United States Patent
Lee et al.

(10) Patent No.: US 11,999,718 B2
(45) Date of Patent: *Jun. 4, 2024

(54) PYRAZOLE DERIVATIVES

(71) Applicant: Aptabio Therapeutics Inc., Yongin-si (KR)

(72) Inventors: Soo Jin Lee, Suwon-si (KR); Sung Hwan Moon, Suwon-si (KR); Sooho Ban, Suwon-si (KR); Eunsil Lee, Suwon-si (KR); Eun Jung Shin, Suwon-si (KR); Yoo-Kyung Goh, Suwon-si (KR)

(73) Assignee: APTABIO THERAPEUTICS INC., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/150,955

(22) Filed: Jan. 6, 2023

(65) Prior Publication Data

US 2023/0234940 A1     Jul. 27, 2023

Related U.S. Application Data

(63) Continuation of application No. PCT/KR2022/002802, filed on Feb. 25, 2022.

(30) Foreign Application Priority Data

Feb. 25, 2021   (KR) .................. 10-2021-0025694

(51) Int. Cl.
| | | |
|---|---|---|
| *C07D 401/14* | (2006.01) | |
| *A61P 1/16* | (2006.01) | |
| *A61P 11/00* | (2006.01) | |
| *A61P 35/00* | (2006.01) | |
| *A61P 39/06* | (2006.01) | |
| *C07D 231/54* | (2006.01) | |
| *C07D 401/04* | (2006.01) | |
| *C07D 401/12* | (2006.01) | |
| *C07D 403/04* | (2006.01) | |
| *C07D 405/04* | (2006.01) | |
| *C07D 413/04* | (2006.01) | |
| *C07D 417/04* | (2006.01) | |
| *C07D 471/04* | (2006.01) | |
| *C07D 495/04* | (2006.01) | |

(52) U.S. Cl.
CPC ............ *C07D 401/14* (2013.01); *A61P 1/16* (2018.01); *A61P 11/00* (2018.01); *A61P 35/00* (2018.01); *A61P 39/06* (2018.01); *C07D 231/54* (2013.01); *C07D 401/04* (2013.01); *C07D 401/12* (2013.01); *C07D 403/04* (2013.01); *C07D 405/04* (2013.01); *C07D 413/04* (2013.01); *C07D 417/04* (2013.01); *C07D 471/04* (2013.01); *C07D 495/04* (2013.01)

(58) Field of Classification Search
CPC .. A61P 35/00; A61P 11/00; A61P 1/16; A61P 39/06; C07D 401/14; C07D 401/04; C07D 401/12; C07D 231/54; C07D 403/04; C07D 405/04; C07D 413/04; C07D 417/04; C07D 471/04; C07D 495/04

See application file for complete search history.

(56) References Cited

U.S. PATENT DOCUMENTS

2016/0200739 A1*   7/2016   Blaquiere .............. A61P 25/00
548/362.5

FOREIGN PATENT DOCUMENTS

| CN | 1071424 | 4/1993 |
|---|---|---|
| CN | 101484425 | 7/2009 |
| CN | 102939087 | 2/2013 |
| CN | 110023311 | 7/2019 |
| DE | 2701467 | 7/1977 |
| EA | 015675 | 10/2011 |
| EP | 1582517 | 10/2005 |
| GB | 1539846 | 2/1979 |
| JP | H06-287187 | 10/1994 |
| JP | 2004-123700 | 4/2004 |
| JP | 2005-029573 | 2/2005 |
| JP | 2005-162639 | 6/2005 |
| JP | 2011-026305 | 2/2011 |
| JP | 2015-512953 | 4/2015 |
| JP | 2023-511302 | 3/2023 |
| KR | 10-2005-0114606 | 12/2005 |

(Continued)

OTHER PUBLICATIONS

KIPO, PCT Search Report & Written Opinion of PCT/KR2022/002802 dated Jun. 9, 2022.

(Continued)

*Primary Examiner* — Noble E Jarrell
*Assistant Examiner* — Richard Grant Peckham
(74) *Attorney, Agent, or Firm* — LEX IP MEISTER, PLLC

(57) ABSTRACT

The Present invention provides a novel pyrazole derivative compound represented by Chemical formula 1, a stereoisomer thereof, a solvate thereof, an isotopic variant thereof, a tautomer thereof, or a pharmaceutically acceptable salt thereof, and a pharmaceutical composition comprising the same.

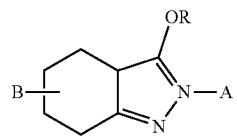

[Chemical formula I]

(In the above, A, B and R, and the like are the same as defined in the description of the invention.)

12 Claims, 9 Drawing Sheets

Specification includes a Sequence Listing.

(56) References Cited

FOREIGN PATENT DOCUMENTS

| WO | 93//07138 | * | 4/1993 |
| WO | 2010-015657 | | 2/2010 |
| WO | 2011-101804 | | 8/2011 |
| WO | 2013-158644 | | 10/2013 |
| WO | 2016-207785 | | 12/2016 |
| WO | 2021-145655 | | 7/2021 |
| WO | 2022-182205 | | 9/2022 |

OTHER PUBLICATIONS

Popova, Gergana, et al. "Optimization of tetrahydroindazoles as inhibitors of human dihydroorotate dehydrogenase and evaluation of their activity and in vitro metabolic stability." Journal of Medicinal Chemistry 63.8 (Mar. 26, 2020): 3915-3934.
Database Registry [Online], CAS Registry No. 2109695-62-5, Entered STN: Aug. 7, 2017.
G. Malcolm Dyson, May's chemistry of synthetic drugs, Fifth Edition, pp. 12-19, Moscow 1959.
Rospatent, Office Action with Search Report of the corresponding RU Patent Application No. 2022134333, dated Aug. 11, 2023.

* cited by examiner

[FIG. 1]
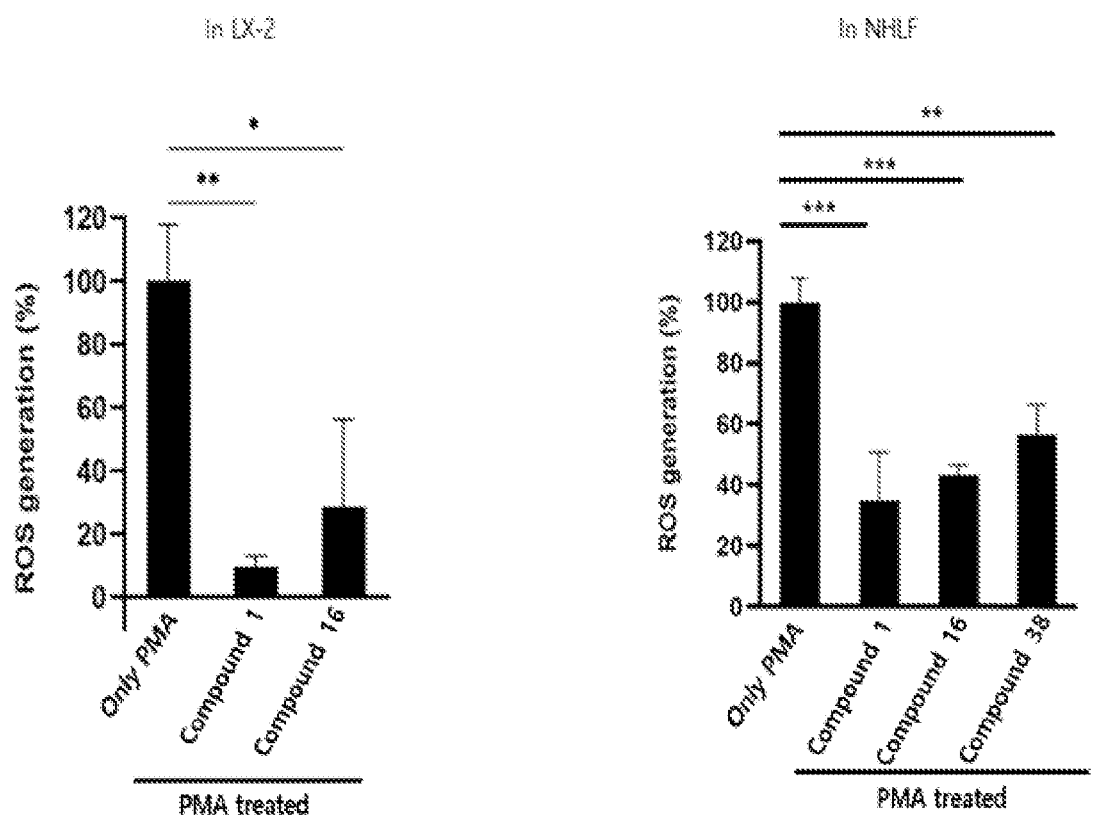

[FIG. 2]
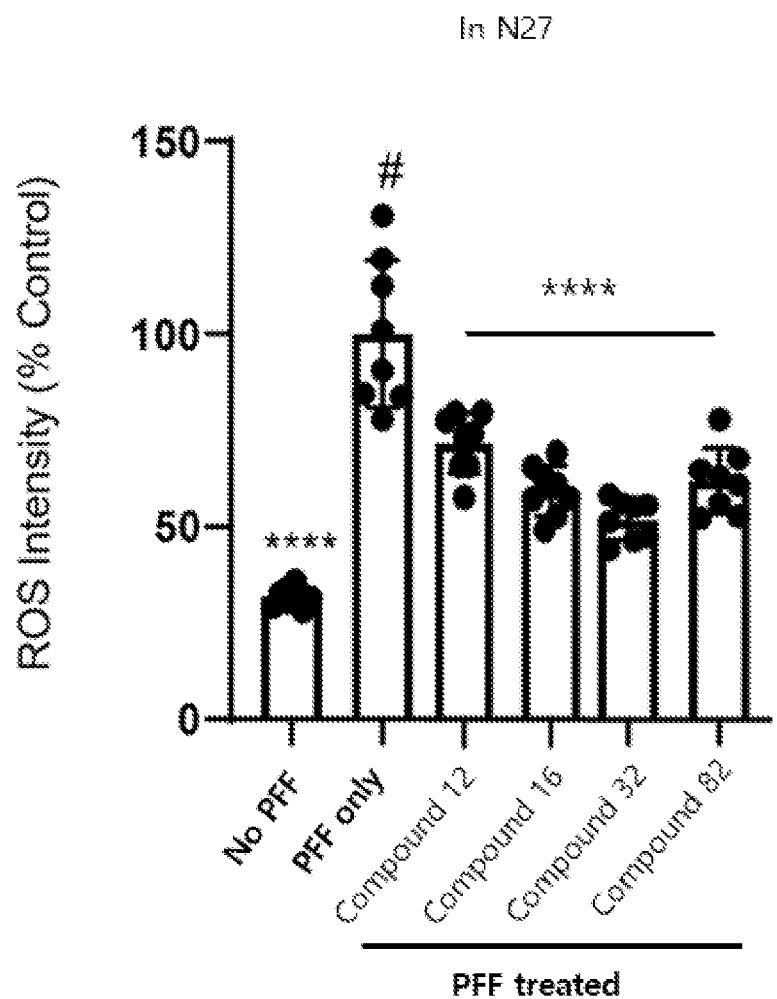

[FIG. 3a]
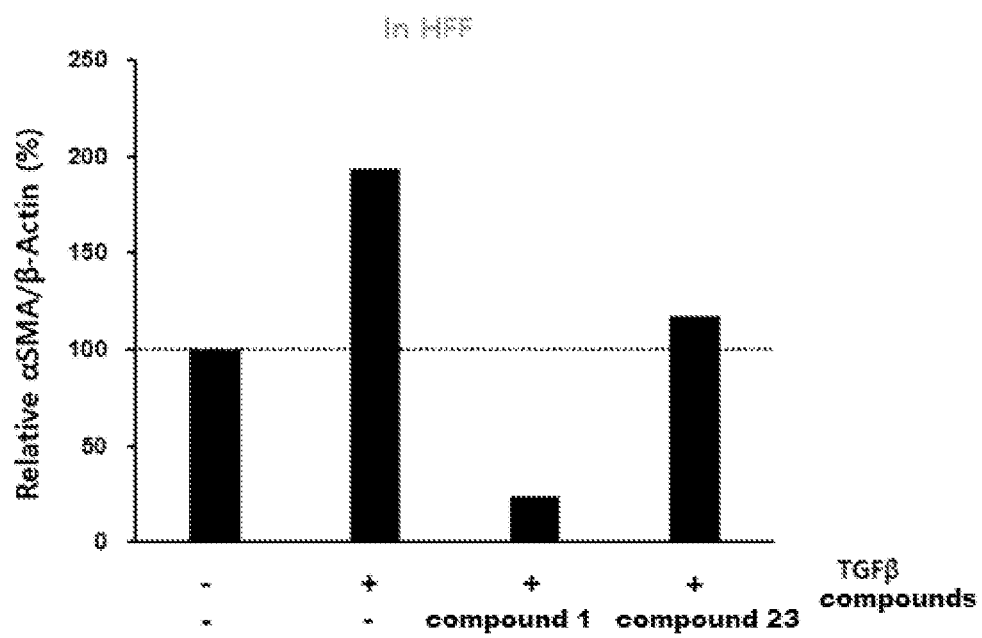
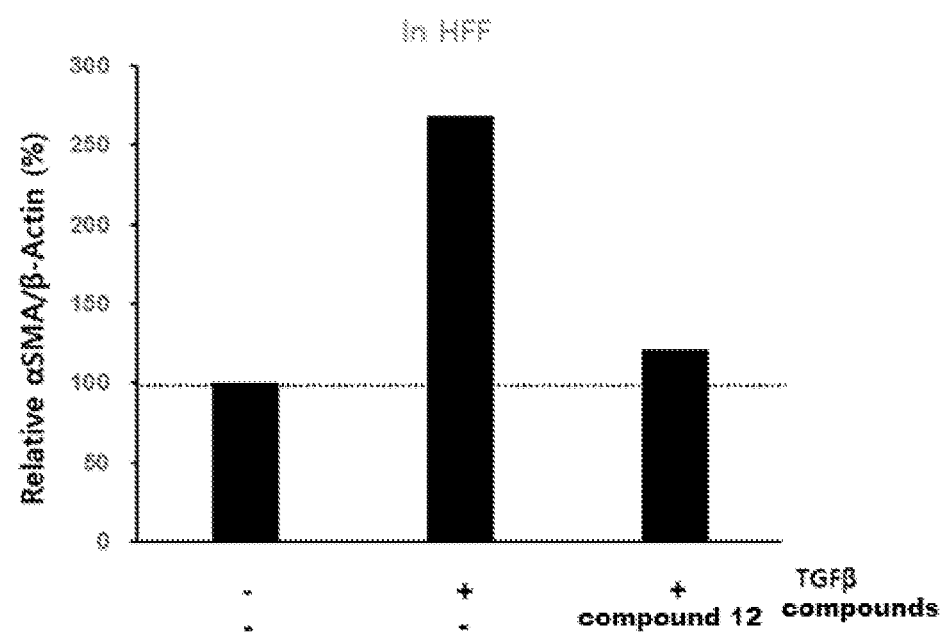

[FIG. 3b]
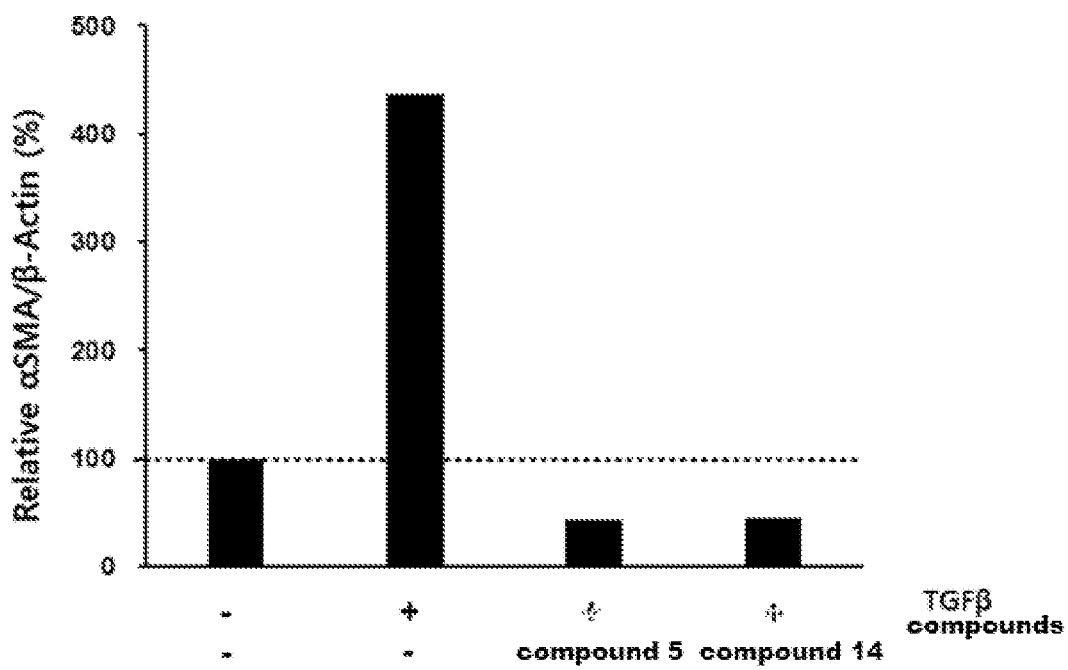
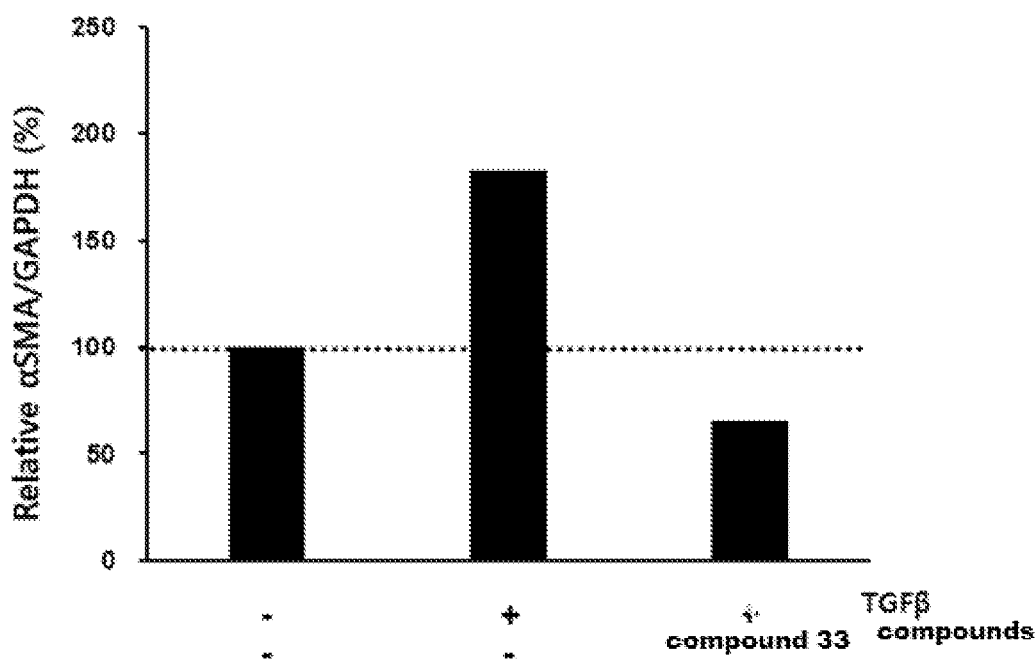

[FIG. 4]
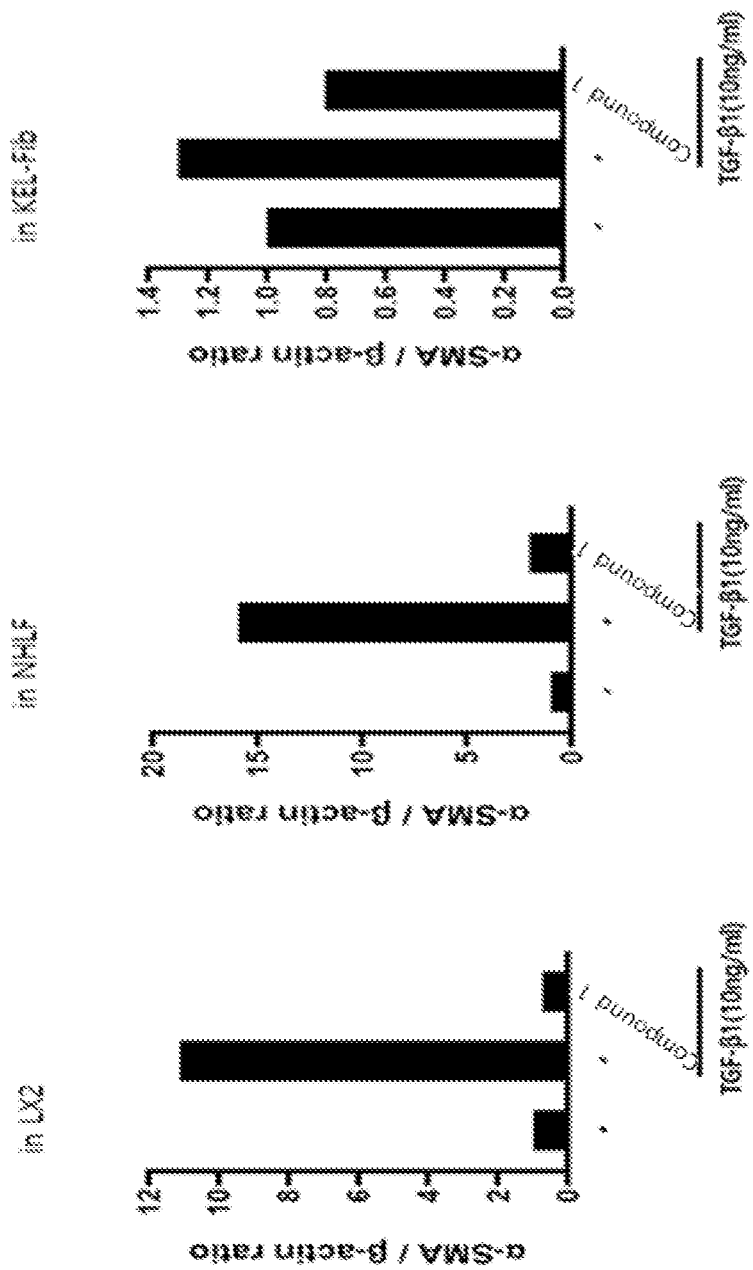

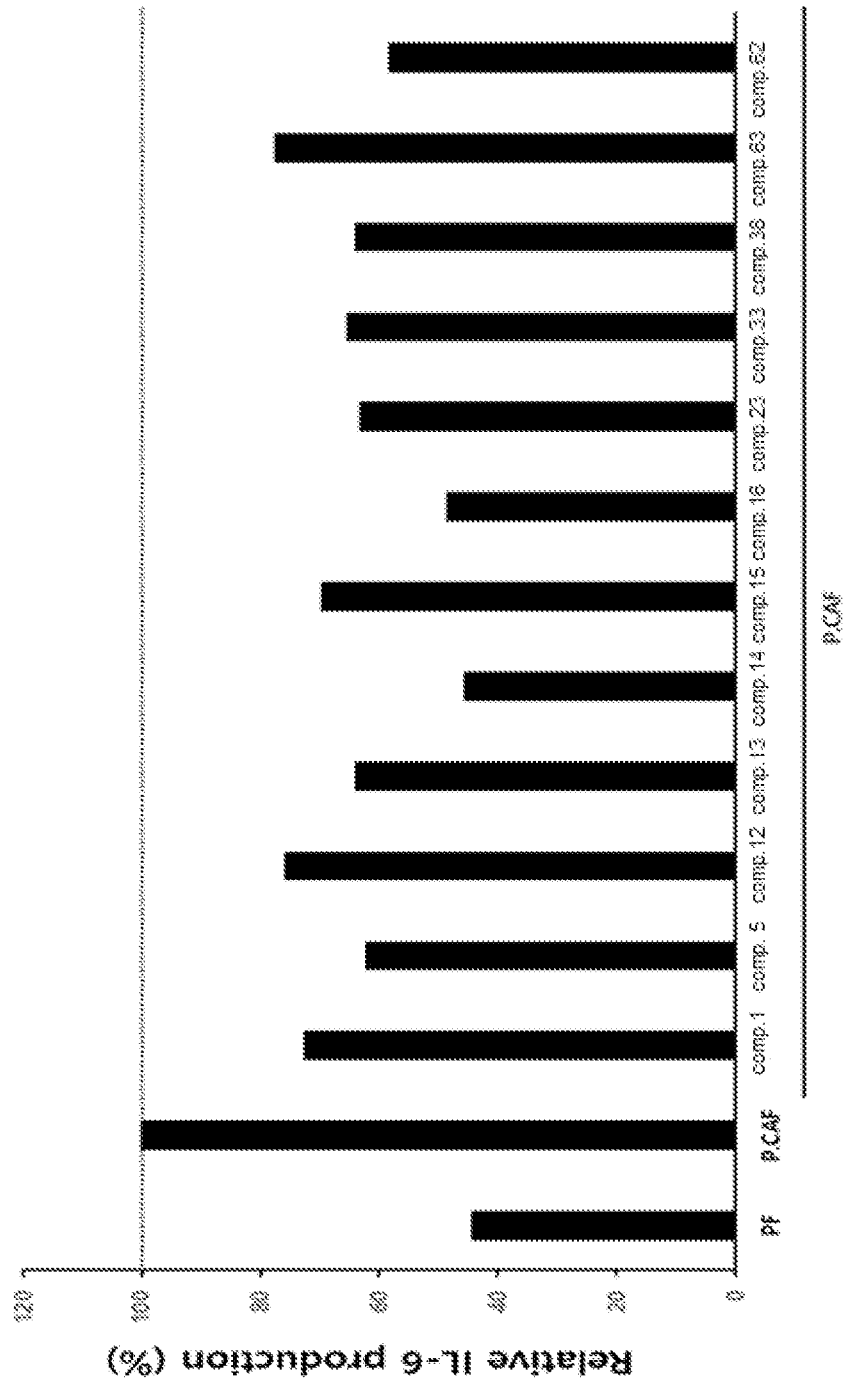
[FIG. 3]

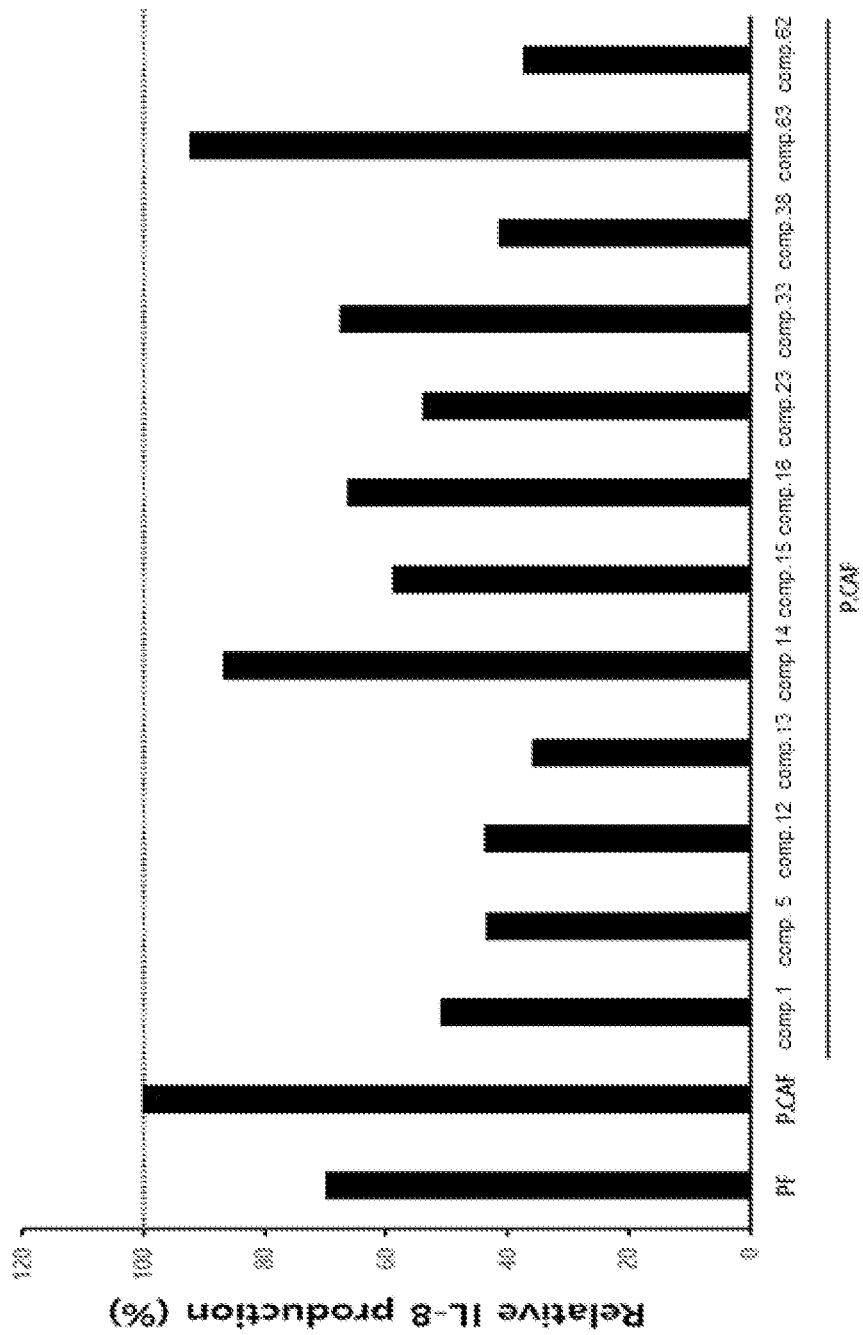
[FIG. 6]

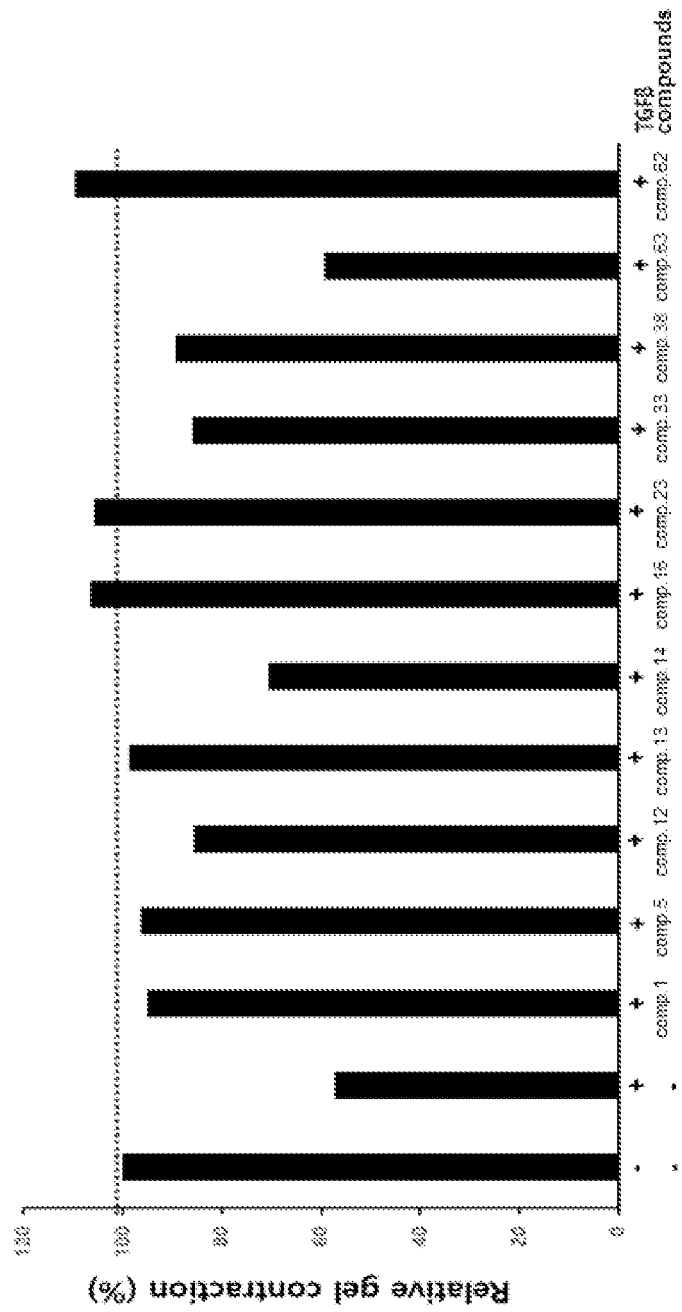
[FIG. 7]

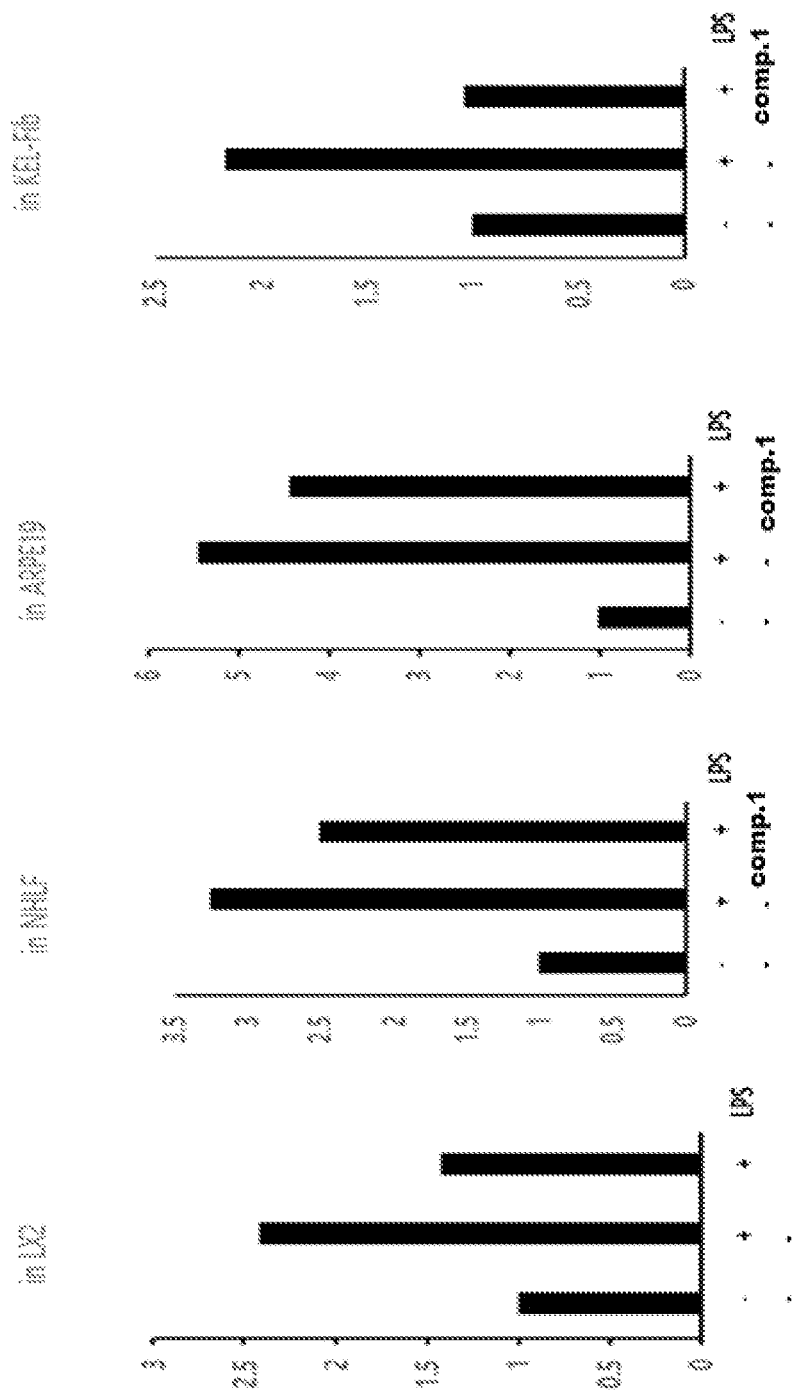
[FIG. 8]

SEQUENCE LISTING

```
Sequence total quantity: 6
SEQ ID NO: 1           moltype = DNA  length = 22
FEATURE                Location/Qualifiers
misc_feature           1..22
                       note = IL-1 beta forward primer
source                 1..22
```

```
                            mol_type = other DNA
                            organism = synthetic construct
SEQUENCE: 1
ccacagacct tccaggagaa tg                                              22

SEQ ID NO: 2                moltype = DNA  length = 23
FEATURE                     Location/Qualifiers
misc_feature                1..23
                            note = IL-1 beta reverse primer
source                      1..23
                            mol_type = other DNA
                            organism = synthetic construct
SEQUENCE: 2
gtgcagttca gtgatcgtac agg                                             23

SEQ ID NO: 3                moltype = DNA  length = 20
FEATURE                     Location/Qualifiers
misc_feature                1..20
                            note = GAPDH forward primer
source                      1..20
                            mol_type = other DNA
                            organism = synthetic construct
SEQUENCE: 3
gtggctggct cagaaaaagg                                                 20

SEQ ID NO: 4                moltype = DNA  length = 20
FEATURE                     Location/Qualifiers
misc_feature                1..20
                            note = GAPDH reverse primer
source                      1..20
                            mol_type = other DNA
                            organism = synthetic construct
SEQUENCE: 4
ggtggtccag gggtcttact                                                 20

SEQ ID NO: 5                moltype = DNA  length = 22
FEATURE                     Location/Qualifiers
misc_feature                1..22
                            note = Beta actin forward primer
source                      1..22
                            mol_type = other DNA
                            organism = synthetic construct
SEQUENCE: 5
caccattggc aatgagcggt tc                                              22

SEQ ID NO: 6                moltype = DNA  length = 22
FEATURE                     Location/Qualifiers
misc_feature                1..22
                            note = Beta actin reverse primer
source                      1..22
                            mol_type = other DNA
                            organism = synthetic construct
SEQUENCE: 6
aggtctttgc ggatgtccac gt                                              22
```

PYRAZOLE DERIVATIVES

REFERENCE TO AN ELECTRONIC SEQUENCE LISTING

The contents of the electronic sequence listing (LPP20226360US_SEQ.xml; Size: 9K bytes; and Date of Creation: Dec. 29, 2022) is herein incorporated by reference in its entirety.

TECHNICAL FIELD

The present invention relates to a novel pyrazole derivative with excellent oxidative stress inhibitory activity, and more specifically, a novel pyrazole derivative showing ability of prevention, improvement or treatment for various related diseases due to excellent oxidative stress inhibitory activity, an optical isomer thereof, a stereoisomer thereof, a solvate thereof, an isotopic variant thereof, a tautomer thereof, or a pharmaceutically acceptable salt thereof, a method for preparing them, and a pharmaceutical composition comprising them.

BACKGROUND ART

Oxidative stress means to a phenomenon in which production of reactive oxygen species or reactive nitrogen species and the antioxidant defense mechanism are out of balance in biomolecules, cells and tissues in vivo, and the production of reactive oxygen species or reactive nitrogen species becomes relatively excessive, and in this case, cell damage and tissue damage are commonly caused.

Reactive oxygen species (ROS) are oxygen free radicals produced due to chemical properties of oxygen and oxygen compounds derived therefrom, and collectively refer to superoxide anion ($O_2$—·), hydrogenperoxide ($H_2O_2$), a hydroxyl group (OH·), an alkoxyl group (RO·), a peroxyl group (ROO·), and the like.

As these reactive oxygen species are chemically very unstable and high reactive, they cause enzyme catalytic reaction, electron transfer in mitochondria, cell signal delivery system and gene expression, activation of transcription factors and inflammation around by causing extensive oxidative damage in biomolecules, cells, tissues, and the like in vivo, and are involved as a major factor in tissue fibrosis. This oxidative damage causes various diseases in all tissues of the human body. Specifically, it is known to be involved in cancer occurrence in tissues such as skin, kidney, heart, joint, lung, brain, blood vessel, intestinal tract, eye, and the like and progression of the occurred cancer, as well as it is known to play an important role in almost all diseases, including cardiovascular disease, inflammation, fibrotic disease, diabetes, and the like.

Recently, it is known that the interaction between the tumor microenvironment and cancer cells plays an important role in tumor growth, metastasis, anticancer agent resistance expression, and then, a cancer associated fibroblast (CAF) acts importantly. The cancer associated fibroblast is known to be activated by ROS to promote tumor immunity escaping, thereby acting on malignancy and metastasis of cancer. Therefore, recently, the cancer associated fibroblast is emerging as a new target for cancer treatment.

It has been reported that, in the liver tissue of patients undergoing hepatic fibrosis, an increase in ROS production of hepatocytes is induced by TGF-β stimulation, thereby increasing expression of collagen and αSMA, which are important for fibrosis. It has been reported that ROS exacerbates pulmonary fibrosis in lung tissue of patients with idiopathic pulmonary fibrosis.

Brain is a highly metabolized tissue and therefore very vulnerable to oxidative damage. Therefore, many studies have been conducted to effectively remove ROS for treatment of various neurodegenerative diseases (Parkinson's disease, Huntington's disease, amyotrophic lateral sclerosis, Alzheimer's disease, multiple sclerosis, ischemic and traumatic brain injury, etc.), but without success. Recently, as ROS was found to be an important factor in these brain diseases, the possibility of treatment through ROS inhibition was reported.

Keloid is a type of benign tumor disease in which the connective tissue of skin proliferates pathologically, making hard bumps, and the epidermis becomes thin and shiny and reddish. It has been reported that the onset and exacerbation of keloid is also one of the reasons for overexpression of connective tissue growth factor (CTGF) by ROS produced by TGF-β stimulation.

In case of diabetes, complications such as diabetic nephropathy and diabetic retinopathy may accompany long-term hyperglycemia, and ROS is known to play an important role in occurrence of complications. In other words, high blood sugar causes an increase in ROS production, and then, the generated ROS may cause diabetic nephropathy and diabetic retinopathy through a series of processes including the death of kidney cells and retinal cells.

In addition, it has been reported that the keloid disease causes retinal fibrosis and macular degeneration, and the like, when the CTGF gene is overexpressed in the retina of eye.

Therefore, the present inventors have studied focusing on that a therapeutic agent for cancer, inflammatory disease, fibrotic disease, neurodegenerative disease, liver disease, skin disease or retinal disease, or the like caused by oxidative stress can be developed using a molecular mechanism inhibiting production of oxidative stress, and as a result, they found that the novel pyrazole derivative of the present invention has an excellent inhibitory activity of ROS production, and confirmed that it can be used for treatment of various disease related to oxidative stress, thereby completing the present invention.

PRIOR ART (Patent document 1) WO 2016-207785

DISCLOSURE

Technical Problem

An object of the present invention is to provide a pyrazole-based compound of Chemical formula 1, an optical isomer thereof, a stereoisomer thereof, a solvate thereof, an isotopic variant thereof, a tautomer thereof, or a pharmaceutically acceptable salt thereof.

An object of the present invention is to provide a pharmaceutical composition comprising the compound of Chemical formula I or stereoisomer thereof, solvate thereof, isotopic variant thereof, tautomer thereof or pharmaceutically acceptable salt thereof and a pharmaceutically acceptable carrier.

An object of the present invention is to provide a method for controlling production of ROS using the compound of Chemical formula I or stereoisomer thereof, solvate thereof, isotopic variant thereof, tautomer thereof or pharmaceutically acceptable salt thereof.

An object of the present invention is to provide a method for treating diseases related to oxidative stress by administering the compound of Chemical formula I or stereoisomer thereof, solvate thereof, isotopic variant thereof, tautomer thereof or pharmaceutically acceptable salt thereof to a subject.

An object of the present invention is to provide a method for preparing the compound of Chemical formula I or stereoisomer thereof, solvate thereof, isotopic variant thereof, tautomer thereof or pharmaceutically acceptable salt thereof.

An object of the present invention is to provide a use of the compound of Chemical formula I, solvate, stereoisomer or pharmaceutically acceptable salt thereof, for preparing a pharmaceutical composition for prevention, improvement or treatment of diseases related to oxidative stress.

Technical Solution

In order to achieve the above objects, as one aspect of the present invention, a novel pyrazole derivative, a compound represented by Chemical formula 1 below, or a stereoisomer thereof, a solvate thereof, an isotopic variant thereof, a tautomer thereof, or a pharmaceutically acceptable salt thereof may be provided.

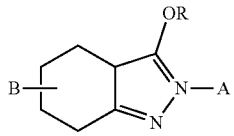

[Chemical formula 1]

In the above formula, A, B and R are as defined below.

As one aspect of the present invention, the present invention provides the compound represented by Chemical formula 1, solvate, stereoisomer or pharmaceutically acceptable salt thereof used for prevention, improvement or treatment of diseases related to oxidative stress.

As one aspect of the present invention, the present invention provides a pharmaceutical composition for treating diseases related to oxidative stress comprising the compound represented by Chemical formula 1, solvate, stereoisomer or pharmaceutically acceptable salt thereof as an active ingredient and an acceptable carrier.

In addition, the present invention provides a method for treating diseases related to oxidative stress comprising administering the compound represented by Chemical formula 1, solvate, stereoisomer or pharmaceutically acceptable salt thereof in an effective amount into a subject in need of treatment.

Furthermore, the present invention provides a use of the compound of Chemical formula 1, solvate, stereoisomer or pharmaceutically acceptable salt thereof, for preparation of a pharmaceutical composition for preventing or treating diseases related to oxidative stress.

Advantageous Effects

The novel pyrazole derivative and pharmaceutical composition comprising the same of the present invention provide an excellent effect for diseases related to oxidative stress.

In addition, the novel pyrazole derivative effectively inhibited oxidative stress and αSMA production in various cells, and in particular, it has an effect for effectively improving cancer, inflammatory disease, fibrotic disease, neurodegenerative disease, liver disease, skin disease or retinal disease, or the like caused by oxidative stress.

BRIEF DESCRIPTION OF THE DRAWINGS

FIG. 1 shows the effect of the compounds of Synthetic examples in inhibiting ROS production induced by PMA in LX-2 and NHLF cells.

FIG. 2 shows the effect of the compound of Synthetic example 3 in inhibiting ROS production induced by alpha-synuclein preformed fibril (PFF) in N27 cells.

FIGS. 3a and 3b shows the effect of the compounds of Synthetic examples (FIG. 3a: Compounds 1, 23 and 12, FIGS. 3b: 5, 14 and 33) in inhibiting expression of αSMA induced by TGF β1 in HFF cells.

FIG. 4 shows the effect of the Synthetic example Compound 1 in inhibiting expression of αSMA induced by TGF β1 in various cells.

FIG. 5 shows the effect of the compounds of Synthetic examples in inhibiting expression of IL6 in P.CAF cells.

FIG. 6 shows the effect of the compounds of Synthetic examples in inhibiting expression of IL8 in P.CAF cells.

FIG. 7 shows the effect of the compounds of Synthetic examples in inhibiting collagen gel contraction induced by TGF β1 in HFF cells.

FIG. 8 shows the effect of the compounds of Synthetic examples in inhibiting expression of IL1β induced by LPS in LX2, NHLF, ARPE19 and KEL-Fib cells.

BEST MODE

Hereinafter, the present invention will be described in more detail.

Unless defined otherwise, all technical terms used herein have the same meaning as commonly understood by those skilled in the art to which the present invention pertains. In addition, numerical values disclosed herein are intended to include the meaning of "about" unless explicitly stated otherwise. All publications and other references mentioned herein are incorporated herein by reference in their entirety.

Definitions of residues used herein are set forth below. In addition, unless there is a separate definition of residues, it is used in the meaning generally understood by those skilled in the art.

The term used herein, "independently" means that when more than one substituent is selected from a number of possible substituents, these substituents may be identical to or different from each other.

The term used herein, "alkyl" refers to an aliphatic carbohydrogen radical, and means a linear or branched monovalent saturated carbohydrogen group. Unless otherwise defined, the alkyl group generally comprises 1~10, 1~8, 1~6, 1~4 or 1~3 carbon atoms. The example of the alkyl group includes methyl, ethyl, propyl (e.g. n-propyl and isopropyl), butyl (e.g. n-butyl, isobutyl, and t-butyl), pentyl (e.g. n-pentyl, isopentyl, and neopentyl), n-hexyl, n-heptyl, n-octyl, n-nonyl and n-decyl.

The term used herein, "alkenyl" refers to an aliphatic carbohydrogen radical comprising one or more carbon-carbon double bonds, and includes linear and branched carbohydrogen radicals. For example, the "alkenyl" is vinyl, allyl, but-1-enyl or but-2-enyl.

The term used herein, "alkynyl" refers to an aliphatic carbohydrogen radical comprising one or more carbon-carbon triple bonds, and includes all linear and branched carbohydrogen radicals. For example, the "alkynyl" is ethynyl, propynyl or butynyl.

The term used herein, "haloalkyl" means an alkyl group having one or more halogen substituents. The haloalkyl includes —CF$_3$, —C$_2$F5, —CHF$_2$, —CCl$_3$, —CHCl$_2$, and —C$_2$Cl$_5$. Unless otherwise defined, the haloalkyl group generally includes 1~6, 1~5, 1~4 or 1~3 carbon atoms, and may be additionally substituted by other substituents.

The term used herein, "alkoxy" may be a linear chain, branched chain or ring chain. The carbon number of the alkoxy group is not particularly limited, but the carbon number of 1~10, 1~8, 1~6, 1~4 or 1~3 is preferable. Specifically, it may be methoxy, ethoxy, n-propoxy, isopropoxy, n-butoxy, isobutoxy, tert-butoxy, sec-butoxy, n-pentyloxy, neopentyloxy, isopentyloxy, and the like, but not limited thereto.

The term used herein, "hydroxy" or "hydroxyl" means —HO alone or in combination with other term.

The term used herein, "amino" means —NH$_2$.

The term used herein, "halo", "halogen" and "halide(s)" represent fluoro, chloro, bromo and iodo.

Herein, the term "cycloalkyl" represents a non-aromatic carbocyclic ring including cyclic alkyl, alkenyl and alkynyl groups. The cycloalkyl group may comprise a monocyclic or polycyclic ring. The polycyclic ring has for example, 2, 3 or 4 fused rings. Unless otherwise defined, the cycloalkyl group generally comprises 3 to 10, or 3 to 7 cyclic carbon atoms. The cycloalkyl group includes cyclopropyl, cyclobutyl, cyclopentyl, cyclohexyl, cycloheptyl, cyclohexadienyl, cycloheptatrienyl, and the like, and may be further substituted by other substituents.

Herein, the term "aryl" means an aromatic carbohydrogen group having a monocyclic or polycyclic ring, and may be further substituted by other substituents. Herein, the polycyclic means a group in which an aryl group is directly connected or condensed with another cyclic group. Herein, another cyclic group may be an aryl group, but may be other type of cyclic group, for example, cycloalkyl group, heteroaryl group, and the like. The polycyclic may have for example, 2, 3, or 4 rings. Unless otherwise defined, the aryl group generally has 5 to 20, 6 to 15, 6 to 12, or 6 to 10 carbon cyclic atoms. The aryl group includes for example, phenyl, naphthyl (e.g., naphthyl-1-yl and naphthyl-2-yl), non-phenyl, anthracenyl, phenanthrenyl, and the like.

Used herein, "heterocycle" represents an aromatic, saturated or partially unsaturated mono-, bi-, di- or poly-cyclic system containing a designated number of cyclic atoms, and includes one or more heteroatoms selected from N, O and S. A ring member, herein heterocyclic ring is connected to the base molecule through a cyclic atom (may be C or N). The bicyclic system may be connected by 1,1-fusion (spiro), 1,2-fusion (fused) or 1,>2-fusion (bridgehead).

Herein, the term "heteroaryl" means a monovalent aromatic group having one or more heteroatoms selected from N, O and S as a ring member. The heteroaryl group includes a monocyclic or polycyclic structure. The polycyclic may have for example, 2, 3 or 4 fused rings. Unless otherwise defined, the heteroaryl group generally comprises 3 to 10, 3 to 7, or 3 to 5 cyclic atoms. The heteroaryl group may comprise 1, 2, or 3 heteroatoms. The heteroaryl group includes for example, furanyl, pyridyl, N-oxopyridyl, pyrimidinyl, pyrazinyl, pyridazinyl, triazinyl, furyl, quinolyl, isoquinolyl, dihydroisoquinolyl, thienyl, imidazolyl, furanyl, thiazolyl, indolyl, pyryl, oxazolyl, benzofuryl, benzothienyl, benzthiazolyl, isooxazolyl, pyrazolyl, triazolyl, tetrazolyl, indazolyl, 1,2,4-thiadiazolyl, isothiazolyl, benzothienyl, furynyl, benzimidazolyl, indolinyl, and the like, and may be further substituted by other substituents.

Used herein, "heterocycloalkyl" refers to a monocyclic, bicyclic, tricyclic or polycyclic alkyl having 3 to 10 carbocyclic members containing one or more, for example, 1 to 4, 1 to 3, or 1 to 2 heteroatoms selected from N, O and S. In addition, the heterocycle according to the present invention may be also fused or crosslinked heterocycloalkyl. The example of the non-aromatic ring may be azetidinyl, oxetanyl, tetrahydro, tetrahydrofuran, pyrrole, pyrrolidinyl, imidazolinyl, imaidazolidinyl, oxazolinyl, oxazolidinyl, piperidinyl, piperazinyl, tetrahydropyranyl, dihydropyranyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, tetrahydropyrazolopyridinyl, morpholinyl, indolinyl, azethiomorpholinyl, and the like.

Attachment of the heterocycloalkyl substituent may occur by a carbon atom or heteroatom. The heterocycloalkyl group may be randomly substituted with one or more appropriate groups by one or more aforementioned groups. Unless otherwise defined, the heterocycloalkyl refers to 4 to 12-membered heterocycloalkyl, preferably, 4 to 10-membered heterocycloalkyl, more preferably, 4 to 7-membered heterocycloalkyl.

Herein, the term "arylalkyl" represents an alkyl group substituted by an aryl group. The "aryl" and "alkyl" are same as defined above.

Herein, the term "heteroarylalkyl" represents an alkyl group substituted by a heteroaryl group. The "heteroaryl" and "alkyl" are same as defined above.

Herein, the term "alkylheterocycloalkyl" represents a heterocycloalkyl group substituted with an alkyl group. The "alkyl" and "heterocycloalkyl" are same as defined above.

Herein, the "substituted or unsubstituted amine group" may be selected from the group consisting of monoalkylamine group, —NH2, and dialkylamine group, and the "alkyl" is same as defined above. The specific example of the substituted or unsubstituted amine group includes NH2, methylamine group, dimethylamine group, ethylamine group, diethylamine, and the like, but not limited thereto.

Herein, the "alkylene group" means an alkyl group having two binding sites, namely, a divalent group. The description of the aforementioned alkyl group may be applied for them except that they are bivalent, respectively.

Herein, the term "substitution" means that a hydrogen atom bound to a carbon atom of a compound is substituted with another substituent, and the position to be substituted is not limited as long as the position at which the hydrogen atom is substituted, that is, a position where a substituent is substitutable is not limited, and when 2 or more substituents are substituted, 2 or more substituents may be identical or different, and 2 or more identical or different substituents may be connected and substituted.

Herein, the term "substituted alkyl" is a form in which the following substituent is substituted at a carbon atom of C1-C10 linear or branched alkyl. Specifically, it is a form in which one or more substituents or same or different 2 or more substituents are connected and substituted, which are selected from heavy hydrogen, halogen, cyano, nitro, carboxyl, substituted or unsubstituted amine, substituted or unsubstituted C5-C20 aryl or C5-C20 heteroaryl, C1-C5 alkoxy, C1-C5 haloalkyl. As an exemplary substituent, trifluoromethyl, halogen, cyano, methoxy, carboxyl, methyl, amino, nitro, dimethylamino, cyclopropyl substituted imidazole, pyridine, substituted or unsubstituted sulfonyl, and the like may be used, but not limited thereto.

The term herein, "substituted cycloalkyl" is a form in which one or more substituents or same or different 2 or more substituents are connected and substituted to C3-C8 cycloalkyl, which are selected from heavy hydrogen, halogen, cyano, nitro, carboxyl, substituted or unsubstituted amine, substituted or unsubstituted C5-C20 aryl or C5-C20 heteroaryl, C1-C5 alkoxy, C1-C5 haloalkyl. As an exemplary substituent, trifluoromethyl, halogen, cyano, methoxy, carboxyl, methyl, amino, nitro, dimethylamino, cyclopropyl, substituted imidazole, substituted or unsubstituted sulfonyl, and the like may be used, but not limited thereto.

The term herein, "substituted aryl" or "substituted heteroaryl" is a form in which one or more substituents, or same or different 2 or more substituents are connected and substituted to C5-C20 aryl or C5-C50 heteroaryl, which are selected from heavy hydrogen, halo, cyano, nitro, carboxyl, substituted or unsubstituted amine, C1-C5 alkoxy, C1-C5 haloalkyl, C1-C10 alkyl, C3-C8 cycloalkyl or C3-C8 heterocycloalkyl, C3-C8 cycloalkyl C1-C10 alkyl, C5-C20 aryl C1-C10 alkyl. As an exemplary substituent, trifluoromethyl, halogen, cyano, methoxy, carboxyl, methyl, amino, nitro, dimethylamino, cyclopropyl substituted imidazole, methyl piperazine, substituted imidazopyrimidine, substituted or unsubstituted sulfonyl, and the like may be used, but not limited thereto.

Herein, the "adjacent" group may mean a substituent substituted on an atom directly connected to an atom in which the corresponding substituent is substituted, a substituent sterically closest to the corresponding substituent, or another substituent substituted on an atom in which the corresponding substituent is substituted. For example, two substituents substituted at the ortho position in the benzene ring and two substituents substituted at the same carbon in the aliphatic ring may be interpreted as "adjacent" to each other.

When used in regard of a compound, an "effective dose" is an amount effective to treat or prevent disease in a subject as described herein.

Compound

In order to achieve the above objects, the present invention provides a compound of Chemical formula I below, or a stereoisomer thereof, a solvate thereof, an isotopic variant thereof, a tautomer thereof, or a pharmaceutically acceptable salt thereof:

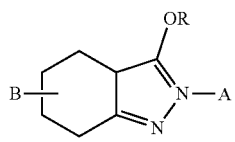

in the formula,

A is a substituted or unsubstituted 5-membered to 20-membered heteroaryl or substituted or unsubstituted $C_5$-$C_{20}$ aryl; and then, the 5-membered to 20-membered heteroaryl or $C_5$-$C_{20}$ aryl may be unsubstituted, or may be substituted with 1, 2, 3 or 4 kinds of substituents consisting of cyano, halo, haloalkyl, nitro, —C(=O)$R_1$, —C(=O)O$R_1$, —NH—C(=O)$R_1$, $C_1$-$C_{10}$ alkoxy group, substituted or unsubstituted $C_1$-$C_{10}$ alkyl, substituted or unsubstituted $C_3$-$C_5$ cycloalkyl, substituted or unsubstituted amine, substituted or unsubstituted $C_5$-$C_{20}$ aryl, substituted or unsubstituted 5-membered to 20-membered heteroaryl and substituted or unsubstituted 5-membered to 20-membered heterocycloalkyl, and then, the $R_1$ may be hydrogen, heavy hydrogen, $C_1$-$C_{10}$ alkyl; and two or more adjacent groups may combine with each other to form a substituted or unsubstituted aromatic hydrocarbon ring, wherein the aromatic hydrocarbon ring may form a 5-membered to 10-membered heteroaryl ring or a $C_5$-$C_{10}$ aryl ring comprising 0, 1, 2 or 3 heteroatoms selected from N, O and S; and R is hydrogen, heavy hydrogen, cyano, halo, nitro, haloalkyl, substituted or unsubstituted $C_1$-$C_{10}$ alkyl, substituted or unsubstituted $C_3$-$C_8$ cycloalkyl, substituted or unsubstituted $C_5$-$C_{20}$ aryl, substituted or unsubstituted 5-membered to 20-membered heteroaryl, or —C(=O)$R_2$, and then, the $R_2$ is $C_3$-$C_8$ cycloalkyl, $C_1$-$C_{10}$ alkyl, $C_2$-$C_{10}$ alkenyl, or $C_6$-$C_{10}$ aryl; and B is -NKM or substituted or unsubstituted 5-membered to 20-membered heteroaryl or substituted or unsubstituted 5-membered to 20-membered heterocycloalkyl; and K and M are each independently hydrogen, heavy hydrogen, cyano, halo, nitro, haloalkyl, substituted or unsubstituted $C_1$-$C_{10}$ alkyl, substituted or unsubstituted $C_1$-$C_{10}$ alkoxy, substituted or unsubstituted $C_3$-$C_8$ cycloalkyl, substituted or unsubstituted $C_5$-$C_{20}$ aryl, substituted or unsubstituted $C_5$-$C_{20}$ aryl $C_1$-$C_{10}$ alkyl, substituted or unsubstituted 5-membered to 20-membered heteroaryl or substituted or unsubstituted 5-membered to 20-membered heteroaryl $C_1$-$C_{10}$ alkyl;

wherein the $C_1$-$C_{10}$ alkyl may be unsubstituted, or substituted with 1, 2, 3 or 4 kinds of substituents selected from the group consisting of heavy hydrogen, halo, hydroxy, cyano, nitro, carboxyl, substituted or unsubstituted amino, substituted or unsubstituted $C_1$-$C_{10}$ alkyl, substituted or unsubstituted $C_1$-$C_{10}$ haloalkyl, substituted or unsubstituted $C_1$-$C_{10}$ hydroxyalkyl, substituted or unsubstituted $C_3$-$C_8$ cycloalkyl, $C_1$-$C_{10}$ alkoxy, $C_1$-$C_{10}$ alkylsulfonyl, $C_5$-$C_{20}$ arylsulfonyl, $C_5$-$C_{20}$ aryloxy, substituted or unsubstituted $C_5$-$C_{20}$ aryl, substituted or unsubstituted 5-membered to 20-membered heteroaryl and substituted or unsubstituted 5-membered to 20-membered heterocycloalkyl; and the $C_3$-$C_8$ cycloalkyl may be unsubstituted, or substituted with 1, 2, 3 or 4 kinds of substituents selected from the group consisting of heavy hydrogen, halogen, cyano, nitro, carboxyl, substituted or unsubstituted amine, substituted or unsubstituted $C_5$-$C_{20}$ aryl or 5-membered to 20-membered heteroaryl, $C_1$-$C_{10}$ alkoxy and $C_1$-$C_{10}$ haloalkyl; and the 5-membered to 20-membered heteroaryl, 5-membered to 20-membered heterocycloalkyl, or $C_5$-$C_{20}$ aryl may be unsubstituted, or substituted with 1, 2, 3 or 4 kinds of substituents selected from the group consisting of heavy hydrogen, halo, cyano, nitro, —C(=O)R', —C(=O)OR', —NH—C(=O)R", substituted or unsubstituted amino, substituted or unsubstituted $C_1$-$C_{10}$ alkyl, substituted or unsubstituted $C_1$-$C_{10}$ alkoxy, substituted or unsubstituted $C_1$-$C_{10}$ haloalkyl, substituted or unsubstituted $C_1$-$C_{10}$ hydroxyalkyl, substituted or unsubstituted $C_1$-$C_{10}$alkylsulfonyl, substituted or unsubstituted $C_5$-$C_{20}$arylsulfonyl, substituted or unsubstituted $C_3$-$C_8$ cycloalkyl, substituted or unsubstituted $C_3$-$C_8$ cycloalkyl $C_1$-$C_{10}$alkyl, substituted or unsubstituted $C_5$-$C_{20}$aryl, substituted or unsubstituted $C_5$-$C_{20}$ aryl $C_1$-$C_{10}$ alkyl, substituted or unsubstituted 5-membered to 12-memberedheterocycloalkyl, substituted or unsubstituted $C_1$-$C_{10}$alkyl $C_3$-$C_8$ cycloalkyl and substituted or unsubstituted $C_1$-$C_{10}$ alkyl 5-membered to 20-membered heterocycloalkyl, and then, the R' and R" are each independently hydrogen, heavy hydrogen, substituted or unsubstituted amine, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_6$-$C_{10}$ aryl or substituted or unsubstituted $C_6$-$C_{10}$ aryl, or $C_1$-$C_6$ alkyl; and the substituted amino group may be substituted with 1 kind or 2 kinds of $C_1$-$C_{10}$ alkyl groups; and the heteroatom of the heterocycloalkyl or heteroaryl ring may be one or more kinds selected from N, S and O.

As one specific aspect, the A is a unsubstituted, or substituted 5-membered to 12-membered heteroaryl or $C_6$-$C_{10}$ aryl, and then, the 5-membered to 12-membered heteroaryl or $C_6$-$C_{10}$ aryl may be substituted with 1, 2, 3 or 4 kinds of substituents selected from the group consisting of cyano, halo, $C_1$-$C_6$ haloalkyl, nitro, —C(=O)$R_1$, —C(=O)O$R_1$, —NH—C(=O)$R_1$, $C_1$-$C_6$ alkyl, $C_1$-$C_6$ alkoxy, $C_3$-$C_6$ cycloalkyl, amino, $C_6$-$C_{10}$ aryl, 5-membered to 12-membered heteroaryl, and 5-membered to 12-membered heterocycloalkyl, and then the $R_1$ is hydrogen, heavy hydrogen or $C_1$-$C_6$ alkyl; and two or more adjacent groups may combine with each other to form a substituted or unsubstituted aromatic hydrocarbon ring, wherein the aromatic hydrocarbon ring may form a 5-membered to 7-membered heteroaryl ring or a $C_6$-$C_9$ aryl ring comprising 0, 1, 2 or 3 heteroatoms selected from N, O and S.

As one specific aspect, the A may be 5-membered to 10-membered heteroaryl or $C_6$-$C_9$ aryl having 1, 2, 3 or 4 heteroatoms selected from the group consisting of N, O and S.

As one specific aspect, the A may be pyridinyl, pyrimidinyl, pyrazinyl, triazolyl, thiazolyl, phenyl or thieno[3,2]pyridine.

As one specific aspect, the A may be substituted with 1 kind, 2 kinds, 3 kinds or 4 kinds of $C_1$-$C_6$ alkyl, $C_1$-$C_6$ alkoxy, F, Cl, Br, I, cyano, amino, nitro, —C(=O)$R_1$, —C(=O)O$R_1$, —NH—C(=O)$R_1$, 5-membered to 12-membered heterocycloalkyl, and then, the $R_a$ may be hydrogen, heavy hydrogen, $C_1$-$C_6$ alkyl.

As one specific aspect, the A may be substituted with 1 kind, 2 kinds, 3 kinds or 4 kinds of methyl, ethyl, propyl, butyl, methoxy, ethoxy, propoxy, butoxy, F, Cl, Br, I, cyano, amino, nitro, —C(=O)OH, —C(=O)$CH_3$, —NH—C(=O)$CH_3$, morpholino, or piperidino.

As one specific aspect, the R is hydrogen, heavy hydrogen, cyano, halo, nitro, unsubstituted or $C_3$-$C_6$ cycloalkyl-substituted $C_1$-$C_6$alkyl, $C_1$-$C_6$haloalkyl, $C_3$-$C_6$cycloalkyl, $C_6$-$C_{10}$ aryl, 5-membered to 12-membered heteroaryl, —C(=O)$R_2$, and then, the $R^2$ is $C_3$-$C_6$ cycloalkyl, $C_1$-$C_6$ alkyl, $C_2$-$C_6$ alkenyl, or $C_6$-$C_{10}$ aryl.

As one specific aspect, the $R_2$ may be cyclopropyl, methyl, ethyl, propyl, ethenyl, propenyl or phenyl.

As one specific aspect, the R may be hydrogen, heavy hydrogen, cyano, halo, nitro, methyl, ethyl, propyl, butyl, cyclopropylmethyl, $CF_3$, —C(=O)-cyclopropyl, —C(=O)-ethenyl, or benzoyl.

As one specific aspect, the B is -NKM or 5-membered to 12-membered heteroaryl or 5-membered to 12-membered heterocycloalkyl, and then, the 5-membered to 12-membered heteroaryl or 5-membered to 12-membered heterocycloalkyl is unsubstituted, or substituted with 1, 2, 3 or 4 kinds of heavy hydrogen, halo, cyano, nitro, —$NR_3R_4$, $C_1$-$C_6$ alkyl, $C_1$-$C_6$ alkoxy, $C_6$-$C_{10}$ aryl, —C(=O)$R_5$, —$SO_2$—$R_6$, and then, the $C_1$-$C_6$ alkyl, $C_1$-$C_6$ alkoxy or $C_6$-$C_{10}$ aryl may be unsubstituted, or substituted with 1, 2, 3 or 4 kinds of hydroxy, $C_1$-$C_6$ alkyl, $C_1$-$C_6$ alkoxy, $C_6$-$C_{10}$ aryloxy, or unsubstituted or $C_1$-$C_6$ alkyl, $C_6$-$C_{10}$ aryl $C_1$-$C_6$ alkyl or $C_1$-$C_6$ alkylcarbonyl-substituted 4-membered to 12-membered heterocycloalkyl, and the $R_3$ and $R_4$ are each independently hydrogen, heavy hydrogen, —C(=O)—$R_a$, $C_1$-$C_6$ alkyl or $C_6$-$C_{10}$ aryl, and the $C_1$-$C_6$ alkyl or $C_6$-$C_{10}$ aryl is unsubstituted or substituted with 1, 2, 3 or 4 kinds of halo, hydroxy, $C_1$-$C_6$ alkyl, $C_1$-$C_6$ alkoxy or $C_6$-$C_{10}$ aryloxy, and then the $R_a$ is hydrogen, heavy hydrogen, $C_1$-$C_6$ alkyl or $C_1$-$C_6$ haloalkyl; and the $R_5$ is —$OR_b$, —$NR_cR_d$, $C_1$-$C_6$ alkyl, $C_2$-$C_6$ alkenyl, $C_2$-$C_6$ alkynyl, $C_3$-$C_8$ cycloalkyl, and then, the $C_1$-$C_6$ alkyl, $C_2$-$C_6$ alkenyl or $C_2$-$C_6$ alkynyl may be unsubstituted, or substituted with 1, 2, 3 or 4 kinds of mono $C_1$-$C_6$ alkylamine or di $C_1$-$C_6$ alkylamine, and then the $R_b$, $R_c$ and $R_d$ are each independently hydrogen, heavy hydrogen, $C_6$-$C_{10}$ aryl or $C_6$-$C_{10}$ aryl $C_1$-$C_6$ alkyl, and the $R_6$ is $C_1$-$C_6$ alkyl, unsubstituted or 1, 2, 3 or 4 kinds of $C_1$-$C_6$ alkyl-substituted $C_6$-$C_{10}$aryl, and the K and M are each independently hydrogen, heavy hydrogen, cyano, halo, nitro, $C_1$-$C_6$ haloalkyl, $C_1$-$C_6$ alkyl, $C_1$-$C_6$ alkoxy, $C_3$-$C_8$ cycloalkyl, $C_6$-$C_{10}$ aryl, $C_6$-$C_{10}$ aryl $C_1$-$C_6$ alkyl-, 5-membered to 12-membered heteroaryl, 5-membered to 12-membered heteroaryl $C_1$-$C_6$ alkyl, and then the $C_1$-$C_6$ alkyl, $C_1$-$C_6$ alkoxy, $C_6$-$C_{10}$ aryl, $C_3$-$C_5$ cycloalkyl or 5-membered to 12-membered heteroaryl may be substituted with 1, 2, 3 or 4 kinds of cyano, halo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylsulfonyl, $C_6$-$C_{10}$ arylsulfonyl, —$NR_7R_8$, —C(=O)$R_9$, 5-membered to 12-membered heterocyclyl, hydroxy, nitro, $C_6$-$C_{10}$ aryl, and then, the 5-membered to 12-membered heterocyclyl or $C_6$-$C_{10}$ aryl may be unsubstituted or substituted with $C_1$-$C_6$ alkyl, and the $R_9$ is —$OR_e$, —$NR_eR_f$, unsubstituted or 1, 2, 3 or 4 kinds of —$NR_eR_f$-substituted $C_2$-$C_6$ alkenyl, or $C_6$-$C_{10}$ aryl, and then, the $R_e$ and $R_f$ are each independently hydrogen, heavy hydrogen, $C_1$-$C_6$ alkyl, $C_6$-$C_{10}$ aryl, or $C_1$-$C_6$ alkyl.

As one specific aspect, the B may be 5-membered to 10-membered heteroaryl or 5-membered to 10-membered heterocycloalkyl having 1 kind to 3 kinds heteroatoms selected from the group consisting of N, O and S, and they may be substituted with the aforementioned substituents or unsubstituted.

As one specific aspect, the B may be pyrrolidine, piperazine, dihydroisoquinoline, morpholine or piperidine, and they may be substituted with the aforementioned substituents or unsubstituted.

As one specific aspect, the compound of Chemical formula I may be a compound of Chemical formula I-1 below:

[Chemical formula I-1]

in the formula, the definition of K, M and R is same as the Chemical formula I; and D is $CR_{10}$, N, O or S, or E is $CR_{11}$, N, O or S, or F is $CR_{12}$, N, O or S, or G is $CR_{13}$, N, O or S, or J is $CR_{14}$, N or S, but N, O and S are one or more; and the $R_{10}$ to $R_{14}$ are same or different, and may be each dependently substituted with 1, 2, 3 or 4 kinds of substituents consisting cyano, halo, haloalkyl, nitro, —C(=O)$R_1$, —C(=O)OR$_1$, —NH—C(=O)R$_1$, C$_1$-C$_{10}$ alkoxy, substituted or unsubstituted C$_1$-C$_{10}$ alkyl, substituted or unsubstituted C$_3$-C$_8$ cycloalkyl, substituted or unsubstituted amine, substituted or unsubstituted C$_5$-C$_{20}$ aryl, substituted or unsubstituted 5-membered to 12-membered heteroaryl and substituted or unsubstituted 5-membered to 12-membered heterocycloalkyl, and then the R$_1$ may be hydrogen, heavy hydrogen, C$_1$-C$_{10}$alkyl; and two or more adjacent groups may combine with each other to form a substituted or unsubstituted aromatic hydrocarbon ring, wherein the aromatic hydrocarbon ring may form a 5-membered to 10-membered heteroaryl ring or a C$_6$-C$_{10}$ aryl ring comprising 0, 1, 2 or 3 heteroatoms selected from N, O and S.

As one specific aspect, the compound of Chemical formula I may be a compound of Chemical formula I-2 below:

[Chemical formula I-2]

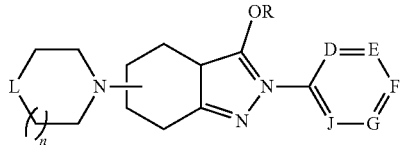

in the formula,
the definition of the R, D, E, F, G and J is same as the Chemical formula I-1; and
n is an integer of 0, 1 or 2; and
L is CH$_2$, NH or O; and

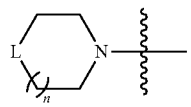

may be unsubstituted, or substituted with 1, 2, 3 or 4 kinds of heavy hydrogen, halo, cyano, nitro, —NR$_3$R$_4$, C$_1$-C$_6$ alkyl, C$_1$-C$_6$ alkoxy, C$_6$-C$_{10}$ aryl, —C(=O)R$_5$, —SO$_2$—R$_6$, and then, when the substituent is 2 kinds or more, two or more adjacent groups may combine with each other to form a substituted or unsubstituted 5-membered to 20-membered heteroaryl or substituted or unsubstituted 5-membered to 20-membered heterocycloalkyl with

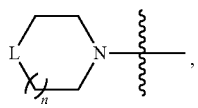

and
then the C$_1$-C$_6$ alkyl, C$_1$-C$_6$ alkoxy or C$_6$-C$_{10}$ aryl may be unsubstituted, or substituted with 1, 2, 3 or 4 kinds of hydroxy, C$_1$-C$_6$ alkyl, C$_1$-C$_6$ alkoxy, C$_6$-C$_{10}$ aryloxy, or unsubstituted or C$_1$-C$_6$ alkyl, C$_6$-C$_{10}$ aryl C$_1$-C$_6$ alkyl or C$_1$-C$_6$ alkylcarbonyl-substituted 4-membered to 12-membered heterocycloalkyl, and the R$_3$ and R$_4$ are each independently hydrogen, heavy hydrogen, —C(=O)—R$_a$, C$_1$-C$_6$ alkyl or C$_6$-C$_{10}$ aryl, and the C$_1$-C$_6$ alkyl or C$_6$-C$_{10}$ aryl may be unsubstituted or substituted with 1, 2, 3 or 4 kinds of halo, hydroxy, C$_1$-C$_6$ alkyl, C$_1$-C$_6$ alkoxy or C$_6$-C$_{10}$ aryloxy, and then the Ra is hydrogen, heavy hydrogen, C$_1$-C$_6$ alkyl or C$_1$-C$_6$haloalkyl; and the R$_5$ is —OR$_b$, —NR$_c$R$_d$, C$_1$-C$_6$ alkyl, C2-C6 alkenyl, C2-C6 alkynyl, C3-C8 cycloalkyl, and then, the C$_1$-C$_6$ alkyl, C2-C6 alkenyl or C2-C6 alkynyl may be unsubstituted, or substituted with 1, 2, 3 or 4 kinds of mono C$_1$-C$_6$ alkylamine or di C$_1$-C$_6$ alkylamine, and the R$_b$, R$_c$ and R$_d$ are each independently hydrogen, heavy hydrogen, C$_6$-C$_{10}$ aryl or C$_6$-C$_{10}$ aryl C$_1$-C$_6$ alkyl, and the R$_6$ is C$_1$-C$_6$ alkyl, unsubstituted or 1, 2, 3 or 4 kinds of C$_1$-C$_6$ alkyl-substituted C$_6$-C$_{10}$ aryl.

In one specific aspect, when the L of is

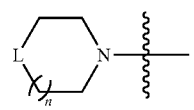

substituted, the L is CH$_2$ or NH, and among them, one kind or 2 kinds of H may be substituted with the above substituents.

As one specific aspect, the compound of Chemical formula I may be a compound of Chemical formula I-3 below:

[Chemical formula I-3]

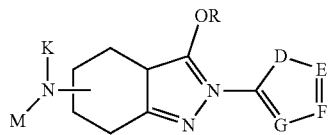

in the formula,
the definition of K, M, R, D, E, F and G is same as the Chemical formula I-1.

As one specific aspect, the compound of Chemical formula I may be a compound of Chemical formula I-4 below

[Chemical formula I-4]

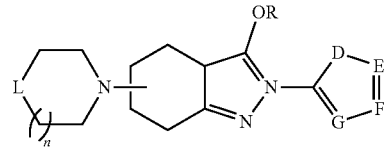

in the formula,
the definition of L, n, R, D, E, F and G is same as the Chemical formula I-2.

As one aspect, the compounds of Chemical formula I according to the present invention may be one or more selected from the group consisting of the following compounds 1) to 161), but not limited thereto.

1) 5-(Benzylmethylamino)-2-(pyridin-2-yl)-4,5,6,7-tetrahydro-2H-indazol-3-ol;
2) 5-(Benzylcyclopropylamino)-2-(pyridin-2-yl)-4,5,6,7-tetrahydro-2H-indazol-3-ol;
3) 4-{[(3-Hydroxy-2-(pyridin-2-yl)-4,5,6,7-tetrahydro-2H-indazol-5-yl)methylamino]methyl}benzonitrile;
4) 5-[(4-Fluorobenzyl)methylamino]-2-(pyridin-2-yl)-4,5,6,7-tetrahydro-2H-indazol-3-ol;
5) 5-[(2,4-Difluorobenzyl)methylamino]-2-(pyridin-2-yl)-4,5,6,7-tetrahydro-2H-indazol-3-ol;

6) 5-[(2-Chlorobenzyl)methylamino]-2-(pyridin-2-yl)-4,5,6,7-tetrahydro-2H-indazol-3-ol;
7) 5-[(3-Chlorobenzyl)methylamino]-2-(pyridin-2-yl)-4,5,6,7-tetrahydro-2H-indazol-3-ol;
8) 5-[Methyl-(4-trifluoromethylbenzyl)amino]-2-pyridin-2-yl-4,5,6,7-tetrahydro-2H-indazol-3-ol;
9) 5-[Methyl-(3-methylbenzyl)amino]-2-(pyridin-2-yl)-4,5,6,7-tetrahydro-2H-indazol-3-ol;
10) 5-[Methyl-(3-trifluoromethylbenzyl)-amino]-2-pyridin-2-yl-4,5,6,7-tetrahydro-2H-indazol-3-ol;
11) 5-[Methyl-(2-trifluoromethylbenzyl)-amino]-2-pyridin-2-yl-4,5,6,7-tetrahydro-2H-indazol-3-ol;
12) 5-[(4-Methanesulfonylbenzyl)methylamino]-2-(pyridin-2-yl)-4,5,6,7-tetrahydro-2H-indazol-3-ol;
13) 5-[(3-Methoxybenzyl)methylamino]-2-(pyridin-2-yl)-4,5,6,7-tetrahydro-2H-indazol-3-ol;
14) 5-Piperidin-1-yl-2-(pyridin-2-yl)-4,5,6,7-tetrahydro-2H-indazol-3-ol;
15) 5-Morpholino-4-yl-2-(pyridin-2-yl)-4,5,6,7-tetrahydro-2H-indazol-3-ol;
16) 5-(4-Methylpiperazin-1-yl)-2-(pyridin-2-yl)-4,5,6,7-tetrahydro-2H-indazol-3-ol;
17) 5-(4-(2-(2-Hydroxymethoxy)ethyl)piperazin-1-yl)-2-(pyridin-2-yl)-4,5,6,7-tetrahydro-2H-indazol-3-ol;
18) 5-(3,4-Dihydro-1H-isoquinolin-2-yl)-2-(pyridin-2-yl)-4,5,6,7-tetrahydro-2H-indazol-3-ol;
19) 5-[(4-Chlorobenzyl)methylamino]-2-(pyridin-2-yl)-4,5,6,7-tetrahydro-2H-indazol-3-ol;
20) 5-(Benzylethylamino)-2-(pyridin-2-yl)-4,5,6,7-tetrahydro-2H-indazol-3-ol;
21) 5-(Benzylpropylamino)-2-(pyridin-2-yl)-4,5,6,7-tetrahydro-2H-indazol-3-ol;
22) 5-(Benzylbutylamino)-2-(pyridin-2-yl)-4,5,6,7-tetrahydro-2H-indazol-3-ol;
23) 5-[Methyl(3-methylsulfonylbenzyl)amino]-2-(pyridin-2-yl)-4,5,6,7-tetrahydro-2H-indazol-3-ol;
24) 5-[Methyl-(4-methylbenzyl)amino]-2-(pyridin-2-yl)-4,5,6,7-tetrahydro-2H-indazol-3-ol;
25) 3-{[(3-Hydroxy-2-(pyridin-2-yl)-4,5,6,7-tetrahydro-2H-indazol-5-yl)methylamino]methyl}benzonitrile;
26) 5-[(2-Methoxybenzyl)-methylamino]-2-(pyridin-2-yl)-4,5,6,7-tetrahydro-2H-indazol-3-ol;
27) 5-[(3-Fluorobenzyl)methylamino]-2-(pyridin-2-yl)-4,5,6,7-tetrahydro-2H-indazol-3-ol;
28) 5-[(4-Methoxybenzyl)methylamino]-2-(pyridin-2-yl)-4,5,6,7-tetrahydro-2H-indazol-3-ol;
29) 5-[Methyl-(2-methylbenzyl)amino]-2-(pyridin-2-yl)-4,5,6,7-tetrahydro-2H-indazol-3-ol;
30) 5-[(2,4-Dichlorobenzyl)methylamino]-2-(pyridin-2-yl)-4,5,6,7-tetrahydro-2H-indazol-3-ol;
31) 5-[(3,4-Dichlorobenzyl)methylamino]-2-(pyridin-2-yl)-4,5,6,7-tetrahydro-2H-indazol-3-ol;
32) 5-(3,4-Difluorophenylamino)-2-(pyridin-2-yl)-4,5,6,7-tetrahydro-2H-indazol-3-ol;
33) 5-[Methyl(5,6,7,8-tetrahydroquinolin-8-yl)amino]-2-(pyridin-2-yl)-4,5,6,7-tetrahydro-2H-indazol-3-ol;
34) 5-(((3-(Hydroxymethyl)-5-(4-methylpiperazin-1-yl)imidazo[1,2-a]pyridin-2-yl)methyl)(methyl)amino)-2-(pyridin-2-yl)-4,5,6,7-tetrahydro-2H-indazol-3-ol;
35) 5-{[(3-(Hydroxymethyl)-5-(4-methylpiperazin-1-yl)imidazo[1,2-a]pyridin-2-yl)methyl]methylamino}-2-(pyridin-2-yl)-4,5,6,7-tetrahydro-2H-indazol-3-ol;
36) 5-{Methyl[3-methyl-5-(4-methylpiperazin-1-yl)imidazo[1,2-a]pyridin-2-yl]methylamino}-2-(pyridin-2-yl)-4,5,6,7-tetrahydro-2H-indazol-3-ol;
37) 5-{Methyl[5-(4-methylpiperazin-1-yl)imidazo[1,2-a]pyridin-2-yl]methylamino}-2-(pyridin-2-yl)-4,5,6,7-tetrahydro-2H-indazol-3-ol;
38) Cyclopropyl[4-(3-hydroxy-2-(pyridin-2-yl)-4,5,6,7-tetrahydro-2-indazol-5-yl)piperazin-1-yl]methanone;
39) 5-(Benzylmethylamino)-2-(5-trifluoromethylpyridin-2-yl)-4,5,6,7-tetrahydro-2H-indazol-3-ol;
40) 5-(Benzylmethylamino)-2-(5-chloropyridin-2-yl)-4,5,6,7-tetrahydro-2H-indazol-3-ol;
41) 5-(Benzylmethylamino)-2-(6-(trifluoromethyl)pyridin-2-yl)-4,5,6,7-tetrahydro-2H-indazol-3-ol;
42) 5-(Benzylmethylamino)-2-(6-methylpyridin-2-yl)-4,5,6,7-tetrahydro-2H-indazol-3-ol;
43) 5-(Benzylmethylamino)-2-(3-fluoropyridin-2-yl)-4,5,6,7-tetrahydro-2H-indazol-3-ol;
44) 6-(5-(Benzylmethylamino)-3-hydroxy-4,5,6,7-tetrahydro-2H-indazol-2-yl)nicotinonitrile;
45) 5-(Benzylmethylamino)-2-(6-methyl-4-trifluoromethylpyridin-2-yl)-4,5,6,7-tetrahydro-2H-indazol-3-ol;
46) 5-(Benzylamino)-2-(pyridin-2-yl)-4,5,6,7-tetrahydro-2H-indazol-3-ol;
47) 2-(Pyridin-2-yl)-5-[(pyridin-2-ylmethyl)amino]-4,5,6,7-tetrahydro-2H-indazol-3-ol;
48) 5-[Methyl(pyridin-2-ylmethyl)amino]-2-(pyridin-2-yl)-4,5,6,7-tetrahydro-2H-indazol-3-ol;
49) 5-[Methyl(pyridin-4-ylmethyl)amino]-2-(5-trifluoromethylpyridin-2-yl)-4,5,6,7-tetrahydro-2H-indazol-3-ol;
50) 2-(5-Chloropyridin-2-yl)-5-[methyl(pyridin-4-ylmethyl)amino]-4,5,6,7-tetrahydro-2H-indazol-3-ol;
51) 5-[Methyl(pyridin-4-ylmethyl)amino]-2-(pyridin-2-yl)-4,5,6,7-tetrahydro-2H-indazol-3-ol;
52) 2-(4-Bromophenyl)-5-[methyl(pyridin-4-ylmethyl)amino]-4,5,6,7,-tetrahydro-2H-indazol-3-ol;
53) 5-(Benzylmethylamino)-2-(thieno[3,2-c]pyridin-4-yl)-4,5,6,7-tetrahydro-2H-indazol-3-ol;
54) 2-(6-Aminopyridin-2-yl)-5-(benzylmethylamino)-4,5,6,7-tetrahydro-2H-indazol-3-ol;
55) 5-Phenylamino-2-(pyridin-2-yl)-4,5,6,7-tetrahydro-2H-indazol-3-ol;
56) 5-[(2,5-Dimethylphenyl)amino]-2-(pyridin-2-yl)-4,5,6,7-tetrahydro-2H-indazol-3-ol;
57) 5-[(4-Nitrophenyl)amino]-2-(pyridin-2-yl)-4,5,6,7-tetrahydro-2H-indazol-3-ol;
58) 5-[(4-Methoxyphenyl)amino]-2-(pyridin-2-yl)-4,5,6,7-tetrahydro-2H-indazol-3-ol;
59) 5-(Phenylamino)-2-(pyridin-2-yl)-4,5,6,7-tetrahydro-2H-indazol-3-ol;
60) 2-(Pyridin-2-yl)-5-(quinolin-3-ylamino)-4,5,6,7-tetrahydro-2H-indazol-3-ol;
61) 5-[Methyl(naphathalen-2-ylmethyl)amino]-2-(pyridin-2-yl)-4,5,6,7-tetrahydro-2H-indazol-3-ol;
62) 5-[(Isoquinolin-3-ylmethyl)methylamino]-2-(pyridin-2-yl)-4,5,6,7-tetrahydro-2H-indazol-3-ol;
63) 5-[Methyl(quinolin-6-ylmethyl)amino]-2-(pyridin-2-yl)-4,5,6,7-tetrahydro-2H-indazol-3-ol;
64) 5-[(Isoquinolin-3-ylmethyl)amino]-2-(pyridin-2-yl)-4,5,6,7-tetrahydro-2H-indazol-3-ol;
65) 5-[Methyl(pyridin-2-ylmethyl)amino]-2-phenyl-4,5,6,7-tetrahydro-2H-indazol-3-ol;
66) 5-[Ethyl(pyridin-4-ylmethyl)amino]-2-(pyridin-2-yl)-4,5,6,7-tetrahydro-2H-indazol-3-ol;
67) 5-[(3-Dimethylaminobenzyl)amino]-2-(pyridin-2-yl)-4,5,6,7-tetrahydro-2H-indazol-3-ol;
68) 5-[(4-Dimethylaminobenzyl)amino]-2-(pyridin-2-yl)-4,5,6,7-tetrahydro-2H-indazol-2-ol;

69) 5-[(3-Dimethylaminobenzyl)methylamino)]-2-(pyridin-2-yl)-4,5,6,7-tetrahydro-2H-indazol-3-ol;
70) 5-[(4-Dimethylamino)benzylmethylamino]-2-(pyridin-2-yl)-4,5,6,7-tetrahydro-2H-indazol-3-ol;
71) 5-[(2-Dimethylamino)benzylmethylamino]-2-(pyridin-2-yl)-4,5,6,7-tetrahydro-2H-indazol-3-ol;
72) 5-(Benzylmethylamino)-2-phenyl-4,5,6,7-tetrahydro-2H-indazol-3-ol;
73) 4-[(5-Benzylmethylamino)-3-hydroxy-4,5,6,7-tetrahydro-2H-indazol-2-yl]benzoic acid;
74) 5-(Benzylmethylamino)-2-(4-bromophenyl)-4,5,6,7-tetrahydro-2H-indazol-3-ol;
75) 5-(Benzylmethylamino)-2-(2-chlorophenyl)-4,5,6,7-tetrahydro-2H-indazol-3-ol;
76) 5-(Benzylmethylamino)-2-(2-methoxyphenyl)-4,5,6,7-tetrahydro-2H-indazol-3-ol;
77) 2-(2-Chlorophenyl)-5-[(3-다ㅇmethylaminobenzyl)methylamino]-4,5,6,7-tetrahydro-2H-indazol-3-ol;
78) 4-(((3-Hydroxy-2-(pyridin-2-yl)-4,5,6,7-tetrahydro-2H-indazol-5-yl)(methyl)amino)methyl)bezoic acid;
79) 4-(((3-Hydroxy-2-(pyridin-2-yl)-4,5,6,7-tetrahydro-2H-indazol-5-yl)(methyl)amino)methyl)benzamide;
80) 4-(((3-Hydroxy-2-(pyridin-2-yl)-4,5,6,7-tetrahydro-2H-indazol-5-yl)(methyl)amino)methyl)-N-methylbenzamide;
81) 4-(((3-Hydroxy-2-(pyridin-2-yl)-4,5,6,7-tetrahydro-2H-indazol-5-yl)(methyl)amino)methyl)-N,N-dimethylbenzamide;
82) 5-(4-Methylpiperazin-1-yl)-2-(5-(trifluoromethyl)pyridin-2-yl)-4,5,6,7-tetrahydro-2H-indazol-3-ol;
83) 2-(6-Chloropyridin-2-yl)-5-(4-methylpiperazin-1-yl)-4,5,6,7-tetrahydro-2H-indazol-3-ol;
84) 2-(6-Methyl-4-(trifluoromethyl)pyridin-2-yl)-5-(4-methylpiperazin-1-yl)-4,5,6,7-tetrahydro-2H-indazol-3-ol;
85) 5-(4-Methylpiperazin-1-yl)-2-(thieno[3,2-c]pyridin-4-yl)-4,5,6,7-tetrahydro-2H-indazol-3-ol;
86) 2-(3-Fluoropyridin-2-yl)-5-(4-methylpiperazin-1-yl)-4,5,6,7-tetrahydro-2H-indazol-3-ol;
87) 2-(Pyridin-2-yl)-5-(4-(pyridin-2-ylmethyl)piperazin-1-yl)-4,5,6,7-tetrahydro-2H-indazol-3-ol;
88) 5-((4-Methoxybenzyl)amino)-2-(pyridin-2-yl)-4,5,6,7-tetrahydro-2H-indazol-3-ol;
89) 1-(4-(3-Hydroxy-2-(pyridin-2-yl)-4,5,6,7-tetrahydro-2H-indazol-5-yl)piperazin-1-yl)but-2-en-1-one;
90) 2-(Pyridin-2-yl)-5-(4-(quinolin-6-ylmethyl)piperazin-1-yl)-4,5,6,7-tetrahydro-2H-indazol-3-ol;
91) 5-(4-Ethylpiperazin-1-yl)-2-(pyridin-2-yl)-4,5,6,7-tetrahydro-2H-indazol-3-ol;
92) 5-(Phenylamino)-2-(pyridin-2-yl)-4,5,6,7-tetrahydro-2H-indazol-3-ol;
93) 5-(Penethylamino)-2-(pyridin-2-yl)-4,5,6,7-tetrahydro-2H-indazol-3-ol;
94) 2-(4-Chlorophenyl)-5-(4-methylpiperazin-1-yl)-4,5,6,7-tetrahydro-2H-indazol-3-ol;
95) 5-(4-Methylpiperazin-1-yl)-2-(4-(trifluoromethyl)phenyl)-4,5,6,7-tetrahydro-2H-indazol-3-ol;
96) 2-(Pyridin-2-yl)-5-(pyrrolidin-1-yl)-4,5,6,7-tetrahydro-2H-indazol-3-ol;
97) 1-(4-(3-Hydroxy-2-(pyridin-2-yl)-4,5,6,7-tetrahydro-2H-indazol-5-yl)piperazin-1-yl)prop-2-en-1-one;
98) (E)-4-(dimethylamino)-1-(4-(3-hydroxy-2-(pyridin-2-yl)-4,5,6,7-tetrahydro-2H-indazol-5-yl)piperazin-1-yl)but-2-en-1-one;
99) (E)-4-(dimethylamino)-N-(3-hydroxy-2-(pyridin-2-yl)-4,5,6,7-tetrahydro-2H-indazol-5-yl)-N-methylbut-2-enamide;
100) 5-(4-Propylpiperazin-1-yl)-2-(pyridin-2-yl)-4,5,6,7-tetrahydro-2H-indazol-3-ol;
101) 2-(4-Bromophenyl)-5-(4-methylpiperazin-1-yl)-4,5,6,7-tetrahydro-2H-indazol-3-ol;
102) 2-(4-Fluorophenyl)-5-(4-methylpiperazin-1-yl)-4,5,6,7-tetrahydro-2H-indazol-3-ol;
103) 4-(3-Hydroxy-5-(4-methylpiperazin-1-yl)-4,5,6,7-tetrahydro-2H-indazol-2-yl)benzonitrile;
104) 5-(4-Penethylpiperazin-1-yl)-2-(pyridin-2-yl)-4,5,6,7-tetrahydro-2H-indazol-3-ol;
105) 5-(4-Benzylpiperazin-1-yl)-2-(pyridin-2-yl)-4,5,6,7-tetrahydro-2H-indazol-3-ol;
106) 5-(4-(Cyclohexylmethyl)piperazin-1-yl)-2-(pyridin-2-yl)-4,5,6,7-tetrahydro-2H-indazol-3-ol;
107) 5-(4-(3-Phenylpropyl)piperazin-1-yl)-2-(pyridin-2-yl)-4,5,6,7-tetrahydro-2H-indazol-3-ol;
108) 5-(4-Methylpiperazin-1-yl)-2-(pyrimidin-2-yl)-4,5,6,7-tetrahydro-2H-indazol-3-ol;
109) 5-(Piperazin-1-yl)-2-(pyridin-2-yl)-4,5,6,7-tetrahydro-2H-indazol-3-ol;
110) 5-(4-(Methylsulfonyl)piperazin-1-yl)-2-(pyridin-2-yl)-4,5,6,7-tetrahydro-2H-indazol-3-ol;
111) 5-(4-(Phenylsulfonyl)piperazin-1-yl)-2-(pyridin-2-yl)-4,5,6,7-tetrahydro-2H-indazol-3-ol;
112) 2-(Pyridin-2-yl)-5-(4-tosylpiperazin-1-yl)-4,5,6,7-tetrahydro-2H-indazol-3-ol;
113) 4-(3-Hydroxy-2-(pyridin-2-yl)-4,5,6,7-tetrahydro-2H-indazol-5-yl)-N-phenylpiperazin-1-carboxamide;
114) Benzyl 4-(3-hydroxy-2-(pyridin-2-yl)-4,5,6,7-tetrahydro-2H-indazol-5-yl)piperazin-1-carboxylate;
115) 2-(1-Methyl-1H-pyrrol-2-yl)-5-(4-methylpiperazin-1-yl)-4,5,6,7-tetrahydro-2H-indazol-3-ol;
116) 5-(4-Methylpiperazin-1-yl)-2-(thiazol-2-yl)-4,5,6,7-tetrahydro-2H-indazol-3-ol;
117) 5-(4-Methylpiperazin-1-yl)-2-(oxazol-2-yl)-4,5,6,7-tetrahydro-2H-indazol-3-ol;
118) 2-(1-Methyl-1H-pyrazol-5-yl)-5-(4-methylpiperazin-1-yl)-4,5,6,7-tetrahydro-2H-indazol-3-ol;
119) 2-(1-Methyl-1H-imidazol-5-yl)-5-(4-methylpiperazin-1-yl)-4,5,6,7-tetrahydro-2H-indazol-3-ol;
120) 2-(1-Methyl-1H-imidazol-5-yl)-5-(4-methylpiperazin-1-yl)-4,5,6,7-tetrahydro-2H-indazol-3-ol;
121) 5-(Benzyl(methyl)amino)-2-(pyrimidin-2-yl)-4,5,6,7-tetrahydro-2H-indazol-3-ol;
122) 5-(Benzyl(methyl)amino)-2-(1-methyl-1H-pyrrol-2-yl)-4,5,6,7-tetrahydro-2H-indazol-3-ol;
123) 5-(Benzyl(methyl)amino)-2-(1-methyl-1H-pyrazol-5-yl)-4,5,6,7-tetrahydro-2H-indazol-3-ol;
124) 5-(Benzyl(methyl)amino)-2-(1-methyl-1H-imidazol-5-yl)-4,5,6,7-tetrahydro-2H-indazol-3-ol;
125) 5-(Benzyl(methyl)amino)-2-(oxazol-2-yl)-4,5,6,7-tetrahydro-2H-indazol-3-ol;
126) 2-(Pyridin-2-yl)-5-(4-(p-tolyl)piperazin-1-yl)-4,5,6,7-tetrahydro-2H-indazol-3-ol;
127) 5-(4-(4-Hydroxyphenyl)piperazin-1-yl)-2-(pyridin-2-yl)-4,5,6,7-tetrahydro-2H-indazol-3-ol;
128) 5-(4-(3,4-Difluorophenyl)piperazin-1-yl)-2-(pyridin-2-yl)-4,5,6,7-tetrahydro-2H-indazol-3-ol;
129) 5-(4-(4-Methoxyphenyl)piperazin-1-yl)-2-(pyridin-2-yl)-4,5,6,7-tetrahydro-2H-indazol-3-ol;
130) 1-(4-(4-(3-Hydroxy-2-(pyridin-2-yl)-4,5,6,7-tetrahydro-2H-indazol-5-yl)piperazin-1-yl)phenyl)ethan-1-one;

131) 5-(4-(4-(Methylsulfonyl)phenyl)piperazin-1-yl)-2-(pyridin-2-yl)-4,5,6,7-tetrahydro-2H-indazol-3-ol;
132) 5-(4-(4-Phenoxyphenyl)piperazin-1-yl)-2-(pyridin-2-yl)-4,5,6,7-tetrahydro-2H-indazol-3-ol;
133) 5-(4-(Piperidin-4-ylmethyl)piperazin-1-yl)-2-(pyridin-2-yl)-4,5,6,7-tetrahydro-2H-indazol-3-ol;
134) 5-(4-((1-Methylpiperidin-4-yl)methyl)piperazin-1-yl)-2-(pyridin-2-yl)-4,5,6,7-tetrahydro-2H-indazol-3-ol;
135) 5-(4-((1-Benzylpiperidin-4-yl)methyl)piperazin-1-yl)-2-(pyridin-2-yl)-4,5,6,7-tetrahydro-2H-indazol-3-ol;
136) 1-(4-((4-(3-Hydroxy-2-(pyridin-2-yl)-4,5,6,7-tetrahydro-2H-indazol-5-yl)piperazin-1-yl)methyl)piperidin-1-yl)ethan-1-one;
137) N-(3-Hydroxy-2-(pyridin-2-yl)-4,5,6,7-tetrahydro-2H-indazol-5-yl)benzamide;
138) N-(3-Hydroxy-2-(pyridin-2-yl)-4,5,6,7-tetrahydro-2H-indazol-5-yl)-2-phenylacetamide;
139) 1-(3-Hydroxy-2-(pyridin-2-yl)-4,5,6,7-tetrahydro-2H-indazol-5-yl)-3-phenylurea;
140) 1-Benzyl-3-(3-hydroxy-2-(pyridin-2-yl)-4,5,6,7-tetrahydro-2H-indazol-5-yl)urea;
141) N-(3-Hydroxy-2-(pyridin-2-yl)-4,5,6,7-tetrahydro-2H-indazol-5-yl)benzenesulfonamide;
142) N-(3-hydroxy-2-(pyridin-2-yl)-4,5,6,7-tetrahydro-2H-indazol-5-yl)-4-methyl benzenesulfonamide;
143) Benzyl (3-hydroxy-2-(pyridin-2-yl)-4,5,6,7-tetrahydro-2H-indazol-5-yl)carbamate;
144) 2-(5-Fluoro-4-morpholinopyrimidin-2-yl)-5-(4-methylpiperazin-1-yl)-4,5,6,7-tetrahydro-2H-indazol-3-ol;
145) N-benzyl-3-methoxy-N-methyl-2-(pyridin-2-yl)-4,5,6,7-tetrahydro-2H-indazol-5-amine;
146) N-benzyl-3-(cyclopropylmethoxy)-N-methyl-2-(pyridin-2-yl)-4,5,6,7-tetrahydro-2H-indazol-5-amine;
147) 5-(Benzyl(methyl)amino)-2-(pyridin-2-yl)-4,5,6,7-tetrahydro-2H-indazol-3-yl cyclopropane carboxylate;
148) 5-(Benzyl(methyl)amino)-2-(pyridin-2-yl)-4,5,6,7-tetrahydro-2H-indazol-3-yl acrylate;
149) 5-(Benzyl(methyl)amino)-2-(pyridin-2-yl)-4,5,6,7-tetrahydro-2H-indazol-3-yl benzoate;
150) 2-(5-(Benzyl(methyl)amino)-3-hydroxy-4,5,6,7-tetrahydro-2H-indazol-2-yl)pyrimidin-5-carboxylic acid;
151) Methyl 2-(5-(benzyl(methyl)amino)-3-hydroxy-4,5,6,7-tetrahydro-2H-indazol-2-yl)nicotinate;
152) N-(6-(5-(benzyl(methyl)amino)-3-hydroxy-4,5,6,7-tetrahydro-2H-indazol-2-yl)pyridin-2-yl)acetamide;
153) 5-(Benzyl(methyl)amino)-2-(4,6-dimethoxy-1,3,5-triazin-2-yl)-4,5,6,7-tetrahydro-2H-indazol-3-ol;
154) 5-(4-Methylpiperazin-1-yl)-2-(pyrimidin-4-yl)-4,5,6,7-tetrahydro-2H-indazol-3-ol;
155) 2-(5-Chloropyridazin-3-yl)-5-(4-methylpiperazin-1-yl)-4,5,6,7-tetrahydro-2H-indazol-3-ol;
156) 2-(Pyridin-2-yl)-5-(4-(pyrimidin-2-yl)piperazin-1-yl)-4,5,6,7-tetrahydro-2H-indazol-3-ol;
157) 5-(Benzyl(methyl)amino)-2-(5-nitropyrimidin-2-yl)-4,5,6,7-tetrahydro-2H-indazol-3-ol;
158) 5-((4-Hydroxybenzyl)(methyl)amino)-2-(pyridin-2-yl)-4,5,6,7-tetrahydro-2H-indazol-3-ol;
159) 5-(Methyl(4-nitrobenzyl)amino)-2-(pyridin-2-yl)-4,5,6,7-tetrahydro-2H-indazol-3-ol;
160) 5-(3-(Ethyl(methyl)amino)pyrrolidin-1-yl)-2-(pyridin-2-yl)-4,5,6,7-tetrahydro-2H-indazol-3-ol; and
161) 2,2,2-Trifluoro-N-(1-(3-hydroxy-2-(pyridin-2-yl)-4,5,6,7-tetrahydro-2H-indazol-5-yl)pyrrolidin-3-yl)acetamide.

Unless otherwise specified, Chemical formulas or names given in the present description and claims refer to tautomers and all stereoscopic, optical and geometric isomers (for example, enantiomers, diastereomers, E/Z isomers, etc.) and their racemates, as well as mixtures of distinct enantiomers in different proportions, mixtures of diastereomers, or mixtures of any of the above forms in which isomers and enantiomers exist, and pharmaceutically acceptable salts thereof and solvates thereof such as hydrates comprising for example, solvates and hydrates of free compounds, or solvates and hydrates of salts of the corresponding compound.

In one embodiment, the compound of the present invention may be present in a pharmaceutically acceptable salt form. The salt means a commonly used salt in the medical field to which the present invention pertains, and an acid addition salt formed by pharmaceutically acceptable free acid is useful. The term of the present invention, "pharmaceutically acceptable salt" refers to any organic or inorganic addition salt of the compound in which side effects attributed by this salt do not diminish beneficial efficacy of the compound according to the present invention, at a concentration having an effective action that is relatively non-toxic and harmless to a patient.

The acid addition salt is prepared by a common method, for example, by dissolving a compound in an excessive amount of acid aqueous solution and precipitating this salt using a water-miscible organic solvent, for example, methanol, ethanol, acetone or acetonitrile. An equal molar amount of compound and acid or alcohol (e.g., glycol monoethylether) in water may be heated, and then the mixture may be evaporated to dry it, or the precipitated salt may be filtered with suction.

Then, as the free acid, organic acid and inorganic acid may be used, and as the inorganic acid, hydrochloric acid, phosphoric acid, sulfuric acid, nitric acid, tartaric acid, and the like may be used, and as the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydriodic acid, and the like may be used, but not limited thereto.

In addition, using a base, a pharmaceutically acceptable metal salt may be produced. The alkali metal salt or alkali earth metal salt is obtained, for example, by dissolving a compound in an excess alkali metal hydroxide or alkali earth metal hydroxide solution, filtering the undissolved compound salt and then evaporating and drying the filtrate. Then, as the metal salt, it is pharmaceutically suitable to prepare sodium, potassium or calcium salts, but not limited thereto. In addition, the silver salt corresponding thereto may be obtained by reacting an alkali metal or alkali earth metal salt with a suitable silver salt (e.g., silver nitrate).

The pharmaceutically acceptable salt of the compound of the present invention, unless otherwise indicated, includes salts of acidic or basic groups that may be present in the compounds described in Chemical formula I above. For example, as the pharmaceutically acceptable salt, sodium, calcium and potassium salts of a hydroxy group may be comprised, and other pharmaceutically acceptable salt of the amino group includes hydrobromide, sulfate, hydrogen sulfate, phosphate, hydrogen phosphate, dihydrogen phosphate, acetate, succinate, citrate, tartrate, lactate, mandelate, methanesulfonate (methylate) and p-toluenesulfonate (tosylate)

salts, and the like, and it may be prepared by a preparation method of salts known in the art.

As the salt of the compound described in Chemical formula I above of the present invention, any pharmaceutically acceptable salt, which is a salt of the compound described in Chemical formula I above showing the equal pharmacological activity to the compound described in Table 1, may be used without limitation.

In addition, the compound of the present invention may be also in a form of stereoisomer thereof. The stereoisomer includes all stereoisomers such as enantiomers and diastereomers. The compound may be a stereoisomerically pure form or a mixture of one or more stereoisomers, for example, racemic mixture. Separation of specific stereoisomers may be performed by one of the common methods known in the art. Some examples of the compound of the present invention may have a greater inhibitory effect of oxidative stress of the specific stereoisomer. In this case, by using the specific stereoisomer, the dosage may be reduced. Accordingly, a specific stereoisomer with a great inhibitory effect on oxidative stress, for example, an enantiomer or diastereomer may be separated, thereby efficiently treating diseases related to oxidative stress.

The compound of the present invention may be in a form of solvate thereof. The "solvate" means a composite or aggregate of one or more solute molecules, that is, the compound of Chemical formula I or pharmaceutically acceptable salt thereof, and one or more solvent molecules. The solvate may be for example a composite or aggregate formed by various solvent molecules such as water, methanol, ethanol, isopropanol or acetate, or the like.

Solvates in which water is a solvent molecule are termed hydrates. The hydrate includes a composition containing stoichiometric amount of water as well as a composition containing a varying amount of water.

The compound of the present invention may be also in a form of tautomer thereof.

The term "tautomer" or "tautomer form" means a varying constitutional isomer of different energies that are interconvertible through low energy barriers. Some non-limitative examples of proton tautomers (also known as protic tautomers) include interconversion through proton transfer, such as keto-enol and imine-enamine isomerization. Valence tautomers include interconversion by reorganization of some of bonding electrons.

The compound of the present invention may be also in a form of isotopic variant thereof.

The term "isotopic variant" means a compound in which at least one atom has the same number of atoms for any compound, but is substituted with another atom having an atomic weight different from the atomic weight normally or usually occurring in nature.

The solvate, stereoisomer, tautomer and isotopic variant of the compound of Chemical formula I above may be prepared from the compound using a method known in the art.

In the method for preparation of the present invention, as reactants used in the above reaction formulas, commercially available compounds may be purchased and used as they are, or they may be synthesized by performing one or more reactions known in the art as they are or by appropriately changing them and used. For example, they may be synthesized by performing one or more reactions in a series order in consideration of the presence, type and/or position of the reactive functional group and/or heteroelement included in the framework structure, but not limited thereto.

In one embodiment, the compounds of Synthetic examples of the present invention shows the inhibitory effect for ROS production of 30%, 50%, 70% or more compared to the control group by treating ROS produced by PMA in HL-60 cells (human leukemia cell), and also exhibits the concentration-dependent inhibitory ability, and therefore, the compounds of the present invention may be used for prevention or treatment of diseases related to oxidative stress.

It has been reported that cancer associated fibroblasts (CAF) are formed or fibrosis of various tissues is induced, as fibroblasts differentiate into myofibroblasts. As the result of treating the compounds of Synthetic examples of the present invention into HFF-1 cells (human foreskin fibroblasts) in which fibrosis was induced by TGF-β1 treatment, the effect of inhibiting expression of αSMA, an indicator of fibrosis was shown. Thus, the compounds of the present invention may be used for prevention or treatment of diseases related to fibrosis, and may be used for treatment of cancer through regulation of cancer associated fibroblasts, important indicators for interaction of the tumor microenvironment.

When the ROS level is increased in neuronal cells, lipid oxidation is induced, and this is known as an important factor in neuronal cell death. When MPP+(1-methyl-4-phenylptridinium) inducing ROS and the compounds of Synthetic examples are treated to N27 cells (rat dopaminergic neural cell) at the same time, the effect of effectively inhibiting ROS production was shown. Accordingly, the compounds of the present invention may be used for prevention or treatment of diseases related to neuronal cell death due to oxidative stress.

Extracellular matrix production such as collagen type I, and the like by CTGT from keloid fibroblasts is one of main causes of skin fibrotic disease. When fibrosis was induced by treating the compounds of Synthetic examples and then treating TGF--1 to KEL-FIB (keloid fibroblast) cells, the expression of the CTGF gene and collagen type I gene was effectively inhibited. Therefore, the compounds of the present invention may be used for prevention or treatment of skin keloid diseases.

Pharmaceutical Composition and Medical Use

The compound of the present invention, optical isomer thereof, stereoisomer thereof, solvate thereof, isotopic variant thereof, tautomer thereof or pharmaceutically acceptable salt thereof may be suitable for preventing, improving or treating various diseases caused by oxidative stress, due to their biological characteristics.

The pharmaceutical composition of the present invention may be for treating diseases related to oxidative stress. The disease may be cancer, inflammatory disease, fibrotic disease, neurodegenerative disease, neurological disease, liver disease, skin disease, mitochondria disorder, aging, chronic alcoholism, stem cell dysfunction, claudication, metabolic syndrome, Down's syndrome, sterility, overproduction of lipid peroxides in tissue, muscle-related disease, lipid peroxide accumulation in cell membranes, chronic fatigue or retinal disease.

The cancer may be selected from the group consisting of liver cancer, hepatocellular carcinoma, gastrointestinal malignancy, stomach cancer, intracranial meningioma associated with neurofibroma, pancreatic cancer, leukemia, myeloproliferative/myelodysplastic disease, dermatofibrosarcoma, breast cancer, lung cancer, thyroid cancer, colorectal cancer, prostatic cancer, breast cancer, ovarian cancer, brain tumor, cancer on head and neck, glioblastoma, and the like. In addition, cancer may be secondary cancer metastasized into another organ from the various kinds of cancer.

The metabolic syndrome may be obesity, diabetes, high blood pressure, hyperlipidemia, arteriosclerosis, peripheral vascular disease, ischemic perfusion, myocardial infarction or stroke, or the like.

The inflammatory disease may be inflammation-accompanying rheumarthritis, osteoarthritis, pneumonia, hepatitis, inflammatory colorectal disease, intestinal enteritis, glomerulonephritis, gastritis, vasculitis, pancreatitis, peritonitis, bronchitis, cardiomyositis, encephalitis, inflammation in postischemic reperfusion injury, inflammation resulting from immune rejection after tissue and organ transplantation, various inflammation occurring on skin such as scald, allergic contact dermatitis, and the like, inflammation resulting from multiple organ disorders, diabetic inflammation including diabetic nephropathy, infective inflammation caused by viral or bacterial infection, or autoimmune disease such as atopic disease, lupus, psoriasis, atherosclerosis, and the like.

The fibrotic disease may be metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasitic infection-induced liver fibrosis or cirrhosis, bacterial infection-induced liver fibrosis or cirrhosis, viral infection-induced liver fibrosis or cirrhosis, HBV-infection-induced liver fibrosis or cirrhosis, HCV-infection-induced liver fibrosis or cirrhosis, HIV-infection-induced liver fibrosis or cirrhosis, dual HCV and HIV-infection-induced liver fibrosis or cirrhosis, radiation- or chemotherapy-induced fibrosis or cirrhosis, biliary tract fibrosis, liver fibrosis or cirrhosis caused by any chronic cholestatic disease, digestive tract fibrosis of any etiology, Crohn's disease-induced fibrosis, ulcerative colitis-induced fibrosis, small intestine fibrosis, colon fibrosis, gastric fibrosis, lung fibrosis, skin fibrosis, epidermal fibrosis, endothelial fibrosis, skin fibrosis caused by scleroderma/systemic sclerosis, chronic obstructive pulmonary disease (COPD), asthma, emphysema, smoker's lung, tuberculosis, pulmonary fibrosis, idiopathic pulmonary fibrosis (IPF) followed by lung fibrosis, cardiac fibrosis, renal fibrosis, nephrogenic systemic fibrosis, muscle fibrosis, soft tissue fibrosis, myelofibrosis, articular fibrosis, tendon fibrosis, chondrofibrosis, pancreatic fibrosis, uterine fibrosis, nervous system fibrosis, testicular fibrosis, ovarian fibrosis, adrenal fibrosis, arterial fibrosis, venofibrosis, ocular fibrosis, endomyocardial fibrosis, mediastinal fibrosis, myelofibrosis, retroperitoneal fibrosis, progressive giant fibrosis which is a complication of pneumoconiosis, proliferative fibrosis, neoplastic fibrosis, transplant peripheral fibrosis, asbestosis, articular fibrosis, or adhesive capsulitis.

The neurodegenerative disease may be Alzheimer's disease (including mild or early Alzheimer's disease, mild to moderate Alzheimer's disease, moderate or intermediate Alzheimer's disease, moderate to severe Alzheimer's disease, moderately severe Alzheimer's disease, severe Alzheimer's disease, and Alzheimer's disease with Lewy bodies), Parkinson's disease (including Parkinson's disease chemically induced by exposure to environmental agents such as pesticides, insecticides or herbicides and/or metals such as manganese, aluminum, cadmium, copper or zinc, SNCA gene-associated Parkinson's disease, sporadic or idiopathic Parkinson's disease, or Parkinson's- or LRRK2-associated Parkinson's disease), autosomal dominant Parkinson's disease, diffuse Lewy body disease (DLBD) (also known as dementia with Lewy bodies (DLB)), pure autonomic ataxia, Lewy body dysphagia, fortuitous LBD, genetic LBD (for example, alpha-synuclein gene, PARK3 and PARK4 mutation), multiple system atrophy (including olivopontocerebellar atrophy, striationigral degeneration, Shy-Drager syndrome (MSA)), complex Alzheimer's disease and Parkinson's disease and/or MSA, Huntington's disease, synuclein disease, disorder or condition characterized by presence of Lewy bodies, multiple sclerosis, amyotrophic lateral sclerosis (ALS), dementia (including vascular dementia, Lewy body dementia, Parkinson dementia, and frontotemporal dementia), psychosis (including anxiety caused by neurodegenerative disease or associated with dopamine therapy, for example, Parkinson psychosis, Alzheimer psychosis, Lewy body dementia psychosis (not limited thereto), dyskinesia (including anxiety caused by neurodegenerative disease or associated with dopamine therapy), anxiety (including anxiety caused by neurodegenerative disease or associated with dopamine therapy), condition associated with dopamine therapy (including myodystonia, myoclonia or tremor), synuclein disease, disease related to abnormal expression of α-synuclein, ischemic brain disease, Creutzfeldt-Jakob disease, Machado-Joseph disease, or spino-cerebellar ataxia, or Pick disease.

The liver disease may be metabolic liver disease, non-alcoholic fatty liver disease (NAFLD), non-alcoholic steatohepatitis (NASH), drug-induced liver disease, alcohol-induced liver disease, infectious agent-induced liver disease, inflammatory liver disease, immune system dysfunction-mediated liver disease or dyslipidemia.

The skin disease may be keloid disease, psoriasis or leukoplakia, and the retinal disease may be retinal fibrosis, macular degeneration, diabetic retinopathy, diabetic macular degeneration, retinopathy of prematurity, ischemic refusion-associated retinal damage, retinitis pigmentosa, cataract or neovacular glaucoma.

The mitochondrial disorder may be genetic mitochondrial disorder, Alpers disease, Barth syndrome, chronic progressive extraocular muscle paralysis (CPEO), long chain acyl-CoA dehydrogenase deficiency (LCAD), melas syndrome, Leber hereditary optic neuropathy (LHON), Leigh disease, Leigh-like syndrome, Luft disease, Pearson syndrome, neuropathy, ataxia and retinitis pigmentosa (NARP), Co-Q10 deficiency, MERRF syndrome (MERRF), mitochondria DNA depletion syndrome (MDS), lethal infant cardiomyopathy (LIC), mitochondria nervous gastrointestinal system encephalomyopathy, beta oxidation defect, Friedreich's ataxia (Friedreich's Ataxia FA), Kearns-Sayre syndrome (KSS), or lactic acidosis.

The neurological disease may be bipolar disorder, developmental disorder, autism disorder, Asperger's syndrome, Rett's disorder, vision disorder, optic neuropathy, attention deficit hyperactivity disorder (ADHD), epilepsy, mood disorder, Tourette's syndrome or schizophrenia, or the like. The muscle-related disease may be myopathy, muscular dystrophy, cardiomyopathy, encephalomyopathy, or spinal muscular atrophy, or the like.

Other aspect of the present invention provides a pharmaceutical composition comprising a therapeutically effective dose of the compound of Chemical formula I defined above, or pharmaceutically acceptable salt or solvate or stereoisomer thereof and a pharmaceutically acceptable carrier.

In the composition of the present invention, the compound, or pharmaceutically acceptable salt or solvate or stereoisomer thereof is same as described above.

In the composition of the present invention, the "pharmaceutically acceptable carrier" represents a substance, generally an inert substance, used in combination with an active ingredient to help application of the active ingredient. The carrier includes a common pharmaceutically acceptable excipient, additive or diluent. The carrier may comprise one or more selected from for example, filler, binder, disintegrant, buffer, preservative, anti-oxidant, glydent, flavoring agent, thickener, coloring agent, emulsifier, suspending agent, stabilizer, pH adjusting agent and isotonic agent.

As the diluent, sugar, starch, microcrystalline cellulose, lactose (lactose hydrate), glucose, di-mannitol, alginate, alkali earth metal salt, clay, polyethylene glycol, anhydrous calcium hydrogen phosphate or a mixture thereof, or the like may be used; and for the binder, starch, microcrystalline cellulose, highly dispersible silica, mannitol, di-mannitol, fructose, lactose hydrate, polyethylene glycol, polyvinyl pyrrolidone (povidone), polyvinyl pyrrolidone copolymer (copovidone), hypromellose, hydroxypropyl cellulose, natural gum, synthetic gum, gelatin or a mixture thereof, or the like may be used.

As the disintegrant, starch or modified starch such as starch sodium glyconic acid, corn starch, potato starch, pregelatinized starch, or the like; clay such as bentonite, montmorillonite or veegum, or the like; cellulose such as microcrystalline cellulose, hydroxypropyl cellulose or carboxylmethyl cellulose, or the like; algins such as sodium alginate or alginate, or the like; crosslinked celluloses such as croscarmellose, or the like; gums such as guar gum, xanthan gum, or the like; crosslinked polymers such as crosslinked polyvinyl pyrrolidone (crospovidone), or the like; effervescent agents such as sodium bicarbonate, citrate, or the like or mixtures thereof may be used.

As the lubricant, talc, stearate, magnesium stearate, calcium stearate, sodium lauryl sulfate, hydrogenated plant oil, sodium benzoate, sodium stearyl fumarate, glyceryl monorate, glyceryl monostearate, glyceryl palmitostearate, colloidal silicone dioxide or mixtures thereof, or the like may be used.

As the pH adjusting agent, acidifying agents such as acetate, ascorbic acid, sodium ascorbate, sodium etheric acid, malic acid, succinic acid, tartaric acid, fumaric acid, citric acid (citrate), and alkalizing agents such as precipitated calcium carbonate, ammonia water, meglumine, sodium carbonate, magnesium oxide, magnesium carbonate, sodium citrate and tribasic calcium phosphate, and the like may be used.

As the anti-oxidant, dibutylhydroxy toluene, butylated hydroxyanisole, tocopherol acetate, tocopherol, propyl gallate, sodium bisulfite, sodium pyrosulfite, and the like may be used. In the prior-release compartment of the present invention, as the solubilizer, lauryl sodium sulfate, polyoxyethylene sorbitan fatty acid esters such as polysorbate, docusate sodium, poloxamer, or the like may be used.

In addition, to produce a sustained-release agent, an enteric polymer, a water-insoluble polymer, a hydrophobic compound and a hydrophilic polymer may be comprised.

The enteric polymer refers to a polymer which is insoluble or stable under the acidic condition of less than pH 5, and is dissolved or degraded under a specific pH condition of pH 5 or more, and for example, includes enteric cellulose derivatives such as hypromellose acetate succinate, hypromellose phthalate (hydroxypropylmethyl cellulose phthalate), hydroxymethylethyl cellulose phthalate, cellulose acetate phthalate, cellulose acetate succinate, cellulose acetate malate, cellulose benzoate phthalate, cellulose propionate phthalate, methyl cellulose phthalate, carboxymethylethyl cellulose and ethylhydroxyethyl cellulose phthalate, methylhydroxyethyl cellulose; enteric acrylate-based copolymers such as styrene-acrylate copolymer, acrylate methyl-acrylate copolymer, acrylate methyl methacrylate copolymer (for example, aryl-is), acrylate butyl-styrene-acrylate copolymer, and acrylate methyl-methacrylate-acrylate octyl copolymer; enteric polymethacrylate copolymers such as poly(methacrylate methyl methacrylate) copolymer (for example, Eudragit L, Eudragit S, Evonik, Germany), poly(methacrylate ethylacrylate) copolymer (for example, Eudragit L100-55); enteric maleic acid-based copolymers such as acetate vinyl-maleic acid anhydrous copolymer, styrene-maleic acid anhydrous copolymer, styrene-maleic acid monoesterol copolymer, vinylmethylether-maleic acid anhydrous copolymer, ethylene-maleic acid anhydrous copolymer, vinylbutylether-maleic acid anhydrous copolymer, acrylonitrile-acrylate methyl-maleic acid anhydrous copolymer and acrylate butyl-styrene-maleic acid anhydrous copolymer; and enteric polyvinyl derivatives such as polyvinylalcoholphthalate, polyvinylacetalphthalate, polyvinylbutylatephthalate and polyvinylacetacetalphthalate.

The water-insoluble polymer refers to a pharmaceutically acceptable polymer controlling release of a drug which is not dissolved in water. For example, the water-insoluble polymer includes polyvinylacetate (for example, Kollicoat SR30D), water-insoluble polymethacrylate copolymer [for example, poly(ethylacrylate-methyl methacrylate) copolymer (for example, Eudragit NE30D, poly(ethylacrylate-methylmethacrylate-trimethylaminoethylmethacrylate) copolymer (for example, Eudragit RSPO), etc.), methylcellulose, cellulose ester, cellulose ether, cellulose acylate, cellulose diacylate, cellulose triacylate, cellulose acetate, cellulose diacetate and cellulose triacetate, and the like.

The hydrophobic compound refers to a pharmaceutically acceptable substance controlling release of a drug which is not dissolved in water. For example, it includes fatty acid and fatty acid esters such as glyceryl palmitostearate, glyceryl stearate, glyceryl behenate, cetyl palmitate, glyceryl monooleate and stearate; fatty acid alcohols such as cetostearyl alcohol, cetylalcohol and stearyl alcohol; wax such as carnauba wax, cera and microcrystalline wax; and mineral substances such as talc, precipitated calcium carbonate, calcium hydrogen phosphate, zinc oxide, titanium oxide, kaolin, bentonite, montmorillonite and veegum, and the like.

The hydrophilic polymer refers to a pharmaceutically acceptable polymer substance controlling release of a drug which is dissolved in water. For example, it includes saccharides such as dextrin, polydextrin, dextran, pectin and pectin derivatives, alginate, polygalacturonic acid, xylan, arabinoxylan, arabinogalactan, starch, hydroxypropylstarch, amylose and amylopectin; cellulose derivatives such as hypromellose, hydroxypropylcellulose, hydroxymethylcellulose, hydroxyethylcellulose, methylcellulose and sodium carboxymethylcellulose; gum such as guar gum, locust bean gum, *tragacantha*, carrageenan, acacia gum, Arabia gum, gellan gum and xanthan gum; proteins such as gelatin, casein and zein; polyvinyl derivatives such as polyvinyl alcohol, polyvinyl pyrrolidone and polyvinylacetaldiethylaminoacetate; hydrophilic polymethacrylate copolymers such as poly(butyl methacrylate-(2-dimethylaminoethyl) methacrylate-methylmethacrylate) copolymer (for example, Eudragit E100, Evonik, Germany), poly(ethyl acrylate-methyl methacrylate-triethylaminoethyl-methacrylate chloride) copolymer (for example, Eudragit RL, RS, Evonik, Germany); polyethylene derivatives such as polyethylene glycol and polyethylene oxide; carbomer, and the like.

In addition, as various additives selected from coloring agents and flavoring agents, the formulation of the present invention may be formulated by selecting and using a pharmaceutically acceptable additive.

In the present invention, the range of the additive is not limited by using the above additives, and it may be formulated by containing a dose in a common range by selecting the aforementioned additive.

The pharmaceutical composition according to the present invention may be used as formulated in a form of oral formulation such as powder, granule, tablet, capsule, suspension, emulsion, syrup and aerosol, and external preparation, suppository or sterile injection solution.

The composition of the present invention may be orally administered, or administered parenterally including intravenous, intraperitoneal, subcutaneous, intrectal and local administration.

Other aspect of the present invention provides a method for treating disease in a subject, comprising administering a therapeutically effective dose of the compound of Chemical formula I or pharmaceutically acceptable salt or solvate or stereoisomer thereof into a subject.

In the method, those skilled in the art may appropriately select the administration route when administering according to the condition of a patient. The administration may be oral or parenteral. The parenteral administration includes intravenous, intraperitoneal, subcutaneous, intrectal and local administration.

In the method, the dose may be variously changed according to various factors such as the patient's condition, administration route, judgement of a family doctor, and the like. An effective dose may be estimated from a dose-reaction curve obtained from an in vitro experiment or animal model test. The proportion and concentration of the compound of the present invention present in the composition to be administered may be determined depending on the chemical properties, administration route, therapeutic dose, and the like. The dose may be administered in an effective dose of about 1 μg/kg to about 1 g/kg/day, or about 0.1 mg/kg to about 500 mg/kg/day into a subject. The dose may be changed according to the subject's age, body weight, sensitivity or symptoms.

Moreover, the pharmaceutical composition comprising the compound of the present invention or stereoisomer thereof, solvate thereof, isotopic variant thereof, tautomer thereof, or pharmaceutically acceptable salt thereof as an active ingredient may be used in a method for preventing or treating disease selected from the group consisting of cancer; inflammatory diseases selected from rheumatoid arthritis, osteoarthritis, pneumonia, hepatitis, inflammatory colorectal disease, intestinal enteritis, glomerulonephritis, gastritis, vasculitis, pancreatitis, peritonitis, bronchitis, cardiomyositis, encephalitis, allergic contact dermatitis, diabetic inflammation, infectious inflammation and autoimmune disease; fibrotic diseases selected from hepatic fibrosis, cirrhosis, small intestine fibrosis, large intestine fibrosis, gastric fibrosis, lung fibrosis, skin fibrosis, epidermal fibrosis, dermal sclerosis/systemic sclerosis, heart fibrosis and kidney fibrosis; neurodegenerative diseases selected from Parkinson's disease, Huntington's disease, amylotrophic lateral sclerosis, Alzheimer's disease, multiple sclerosis, ischemic and traumatic brain damage; neurological diseases selected from bipolar disorder, developmental disorder, autistic disorder, Asperger syndrome, Rett's disorder, visual impairment, optic neuropathy, attention deficit hyperactivity disorder (ADHD), epilepsy, mood disorder, Tourette's syndrome and schizophrenia; liver diseases; skin diseases; mitochondria disorders selected from genetic mitochondria disorder, Alpers disease, Barth syndrome, chronic progressive extraocular muscle paralysis (CPEO), long chain acyl-CoA dehydrogenase deficiency (LCAD), melas syndrome, Leber hereditary optic neuropathy (LHON), Leigh disease, Leigh-like syndrome, Luft disease, Pearson syndrome, neuropathy, ataxia and retinitis pigmentosa (NARP), Co-Q10 deficiency, MERRF syndrome (MERRF), mitochondria DNA depletion syndrome (MDS), lethal infant cardiomyopathy (LIC), mitochondria nervous gastrointestinal system encephalomyopathy, beta oxidation defect, Friedreich's ataxia (Friedreich's Ataxia FA), Kearns-Sayre syndrome (KSS), or lactic acidosis; aging; chronic alcoholism; stem cell dysfunction; claudication; metabolic syndromes selected from obesity, diabetes, high blood pressure, hyperlipidemia, arteriosclerosis, peripheral vascular disease, ischemic perfusion, myocardial infarction and stroke; Down's syndrome; sterility; overproduction of lipid peroxides in tissue; muscle-related diseases selected from myopathy, muscular dystrophy, myocardiopathy, encephalomyopathy and back muscular atrophy; lipid peroxide accumulation in cell membranes; chronic fatigue; and retinal diseases selected from retinal fibrosis, macular degeneration, diabetic retinopathy, cataract and neovascular glaucoma, comprising administering it into a subject in need thereof.

MODE FOR INVENTION

EXAMPLE

Hereinafter, the present invention will be described in more detail by examples. These examples are intended to illustrate the present invention more specifically, and it is obvious to those skilled in the art that the scope of the present invention is not limited by these examples.

Reference Example—Preparation of Intermediates 1 to 3

Intermediate 1: Preparation of methyl 8-oxo-1,4-dioxaspiro[4,5]decan-7-carboxylate 4-Dioxaspiro[4.5]decan-8-one (10.0 g, 64 mmol) was dissolved in 250 mL tetrahydrofuran, and then sodium hydride (1.84 g, 77 mmol, 1.2 eq) was added at a room temperature. The reaction mixture was stirred at a room temperature for 30 minutes, and then dimethyl carbonate (11.5 g, 128 mmol, 2 eq) was added. After stirring at a room temperature for 12 hours, 200 mL saturated ammonium chloride aqueous solution was added to terminate the reaction. The reaction mixture was extracted with ethyl acetate (100 mL×3) and salt water and dried with anhydrous sodium sulfate and then concentrated under reduced pressure. The residue was purified by silica gel column chromatography (petroleum ether/ethyl acetate=18/1) to obtain the title compound (6.94 g, 56%) as colorless oil.

$^1$H NMR (400 MHz, CDCl$_3$): δ 12.19 (s, 1H), 4.04 (s, 4H), 3.79 (s, 3H), 2.60-2.50 (m, 4H), 2.30-2.05 (m, 1H), 1.88 (t, J=4.8 Hz, 2H).

4-Dioxaspiro[4.5]decan-8-one (15.0 g, 96.04 mmol) was dissolved in 250 mL anhydrous tetrahydrofuran, and then sodium hydride (9.22 g, 192.08 mmol, 2 eq) was added at a room temperature. The reaction mixture was refluxed at 50° C. for 30 minutes, and then dimethyl carbonate (17.3 g, 192.08 mmol, 2 eq) was added. The reaction mixture was refluxed for 4 hours and then cooled to a room temperature, and then neutralized at 0° C. using 2M hydrochloric acid aqueous solution. The reaction mixture was extracted with ethyl acetate (100 mL×3) and salt water, and dried with anhydrous sodium sulfate, and then concentrated under reduced pressure. The residue was purified by silica gel column chromatography (hexane/ethyl acetate=3/1) to obtain the title compound as a white solid (18.10 g, 88%).

Intermediate 2: Preparation of 2'-(pyridin-2-yl)-2',4',6',7'-tetrahydrospiro[[1,3]dioxolane-2,5'-indazol]-3'-ol Methyl 8-oxo-1,4-dioxaspiro[4,5]decane-7-carboxylate (2.0 g, 10.3 mmol) was dissolved in 20 mL ethanol and then 2-hydrazinyl pyridine (1.1 g, 10.3 mmol, 1.0 eq) was added. The reaction mixture was refluxed for 12 hours, and then concentrated under reduced pressure. The residue was recrystallized with ethyl acetate to obtain the title compound as a yellow solid (1.5 g, 54%).

$^1$H NMR (400 MHz, DMSO-$d_6$): δ 11.56 (s, 1H), 8.41 (t, J=4.8 Hz, 2H), 7.88 (t, J=8.0 Hz, 1H), 7.19 (t, J=6.0 Hz, 1H), 3.95-3.90 (m, 4H), 2.60-2.52 (m, 2H), 2.38-2.33 (m, 2H), 1.89-1.84 (m, 2H).

Methyl 8-oxo-1,4-dioxaspiro[4,5]decane-7-carboxylate (18.1 g, 84.53 mmol) was dissolved in 120 mL ethanol, and then 2-hydrazinyl pyridine (9.22 g, 84.53 mmol, 1.0 eq) was added. The reaction mixture was refluxed at 100° C. for 4 hours, and then concentrated under reduced pressure. The residue was recrystallized with ethyl acetate to obtain the title compound as a yellow solid (16.39 g, 71%).

Intermediate 3: Preparation of 3-hydroxy-2-pyridin-2-yl-2,4,6,7-tetrahydroindazol-5-one 2'-(Pyridin-2-yl)-2',4',6',7'-tetrahydrospiro[[1,3]dioxolane-2,5'-indazol]-3'-ol (5.0 g, 18.3 mmol, 1.0 eq) was dissolved in 40 mL dichloromethane, and then trifluoroacetate (80 mL) was added. The reaction mixture was refluxed at 50° C. for 12 hours and then concentrated under reduced pressure. The reaction mixture was diluted with dichloromethane, and then it was adjusted to pH 6 using sodium hydrogen carbonate. The reaction mixture was extracted using dichloromethane and water, and then dried with sodium sulfate, filtered, and concentrated under reduced pressure. The residue was purified by silica gel column chromatography (solvent dichloromethane/methanol=20/1) to obtain the title compound as a brown solid (2.3 g, 54.9%).

$^1$H NMR (400 MHz, DMSO-$d_6$): δ 8.48-8.40 (m, 1H), 8.31 (d, J=8.4 Hz, 1H), 8.00-7.90 (m, 1H), 7.25-7.22 (m, 1H), 3.09 (s, 2H), 2.93 (t, J=6.8 Hz, 2H), 2.62 (t, J=6.8 Hz, 2H). MS Calcd.: 229.2; MS Found: 230.2 ([M+H]$^+$).

2'-(Pyridin-2-yl)-2',4',6',7'-tetrahydrospiro[[1,3]dioxolane-2,5'-indazol]-3'-ol (12.99 g, 47.56 mmol) was dissolved in 120 mL dichloromethane, and then trifluoroacetate (240 mL) was added. The reaction mixture was refluxed at 60° C. for 12 hours and then concentrated under reduced pressure. The reaction mixture was recrystallized with diethylether to obtain the title compound as a light brown solid (10.88 g, 99%).

Synthetic Example

Synthetic Example 1. Preparation of methyl 8-oxo-1,4-dioxaspiro[4,5]decane-7-carboxylate 4-Dioxaspiro[4,5]decan-8-one (10.0 g, 64 mmol) was dissolved in 250 mL tetrahydrofuran, and then sodium hydride (1.84 g, 77 mmol, 1.2 eq) was added at a room temperature. The reaction mixture was stirred at a room temperature for 30 minutes, and then dimethyl carbonate (11.5 g, 128 mmol, 2 eq) was added. After stirring at a room temperature for 12 hours, 200 mL saturated ammonium chloride aqueous solution was added to terminate the reaction. The reaction mixture was extracted with ethyl acetate (100 mL×3) and salt water and dried with anhydrous sodium sulfate and then concentrated under reduced pressure. The residue was purified by silica gel column chromatography (petroleum ether/ethyl acetate=18/1) to obtain the title compound as colorless oil (6.94 g, 56%).

$^1$H NMR (400 MHz, CDCl$_3$): δ 12.19 (s, 1H), 4.04 (s, 4H), 3.79 (s, 3H), 2.60-2.50 (m, 4H), 2.30-2.05 (m, 1H), 1.88 (t, J=4.8 Hz, 2H).

4-Dioxaspiro[4,5]decan-8-one (15.0 g, 96.04 mmol) was dissolved in 250 mL anhydrous tetrahydrofuran, and then sodium hydride (9.22 g, 192.08 mmol, 2 eq) was added at a room temperature. The reaction mixture was refluxed at 50° C. for 30 minutes, and then dimethyl carbonate (17.3 g, 192.08 mmol, 2 eq) was added. The reaction mixture was refluxed for 4 hours, and then cooled to a room temperature, and then neutralized at 0° C. using 2M hydrochloric acid aqueous solution. The reaction mixture was extracted with ethyl acetate (100 mL×3) and salt water and dried with anhydrous sodium sulfate and then concentrated under reduced pressure. The residue was purified by silica gel column chromatography (hexane/ethyl acetate=3/1) to obtain the title compound as a white solid (18.10 g, 88%).

Synthetic Example 2. Preparation of 2'-(pyridin-2-yl)-2',4',6',7'-tetrahydrospiro[[1,3]dioxolane-2,5'-indazol]-3'-ol Methyl 8-oxo-1,4-dioxaspiro[4,5]decane-7-carboxylate (2.0 g, 10.3 mmol) was dissolved in 20 mL ethanol and then 2-hydrazinyl pyridine (1.1 g, 10.3 mmol, 1.0 eq) was added. The reaction mixture was refluxed for 12 hours and then concentrated under reduced pressure. The residue was recrystallized with ethyl acetate to obtain the title compound as a yellow solid (1.5 g, 54%).

$^1$H NMR (400 MHz, DMSO-$d_6$): δ 11.56 (s, 1H), 8.41 (t, J=4.8 Hz, 2H), 7.88 (t, J=8.0 Hz, 1H), 7.19 (t, J=6.0 Hz, 1H), 3.95-3.90 (m, 4H), 2.60-2.52 (m, 2H), 2.38-2.33 (m, 2H), 1.89-1.84 (m, 2H).

Methyl 8-oxo-1,4-dioxaspiro[4,5]decane-7-carboxylate (18.1 g, 84.53 mmol) was dissolved in 120 mL ethanol, and then 2-hydrazinyl pyridine (9.22 g, 84.53 mmol, 1.0 eq) was added. The reaction mixture was refluxed at 100° C. for 4 hours. The residue was recrystallized with ethyl acetate to obtain the title compound as a yellow solid (16.39 g, 71%).

Synthetic Example 3. Preparation of 3-hydroxy-2-pyridin-2-yl-2,4,6,7-tetrahydroindazol-5-one 2'-(Pyridin-2-yl)-2',4',6',7'-tetrahydrospiro[[1,3]dioxolane-2,5'-indazol]-3'-ol (5.0 g, 18.3 mmol, 1.0 eq) was dissolved in 40 mL dichloromethane, and then trifluoroacetate (80 mL) was added. The reaction mixture was refluxed at 50° C. for 12 hours and then concentrated under reduced pressure. The reaction mixture was diluted with dichloromethane, and then it was adjusted to pH 6 using dichloromethane and water. The reaction mixture was extracted with dichloromethane and water and then dried with sodium sulfate and filtered and concentrated under reduced pressure. The residue was purified by silica gel column chromatography (solvent: dichloromethane/methanol=20/1) to obtain the title compound as a yellow solid (2.3 g, 54.9%).

$^1$H NMR (400 MHz, DMSO-$d_6$): δ 8.48-8.40 (m, 1H), 8.31 (d, J=8.4 Hz, 1H), 8.00-7.90 (m, 1H), 7.25-7.22 (m,

1H), 3.09 (s, 2H), 2.93 (t, J=6.8 Hz, 2H), 2.62 (t, J=6.8 Hz, 2H). MS Calcd.: 229.2; MS Found: 230.2 ([M+H]$^+$).

2'-(Pyridin-2-yl)-2',4',6',7'-tetrahydrospiro[[1,3]dioxolane-2,5'-indazol]-3'-ol (12.99 g, 47.56 mmol) was dissolved in 120 mL dichloromethane and then trifluoroacetate (240 mL) was added. The reaction mixture was recrystallized with diethylether to obtain the title compound as a light brown solid (10.88 g, 99%).

Synthetic Example 4. Preparation of 5-(benzyl propylamino)-2-pyridin-2-yl-4,5,6,7-tetrahydro-2H-indazol-3-ol hydrochloride (Compound 21)

3-Hydroxy-2-pyridin-2-yl-2,4,6,7-tetrahydroindazol-5-one (500 mg, 2.18 mmol, 1.0 eq) was dissolved in 30 mL dichloromethane, and then under nitrogen flow, tertiary-butyldimethylsilyl chloride (494 mg, 3.27 mmol, 1.5 eq) and triethylamine (0.6 mL, 4.36 mmol, 2.0 eq) was slowly added. The reaction mixture was stirred at a room temperature for 12 hours, and then extracted using water and salt water. The organic layer was dried with anhydrous sodium sulfate and then the mixture was used for the next step without additional purification.

To the compound obtained in the reaction, N-benzyl propane-1-amine (649 mg, 4.36 mmol, 2.0 eq), sodium triacetoxyborohydride (1.39 g, 6.54 mmol, 3.0 eq) and acetate (4 drops) were added and then stirred at a room temperature for 12 hours. To the reaction mixture, saturated sodium hydrogen carbonate aqueous solution (50 mL) was added to adjust pH to about 8, and then it was extracted with dichloromethane (30 mL×3). The organic layer was dried with anhydrous sodium sulfate and then concentrated under reduced pressure. The residue was primarily purified through a silica gel column (solvent: dichloromethane/methanol=20/1) to obtain Mixture 6 (400 mg). The primarily purified mixture was secondarily purified by sorting high performance liquid chromatography to obtain the title compound as a yellow solid (104 mg, 13.1%).

$^1$H NMR (400 MHz, CD$_3$OD): δ 8.40 (s, 1H), 8.15-8.11 (m, 1H), 8.08-8.01 (m, 1H), 7.56-7.53 (m, 2H), 7.41 (s, 3H), 7.34 (t, J=6.4 Hz, 1H), 4.58-4.51 (m, 1H), 4.38-4.31 (m, 1H), 3.72-3.68 (m, 1H), 3.25-3.18 (m, 1H), 3.15-2.83 (m, 3H), 2.80-2.70 (m, 2H), 2.50-2.42 (m, 1H), 2.20-2.08 (m, 1H), 1.75-1.60 (m, 1H), 1.60-1.57 (m, 1H), 0.90-0.81 (m, 3H). MS Calcd.: 362.2; MS Found: 363.3 ([M+H]$^+$).

Synthetic Example 5. Preparation of 5-(benzylethylamino)-2-pyridin-2-yl-4,5,6,7-tetrahydro-2H-indazol-3-ol hydrochloride (Compound 20)

According to the method for preparation of the Compound 21, the title compound as a yellow solid (120 mg, 15.8%) was obtained.

$^1$H NMR (400 MHz, CD$_3$OD): δ 9.55-9.40 (m, 1H), 8.42 (d, J=4.0 Hz, 1H), 8.40-8.30 (br, 1H), 7.92 (t, J=8.0 Hz, 1H), 7.60-7.45 (m, 4H), 7.23 (t, J=6.8 Hz, 1H), 4.68 (t, J=13.6 Hz, 1H), 4.50-4.44 (m, 1H), 3.90-3.86 (m, 1H), 3.47-3.37 (m, 2H), 3.20-3.02 (m, 2H), 2.95-2.90 (m, 2H), 2.60-2.50 (m, 1H), 2.35-2.25 (m, 1H), 1.47-1.37 (m, 3H). MS Calcd.: 347.5; MS Found: 349.2 ([M+H]$^+$).

Synthetic Example 6. Preparation of 5-(benzylbutylamino)-2-pyrizin-2-yl-4,5,6,7-tetrahydro-2H-indazol-3-ol hydrochloride (Compound 22)

According to the method for preparation of the Compound 21, the title compound as a yellow solid (100 mg, 12.1%) was obtained.

$^1$H NMR (400 MHz, CD$_3$OD): δ 9.55-9.40 (m, 1H), 8.42 (d, J=4.0 Hz, 1H), 8.40-8.30 (br, 1H), 7.92 (t, J=8.0 Hz, 1H), 7.60-7.45 (m, 5H), 7.23 (t, J=6.8 Hz, 1H), 4.61-4.50 (m, 1H), 4.40-4.35 (m, 1H), 3.66-3.50 (m, 2H), 3.30-3.15 (m, 2H), 3.10-2.90 (m, 1H), 2.80-2.55 (m, 4H), 2.45-2.30 (m, 1H), 2.15-1.80 (m, 1H), 1.75-1.60 (m, 1H), 1.60-1.40 (m, 1H), 1.35-1.22 (m, 3H). MS Calcd.: 376.2; MS Found: 377.2 ([M+H]$^+$).

Synthetic Example 7. Preparation of 5-[(2-methoxybenzyl)-methylamino]-2-pyridin-2-yl-4,5,6,7-tetrahydro-2H-indazol-3-ol hydrochloride (Compound 26)

3-Hydroxy-2-pyridin-2-yl-2,4,6,7-tetrahydroindazol-5-one (500 mg, 2.18 mmol, 1.0 eq) was dissolved in 30 mL dichloromethane, and then 1-(2-methoxyphenyl)-N-methyl-methane amine (658 mg, 4.36 mmol, 2.0 eq) and sodium triacetoxyborohydride (1.39 g, 6.54 mmol, 3.0 eq), and acetate 4 drops were added. The reaction mixture was stirred at a room temperature for 12 hours. To the reaction mixture, saturated sodium hydrogen carbonate aqueous solution (50 mL) was added, and then extracted with dichloromethane (50 mL×2). After washing the organic layer with salt water, it was dried with anhydrous sodium sulfate and concentrated under reduced pressure. The residue was purified by sorting high performance liquid chromatography to obtain the yellow solid of title compound (200 mg, 34.0%). Compounds 39 to 60, 64 to 68, 72 to 76, 78 to 81, 121 to 125, 146 to 153, and 157 to 159 were also prepared by the above method.

$^1$H NMR (400 MHz, CD$_3$OD): δ 8.56 (d, J=5.2 Hz, 1H), 8.30-8.22 (m, 2H), 7.59-7.52 (m, 3H), 7.19 (d, J=8.4 Hz, 1H), 7.10 (t, J=7.6 Hz, 1H), 4.78 (dd, J$_1$=12.8 Hz, J$_2$=19.2 Hz, 1H), 4.20 (dd, J$_1$=12.8 Hz, J$_2$=27.6 Hz, 1H), 4.00 (s, 3H), 3.90-3.85 (m, 1H), 3.15-3.08 (m, 2H), 3.00-2.85 (m, 5H), 2.60-2.50 (m, 1H), 2.40-2.10 (m, 1H). MS Calcd.: 364.2; MS Found: 365.3 ([M+H]$^+$).

Synthetic Example 8. Preparation of 5-(benzylmethylamino)-2-pyridin-2-yl-4,5,6,7-tetrahydro-2H-indazol-3-ol (Compound 1)

According to the method for preparation of Compound 26, the title compound as a white solid (200 mg, 27.4%) was obtained.

$^1$H NMR (400 MHz, DMSO-d$_6$): δ 10.8-10.50 (br, 1H), 8.45-8.38 (m, 2H), 7.88 (t, J=11.2 Hz, 1H), 7.40-7.15 (m, 6H), 3.63 (q, J$_1$=18.4 Hz, J$_2$=34.4 Hz, 2H), 2.80-2.70 (m, 1H), 2.65-2.55 (m, 1H), 2.52-2.50 (m, 1H), 2.48-2.30 (m, 1H), 2.31-2.25 (m, 1H), 2.16 (s, 3H), 2.05-1.85 (m, 1H), 1.71-1.65 (m, 1H). MS Calcd.: 334.2; MS Found: 335.2 ([M+H]$^+$).

Synthetic Example 9. Preparation of 5-(benzylcyclopropylamino)-2-pyridin-2-yl-4,5,6,7-tetrahydro-2H-indazol-3-ol (Compound 2)

According to the method for preparation of Compound 26, the title compound as a yellow solid (94 mg, 11.9%) was obtained.

$^1$H NMR (400 MHz, DMSO-d$_6$): δ 11.39 (s, 1H), 8.42-8.37 (m, 2H), 7.92-7.85 (m, 1H), 7.31-7.15 (m, 6H), 3.82 (s, 2H), 2.80-2.70 (m, 1H), 2.60-2.52 (m, 1H), 2.50-2.35 (m, 2H), 2.13-2.00 (m, 2H), 1.77-1.72 (m, 1H), 0.48-0.43 (m, 2H), 0.30-0.26 (m, 2H). MS Calcd.: 360.2; MS Found: 361.0 ([M+H]$^+$).

Synthetic Example 10. Preparation of 4-{[(3-hydroxy-2-pyridin-2-yl-4,5,6,7-tetrahydro-2H-indazol-5-yl)methylamino]methyl}benzonitrile (Compound 3)

According to the method for preparation of Compound 26, the title compound as a yellow solid (103 mg, 16.4%) was obtained.

$^1$H NMR (400 MHz, DMSO-d$_6$): δ 8.40 (s, 1H), 7.96-7.60 (m, 4H), 7.60-7.55 (m, 2H), 7.22-7.18 (m, 0.5H), 6.95-6.90 (m, 0.5H), 3.80-3.62 (m, 2H), 2.90-2.75 (m, 1H), 2.75-2.60 (m, 2H), 2.50-2.22 (m, 2H), 2.21-2.04 (m, 3H), 2.05-1.92 (m, 1H), 1.75-1.62 (m, 1H). MS Calcd.: 359.4; MS Found: 360.2 ([M+H]$^+$).

Synthetic Example 11. Preparation of 5-[(4-fluorobenzyl)methylamino]-2-pyridin-2-yl-4,5,6,7-tetrahydro-2H-indazol-3-ol (Compound 4)

According to the method for preparation of Compound 26, the title compound as a white solid (189 mg, 30.8%) was obtained.

$^1$H NMR (400 MHz, DMSO-d$_6$): δ 8.40-8.33 (m, 2H), 7.90-7.83 (m, 1H), 7.40-7.30 (m, 2H), 7.22-7.10 (m, 3H), 3.58 (q, J$_1$=13.6 Hz, J$_2$=30.0 Hz, 2H), 2.75-2.60 (m, 2H), 2.50-2.22 (m, 1H), 2.21-2.04 (m, 1H), 2.15 (s, 3H), 2.03-1.96 (m, 1H), 1.68-1.52 (m, 1H). MS Calcd.: 352.2; MS Found: 353.1 ([M+H]$^+$).

Synthetic Example 12. Preparation of 5-[(2,4-difluorobenzyl)methylamino]-2-pyridin-2-yl-4,5,6,7-tetrahydro-2H-indazol-3-ol (Compound 5)

According to the method for preparation of Compound 26, the title compound as a brown solid (150 mg, 23.3%) was obtained.

$^1$H NMR (400 MHz, DMSO-d$_6$): δ 11.60-11.45 (br, 1H), 8.50-8.36 (m, 2H), 7.96-7.92 (m, 1H), 7.46 (q, J$_1$=11.2 Hz, J$_2$=20.4 Hz, 2H), 7.22-7.16 (m, 2H), 7.10-7.05 (m, 1H), 3.63 (q, J$_1$=9.6 Hz, J$_2$=28.0 Hz, 2H), 2.75-2.60 (m, 2H), 2.60-2.50 (m, 1H), 2.50-2.42 (m, 1H), 2.42-2.20 (m, 1H), 2.20 (s, 3H), 2.03-1.96 (m, 1H), 1.72-1.68 (m, 1H). MS Calcd.: 370.2; MS Found: 371.1 ([M+H]$^+$)

Synthetic Example 13. Preparation of 5-[(2-chlorobenzyl)methylamino]-2-pyridin-2-yl-4,5,6,7-tetrahydro-2H-indazol-3-ol (Compound 6)

According to the method for preparation of Compound 26, the title compound as a brown solid (270 mg, 42.0%) was obtained.

$^1$H NMR (400 MHz, DMSO-d$_6$): δ 11.60-11.45 (br, 1H), 8.50-8.38 (m, 2H), 7.92-7.90 (m, 1H), 7.53 (d, J=7.2 Hz, 1H), 7.42 (d, J=7.6 Hz, 1H), 7.40-7.35 (m, 1H), 7.35-7.30 (m, 1H), 7.20-7.17 (m, 1H), 3.76-3.68 (m, 2H), 2.85-2.70 (m, 2H), 2.65-2.55 (m, 1H), 2.55-2.50 (m, 1H), 2.42-2.20 (m, 2H), 2.20 (s, 3H), 2.03-1.96 (m, 1H), 1.72-1.68 (m, 1H). MS Calcd.: 368.9; MS Found: 369.1 ([M+H]$^+$)

Synthetic Example 14. Preparation of 5-[(3-chlorobenzyl)methylamino]-2-pyridin-2-yl-4,5,6,7-tetrahydro-2H-indazol-3-ol (Compound 7)

According to the method for preparation of Compound 26, the title compound as a white solid (150 mg, 23.4%) was obtained.

$^1$H NMR (400 MHz, DMSO-d$_6$): δ 11.50-11.42 (br, 1H), 8.50-8.38 (m, 2H), 7.90-7.80 (m, 1H), 7.40-7.23 (m, 4H), 7.30-7.23 (m, 1H), 3.65 (q, J$_1$=14.0 Hz, J$_2$=32.0 Hz, 2H), 2.85-2.70 (m, 1H), 2.65-2.55 (m, 1H), 2.55-2.50 (m, 1H), 2.42-2.20 (m, 1H), 2.20 (s, 3H), 2.03-1.96 (m, 1H), 1.68-1.60 (m, 1H). MS Calcd.: 368.1; MS Found: 369.1 ([M+H]$^+$)

Synthetic Example 15. Preparation of 5-[methyl-(4-trifluoromethylbenzyl)amino]-2-pyridin-2-yl-4,5,6,7-tetrahydro-2H-indazol-3-ol (Compound 8)

According to the method for preparation of Compound 26, the title compound as a white solid (304 mg, 43.5%) was obtained.

$^1$H NMR (400 MHz, DMSO-d$_6$): δ11.43 (s, 1H), 8.44-8.38 (m, 2H), 7.92-7.90 (m, 1H) 7.67 (d, J=8.0 Hz, 2H), 7.58 (d, J=8.0 Hz, 2H), 7.17 (t, J=5.6 Hz, 1H), 3.70 (q, J$_1$=14.4 Hz, J$_2$=31.2 Hz, 2H), 2.85-2.70 (m, 1H), 2.65-2.55 (m, 1H), 2.55-2.50 (m, 1H), 2.42-2.30 (m, 1H), 2.30-2.20 (m, 1H), 2.20 (s, 3H), 2.03-1.96 (m, 1H), 1.72-1.68 (m, 1H). MS Calcd.: 402.4; MS Found: 403.1 ([M+H]$^+$)

Synthetic Example 16. Preparation of 5-[methyl-(3-methylbenzyl)amino]-2-pyridin-2-yl-4,5,6,7-tetrahydro-2H-indazol-3-ol (Compound 9)

According to the method for preparation of Compound 26, the title compound as a brown solid (103 mg, 17.0%) was obtained.

$^1$H NMR (400 MHz, DMSO-d$_6$): δ 11.43 (s, 1H), 8.44-8.38 (m, 2H), 7.92-7.90 (m, 1H), 7.21-7.04 (m, 4H), 7.04-7.02 (m, 1H), 3.60-3.48 (m, 2H), 2.80-2.72 (m, 1H), 2.70-2.66 (m, 1H), 2.48-2.40 (m, 1H), 2.29 (s, 3H), 2.20-2.16 (m, 1H), 2.19 (s, 3H), 2.03-1.96 (m, 2H), 1.70-1.62 (m, 1H). MS Calcd.: 348.4; MS Found: 349.2 ([M+H]$^+$)

Synthetic Example 17. Preparation of 5-[methyl-(3-trifluoromethylbenzyl)-amino]-2-pyridin-2-yl-4,5,6,7-tetrahydro-2H-indazol-3-ol (Compound 10)

According to the method for preparation of Compound 26, the title compound as a white solid (292 mg, 57.5%) was obtained.

$^1$H NMR (400 MHz, DMSO-d$_6$): δ 11.43 (s, 1H), 8.44-8.38 (m, 2H), 7.92-7.90 (m, 1H), 7.71-7.52 (m, 4H), 7.19-7.16 (m, 1H), 3.70 (q, J$_1$=12.0 Hz, J$_2$=30.4 Hz, 2H), 2.85-2.70 (m, 1H), 2.65-2.55 (m, 1H), 2.55-2.50 (m, 1H), 2.45-2.20 (m, 2H), 2.20 (s, 3H), 2.03-1.96 (m, 1H), 1.73-1.68 (m, 1H). MS Calcd.: 402.4; MS Found: 403.2 ([M+H]$^+$)

Synthetic Example 18. Preparation of 5-[methyl-(2-trifluoromethylbenzyl)-amino]-2-pyridin-2-yl-4,5,6,7-tetrahydro-2H-indazol-3-ol (Compound 11)

According to the method for preparation of Compound 26, the title compound as a brown solid (117 mg, 16.7%) was obtained.

$^1$H NMR (400 MHz, DMSO-d$_6$): δ 11.52-11.47 (br, 1H), 8.50-8.38 (m, 2H), 7.89-7.83 (m, 2H), 7.70-7.65 (m, 2H), 7.45 (t, J=7.6 Hz, 1H), 7.18 (br, 1H), 3.80 (q, J$_1$=10.0 Hz, J$_2$=25.0 Hz, 2H), 2.86-2.70 (m, 1H), 2.65-2.55 (m, 1H), 2.53-2.50 (m, 1H), 2.42-2.31 (m, 1H), 2.29-2.20 (m, 1H), 2.20 (s, 3H), 2.05-1.96 (m, 1H), 1.72-1.68 (m, 1H). MS Calcd.: 402.4; MS Found: 403.1 ([M+H]$^+$)

Synthetic Example 19. Preparation of 5-[(4-methanesulfonylbenzyl)methylamino]-2-pyridin-2-yl-4,5,6,7-tetrahydro-2H-indazol-3-ol (Compound 12)

According to the method for preparation of Compound 26, the title compound as a white solid (100 mg, 11.1%) was obtained.

$^1$H NMR (400 MHz, DMSO-d$_6$): δ 11.45 (s, 1H), 8.44-8.38 (m, 2H), 7.89 (d, J=8.0 Hz, 3H), 7.60 (d, J=8.0 Hz, 2H), 7.19-7.16 (m, 1H), 3.72 (q, J$_1$=14.8 Hz, J$_2$=31.2 Hz, 2H), 3.19 (s, 3H), 2.84-2.80 (m, 1H), 2.65-2.55 (m, 1H), 2.55-2.50 (m, 1H), 2.42-2.32 (m, 1H), 2.28-2.20 (m, 1H), 2.20 (s, 3H), 2.05-1.98 (m, 1H), 1.72-1.68 (m, 1H). MS Calcd.: 412.1; MS Found: 413.1 ([M+H]$^+$)

Synthetic Example 20. Preparation of 5-[(3-methanesulfonylbenzyl)methylamino]-2-pyridin-2-yl-4,5,6,7-tetrahydro-2H-indazol-3-ol (Compound 23)

According to the method for preparation of Compound 26, the title compound as a white solid (50 mg, 5.5%) was obtained.

$^1$H NMR (400 MHz, DMSO-d$_6$): δ 8.51-8.30 (m, 2H), 7.95-7.85 (m, 2H), 7.81 (d, J=8.0 Hz, 1H), 7.70 (d, J=8.0 Hz, 1H), 7.60 (t, J=8.0 Hz, 1H), 7.25-7.15 (m, 1H), 3.76 (dd, J$_1$=14.0 Hz, J$_2$=31.6 Hz, 2H), 3.21 (s, 3H), 2.90-2.80 (m, 1H), 2.70-2.60 (m, 1H), 2.60-2.50 (m, 1H), 2.50-2.40 (m, 1H), 2.30-2.15 (m, 4H), 2.10-2.00 (m, 1H), 1.70-1.60 (m, 1H). MS Calcd.: 412.5; MS Found: 413.1 ([M+H]$^+$).

Synthetic Example 21. Preparation of 5-[methyl-(4-methylbenzyl)amino]-2-pyridin-2-yl-4,5,6,7-tetrahydro-2H-indazol-3-ol hydrochloride (Compound 24)

According to the method for preparation of Compound 26, the title compound as a bright yellow solid (50 mg, 5.5%) was obtained.

$^1$H NMR (400 MHz, CD$_3$OD): δ 8.51-8.50 (m, 1H), 8.35-8.20 (m, 2H), 7.65-7.47 (m, 3H), 7.34 (d, J=8.0 Hz, 2H), 4.63 (t, J=13.2 Hz, 1H), 4.34 (t, J=13.6 Hz, 1H), 3.90-3.70 (m, 1H), 3.20-3.00 (m, 2H), 3.00-2.75 (m, 5H), 2.65-2.52 (m, 1H), 2.41 (s, 3H), 2.25-2.10 (m, 1H). MS Calcd.: 348.2; MS Found: 349.2 ([M+H]$^+$).

Synthetic Example 22. Preparation of 5-[(3-methoxybenzyl)methylamino]-2-pyridin-2-yl-4,5,6,7-tetrahydro-2H-indazol-3-ol (Compound 13)

According to the method for preparation of Compound 26, the title compound as a brown solid (105 mg, 13.2%) was obtained.

$^1$H NMR (400 MHz, CDCl$_3$) δ 8.24 (br, 1H), 7.82 (m, 2H), 7.26-7.22 (m, 1H), 7.14-7.02 (m, 1H), 7.00-6.90 (m, 2H), 6.80-6.75 (m, 1H), 3.85-3.80 (m, 3H), 3.65 (s, 2H), 2.95-2.78 (m, 2H), 2.65-2.52 (m, 2H), 2.50-2.40 (m, 1H), 2.32-2.28 (m, 3H), 2.27-2.16 (m, 1H), 1.72-1.58 (m, 1H). MS Calcd.: 364.2; MS Found: 365.1 ([M+H]$^+$)

Synthetic Example 23. Preparation of 5-piperidin-1-yl-2-pyridin-2-yl-4,5,6,7-tetrahydro-2H-indazol-3-ol (Compound 14)

According to the method for preparation of Compound 26, the title compound as a brown solid (70 mg, 10.7%) was obtained.

$^1$H NMR (400 MHz, DMSO-d$_6$): δ 9.74 (br, 1H), 8.42 (d, J=4.4 Hz, 1H), 8.35 (d, J=8.0 Hz, 1H), 7.92 (t, J=8.4 Hz, 1H), 7.23 (t, J=6.8 Hz, 1H), 3.60-3.40 (m, 3H), 3.12-3.02 (m, 2H), 2.75-2.60 (m, 3H), 2.55-2.48 (m, 1H), 2.30-2.27 (m, 1H), 1.90-1.70 (m, 6H), 1.50-1.42 (m, 1H). MS Calcd.: 298.2; MS Found: 299.2 ([M+H]$^+$)

Synthetic Example 24. Preparation of 5-morpholin-4-yl-2-pyridin-2-yl-4,5,6,7-tetrahydro-2H-indazol-3-ol (Compound 15)

According to the method for preparation of Compound 26, the title compound as a brown solid (80 mg, 11.3%) was obtained.

$^1$H NMR (400 MHz, DMSO-d$_6$): δ 11.65-11.47 (br, 1H), 8.39-8.33 (m, 2H), 7.89 (t, J=7.2 Hz, 1H), 7.18 (t, J=5.6 Hz, 1H), 3.59-3.53 (m, 4H), 2.60-2.55 (m, 2H), 2.55-2.45 (m, 4H), 2.45-2.40 (m, 1H), 2.20-2.05 (m, 1H), 2.01-1.98 (m, 1H), 1.62-1.50 (m, 1H). MS Calcd.: 300.4; MS Found: 301.2 ([M+H]$^+$)

Synthetic Example 25. Preparation of 5-(4-methylpiperazin-1-yl)-2-pyridin-2-yl-4,5,6,7-tetrahydro-2H-indazol-3-ol (Compound 16)

According to the method for preparation of Compound 26, the title compound as a gray solid (195 mg, 28.5%) was obtained.

$^1$H NMR (400 MHz, DMSO-d$_6$): δ 8.42 (d, J=4.4 Hz, 1H), 8.35 (d, J=8.4 Hz, 1H), 7.91 (t, J=7.6 Hz, 1H), 7.22 (t, J=5.6 Hz, 1H), 3.70-3.20 (br, 9H), 2.88 (s, 3H), 2.74-2.51 (m, 3H), 2.42-2.37 (m, 1H), 2.26-2.23 (m, 1H), 1.82-1.72 (m, 1H). MS Calcd.: 313.4; MS Found: 314.2 ([M+H]$^+$)

Synthetic Example 26. Preparation of 5-(3,4-dihydro-1H-isoquinolin-2-yl)-2-pyridin-2-yl-4,5,6,7-tetrahydro-2H-indazol-3-ol (Compound 18)

According to the method for preparation of Compound 26, the title compound as a white solid (120 mg, 16.0%) was obtained.

$^1$H NMR (400 MHz, DMSO-d$_6$): δ 11.47 (s, 1H), 8.44-8.38 (m, 2H), 7.91-7.88 (m, 1H), 7.19-7.16 (m, 1H), 7.10-7.04 (m, 4H), 3.76 (s, 2H), 2.91-2.50 (m, 7H), 2.50-2.40 (m, 1H), 2.40-2.25 (m, 1H), 2.20-2.02 (m, 1H), 1.78-1.70 (m, 1H). MS Calcd.: 346.2; MS Found: 347.2 ([M+H]$^+$)

Synthetic Example 27. Preparation of 3-{[(3-hydroxy-2-pyridin-2-yl-4,5,6,7-tetrahydro-2H-indazol-5-yl)methylamino]methyl}benzonitrile hydrochloride (Compound 25)

According to the method for preparation of Compound 26, the title compound as a yellow solid (104 mg, 13.3%) was obtained.

$^1$H NMR (400 MHz, CD$_3$OD): δ 8.5 (d, J=6.0 Hz, 1H), 8.40-8.32 (m, 1H), 8.21 (d, J=8.4 Hz, 1H), 8.16-8.10 (m, 1H), 8.08-8.00 (m, 1H), 7.90 (d, J=8.0 Hz, 1H), 7.72 (t, J=8.0 Hz, 1H), 7.66-7.56 (m, 1H), 4.80-4.75 (m, 1H), 4.62-4.45 (m, 1H), 4.00-3.80 (m, 1H), 3.25-3.00 (m, 2H), 3.00-2.80 (m, 5H), 2.70-2.60 (m, 1H), 2.30-2.15 (m, 1H). MS Calcd.: 359.1, MS Found: 360.1 ([M+H]$^+$).

Synthetic Example 28. Preparation of 5-[(4-chlorobenzyl)methylamino]-2-pyridin-2-yl-4,5,6,7-tetrahydro-2H-indazol-3-ol (Compound 19)

According to the method for preparation of Compound 26, the title compound as a brown solid (144 mg, 22.5%) was obtained.

¹H NMR (400 MHz, DMSO-d₆): δ 11.42 (s, 1H), 8.44-8.38 (m, 2H), 7.87 (m, 1H), 7.39-7.33 (m, 4H), 7.19-7.16 (m, 1H), 3.72 (q, J$_1$=13.6 Hz, J$_2$=30.4 Hz, 2H), 2.83-2.80 (m, 1H), 2.65-2.55 (m, 1H), 2.55-2.50 (m, 1H), 2.42-2.32 (m, 1H), 2.28-2.20 (m, 1H), 2.16 (s, 3H), 2.05-1.98 (m, 1H), 1.72-1.68 (m, 1H). MS Calcd.: 368.1; MS Found: 369.1 ([M+H]⁺)

Synthetic Example 29. Preparation of 5-[(3-fluorobenzyl)methylamino]-2-pyridin-2-yl-4,5,6,7-tetrahydro-2H-indazol-3-ol hydrochloride (Compound 27)

According to the method for preparation of Compound 26, the title compound as a yellow solid (95 mg, 12.3%) was obtained.
¹H NMR (400 MHz, CD₃OD): δ 8.44 (d, J=5.6 Hz, 1H), 8.25-8.15 (m, 1H), 8.15-8.10 (m, 1H), 7.50-7.45 (m, 2H), 7.39 (d, J=8.4 Hz, 2H), 7.25-7.10 (m, 1H), 4.65-4.55 (m, 1H), 4.40-4.28 (m, 1H), 3.80-3.65 (m, 1H), 3.10-2.90 (m, 2H), 2.85-2.65 (m, 5H), 2.50-2.40 (m, 1H), 2.15-2.00 (m, 1H). MS Calcd.: 352.2; MS Found: 353.1 ([M+H]⁺).

Synthetic Example 30. Preparation of 5-[(4-methoxybenzyl)methylamino]-2-pyridin-2-yl-4,5,6,7-tetrahydro-2H-indazol-3-ol hydrochloride (Compound 28)

According to the method for preparation of Compound 26, the of title compound as yellow oil (80 mg, 10.7%) was obtained.
¹H NMR (400 MHz, CD₃OD): δ 8.44 (d, J=5.2 Hz, 1H), 8.30-8.20 (m, 1H), 8.15-8.05 (m, 1H), 7.55-7.40 (m, 3H), 6.94 (d, J=8.4 Hz, 2H), 4.50 (t, J=12.8 Hz, 1H), 4.22 (t, J=14.0 Hz, 1H), 3.76-3.64 (m, 4H), 3.10-2.93 (m, 2H), 2.92-2.70 (m, 5H), 2.50-2.42 (m, 1H), 2.10-2.00 (m, 1H). MS Calcd.: 364.2; MS Found: 365.2 ([M+H]⁺).

Synthetic Example 31. Preparation of 5-[methyl-(2-methylbenzyl)amino]-2-pyridin-2-yl-4,5,6,7-tetrahydro-2H-indazol-3-ol hydrochloride (Compound 29)

According to the method for preparation of Compound 26, the title compound as a white solid (300 mg, 39.5%) was obtained.
¹H NMR (400 MHz, CD₃OD): δ 8.43 (d, J=5.2 Hz, 1H), 8.20-8.10 (m, 2H), 7.50-7.37 (m, 2H), 7.35-7.20 (m, 3H), 4.68 (dd, J$_1$=13.6 Hz, J$_2$=23.6 Hz, 1H), 4.21 (dd, J$_1$=13.2 Hz, J$_2$=32.8 Hz, 1H), 3.90-3.73 (m, 1H), 3.10-2.85 (m, 2H), 2.84-2.65 (m, 5H), 2.51-2.45 (m, 1H), 2.43 (s, 3H), 2.30-2.00 (m, 1H). MS Calcd.: 348.2; MS Found: 349.2 ([M+H]⁺).

Synthetic Example 32. Preparation of 5-[(2,4-dichlorobenzyl)methylamino]-2-pyridin-2-yl-4,5,6,7-tetrahydro-2H-indazol-3-ol hydrochloride (Compound 30)

According to the method for preparation of Compound 26, the title compound as a white solid (127 mg, 13.3%) was obtained.
¹H NMR (400 MHz, CD₃OD): δ 8.42 (d, J=5.2 Hz, 1H), 8.20-8.07 (m, 2H), 7.71 (d, J=8.0 Hz, 1H), 7.61 (d, J=2.0 Hz, 1H), 7.49-7.35 (m, 2H), 4.78-4.68 (m, 1H), 4.50-4.30 (m, 1H), 3.90-3.70 (m, 1H), 3.10-2.90 (m, 2H), 2.90-2.65 (m, 5H), 2.55-2.45 (m, 1H), 2.30-2.05 (m, 1H). MS Calcd.: 402.1; MS Found: 403.1 ([M+H]⁺).

Synthetic Example 33. Preparation of 5-[(3,4-dichlorobenzyl)methylamino]-2-pyridin-2-yl-4,5,6,7-tetrahydro-2H-indazol-3-ol hydrochloride (Compound 31)

According to the method for preparation of Compound 26, the title compound as a yellow solid (144 mg, 16.4%) was obtained.
¹H NMR (400 MHz, CD₃OD): δ 8.54 (d, J=5.2 Hz, 1H), 8.30-8.20 (m, 2H), 7.93 (d, J=1.6 Hz, 1H), 7.75-7.60 (m, 2H), 7.58-7.50 (m, 1H), 4.75-4.60 (m, 1H), 4.50-4.35 (m, 1H), 3.95-3.76 (m, 1H), 3.20-3.00 (m, 2H), 3.00-2.77 (m, 5H), 2.62-2.55 (m, 1H), 2.23-2.15 (m, 1H). MS Calcd.: 402.1; MS Found: 403.1 ([M+H]⁺).

Synthetic Example 34. Preparation of 5-(methyl(5,6,7,8-tetrahydroquinolin-8-yl)amino)-2-(pyridin-2-yl)-4,5,6,7-tetrahydro-2H-indazol-3-ol (Compound 33)

1) Preparation of N-methyl-5,6,7,8-tetrahydroquinolin-8-amine
6,7-Dihydroquinolin-8(5H)-one (2.0 g, 13.59 mmol) was dissolved in 40 mL dichloroethane and then methylamine (3.39 mL, 27.18 mmol, 2.0 eq) and acetate 7 drops were added. The reaction mixture was stirred at a room temperature for 1 hour and then sodium triacetoxyborohydride (5.7 g, 27.18 mmol, 2.0 eq) was added. The reaction mixture was stirred at a room temperature for 12 hours and then 10% ammonium chloride aqueous solution was added to adjust pH to ~8.0. The reaction mixture was extracted with dichloromethane (60 mL×2) and then the organic layer was dried with anhydrous sodium sulfate and then concentrated under reduced pressure to obtain the title compound (1.98 g, 90.0%).
¹H NMR (600 MHz, CDCl₃): δ 8.33 (d, J=4.1 Hz, 1H), 7.25-7.32 (m, 1H), 7.01 (q, J=4.1 Hz, 1H), 3.66 (m, 1H), 2.73-2.78 (m, 1H), 2.66-2.70 (m, 1H), 2.49 (s, 3H), 2.07-2.11 (m, 1H), 1.91-1.96 (m, 1H), 1.66-1.76 (m, 2H).
2) Preparation of 5-(methyl(5,6,7,8-tetrahydroquinolin-8-yl)amino)-2-(pyridin-2-yl)-4,5,6,7-tetrahydro-2H-indazol-3-ol
3-Hydroxy-2-(pyridin-2-yl)-2,4,6,7-tetrahydro-5H-indazol-5-one (0.03 g, 0.13 mmol) was dissolved in 8 mL dichloroethane and then N-methyl-5,6,7,8-tetrahydroquinolin-8-amine (0.02 g, 0.13 mmol, 1.0 eq), and acetate 2 drops were added. The reaction mixture was stirred at a room temperature for 1 hour and then sodium cyanoborohydride (0.01 g, 0.16 mmol, 1.2 eq) was added. The reaction mixture was stirred at a room temperature for 12 hours, and then 10% ammonium chloride aqueous solution was added to adjust pH to about ~8.0. The reaction mixture was extracted with dichloromethane (20 mL×2) and then the organic layer was dried with anhydrous sodium sulfate and concentrated under reduced pressure. The residue was purified by silica gel chromatography (dichloromethane/methanol=5/1+0.1% triethylamine) to obtain the title compound as a brown solid (0.05 g, 11.0%).
¹H NMR (600 MHz, CDCl₃): δ 8.50-8.44 (m, 1H), 8.23-8.17 (m, 1H), 7.90-7.70 (m, 2H), 7.33 (d, J=7.4 Hz, 1H), 7.10-6.97 (m, 2H), 4.20-4.12 (m, 1H), 3.15-2.95 (m, 1H), 2.85-2.77 (m, 3H), 2.71-2.65 (m, 1H), 2.60-2.42 (m, 2H), 2.29 (s, 3H), 2.27-2.20 (m, 1H), 2.05-1.95 (m, 2H), 1.83-1.67 (m, 3H). MS Calcd.: 375.2; MS Found: 376.1 ([M+H]$^+$).

Synthetic Example 35. Preparation of cyclopropyl (4-(3-hydroxy-2-(pyridin-2-yl)-4,5,6,7-tetrahydro-2H-indazol-5-yl)piperazin-1-yl)methanone. (Compound 38)

3-Hydroxy-2-(pyridin-2-yl)-2,4,6,7-tetrahydro-5H-indazol-5-one (2.5 g, 10.9 mmol) was dissolved in 100 mL dichloromethane/dichloroethane (1/1) and then cyclopropyl (piperazin-1-yl)methanone hydrochloride (3.1 g, 16.4 mmol, 1.5 eq), diaisopropylethylamine (2.8 ml, 16.4 mmol, 1.5 eq), acetate (1.0 ml, 16.4 mmol, 1.5 eq) were added. The reaction mixture was stirred at a room temperature for 3 hours and then sodium triacetoxyborohydride (4.6 g, 21.8 mmol, 2.0 eq) was added. The reaction mixture was stirred at a room temperature for 48 hours and then 2 M sodium hydroxide aqueous solution was added to adjust pH to about ~8.0. The reaction mixture was extracted with dichloromethane (20 mL×2) and then the organic layer was dried with anhydrous sodium sulfate and concentrated under reduced pressure. The residue was primarily purified by silica gel column chromatography (dichloromethane/methanol=5/1) and then recrystallized with diethylether to obtain the title compound as a light brown solid (2.8 g, 70.0%).
$^1$H NMR (600 MHz, CDCl$_3$): δ 8.23 (d, J=5.5 Hz, 1H), 7.82 (t, J=3.4 Hz, 2H), 7.10 (q, J=4.1 Hz, 1H), 3.74-3.61 (m, 4H), 2.91-2.81 (m, 1H), 2.81-2.52 (m, 8H), 2.44-2.35 (m, 1H), 2.15-2.07 (m, 1H), 1.76-1.70 (m, 1H), 1.04-0.95 (m, 2H), 0.79-0.70 (m, 2H). MS Calcd.: 367.2; MS Found: 368.1 ([M+H]$^+$).

Synthetic Example 36. Preparation of 5-((4-(dimethylamino)benzyl)(methyl)amino)-2-(pyridin-2-yl)-4,5,6,7-tetrahydro-2H-indazol-3-ol. (Compound 70)

3-Hydroxy-2-(pyridin-2-yl)-2,4,6,7-tetrahydro-5H-indazol-5-one (0.70 g, 3.04 mmol) was dissolved in 40 mL dichloromethane/dichloroethane (1/1) and then N,N-dimethyl-4-((methylamino)methyl)aniline (0.50 g, 3.04 mmol, 1.0 eq), and acetate (0.19 ml, 3.04 mmol, 1.0 eq) were added. The reaction mixture was stirred at a room temperature for 1 hour and then sodium triacetoxyborohydride (0.64 g, 3.04 mmol, 1.0 eq) was added. The reaction mixture was stirred at a room temperature for 18 hours and then 2 M sodium hydroxide aqueous solution was added to adjust pH to about ~8.0. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1) to obtain the title compound as a black solid (0.094 g, 8.0%).
$^1$H NMR (600 MHz, CD$_3$OD): δ 8.42-8.34 (m, 1H), 8.25 (d, J=8.8 Hz, 1H), 7.90-7.79 (m, 1H), 7.27 (d, J=9.0 Hz, 2H), 7.18 (dd, J=8.0, 5.4 Hz, 1H), 6.77 (d, J=9.1 Hz, 2H), 4.11 (dd, J=23.9, 13.5 Hz, 2H), 3.55-3.37 (m, 1H), 2.93 (s, 6H), 2.87-2.72 (m, 2H), 2.63 (s, 3H), 2.58-2.47 (m, 2H), 2.34-2.25 (m, 1H), 2.02-1.92 (m, 1H).
MS Calcd.: 377.2; MS Found: 378.3 ([M+H]$^+$).

Synthetic Example 37. Preparation of 2-pyridin-2-yl-5-pyrrolidin-1-yl-4,5,6,7-tetrahydro-2H-indazol-3-ol. (Compound 96)

3-Hydroxy-2-(pyridin-2-yl)-2,4,6,7-tetrahydro-5H-indazol-5-one (0.30 g, 1.30 mmol) was dissolved in 10 mL dichloromethane and then pyrrolidine (0.32 ml, 3.91 mmol, 3.0 eq), and acetate (0.16 ml, 2.61 mmol, 2.0 eq) were added. The reaction mixture was stirred at a room temperature for 12 hours and then sodium triacetoxyborohydride (0.35 g, 1.65 mmol, 1.3 eq) was added. The reaction mixture was stirred at a room temperature for 12 hours and then 10% sodium hydrogen carbonate aqueous solution was added to adjust pH to about ~8.0. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1) to obtain the title compound as brown gel (0.085 g, 23.0%). By the same method as above, Compounds 17, 160 and 161 were prepared.
$^1$H NMR (600 MHz, CDCl$_3$): δ 10.45 (brs, 1H), 8.23 (s, 1H), 7.98-7.75 (m, 2H), 7.21-7.05 (m, 1H), 3.51-3.20 (m, 5H), 3.00-2.80 (m, 2H), 2.77-2.59 (m, 2H), 2.45-2.30 (m, 1H), 2.15-2.00 (m, 5H). MS Calcd.: 284.2; MS Found: 285.4 ([M+H]$^+$).

Synthetic Example 38. Preparation of 5-(4-methoxybenzylamino)-2-pyridin-2-yl-4,5,6,7-tetrahydro-2H-indazol-3-ol. (Compound 88)

According to the method for preparation of Compound 96, the title compound as a dark gray solid (0.30 g, 39.3%) was obtained.
$^1$H NMR (600 MHz, CDCl$_3$): δ 8.23 (d, J=4.8 Hz, 1H), 7.93-7.85 (m, 1H), 7.83-7.77 (m, 1H), 7.36 (d, J=8.6 Hz, 2H), 7.09 (dd, J=7.5, 5.3 Hz, 1H), 6.86 (d, J=8.7 Hz, 2H), 3.93 (dd, J=50.4, 13.1 Hz, 2H), 3.06 (ddd, J=12.3, 5.1, 2.6 Hz, 1H), 2.90 (dd, J=14.7, 5.0 Hz, 1H), 2.78 (ddd, J=16.7, 4.9, 3.9 Hz, 1H), 2.58 (ddd, J=16.8, 11.1, 5.7 Hz, 1H), 2.50 (dd, J=14.6, 9.6 Hz, 1H), 2.26-2.14 (m, 1H), 1.91-1.81 (m, 1H). MS Calcd.: 350.2; MS Found: 351.3 ([M+H]$^+$).

Synthetic Example 39. Preparation of 5-phenethylamino-2-pyridin-2-yl-4,5,6,7-tetrahydro-2H-indazol-3-ol. (Compound 93)

According to the method for preparation of Compound 96, the title compound as a dark gray solid (0.30 g, 39.3%) was obtained.
$^1$H NMR (600 MHz, DMSO-d$_6$): δ 8.44-8.23 (m, 2H), 7.85 (t, J=7.1 Hz, 1H), 7.27-7.23 (m, 2H), 7.21-7.18 (m, 2H), 7.15-7.12 (m, 2H), 2.90-2.75 (m, 3H), 2.72-2.65 (m, 2H), 2.60-2.50 (m, 1H), 2.48-2.35 (m, 2H), 1.95-1.89 (m, 2H), 1.56-1.44 (m, 1H). MS Calcd.: 334.2; MS Found: 335.3 ([M+H]$^+$).

Synthetic Example 40. Preparation of 5-phenylamino-2-pyridin-2-yl-4,5,6,7-tetrahydro-2H-indazol-3-ol. (Compound 92)

According to the method for preparation of Compound 96, the title compound as a brown solid (0.21 g, 53.2%) was obtained.
$^1$H NMR (600 MHz, CDCl$_3$OD): δ 8.27-8.21 (m, 1H), 7.87-7.79 (m, 2H), 7.20-7.13 (m, 2H), 7.13-7.03 (m, 1H), 6.74-6.66 (m, 1H), 6.66-6.58 (m, 2H), 3.90-3.73 (m, 1H), 2.95 (ddd, J=16.0, 9.0, 4.5 Hz, 1H), 2.85-2.69 (m, 2H), 2.45-2.33 (m, 1H), 2.23-2.07 (m, 1H), 1.95-1.79 (m, 1H). MS Calcd.: 306.2; MS Found: 307.3 ([M+H]$^+$).

Synthetic Example 41. Preparation of 5-(3,4-difluorophenylamino)-2-pyridin-2-yl-4,5,6,7-tetrahydro-2H-indazol-3-ol. (Compound 32)

According to the method for preparation of Compound 96, the title compound as a dark gray solid (0.22 g, 74.2%) was obtained.

$^1$H NMR (600 MHz, DMSO-$d_6$): δ 11.50 (s, 1H), 8.39 (d, J=8.4 Hz, 1H), 8.36 (d, J=4.0 Hz, 1H), 7.84 (t, J=7.2 Hz, 1H), 7.14 (dd, J=6.9, 5.2 Hz, 1H), 7.06 (q, J=9.7 Hz, 1H), 6.58 (ddd, J=13.7, 6.8, 2.4 Hz, 1H), 6.37 (d, J=9.1 Hz, 1H), 5.80 (d, J=8.1 Hz, 1H), 3.62-3.50 (m, 1H), 2.64-2.55 (m, 2H), 2.51 (dd, J=15.1, 5.1 Hz, 1H), 2.06-2.00 (m, 1H), 2.00-1.93 (m, 1H), 1.64-1.53 (m, 1H). MS Calcd.: 342.1; MS Found: 343.2 ([M+H]$^+$).

Synthetic Example 42. Preparation of 5-(4-ethylpiperazin-1-yl)-2-pyridin-2-yl-4,5,6,7-tetrahydro-2H-indazol-3-ol. (Compound 91)

According to the method for preparation of Compound 96, the title compound as brown gel (0.20 g, 47.0%) was obtained.

$^1$H NMR (600 MHz, CDCl$_3$): δ 8.28-8.00 (m, 1H), 7.95-7.80 (m, 1H), 7.80-7.65 (m, 1H), 7.10-6.95 (m, 1H), 2.85-2.50 (m, 12H), 2.35-2.25 (m, 1H), 2.15-2.05 (m, 1H), 2.05-1.95 (m, 2H), 1.70-1.55 (m, 1H), 1.50-1.15 (m, 3H). MS Calcd.: 327.2; MS Found: 328.4 ([M+H]$^+$).

Synthetic Example 43. Preparation of 5-(4-propylpiperazin-1-yl)-2-pyridin-2-yl-4,5,6,7-tetrahydro-2H-indazol-3-ol. (Compound 100)

3-Hydroxy-2-(pyridin-2-yl)-2,4,6,7-tetrahydro-5H-indazol-5-one (0.25 g, 1.09 mmol) was dissolved in 14 mL dichloromethane/dichloroethane (1/1) and then 1-propylpiperadine dihydrobromide (0.41 g, 1.42 mmol, 1.3 eq), and diaisopropylethylamine (0.50 ml, 2.84 mmol, 2.6 eq) were added. The reaction mixture was stirred at a room temperature for 1 hour and then sodium triacetoxyborohydride (0.30 g, 1.42 mmol, 1.3 eq) was added. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1) to obtain the title compound as a brown solid (0.11 g, 29.0%). By the same method as above, Compounds 127 and 128 were also prepared.

$^1$H NMR (600 MHz, CDCl$_3$OD): δ 8.28-8.16 (m, 1H), 8.00-7.58 (m, 2H), 7.17-6.97 (m, 1H), 3.05-2.87 (m, 8H), 2.85-2.75 (m, 2H), 2.71 (dd, J=14.5, 4.7 Hz, 1H), 2.68-2.57 (m, 3H), 2.39 (dd, J=14.3, 10.8 Hz, 1H), 2.21-2.12 (m, 1H), 1.75-1.65 (m, 3H), 0.93 (t, J=7.4 Hz, 3H). MS Calcd.: 341.2; MS Found: 342.4 ([M+H]$^+$).

Synthetic Example 44. Preparation of 5-(4-cyclohexylmethylpiperazin-1-yl)-2-pyridin-2-yl-4,5,6,7-tetrahydro-2H-indazol-3-ol. (Compound 106)

According to the method for preparation of Compound 100, the title compound as a brown solid (0.14 g, 33.1%) was obtained.

$^1$H NMR (600 MHz, CD$_3$OD): δ 8.45-8.20 (m, 2H), 7.87 (dd, J=12.7, 5.3 Hz, 1H), 7.19 (dd, J=7.1, 5.3 Hz, 1H), 3.55-3.35 (m, 1H), 3.09-2.53 (m, 10H), 2.40-2.25 (m, 1H), 2.25-2.07 (m 1H), 1.92-1.61 (m, 8H), 1.37-1.28 (m, 4H), 1.26-1.19 (m, 1H), 1.10-0.90 (m, 2H). MS Calcd.: 395.3; MS Found: 396.3 ([M+H]$^+$).

Synthetic Example 45. Preparation of 5-(4-benzylpiperazin-1-yl)-2-pyridin-2-yl-4,5,6,7-tetrahydro-2H-indazol-3-ol. (Compound 105)

According to the method for preparation of Compound 100, the title compound as a brown solid (0.20 g, 47.1%) was obtained.

$^1$H NMR (600 MHz, CDCl$_3$): δ 8.22 (d, J=5.1 Hz, 1H), 7.90-7.70 (m, 2H), 7.39-7.27 (m, 5H), 7.11 (dd, J=7.5, 5.4 Hz, 1H), 3.75 (brs, 2H), 3.31-2.75 (m, 10H), 2.74-2.61 (m, 2H), 2.60-2.42 (m, 1H), 2.41-2.24 (m, 1H), 1.89-1.67 (m, 1H). MS Calcd.: 389.2; MS Found: 390.3 ([M+H]$^+$).

Synthetic Example 46. Preparation of 5-(4-phenethylpiperazin-1-yl)-2-pyridin-2-yl-4,5,6,7-tetrahydro-2H-indazol-3-ol. (Compound 104)

According to the method for preparation of Compound 100, the title compound as a brown solid (0.18 g, 40.9%) was obtained.

$^1$H NMR (600 MHz, CDCl$_3$): δ 10.24 (brs, 1H), 8.24-8.11 (m, 1H), 8.04-7.81 (m, 1H), 7.81-7.69 (m, 1H), 7.27-7.22 (m, 2H), 7.18-7.14 (m, 3H), 7.07-7.02 (m, 1H), 3.70 (ddd, J=6.6, 4.2, 2.5 Hz, 1H), 2.88-2.64 (m, 12H), 2.63-2.52 (m, 2H), 2.36 (dd, J=14.3, 10.7 Hz, 1H), 2.19-2.10 (m, 1H), 1.84-1.76 (m, 1H), 1.68 (ddd, J=23.9, 12.2, 5.2 Hz, 1H). MS Calcd.: 403.2; MS Found: 404.3 ([M+H]$^+$).

Synthetic Example 47. Preparation of 5-[4-(3-phenylpropyl)-piperazin-1-yl]-2-pyridin-2-yl-4,5,6,7-tetrahydro-2H-indazol-3-ol. (Compound 107)

According to the method for preparation of Compound 100, the title compound as a brown solid (0.11 g, 24.2%) was obtained.

$^1$H NMR (600 MHz, CD$_3$OD): δ 8.36 (ddd, J=5.0, 1.9, 0.9 Hz, 1H), 8.27 (d, J=8.4 Hz, 1H), 7.83 (ddd, J=8.4, 7.4, 1.9 Hz, 1H), 7.28-7.22 (m, 2H), 7.21-7.12 (m, 4H), 3.05-2.78 (m, 8H), 2.75 (ddd, J=16.1, 5.3, 3.2 Hz, 3H), 2.67-2.55 (m, 4H), 2.31-2.23 (m, 1H), 2.13 (ddtdd, J=8.1, 5.4, 2.7, 1.3, 0.6 Hz, 1H), 1.96-1.88 (m, 3H), 1.76-1.66 (m, 1H). MS Calcd.: 417.3; MS Found: 418.3 ([M+H]$^+$).

Synthetic Example 48. Preparation of 5-((2-(dimethylamino)benzyl)(methyl)amino)-2-(pyridin-2-yl)-4,5,6,7-tetrahydro-2H-indazol-3-ol. (Compound 71)

5-(Methylamino)-2-(pyridin-2-yl)-4,5,6,7-tetrahydro-2H-indazol-3-ol (0.20 g, 0.82 mmol) was dissolved in 15 mL dichloroethane and then 2-(dimethylamino)benzaldehyde (0.18 g, 1.23 mmol, 1.5 eq), and acetate 2 drops were added. The reaction mixture was stirred at a room temperature for 1 hour and then sodium triacetoxyborohydride (0.35 g, 1.63 mmol, 2.0 eq) was added. The reaction mixture was stirred at a room temperature for 16 hours and then 2 M sodium hydroxide aqueous solution was added. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1) to obtain the title compound as a light brown solid (0.09 g, 29%). By the same method as above, Compounds 69 and 77 were also prepared.

¹H NMR (600 MHz, CD₃OD): δ 8.38-8.35 (m, 1H), 8.23 (d, J=8.4 Hz, 1H), 7.86-7.81 (m, 1H), 7.44-7.37 (m, 2H), 7.34 (d, J=7.4 Hz, 1H), 7.20-7.14 (m, 2H), 4.31 (s, 2H), 3.38 (tdd, J=5.2, 4.5, 2.7 Hz, 1H), 2.83 (ddd, J=16.8, 5.3, 2.5 Hz, 1H), 2.80-2.74 (m, 1H), 2.71 (s, 6H), 2.69-2.64 (m, 1H), 2.65 (s, 3H) 2.61 (dd, J=13.8, 11.1 Hz, 1H), 2.29 (ddd, J=7.0, 5.2, 2.7 Hz, 1H), 2.02 (qd, J=11.9, 5.5 Hz, 1H). MS Calcd.: 377.2; MS Found: 378.3 ([M+H]⁺).

Synthetic Example 49. Preparation of 5-(methylquinolin-6-ylmethylamino)-2-pyridin-2-yl-4,5,6,7-tetrahydro-2H-indazol-3-ol. (Compound 63)

5-Methylamino-2-pyridin-2-yl-4,5,6,7-tetrahydro-2H-indazol-3-ol (0.25 g, 1.02 mmol) was dissolved in 20 mL dichloromethane/dichloroethane (1/1) and then quinolin-6-carboxaldehyde (0.24 g, 1.5 mmol, 1.5 eq), and acetate (0.06 ml, 1.0 mmol, 1 eq) were added. The reaction mixture was stirred at a room temperature for 1 hour and then sodium triacetoxyborohydride (0.09 g, 1.5 mmol, 1.5 eq) was added. The reaction mixture was stirred at a room temperature for 12 hours and then 10% sodium hydroxide aqueous solution was added to adjust pH to about ~8.0. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1+0.1% triethylamine) to obtain the title compound as a brown solid (0.058 g, 14.7%). By the same method as above, Compound 61 was also prepared.

¹H NMR (600 MHz, DMSO-d₆): δ 11.42 (brs, 1H), 8.81 (dd, J=4.2, 1.8 Hz, 1H), 8.42-8.33 (m, 2H), 8.30 (d, J=7.7 Hz, 1H), 7.94 (d, J=8.6 Hz, 1H), 7.84 (s, 2H), 7.72 (dd, J=8.6, 1.7 Hz, 1H), 7.46 (dt, J=4.1, 3.0 Hz, 1H), 7.10-7.20 (m, 1H), 3.78 (dd, J=43.2, 13.9 Hz, 2H), 2.84 (ddd, J=10.8, 5.0, 2.7 Hz, 1H), 2.72-2.61 (m, 1H), 2.57-2.47 (m, 1H), 2.40 (tddd, J=7.9, 6.7, 3.5, 2.1 Hz, 1H), 2.30-2.14 (m, 1H), 2.19 (s, 3H), 2.09-1.99 (m, 1H), 1.70 (qd, J=12.0, 5.4 Hz, 1H). MS Calcd.: 385.2; MS Found: 386.2 ([M+H]⁺).

Synthetic Example 50. Preparation of 5-(isoquinolin-3-ylmethyl-methylamino)-2-pyridin-2-yl-4,5,6,7-tetrahydro-2H-indazol-3-ol. (Compound 62)

According to the method for preparation of Compound 63, the title compound as a brown solid (0.02 g, 6.1%) was obtained.

¹H NMR (600 MHz, DMSO-d₆): δ 11.45 (brs, 1H), 9.21 (s, 1H), 8.47-8.31 (m, 2H), 8.05 (d, J=8.2 Hz, 1H), 7.92 (d, J=8.2 Hz, 1H), 7.89-7.79 (m, 2H), 7.70 (t, J=7.5 Hz, 1H), 7.58 (t, J=7.4 Hz, 1H), 7.10-7.20 (m, 1H), 3.88 (dd, J=41.3, 14.7 Hz, 2H), 2.93-2.81 (m, 1H), 2.71-2.59 (m, 1H), 2.56-2.36 (m, 2H), 2.27 (s, 3H), 2.25-2.14 (m, 1H), 2.09-1.99 (m, 1H), 1.75-1.64 (m, 1H). MS Calcd.: 385.2; MS Found: 386.2 ([M+H]⁺).

Synthetic Example 51. Preparation of 5-(methyl((5-(4-methylpiperazin-1-yl)imidazo[1,2-a]pyridin-2-yl)methyl)amino)-2-(pyridin-2-yl)-4,5,6,7-tetrahydro-2H-indazol-3-ol. (Compound 37)

5-(Methylamino)-2-(pyridin-2-yl)-4,5,6,7-tetrahydro-2H-indazol-3-ol (0.13 g, 0.55 mmol) was dissolved in 6 ml dichloromethane/dichloroethane (1/1) and then 5-(4-methylpiperazin-1-yl)imidazo[1,2-a]pyridin-2-carbaldehyde (0.20 g, 0.82 mmol, 1.5 eq), and acetate 3 drops were added. The reaction mixture was stirred at 45° C. for 16 hours and then sodium cyanoborohydride (0.07 g, 1.09 mmol, 2.0 eq) was added. The reaction mixture was stirred at 45° C. for 24 hours and then 2 M sodium hydroxide aqueous solution was added. The reaction mixture was extracted with dichloromethane (20 mL×2) and then the organic layer was dried with anhydrous sodium sulfate and concentrated under reduced pressure. The residue was purified by silica gel column chromatography (solvent: dichloromethane/methanol=5/1) to obtain the title compound as a light brown solid (0.059 g, 15%). By the same method as above, Compounds 35 and 36 were also prepared.

¹H NMR (600 MHz, CD₃OD): δ 8.39-8.33 (m, 1H), 8.27 (d, J=8.8 Hz, 1H), 7.88-7.78 (m, 1H), 7.67 (s, 1H), 7.28 (ddd, J=31.9, 16.9, 6.7 Hz, 2H), 7.15 (dd, J=8.1, 5.3 Hz, 1H), 6.52-6.40 (m, 1H), 3.94 (dd, J=26.0, 14.0 Hz, 2H), 3.24-3.01 (m, 4H), 3.02-2.93 (m, 1H), 2.82-2.56 (m, 7H), 2.43 (s, 3H), 2.37 (s, 3H), 2.41-2.35 (m, 1H), 2.26-2.19 (m, 1H), 1.80 (qd, J=11.9, 5.4 Hz, 1H). MS Calcd.: 472.2; MS Found: 473.4 ([M+H]⁺).

Synthetic Example 52. Preparation of 5-{methyl-[6-(4-methyl-piperazin-1-yl)-pyrimidin-4-ylmethyl]-amino}-2-pyridin-2-yl-4,5,6,7-tetrahydro-2H-indazol-3-ol. (Compound 34)

According to the method for preparation of Compound 37, the title compound as a brown solid (0.03 g, 12.7%) was obtained.

¹H NMR (600 MHz, CD₃OD): δ 8.40-8.32 (m, 2H), 8.27 (d, J=8.4 Hz, 1H), 7.87-7.79 (m, 1H), 7.16 (dd, J=7.2, 5.0 Hz, 1H), 6.87 (s, 1H), 3.76-3.54 (m, 6H), 2.94-2.87 (m, 1H), 2.80-2.70 (m, 1H), 2.65-2.53 (m, 2H), 2.53-2.42 (m, 5H), 2.35 (s, 3H), 2.29 (s, 3H), 2.15-2.08 (m, 1H), 1.81 (dtd, J=22.2, 11.0, 5.4 Hz, 1H). MS Calcd.: 434.3; MS Found: 435.5([M+H]⁺).

Synthetic Example 53. Preparation of 1-[4-(3-hydroxy-2-pyridin-2-yl-4,5,6,7-tetrahydro-2H-indazol-5-yl)-piperadin-1-yl]-2-butyn-1-one. (Compound 89)

1) Preparation of tert-butyl 4-(3-hydroxy-2-(pyridin-2-yl)-4,5,6,7-tetrahydro-2H-indazol-5-yl)piperazin-1-carboxylate 3-hydroxy-2-pyridin-2-yl-2,4,6,7-tetrahydroindazol-5-one (1.55 g, 6.78 mmol, 1.0 eq) was dissolved in 80 mL dichloromethane/dichloroethane (1/1) and then under nitrogen flow, tert-butyl piperazin-1-carboxylate (3.65 g, 16.97 mmol, 2.5 eq) and acetate (0.4 ml, 6.77 mmol, 1.0 eq) were added. The reaction mixture was stirred at a room temperature for 2 hours and then at 0° C., sodium triacetoxyborohydride (4.31 g, 20.3 mmol, 3.0 eq) was added and then stirred at a room temperature for 3 hours. To the reaction mixture, saturated sodium hydrogen carbonate aqueous solution (20 mL) was added to adjust pH to about 7 and then it was extracted with dichloromethane (30 mL×3). The organic layer was dried with anhydrous sodium sulfate and then concentrated under reduced pressure. The residue was purified by a silica gel column (solvent: dichloromethane/methanol=10/1) to obtain the title compound as a yellow solid (1.59 g, 58.8%). By the same method as above, Compound 109 was also prepared.

¹H NMR (600 MHz, CDCl₃) δ 8.23 (dt, J=5.0, 1.2 Hz, 1H), 7.81 (dd, J=11.0, 4.4 Hz, 2H), 7.09 (dd, J=8.3, 5.1 Hz,

1H), 3.49 (brt, 4H), 2.88-2.78 (m, 2H), 2.73-2.61 (m, 6H), 2.42-2.31 (m, 1H), 2.15 (dd, J=8.4, 5.1 Hz, 1H), 1.77-1.64 (m, 1H), 1.46 (s, 9H).

2) Preparation of 5-(piperazin-1-yl)-2-(pyridin-2-yl)-4,5,6,7-tetrahydro-2H-indazol-3-ol dihydrochloride tert-Butyl 4-(3-hydroxy-2-(pyridin-2-yl)-4,5,6,7-tetrahydro-2H-indazol-5-yl)piperazin-1-carboxylate (1.59 g, 3.98 mmol, 1.0 eq) was dissolved in 30 mL methanol and then under nitrogen flow, 10 ml 4.6N hydrochloric acid isopropanol solution was added. The reaction mixture was stirred at a room temperature for 1 day and concentrated under reduced pressure. The residue was recrystallized with ethyl alcohol and ethyl ether to obtain the title compound as a yellow solid (1.31 g, 87.8%).

$^1$H NMR (600 MHz, CD$_3$OD) δ 8.51-8.44 (m, 1H), 8.26 (dd, J=8.5, 0.8 Hz, 1H), 8.17-8.11 (m, 1H), 7.47-7.35 (m, 1H), 4.01-3.61 (m, 9H), 3.08 (dd, J=14.2, 5.1 Hz, 1H), 3.01 (ddd, J=17.4, 5.4, 2.3 Hz, 1H), 2.89 (ddd, J=17.4, 11.6, 5.7 Hz, 1H), 2.78-2.70 (m, 1H), 2.61-2.53 (m, 1H), 2.13 (qd, J=12.1, 5.5 Hz, 1H).

3) Preparation of 1-[4-(3-hydroxy-2-pyridin-2-yl-4,5,6,7-tetrahydro-2H-indazol-5-yl)-piperadin-1-yl]-2-butyn-1-one To 2-Butenoic acid 2,5-dioxopyrrolidin-1-yl ester (0.12 g, 0.65 mmol), 5-(piperazin-1-yl)-2-(pyridin-2-yl)-4,5,6,7-tetrahydro-2H-indazol-3-ol dihydrochloride (0.24 g, 0.65 mmol, 1.0 eq) was dissolved in 5 mL acetonitrile and then N,N-diisopropylethylamine (0.6 mL, 3.25 mmol, 5.0 eq) was added. The reaction mixture was stirred at a room temperature for 1 day and then it was extracted with water and salt water. The reaction mixture was extracted with dichloromethane (20 mL×2) and then the organic layer was dried with anhydrous sodium sulfate and concentrated under reduced pressure. The residue was purified by silica gel column chromatography (dichloromethane/methanol=5/1) to obtain the title compound as a green solid (0.25 g, 92.6%).

$^1$H NMR (600 MHz, CDCl$_3$): δ 8.22 (d, J=3.3 Hz, 1H), 7.80 (s, 2H), 7.08 (s, 1H), 3.74 (dd, J=10.3, 5.8 Hz, 2H), 3.70-3.58 (m, 2H), 2.89-2.69 (m, 2H), 2.69-2.51 (m, 6H), 2.40-2.27 (m, 1H), 2.07 (d, J=10.4 Hz, 1H), 2.01-1.92 (m, 3H), 1.69 (dt, J=11.4, 7.0 Hz, 1H). MS Calcd.: 365.2; MS Found: 367.2 ([M+H]$^+$).

Synthetic Example 57a. Preparation of 1-[4-(3-hydroxy-2-pyridin-2-yl-4,5,6,7-tetrahydro-2H-indazol-5-yl)-piperazin-1-yl]-propenone. (Compound 97)

5-(Piperazin-1-yl)-2-(pyridin-2-yl)-4,5,6,7-tetrahydro-2H-indazol-3-ol dihydrochloride (0.038 g, 0.10 mmol) was dissolved in 3 mL dichloromethane and then triethylamine (0.04 ml, 0.30 mmol, 3.0 eq) was added. The reaction mixture was stirred at 0° C. for 10 minutes. Acrylyl chloride (0.01 mL, 0.10 mmol, 1.0 eq) was added and stirred at 0° C. for 30 minutes and then sodium hydrogen carbonate aqueous solution was used to adjust neutralization. The reaction mixture was extracted with dichloromethane (10 mL×2) and then the organic layer was dried with anhydrous sodium sulfate and concentrated under reduced pressure. The residue was purified by silica gel column chromatography (dichloromethane/methanol=5/1+1% ammonia water) to obtain the title compound as a brown solid (19 mg, 53.7%).

$^1$H NMR (600 MHz, CDCl$_3$): δ 8.23 (s, 1H), 7.82 (s, 2H), 7.10 (s, 1H), 6.64-6.48 (m, 1H), 6.28 (dd, J=16.8, 1.6 Hz, 1H), 5.76-5.59 (m, 1H), 3.85-3.40 (m, 4H), 2.95-2.50 (m, 7H), 2.44-2.28 (m, 1H), 2.09 (s, 1H), 1.84-1.61 (m, 1H), 0.86 (dd, J=17.6, 10.5 Hz, 1H). MS Calcd.:353.2; MS Found: 354.3([M+H]$^+$).

Synthetic Example 57b. Synthesis reaction of reaction amide, carbonate, urea and sulfonamide derivatives 5-(Piperazin-1-yl)-2-(pyridin-2-yl)-4,5,6,7-tetrahydro-2H-indazol-3-ol dihydrochloride (0.038 g, 0.10 mmol) was dissolved in a mixed solution of 5 mL acetonitrile and 1 mL water, and NaHCO$_3$ saturated solution (200 uL) was added. For synthesis of each derivative, one of carboxyl chloride, chloroformate, isocyanate and sulfonyl chloride was added at a room temperature. The reaction mixture solution was stirred at a room temperature for 1 hour and the completion of the reaction was confirmed by LC-MS, and then ethyl acetate 50 mL was added and diluted, and washed with a mixed saturated solution of salt water and NaHCO$_3$. The product was separated and purified by TLC for purification, and the yield was in the range of 10-70%. Furthermore, the data of Synthetic examples prepared according to the general synthesis method and the synthesis method using specific materials were described. By the same method as above, Compounds 110 to 114 were prepared.

Synthetic Example 54. Preparation of 4-dimethylamino-1-[4-(3-hydroxy-2-pyridin-2-yl-4,5,6,7-tetrahydro-2H-indazol-5-yl)-piperazin-1-yl]-2-buten-1-one. (Compound 98)

5-(Piperazin-1-yl)-2-(pyridin-2-yl)-4,5,6,7-tetrahydro-2H-indazol-3-ol dihydrochloride (0.37 g, 1.00 mmol) was dissolved in 15 mL dichloromethane and then (E)-4-(dimethylamino)-2-butenic acid hydrochloride (0.20 g, 1.20 mmol, 1.2 eq), hydroxybenzotriazole (0.18 g, 1.30 mmol, 1.3eq), and N,N-diisopropylethylamine (1.74 mL, 10.0 mmol, 10.0 eq) were added. The reaction mixture was stirred at 0° C. for 10 minutes and then 1,3-diisopropylcarbodiimide (0.19 mL, 1.20 mmol, 1.2 eq) was added and it was stirred at a room temperature for 8 hours. For the reaction mixture, neutralization was adjusted using sodium hydrogen carbonate aqueous solution and then it was extracted with dichloromethane (10 mL×2). The organic layer was dried with anhydrous sodium sulfate and concentrated under reduced pressure. The residue was purified by silica gel column chromatography (dichloromethane/methanol=5/1+0.1% ammonia water) to obtain the title compound as a brown solid (0.27 g, 65.8%). By the same method as above, Compound 99 was also prepared.

$^1$H NMR (600 MHz, CDCl$_3$): δ 8.25 (d, J=5.0 Hz, 1H), 7.83 (dt, J=14.3, 7.8 Hz, 2H), 7.13-7.07 (m, 1H), 6.84 (dt, J=15.2, 6.3 Hz, 1H), 6.50-6.43 (m, 1H), 3.70 (d, J=0.9 Hz, 2H), 3.52 (s, 2H), 3.30-3.22 (m, 2H), 2.84 (d, J=16.5 Hz, 1H), 2.77-2.69 (m, 1H), 2.69-2.60 (m, 4H), 2.57 (s, 2H), 2.41-2.33 (m, 7H), 2.11-2.04 (m, 1H), 1.70 (qd, J=12.1, 5.3 Hz, 1H). MS Calcd.:410.2; MS Found: 411.3([M+H]$^+$).

Synthetic Example 55. Preparation of 5-(4-methylpiperazin-1-yl)-2-(5-(trifluoromethyl)pyridin-2-yl)-4,5,6,7-tetrahydro-2H-indazol-3-ol. (Compound 82)

Methyl 5-(4-methylpiperazin-1-yl)-2-oxocyclohexane-1-carboxylate (0.19 g, 0.75 mmol) was dissolved in 15 mL ethanol and then 5 drops of acetate and 2-hydrazinyl-5-(trifluoromethyl)pyridine (0.13 g, 0.75 mmol, 1.0 eq) was added. The reaction mixture was stirred at a room temperature for 1 hour and at 100° C. for 4 hours and concentrated under reduced pressure. The residue was recrystallized with ethylacetate/diethylether to obtain the title compound as a light brown solid (0.092 g, 32%). By the same method as above, Compounds 115 to 120, 132, 137 to 145, and 154 to 156 were also prepared.

$^1$H NMR (600 MHz, CD$_3$OD): δ 8.69 (s, 1H), 8.57 (d, J=8.5 Hz, 1H), 8.15 (dd, J=8.9, 2.4 Hz, 1H), 3.55-2.86 (m, 8H), 2.84 (s, 3H), 2.76 (dd, J=5.1, 3.3 Hz, 1H), 2.70-2.61 (m, 2H), 2.59-2.51 (m, 1H), 2.31 (dd, J=14.5, 10.1 Hz, 1H), 2.16-2.09 (m, 1H), 1.80 (qd, J=11.2, 5.5 Hz, 1H). MS Calcd.: 381.2; MS Found: 382.3 ([M+H]$^+$).

Synthetic Example 56. Preparation of 2-(6-chloro-pyridin-2-yl)-5-(4-methyl-piperazin-1-yl)-4,5,6,7-tetrahydro-2H-indazol-3-ol. (Compound 83)

According to the method for preparation of Compound 82, the title compound as a bright gray solid (0.11 g, 59.8%) was obtained.

$^1$H NMR (600 MHz, D$_2$O): δ 7.91 (d, J=8.2 Hz, 1H), 7.80 (t, J=7.9 Hz, 1H), 7.23 (d, J=7.9 Hz, 1H), 3.82-3.30 (m, 8H), 2.97-2.87 (m, 1H), 2.93 (s, 3H), 2.84-2.75 (m, 2H), 2.74-2.65 (m, 1H), 2.48-2.40 (m, 1H), 2.33 (dd, J=8.4, 3.3 Hz, 1H), 1.93 (qd, J=11.9, 5.6 Hz, 1H). MS Calcd.: 347.1; MS Found: 348.2 ([M+H]$^+$).

Synthetic Example 57. Preparation of 5-(4-methyl-piperazin-1-yl)-2-(6-methyl-4-trifluoromethyl-pyridin-2-yl)-4,5,6,7-tetrahydro-2H-indazol-3-ol. (Compound 84)

According to the method for preparation of Compound 82, the title compound as a gray solid (0.12 g, 73.8%) was obtained.

$^1$H NMR (600 MHz, CD$_3$OD): δ 8.41 (s, 1H), 7.73 (s, 1H), 4.16-3.59 (m, 9H), 3.30 (s, 3H), 3.33-3.24 (m, 2H), 3.19 (ddd, J=18.6, 10.1, 3.7 Hz, 1H), 2.84 (s, 3H), 2.91-2.77 (m, 1H), 2.74-2.67 (m, 1H), 2.30 (qd, J=12.0, 5.6 Hz, 1H). MS Calcd.: 395.2; MS Found: 396.3 ([M+H]$^+$).

Synthetic Example 58. Preparation of 5-(4-methyl-piperazin-1-yl)-2-thieno[3,2-c]pyridin-4-yl-4,5,6,7-tetrahydro-2H-indazol-3-ol. (Compound 85)

According to the method for preparation of Compound 82, the title compound as a gray solid (0.11 g, 43.0%) was obtained.

$^1$H NMR (600 MHz, CD$_3$OD): δ 8.22 (d, J=5.6 Hz, 1H), 8.03 (d, J=5.3 Hz, 1H), 7.90 (d, J=5.6 Hz, 1H), 7.74 (d, J=5.7 Hz, 1H), 3.22-2.86 (m, 9H), 2.81 (ddd, J=16.9, 5.0, 3.2 Hz, 1H), 2.76 (s, 3H), 2.73-2.62 (m, 2H), 2.42-2.34 (m, 1H), 2.19-2.12 (m, 1H), 1.79 (qd, J=11.6, 5.4 Hz, 1H). MS Calcd.: 369.1; MS Found: 370.2 ([M+H]$^+$).

Synthetic Example 59. Preparation of 2-(3-fluoro-pyridin-2-yl)-5-(4-methyl-piperazin-1-yl)-4,5,6,7-tetrahydro-2H-indazol-3-ol. (Compound 86)

According to the method for preparation of Compound 82, the title compound as a brown solid (0.41 g, 86.3%) was obtained.

$^1$H NMR (600 MHz, CD$_3$OD): δ 8.34 (d, J=4.6 Hz, 1H), 7.81-7.76 (m, 1H), 7.51-7.43 (m, 1H), 3.00-2.69 (m, 9H), 2.68-2.59 (m, 2H), 2.52 (s, 3H), 2.32 (dd, J=14.8, 10.7 Hz, 1H), 2.20-2.13 (m, 1H), 1.83-1.70 (m, 1H), 0.92-0.79 (m, 1H). MS Calcd.: 331.2; MS Found: 332.3 ([M+H]$^+$).

Synthetic Example 60. Preparation of 2-pyridin-2-yl-5-(4-pyridin-2-ylmethyl-piperazin-1-yl)-4,5,6,7-tetrahydro-2H-indazol-3-ol. (Compound 87)

According to the method for preparation of Compound 82, the title compound as a brown solid (0.064 g, 23.6%) was obtained.

$^1$H NMR (600 MHz, CD$_3$OD): δ 8.47 (d, J=4.4 Hz, 1H), 8.36 (d, J=4.6 Hz, 1H), 8.26 (d, J=8.4 Hz, 1H), 7.87-7.77 (m, 2H), 7.52 (d, J=7.8 Hz, 1H), 7.31 (dd, J=7.3, 5.2 Hz, 1H), 7.16 (dd, J=7.1, 5.1 Hz, 1H), 3.69 (s, 2H), 2.90-2.69 (m, 6H), 2.69-2.50 (m, 6H), 2.34-2.23 (m, 1H), 2.22-2.14 (m, 1H), 1.76-1.64 (m, 1H). MS Calcd.: 390.2; MS Found: 391.3 ([M+H]$^+$).

Synthetic Example 61. Preparation of 2-pyridin-2-yl-5-(4-quinolin-6-ylmethylpiperazin-1-yl)-4,5,6,7-tetrahydro-2H-indazol-3-ol. (Compound 90)

According to the method for preparation of Compound 82, the title compound as a brown solid (0.064 g, 23.6%) was obtained.

$^1$H NMR (600 MHz, DMSO-d$_6$): δ 11.40 (s, 1H), 8.83 (dd, J=4.2, 1.8 Hz, 1H), 8.38 (d, J=8.5 Hz, 1H), 8.36-8.34 (m, 1H), 8.31 (d, J=8.2 Hz, 1H), 7.94 (d, J=8.6 Hz, 1H), 7.83 (d, J=10.9 Hz, 2H), 7.69 (dd, J=8.6, 1.6 Hz, 1H), 7.47 (dd, J=8.3, 4.1 Hz, 1H), 7.17-7.11 (m, 1H), 3.62 (s, 2H), 2.67-2.23 (m, 12H), 2.14-2.01 (m, 1H), 2.00-1.90 (m, 1H), 1.60-1.45 (m, 1H). MS Calcd.: 440.2; MS Found: 441.4 ([M+H]$^+$).

Synthetic Example 62. Preparation of 2-(4-chloro-phenyl)-5-(4-methyl-piperazin-1-yl)-4,5,6,7-tetrahydride-2H-indazol-3-ol hydrochloride. (Compound 94)

According to the method for preparation of Compound 82, the title compound as a beige solid (0.048 g, 39.8%) was obtained.

$^1$H NMR (600 MHz, DMSO-d$_6$): δ 12.47-11.52 (brd, 1H), 7.72 (d, J=9.0 Hz, 2H), 7.45 (d, J=8.9 Hz, 2H), 3.79-3.24 (m, 10H), 2.80 (s, 3H), 2.75-2.65 (m, 1H), 2.60-2.55 (m, 1H), 2.47-2.40 (m, 1H), 2.38-2.21 (m, 1H), 1.90-1.75 (m, 1H). MS Calcd.: 382.1(Free Base: 346.2); MS Found: 347.3 ([M+H]$^+$).

Synthetic Example 63. Preparation of 5-(4-methyl-piperazin-1-yl)-2-(4-trifluoromethylphenyl)-4,5,6,7-tetrahydro-2H-indazol-3-ol. (Compound 95)

According to the method for preparation of Compound 82, the title compound as a brown solid (0.072 g, 68.8%) was obtained.

$^1$H NMR (600 MHz, CD$_3$OD): δ 7.97 (d, J=8.3 Hz, 2H), 7.70 (d, J=7.8 Hz, 2H), 3.00-2.61 (m, 8H), 2.77-2.66 (m, 4H), 2.55 (s, 3H), 2.41-2.11 (m, 2H), 1.75-1.65 (m, 1H). MS Calcd.: 380.2; MS Found: 381.2 ([M+H]$^+$).

Synthetic Example 64. Preparation of 2-(4-bromophenyl)-5-(4-methyl-piperazin-1-yl)-4,5,6,7-tetrahydro-2H-indazol-3-ol. (Compound 101)

According to the method for preparation of Compound 82, the title compound as a brown solid (0.005 g, 6%) was obtained.

$^1$H NMR (600 MHz, CD$_3$OD): δ 7.65 (d, J=8.9 Hz, 2H), 7.50 (d, J=8.9 Hz, 2H), 2.89-2.46 (m, 11 Hz), 2.34 (s, 3H), 2.2-2.30 (m, 1H), 2.19-2.11 (m, 1H), 2.05-1.95 (m, 1H), 1.67 (qd, J=11.8, 5.4 Hz, 1H). MS Calcd.: 390.1; MS Found: 391.2 ([M+H]$^+$).

Synthetic Example 65. Preparation of 2-(4-methyl-piperazin-1-yl)-2-(4-trifluoromethylphenyl)-4,5,6,7-tetrahydro-2H indazol-3-ol. (Compound 102)

According to the method for preparation of Compound 82, the title compound as a brown solid (0.10 g, 55.8%) was obtained.

¹H NMR (600 MHz, CD₃OD): δ 8.53 (dd, J=9.1, 4.8 Hz, 2H), 8.06-8.00 (m, 2H), 3.76-3.61 (m, 4H), 3.61-3.42 (m, 8H), 3.26 (s, 3H), 3.19-3.13 (m, 1H), 3.08-3.02 (m, 1H), 2.59 (ddd, J=24.0, 11.5, 5.4 Hz, 1H). MS Calcd.: 330.2; MS Found: 331.4 ([M+H]⁺).

Synthetic Example 66. Preparation of 4-[3-hydroxy-(4-methylpiperazin-1-yl)-4,5,6,7-tetrahydro-indazol-2-yl]-benzonitrile. (Compound 103)

According to the method for preparation of Compound 82, the title compound as a brown solid (0.035 g, 17.6%) was obtained.

¹H NMR (600 MHz, CD₃OD): δ 8.04 (d, J=8.9 Hz, 2H), 7.68 (d, J=8.9 Hz, 2H), 2.78-3.00 (m, 5H), 2.77-2.66 (m, 4H), 2.66-2.52 (m, 3H), 2.44 (s, 3H), 2.34-2.22 (m, 1H), 2.11-2.17 (m, 1H), 1.69 (ddd, J=24.0, 11.8, 5.3 Hz, 1H). MS Calcd.: 337.2; MS Found: 338.2 ([M+H]⁺).

Synthetic Example 67. Preparation of 5-(4-methylpiperazin-1-yl)-2-pyrimidin-2-yl-4,5,6,7-tetrahydro-2H-indazol-3-ol. (Compound 108)

According to the method for preparation of Compound 82, the title compound as a brown solid (0.10 g, 40.5%) was obtained.

¹H NMR (600 MHz, CD₃OD): δ 8.71 (d, J=4.9 Hz, 2H), 7.23 (t, J=4.9 Hz, 1H), 2.79-2.68 (m, 6H), 2.67-2.52 (m, 5H), 2.36 (s, 3H), 2.34-2.23 (m, 2H), 2.18-2.11 (m, 1H), 1.68 (ddd, J=23.9, 11.8, 5.3 Hz, 1H). MS Calcd.: 314.2; MS Found: 315.3 ([M+H]⁺).

Synthetic Example 68. Preparation of 2-pyridin-2-yl-5-(4-p-tollylpiperazin-1-yl)-4,5,6,7-tetrahydro-2H-indazol-3-ol. (Compound 126)

According to the method for preparation of Compound 96, the title compound as a beige solid (0.14 g, 32.9%) was obtained.

¹H NMR (600 MHz, CDCl₃): δ 8.40-8.34 (m, 1H), 8.32-8.26 (m, 1H), 7.85 (ddd, J=8.6, 7.4, 1.9 Hz, 1H), 7.17 (ddd, J=7.3, 5.0, 0.8 Hz, 1H), 7.04 (d, J=8.3 Hz, 2H), 6.87 (d, J=8.6 Hz, 2H), 3.16 (t, J=5.0 Hz, 4H), 2.94-2.73 (m, 6H), 2.70-2.59 (m, 2H), 2.32 (dd, J=13.9, 10.9 Hz, 1H), 2.27-2.22 (m, 1H), 2.22 (s, 3H), 1.75 (qd, J=11.8, 5.4 Hz, 1H). MS Calcd.: 389.2; MS Found: 390.3 ([M+H]⁺).

Synthetic Example 69. Preparation of 5-[4-(4-methoxyphenyl)-piperazin-1-yl]-2-pyridin-2-yl-4,5,6,7-tetrahydro-2H-indazol-3-ol. (Compound 129)

According to the method for preparation of Compound 96, the title compound as a brown solid (0.10 g, 23.7%) was obtained.

¹H NMR (600 MHz, CDCl₃): δ 8.28-8.19 (m, 1H), 7.90-7.70 (m, 2H), 7.10 (ddd, J=8.4, 4.3, 3.2 Hz, 1H), 6.91 (d, J=9.1 Hz, 2H), 6.83 (d, J=9.1 Hz, 2H), 3.76 (s, 3H), 3.20-3.10 (m, 4H), 3.01-2.72 (m, 7H), 2.73-2.60 (m, 1H), 2.52-2.36 (m, 1H), 2.32-2.19 (m, 1H), 1.76 (qd, J=12.2, 5.1 Hz, 1H). MS Calcd.: 405.2; MS Found: 406.3 ([M+H]⁺).

Synthetic Example 70. Preparation of 1-{4-[4-(3-hydroxy-2-pyridin-2-yl-4,5,6,7-tetrahydro-2H-indazol-5-yl)-piperazin-1-yl]-phenyl}-ethanone. (Compound 130)

According to the method for preparation of Compound 96, the title compound as a gray solid (0.14 g, 30.1%) was obtained.

¹H NMR (600 MHz, CDCl₃): δ 8.30-8.22 (m, 1H), 7.89-7.75 (m, 4H), 7.12-7.05 (m, 1H), 6.91-6.80 (m, 2H), 3.40-3.30 (m, 4H), 2.92-2.59 (m, 8H), 2.50 (s, 3H), 2.45-2.33 (m, 1H), 2.19-2.07 (m, 1H), 1.80-1.65 (m, 1H). MS Calcd.: 417.2; MS Found: 418.3 ([M+H]⁺).

Synthetic Example 71. Preparation of 5-[4-(4-methanesulfonylphenyl)-piperazin-1-yl]-2-pyridin-2-yl-4,5,6,7-tetrahydro-2H-indazol-3-ol. (Compound 131)

According to the method for preparation of Compound 96, the title compound as a light gray solid (0.09 g, 18.1%) was obtained.

¹H NMR (600 MHz, CDCl₃): δ 8.25-8.20 (m, 1H), 7.86-7.79 (m, 2H), 7.76 (d, J=9.0 Hz, 2H), 7.11 (ddd, J=6.8, 5.2, 2.0 Hz, 1H), 6.93 (d, J=9.0 Hz, 2H), 3.43-3.27 (m, 4H), 3.00 (s, 3H), 2.91-2.83 (m, 1H), 2.82-2.75 (m, 6H), 2.70-2.59 (m, 1H), 2.47-2.37 (m, 1H), 2.19-2.10 (m, 1H), 1.74 (dddd, J=12.6, 7.1, 3.3, 0.7 Hz, 1H). MS Calcd.: 453.2; MS Found: 454.2 ([M+H]⁺).

Synthetic Example 72. Preparation of 5-[4-(1-benzylpiperidin-4-ylmethyl)-piperazin-1-yl]-2-pyridin-2-yl-4,5,6,7-tetrahydro-2H-indazol-3-ol. (Compound 135)

5-(Piperazin-1-yl)-2-(pyridin-2-yl)-4,5,6,7-tetrahydro-2H-indazol-3-ol dihydrochloride (0.70 g, 1.88 mmol) was dissolved in 30 mL dichloromethane/dichloroethane (1/1) and then under nitrogen flow, 1-benzylpiperidin-4-carbaldehyde (0.35 mL, 1.88 mmol, 1.0 eq) and triethylamine (0.77 mL, 5.64 mmol, 3.0 eq) were added. The reaction mixture was stirred at a room temperature for 2 hours after adding sodium triacetoxyborohydride (0.79 g, 3.76 mmol, 2.0 eq) at 0° C. To the reaction mixture, saturated sodium hydrogen carbonate aqueous solution (20 mL) was added to adjust pH to about 7 and then it was extracted with dichloromethane (30 mL×3). The organic layer was dried with anhydrous sodium sulfate and then concentrated under reduced pressure. The residue was purified by a silica gel column (solvent: chloroform/methanol=5/1+1% ammonia water) to obtain the title compound as a brown solid (0.65 g, 70.3%). By the same method as above, Compounds 133, 134, and 136 were also prepared.

¹H NMR (600 MHz, CDCl₃): δ 8.26-8.19 (m, 1H), 7.90-7.80 (m, 2H), 7.27-7.17 (m, 5H), 7.10-7.00 (m, 1H), 3.51 (s, 2H), 2.96-2.80 (m, 2H), 2.80-2.27 (m, 11H), 2.17 (d, J=7.1 Hz, 2H), 2.00-1.90 (m, 3H), 1.75-1.64 (m, 2H), 1.55-1.40 (m, 1H), 1.34-1.16 (m, 5H). MS Calcd.: 486.3; MS Found: 487.4 ([M+H]⁺).

Synthetic Example 73. Preparation of 5-{4-[2-(2-hydroxyethoxy)-ethyl]-piperazin-1-yl}-2-pyridin-2-yl-4,5,6,7-tetrahydro-2H-indazol-3-ol. (Compound 17)

According to the method for preparation of Compound 96, the title compound as a yellow solid (0.15 g, 29.5%) was obtained.

¹H NMR (600 MHz, CDCl₃): δ 8.25-8.19 (m, 1H), 7.99-7.73 (m, 2H), 7.11-7.02 (m, 1H), 3.76-3.50 (m, 6H), 2.89-2.55 (m, 14H), 2.39-2.30 (m, 1H), 2.16-2.09 (m, 1H), 1.72-1.60 (m, 1H). MS Calcd.: 387.2; MS Found: 388.3 ([M+H]⁺).

The structure, MS result and IUPAC name of the prepared Synthetic example compounds 1 to 161 were shown in Table 1 below.

TABLE 1

| No. | Structure | MS (ESI+) | IUPAC name |
|---|---|---|---|
| 1 | 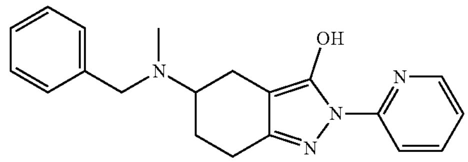 [SMILES: CN(Cc1ccccc1)C1CCc2nn(-c3ccccn3)c(O)c2C1] | 335.2 | 5-(Benzylmethylamino)-2-(pyridin-2-yl)-4,5,6,7-tetrahydro-2H-indazol-3-ol |
| 2 | 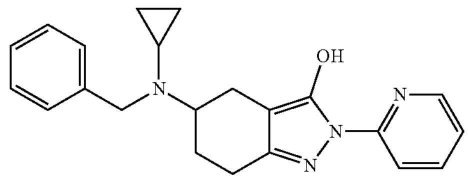 [SMILES: Oc1c2c(nn1-c1ccccn1)CCC(N(Cc1ccccc1)C1CC1)C2] | 361.2 | 5-(Benzylcyclopropylamino)-2-(pyridin-2-yl)-4,5,6,7-tetrahydro-2H-indazol-3-ol |
| 3 | 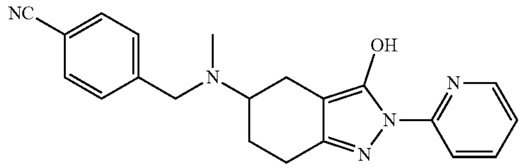 [SMILES: CN(Cc1ccc(C#N)cc1)C1CCc2nn(-c3ccccn3)c(O)c2C1] | 360.2 | 4-{[(3-Hydroxy-2-(pyridin-2-yl)-4,5,6,7-tetrahydro-2H-indazol-5-yl)methylamino]methyl}benzonitrile |
| 4 | 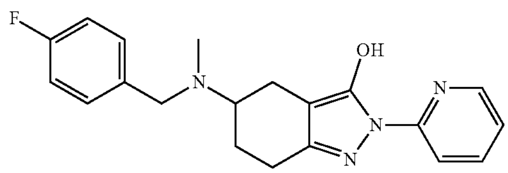 [SMILES: CN(Cc1ccc(F)cc1)C1CCc2nn(-c3ccccn3)c(O)c2C1] | 353.1 | 5-[(4-Fluorobenzyl)methylamino]-2-(pyridin-2-yl)-4,5,6,7-tetrahydro-2H-indazol-3-ol |
| 5 | 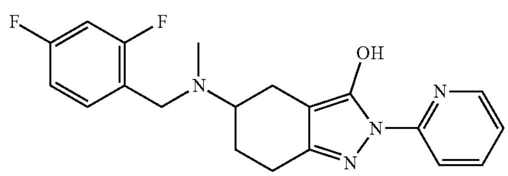 [SMILES: CN(Cc1ccc(F)cc1F)C1CCc2nn(-c3ccccn3)c(O)c2C1] | 371.1 | 5-[(2,4-Difluorobenzyl)methylamino]-2-(pyridin-2-yl)-4,5,6,7-tetrahydro-2H-indazol-3-ol |
| 6 | 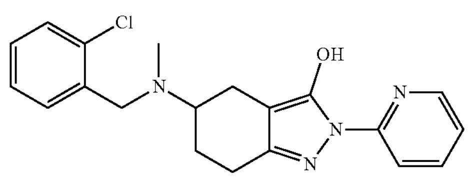 [SMILES: CN(Cc1ccccc1Cl)C1CCc2nn(-c3ccccn3)c(O)c2C1] | 369.1 | 5-[(2-Chlorobenzyl)methylamino]-2-(pyridin-2-yl)-4,5,6,7-tetrahydro-2H-indazol-3-ol |
| 7 | 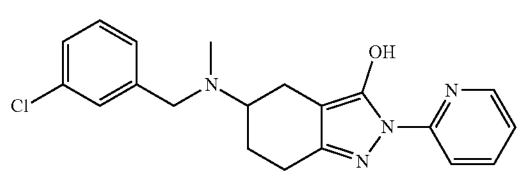 [SMILES: CN(Cc1cccc(Cl)c1)C1CCc2nn(-c3ccccn3)c(O)c2C1] | 369.1 | 5-[(3-Chlorobenzyl)methylamino]-2-(pyridin-2-yl)-4,5,6,7-tetrahydro-2H-indazol-3-ol |
| 8 | 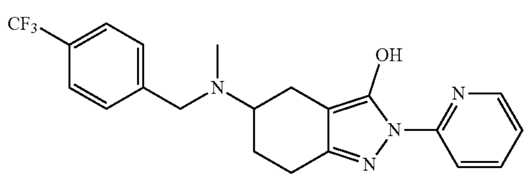 [SMILES: CN(Cc1ccc(C(F)(F)F)cc1)C1CCc2nn(-c3ccccn3)c(O)c2C1] | 403.1 | 5-[Methyl-(4-trifluoromethylbenzyl)amino]-2-pyridin-2-yl-4,5,6,7-tetrahydro-2H-indazol-3-ol |
| 9 | 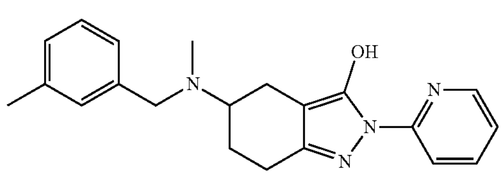 [SMILES: Cc1cccc(CN(C)C2CCc3nn(-c4ccccn4)c(O)c3C2)c1] | 349.2 | 5-[Methyl-(3-methylbenzyl)amino]-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 10 | 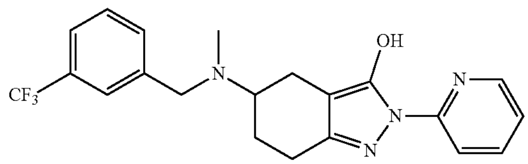 [SMILES: CN(Cc1cccc(C(F)(F)F)c1)C1CCc2nn(-c3ccccn3)c(O)c2C1] | 403.2 | 5-[Methyl-(3-trifluoromethylbenzyl)-amino]-2-pyridin-2-yl-4,5,6,7-tetrahydro-2H-indazol-3-ol |
| 11 | 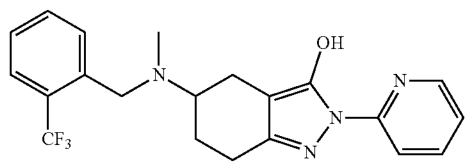 [SMILES: CN(Cc1ccccc1C(F)(F)F)C1CCc2nn(-c3ccccn3)c(O)c2C1] | 403.1 | 5-[Methyl-(2-trifluoromethylbenzyl)-amino]-2-pyridin-2-yl-4,5,6,7-tetrahydro-2H-indazol-3-ol |
| 12 | 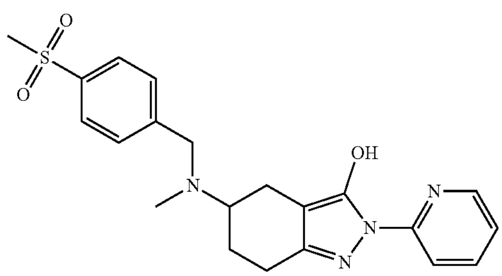 [SMILES: CN(Cc1ccc(S(C)(=O)=O)cc1)C1CCc2nn(-c3ccccn3)c(O)c2C1] | 413.1 | 5-[(4-Methanesulfonylbenzyl)methylamino]-2-(pyridin-2-yl)-4,5,6,7-tetrahydro-2H-indazol-3-ol |
| 13 | 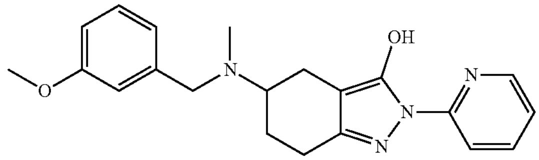 [SMILES: COc1cccc(CN(C)C2CCc3nn(-c4ccccn4)c(O)c3C2)c1] | 365.1 | 5-[(3-Methoxybenzyl)methylamino]-2-(pyridin-2-yl)-4,5,6,7-tetrahydro-2H-indazol-3-ol |
| 14 | 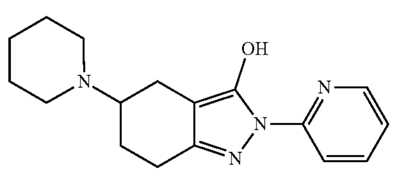 [SMILES: Oc1c2c(nn1-c1ccccn1)CCC(N1CCCCC1)C2] | 299.2 | 5-Piperidin-1-yl-2-(pyridin-2-yl)-4,5,6,7-tetrahydro-2H-indazol-3-ol |
| 15 | 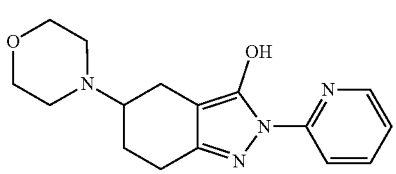 [SMILES: Oc1c2c(nn1-c1ccccn1)CCC(N1CCOCC1)C2] | 301.2 | 5-Morpholino-4-yl-2-(pyridin-2-yl)-4,5,6,7-tetrahydro-2H-indazol-3-ol |
| 16 | 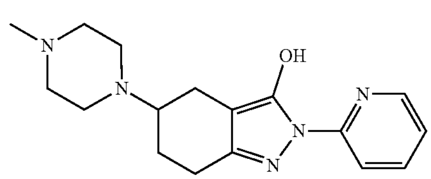 [SMILES: CN1CCN(C2CCc3nn(-c4ccccn4)c(O)c3C2)CC1] | 314.2 | 5-(4-Methylpiperazin-1-yl)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 17 | 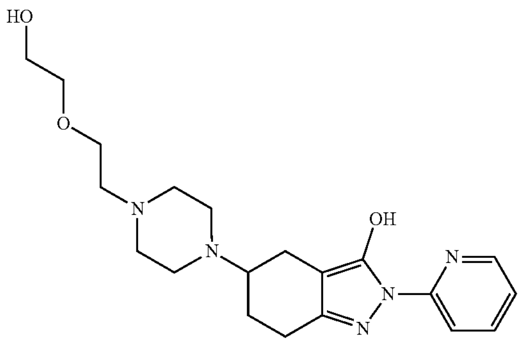 [SMILES: OCCOCCN1CCN(C2CCc3nn(-c4ccccn4)c(O)c3C2)CC1] | 388.3 | 5-(4-(2-(2-Hydroxymethoxy)ethyl)piperazin-1-yl)-2-(pyridin-2-yl)-4,5,6,7-tetrahydro-2H-indazol-3-ol |
| 18 | 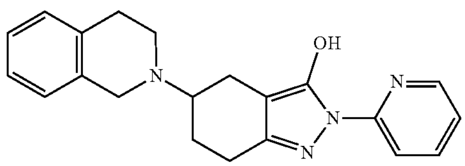 [SMILES: Oc1c2c(nn1-c1ccccn1)CCC(N1CCc3ccccc3C1)C2] | 347.2 | 5-(3,4-Dihydro-1H-isoquinolin-2-yl)-2-(pyridin-2-yl)-4,5,6,7-tetrahydro-2H-indazol-3-ol |
| 19 | 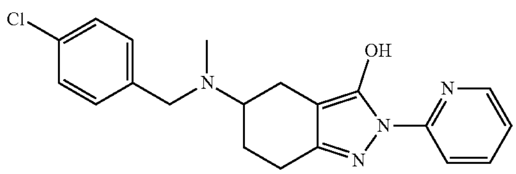 [SMILES: CN(Cc1ccc(Cl)cc1)C1CCc2nn(-c3ccccn3)c(O)c2C1] | 369.1 | 5-[(4-Chlorobenzyl)methylamino]-2-(pyridin-2-yl)-4,5,6,7-tetrahydro-2H-indazol-3-ol |
| 20 | 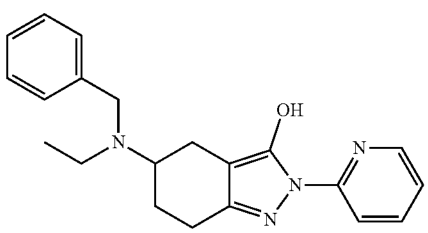 [SMILES: CCN(Cc1ccccc1)C1CCc2nn(-c3ccccn3)c(O)c2C1] | 349.2 | 5-(Benzylethylamino)-2-(pyridin-2-yl)-4,5,6,7-tetrahydro-2H-indazol-3-ol |
| 21 | 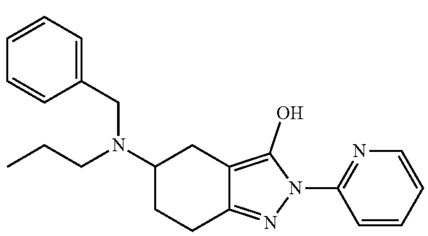 [SMILES: CCCN(Cc1ccccc1)C1CCc2nn(-c3ccccn3)c(O)c2C1] | 363.3 | 5-(Benzylpropylamino)-2-(pyridin-2-yl)-4,5,6,7-tetrahydro-2H-indazol-3-ol |
| 22 | 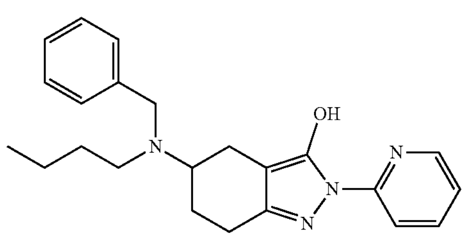 [SMILES: CCCCN(Cc1ccccc1)C1CCc2nn(-c3ccccn3)c(O)c2C1] | 377.2 | 5-(Benzylbutylamino)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 23 | 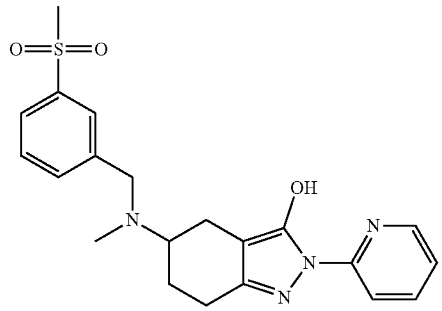 [SMILES: CN(Cc1cccc(S(C)(=O)=O)c1)C1CCc2nn(-c3ccccn3)c(O)c2C1] | 413.1 | 5-[Methyl(3-methylsulfonylbenzyl)amino]-2-(pyridin-2-yl)-4,5,6,7-tetrahydro-2H-indazol-3-ol |
| 24 | 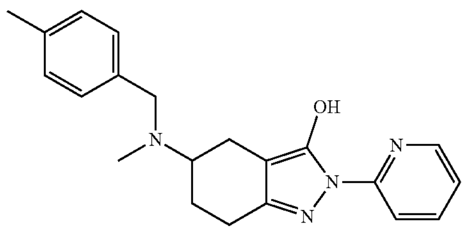 [SMILES: Cc1ccc(CN(C)C2CCc3nn(-c4ccccn4)c(O)c3C2)cc1] | 349.2 | 5-[Methyl-(4-methylbenzyl)amino]-2-(pyridin-2-yl)-4,5,6,7-tetrahydro-2H-indazol-3-ol |
| 25 | 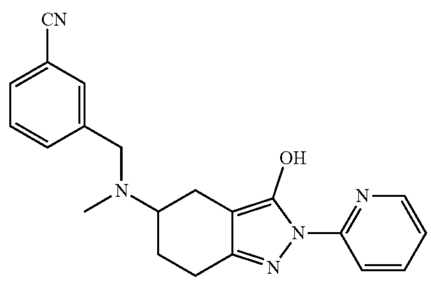 [SMILES: CN(Cc1cccc(C#N)c1)C1CCc2nn(-c3ccccn3)c(O)c2C1] | 360.1 | 3-{[(3-Hydroxy-2-(pyridin-2-yl)-4,5,6,7-tetrahydro-2H-indazol-5-yl)methylamino]methyl}benzonitrile |
| 26 | 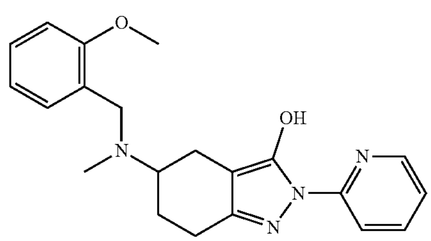 [SMILES: COc1ccccc1CN(C)C1CCc2nn(-c3ccccn3)c(O)c2C1] | 365.3 | 5-[(2-Methoxybenzyl)-methylamino]-2-(pyridin-2-yl)-4,5,6,7-tetrahydro-2H-indazol-3-ol |
| 27 | 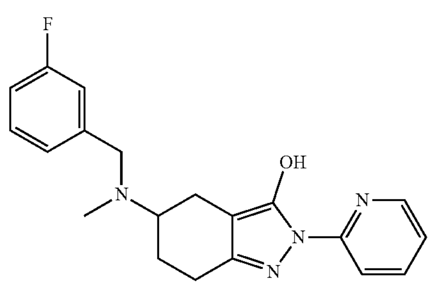 [SMILES: CN(Cc1cccc(F)c1)C1CCc2nn(-c3ccccn3)c(O)c2C1] | 353.1 | 5-[(3-Fluorobenzyl)methylamino]-2-(pyridin-2-yl)-4,5,6,7-tetrahydro-2H-indazol-3-ol |
| 28 | 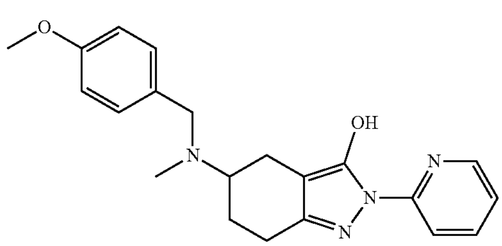 [SMILES: COc1ccc(CN(C)C2CCc3nn(-c4ccccn4)c(O)c3C2)cc1] | 365.2 | 5-[(4-Methoxybenzyl)methylamino]-2-(pyridin-2-yl)-4,5,6,7-tetrahydro-2H-indazol-3-ol |

TABLE 1-continued

| No. | Structure | MS (ESI+) | IUPAC name |
|-----|-----------|-----------|------------|
| 29 | 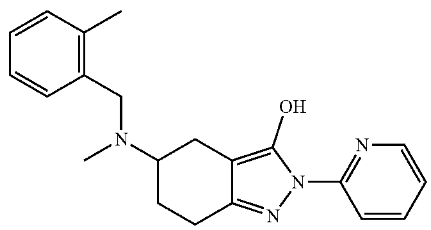 [SMILES: Cc1ccccc1CN(C)C1CCc2nn(-c3ccccn3)c(O)c2C1] | 349.2 | 5-[Methyl-(2-methylbenzyl)amino]-2-(pyridin-2-yl)-4,5,6,7-tetrahydro-2H-indazol-3-ol |
| 30 | 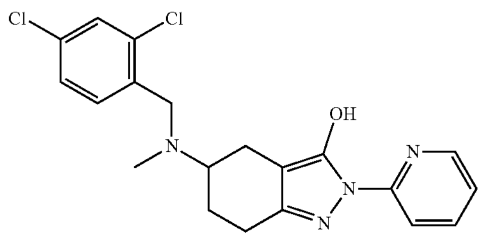 [SMILES: CN(Cc1ccc(Cl)cc1Cl)C1CCc2nn(-c3ccccn3)c(O)c2C1] | 403.1 | 5-[(2,4-Dichlorobenzyl)methylamino]-2-(pyridin-2-yl)-4,5,6,7-tetrahydro-2H-indazol-3-ol |
| 31 | 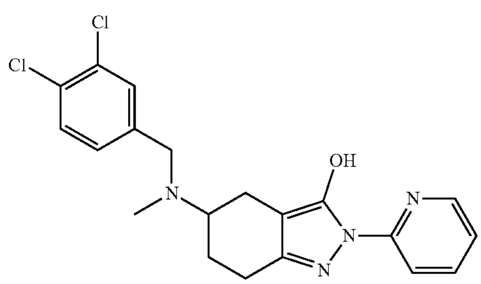 [SMILES: CN(Cc1ccc(Cl)c(Cl)c1)C1CCc2nn(-c3ccccn3)c(O)c2C1] | 403.1 | 5-[(3,4-Dichlorobenzyl)methylamino]-2-(pyridin-2-yl)-4,5,6,7-tetrahydro-2H-indazol-3-ol |
| 32 | 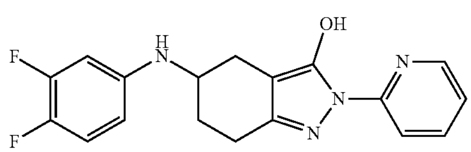 [SMILES: Oc1c2c(nn1-c1ccccn1)CCC(Nc1ccc(F)c(F)c1)C2] | 343.2 | 5-(3,4-Difluorophenylamino)-2-(pyridin-2-yl)-4,5,6,7-tetrahydro-2H-indazol-3-ol |
| 33 | 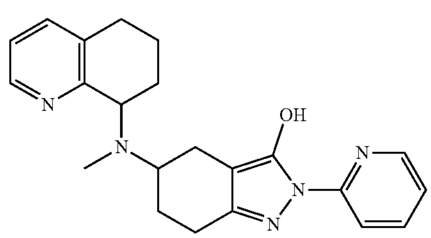 [SMILES: CN(C1CCc2nn(-c3ccccn3)c(O)c2C1)C1CCCc2cccnc21] | 376.1 | 5-[Methyl(5,6,7,8-tetrahydroquinolin-8-yl)amino]-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 34 | 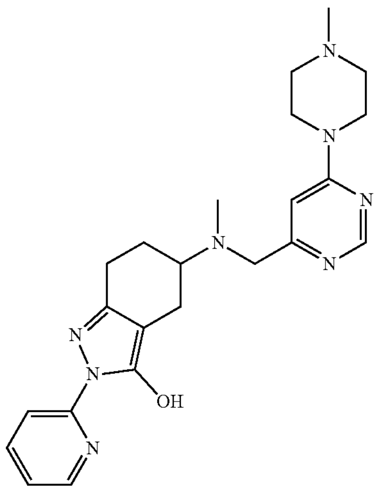 [SMILES: CN1CCN(c2cc(CN(C)C3CCc4nn(-c5ccccn5)c(O)c4C3)ncn2)CC1] | 435.5 | 5-(((3-(Hydroxymethyl)-5-(4-methylpiperazin-1-yl)imidazo[1,2-a]pyridin-2-yl)methyl)(methyl)amino)-2-(pyridin-2-yl)-4,5,6,7-tetrahydro-2H-indazol-3-ol |
| 35 | 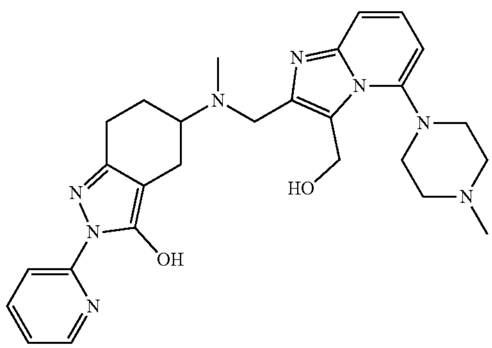 [SMILES: CN1CCN(c2cccc3nc(CN(C)C4CCc5nn(-c6ccccn6)c(O)c5C4)c(CO)n23)CC1] | 503.3 | 5-{[(3-(Hydroxymethyl)-5-(4-methylpiperazin-1-yl)imidazo[1,2-a]pyridin-2-yl)methyl]methylamino}-2-(pyridin-2-yl)-4,5,6,7-tetrahydro-2H-indazol-3-ol |
| 36 | 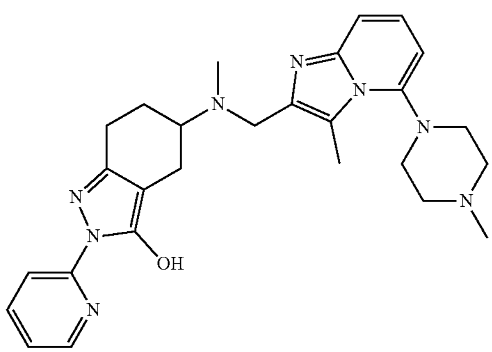 [SMILES: Cc1c(CN(C)C2CCc3nn(-c4ccccn4)c(O)c3C2)nc2cccc(N3CCN(C)CC3)n12] | 487.3 | 5-{Methyl[3-methyl-5-(4-methylpiperazin-1-yl)imidazo[1,2-a]pyridin-2-yl]methylamino}-2-(pyridin-2-yl)-4,5,6,7-tetrahydro-2H-indazol-3-ol |
| 37 | 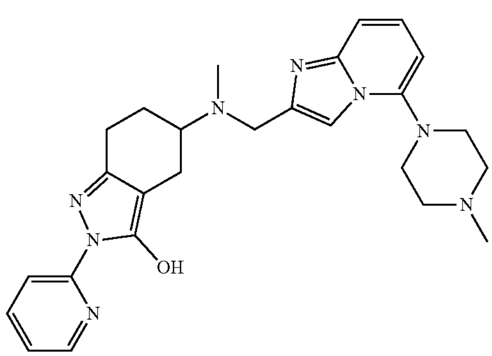 [SMILES: CN1CCN(c2cccc3nc(CN(C)C4CCc5nn(-c6ccccn6)c(O)c5C4)cn23)CC1] | 473.4 | 5-{Methyl[5-(4-methylpiperazin-1-yl)imidazo[1,2-a]pyridin-2-yl]methylamino}-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 38 | 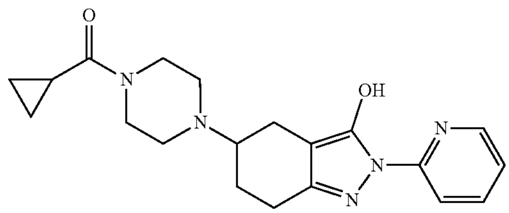 [SMILES: O=C(C1CC1)N1CCN(C2CCc3nn(-c4ccccn4)c(O)c3C2)CC1] | 368.1 | Cyclopropyl[4-(3-hydroxy-2-(pyridin-2-yl)-4,5,6,7-tetrahydro-2-indazol-5-yl)piperazin-1-yl]methanone |
| 39 | 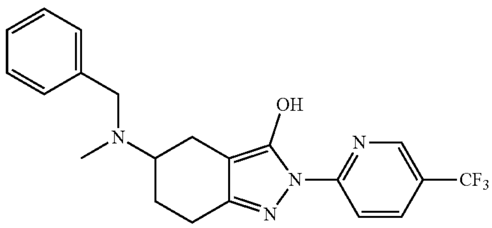 [SMILES: CN(Cc1ccccc1)C1CCc2nn(-c3ccc(C(F)(F)F)cn3)c(O)c2C1] | 403.2 | 5-(Benzylmethylamino)-2-(5-trifluoromethylpyridin-2-yl)-4,5,6,7-tetrahydro-2H-indazol-3-ol |
| 40 | 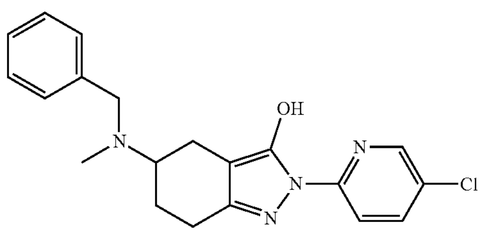 [SMILES: CN(Cc1ccccc1)C1CCc2nn(-c3ccc(Cl)cn3)c(O)c2C1] | 369.1 | 5-(Benzylmethylamino)-2-(5-chloropyridin-2-yl)-4,5,6,7-tetrahydro-2H-indazol-3-ol |
| 41 | 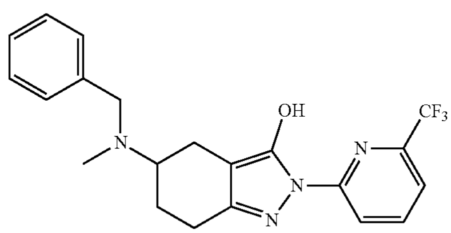 [SMILES: CN(Cc1ccccc1)C1CCc2nn(-c3cccc(C(F)(F)F)n3)c(O)c2C1] | 403.2 | 5-(Benzylmethylamino)-2-(6-(trifluoromethyl)pyridin-2-yl)-4,5,6,7-tetrahydro-2H-indazol-3-ol |
| 42 | 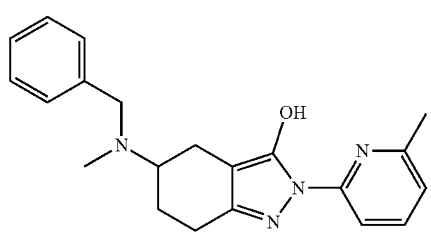 [SMILES: Cc1cccc(-n2nc3c(c2O)CC(N(C)Cc2ccccc2)CC3)n1] | 349.2 | 5-(Benzylmethylamino)-2-(6-methylpyridin-2-yl)-4,5,6,7-tetrahydro-2H-indazol-3-ol |
| 43 | 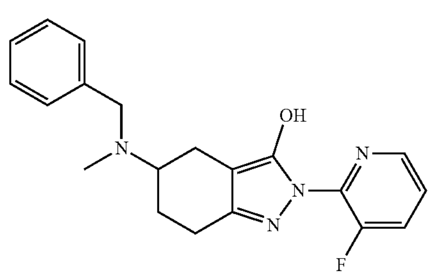 [SMILES: CN(Cc1ccccc1)C1CCc2nn(-c3ncccc3F)c(O)c2C1] | 353.2 | 5-(Benzylmethylamino)-2-(3-fluoropyridin-2-yl)-4,5,6,7-tetrahydro-2H-indazol-3-ol |

TABLE 1-continued

| No. | Structure | MS (ESI+) | IUPAC name |
|---|---|---|---|
| 44 | 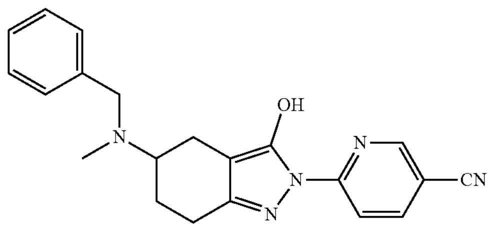 [SMILES: CN(Cc1ccccc1)C1CCc2nn(-c3ccc(C#N)cn3)c(O)c2C1] | 360.2 | 6-(5-(Benzylmethylamino)-3-hydroxy-4,5,6,7-tetrahydro-2H-indazol-2-yl)nicotinonitrile |
| 45 | 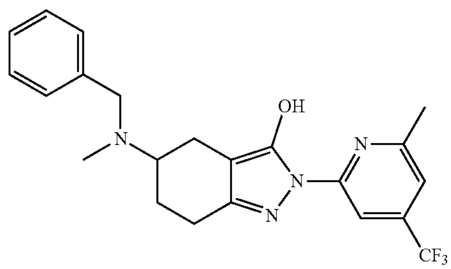 [SMILES: Cc1cc(C(F)(F)F)cc(-n2nc3c(c2O)CC(N(C)Cc2ccccc2)CC3)n1] | 417.2 | 5-(Benzylmethylamino)-2-(6-methyl-4-trifluoromethylpyridin-2-yl)-4,5,6,7-tetrahydro-2H-indazol-3-ol |
| 46 | 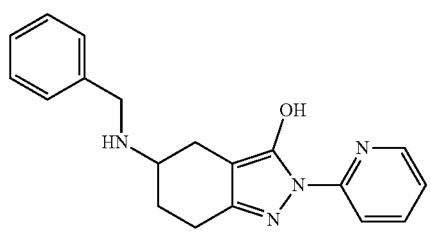 | 321.2 | 5(벤질아미노)-2-(피리딘-2-일)-5-(Benzylamino)-2-(pyridin-2-yl)-4,5,6,7-tetrahydro-2H-indazol-3-ol |
| 47 | 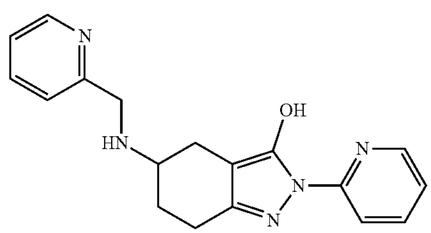 [SMILES: Oc1c2c(nn1-c1ccccn1)CCC(NCc1ccccc1)C2] | 322.2 | 2-(Pyridin-2-yl)-5-[(pyridin-2-ylmethyl)amino]-4,5,6,7-tetrahydro-2H-indazol-3-ol |
| 48 | 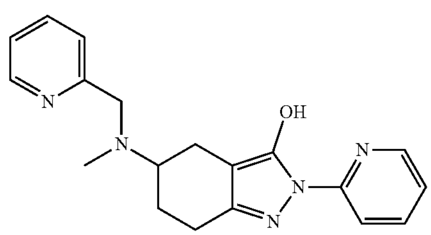 [SMILES: CN(Cc1ccccn1)C1CCc2nn(-c3ccccn3)c(O)c2C1] | 336.2 | 5-[Methyl(pyridin-2-ylmethyl)amino]-2-(pyridin-2-yl)-4,5,6,7-tetrahydro-2H-indazol-3-ol |
| 49 | 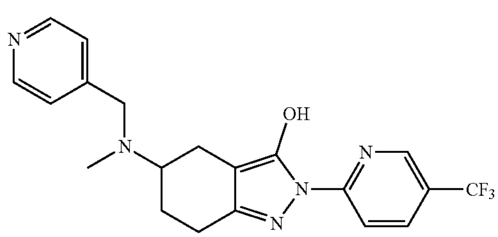 [SMILES: CN(Cc1ccncc1)C1CCc2nn(-c3ccc(C(F)(F)F)cn3)c(O)c2C1] | 404.2 | 5-[Methyl(pyridin-4-ylmethyl)amino]-2-(5-trifluoromethylpyridin-2-yl)-4,5,6,7-tetrahydro-2H-indazol-3-ol |

TABLE 1-continued

| No. | Structure | MS (ESI+) | IUPAC name |
|---|---|---|---|
| 50 | 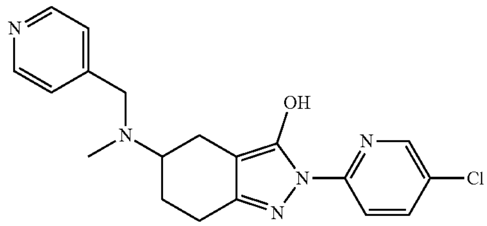 [SMILES: CN(Cc1ccncc1)C1CCc2nn(-c3ccc(Cl)cn3)c(O)c2C1] | 370.1 | 2-(5-Chloropyridin-2-yl)-5-[methyl(pyridin-4-ylmethyl)amino]-4,5,6,7-tetrahydro-2H-indazol-3-ol |
| 51 | 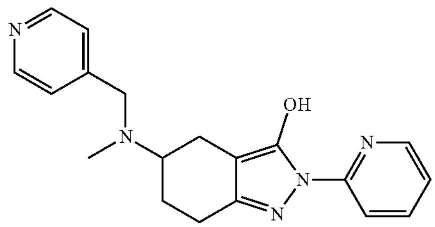 [SMILES: CN(Cc1ccncc1)C1CCc2nn(-c3ccccn3)c(O)c2C1] | 336.2 | 5-[Methyl(pyridin-4-ylmethyl)amino]-2-(pyridin-2-yl)-4,5,6,7-tetrahydro-2H-indazol-3-ol |
| 52 | 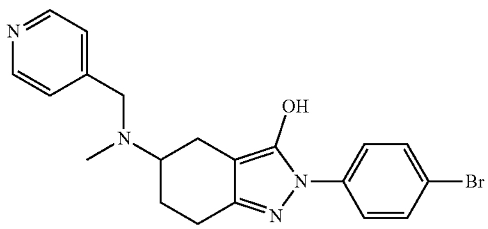 [SMILES: CN(Cc1ccncc1)C1CCc2nn(-c3ccc(Br)cc3)c(O)c2C1] | 413.1 | 2-(4-Bromophenyl)-5-[methyl(pyridin-4-ylmethyl)amino]-4,5,6,7,-tetrahydro-2H-indazol-3-ol |
| 53 | 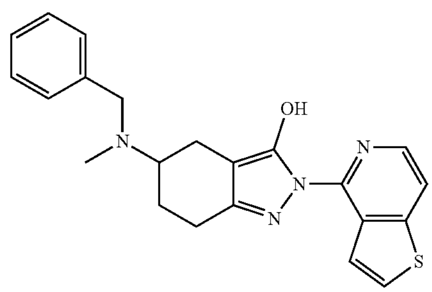 [SMILES: CN(Cc1ccccc1)C1CCc2nn(-c3nccc4sccc34)c(O)c2C1] | 391.2 | 5-(Benzylmethylamino)-2-(thieno[3,2-c]pyridin-4-yl)-4,5,6,7-tetrahydro-2H-indazol-3-ol |
| 54 | 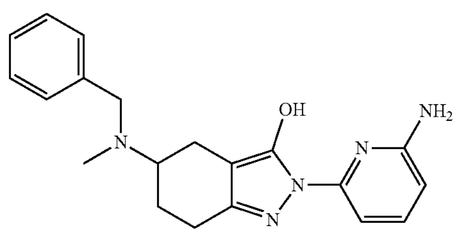 [SMILES: CN(Cc1ccccc1)C1CCc2nn(-c3cccc(N)n3)c(O)c2C1] | 350.2 | 2-(6-Aminopyridin-2-yl)-5-(benzylmethylamino)-4,5,6,7-tetrahydro-2H-indazol-3-ol |
| 55 | 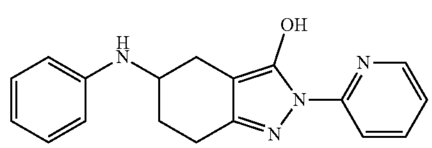 [SMILES: Oc1c2c(nn1-c1ccccn1)CCC(Nc1ccccc1)C2] | 307.2 | 5-Phenylamino-2-(pyridin-2-yl)-4,5,6,7-tetrahydro-2H-indazol-3-ol |
| 56 | 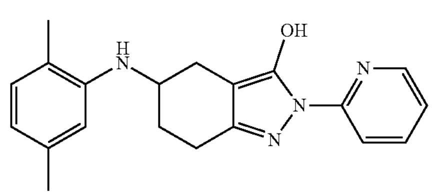 [SMILES: Cc1ccc(C)c(NC2CCc3nn(-c4ccccn4)c(O)c3C2)c1] | 335.2 | 5-[(2,5-Dimethylphenyl)amino]-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 57 | 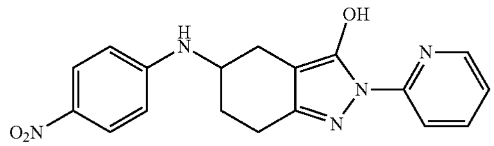 [SMILES: O=[N+]([O-])c1ccc(NC2CCc3nn(-c4ccccn4)c(O)c3C2)cc1] | 352.1 | 5-[(4-Nitrophenyl)amino]-2-(pyridin-2-yl)-4,5,6,7-tetrahydro-2H-indazol-3-ol |
| 58 | 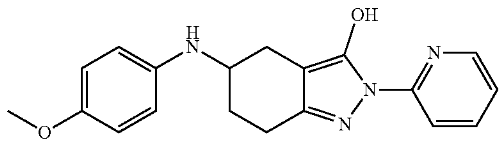 [SMILES: COc1ccc(NC2CCc3nn(-c4ccccn4)c(O)c3C2)cc1] | 337.2 | 5-[(4-Methoxyphenyl)amino]-2-(pyridin-2-yl)-4,5,6,7-tetrahydro-2H-indazol-3-ol |
| 59 | 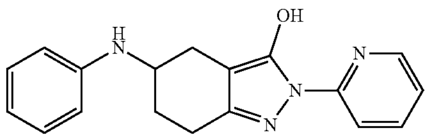 [SMILES: Oc1c2c(nn1-c1ccccn1)CCC(Nc1ccccc1)C2] | 307.2 | 5--(Phenylamino)-2-(pyridin-2-yl)-4,5,6,7-tetrahydro-2H-indazol-3-ol |
| 60 | 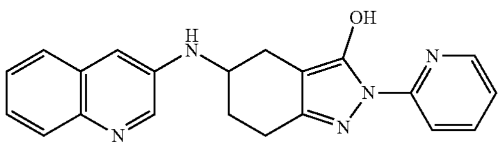 [SMILES: Oc1c2c(nn1-c1ccccn1)CCC(Nc1cnc3ccccc3c1)C2] | 358.2 | 2-(Pyridin-2-yl)-5-(quinolin-3-ylamino)-4,5,6,7-tetrahydro-2H-indazol-3-ol |
| 61 | 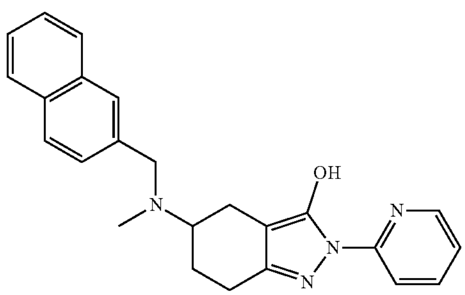 [SMILES: CN(Cc1ccc2ccccc2c1)C1CCc2nn(-c3ccccn3)c(O)c2C1] | 385.2 | 5-[Methyl(naphathalen-2-ylmethyl)amino]-2-(pyridin-2-yl)-4,5,6,7-tetrahydro-2H-indazol-3-ol |
| 62 | 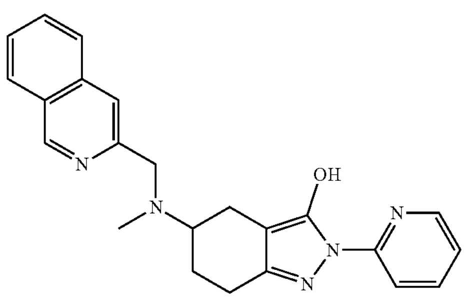 [SMILES: CN(Cc1cc2ccccc2cn1)C1CCc2nn(-c3ccccn3)c(O)c2C1] | 386.2 | 5-[(Isoquinolin-3-ylmethyl)methylamino]-2-(pyridin-2-yl)-4,5,6,7-tetrahydro-2H-indazol-3-ol |
| 63 | 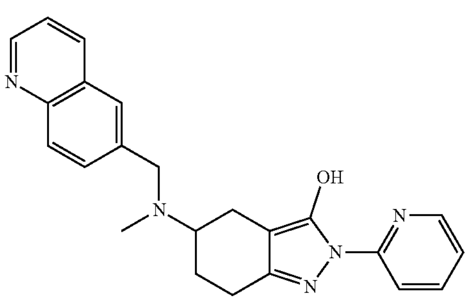 [SMILES: CN(Cc1ccc2ncccc2c1)C1CCc2nn(-c3ccccn3)c(O)c2C1] | 386.2 | 5-[Methyl(quinolin-6-ylmethyl)amino]-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 64 | 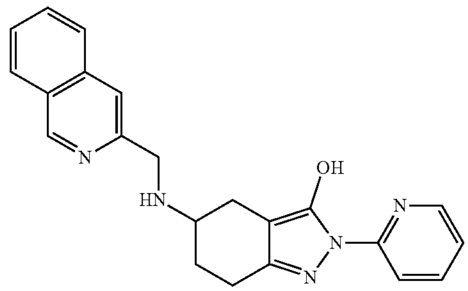 [SMILES: Oc1c2c(nn1-c1ccccn1)CCC(NCc1cc3ccccc3cn1)C2] | 372.2 | 5-[(Isoquinolin-3-ylmethyl)amino]-2-(pyridin-2-yl)-4,5,6,7-tetrahydro-2H-indazol-3-ol |
| 65 | 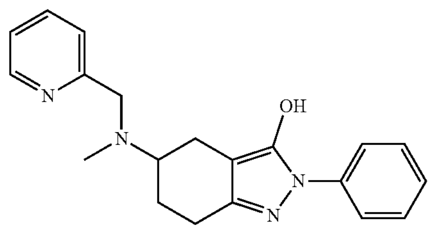 [SMILES: CN(Cc1ccccn1)C1CCc2nn(-c3ccccc3)c(O)c2C1] | 335.2 | 5-[Methyl(pyridin-2-ylmethyl)amino-2-phenyl-4,5,6,7-tetrahydro-2H-indazol-3-ol |
| 66 | 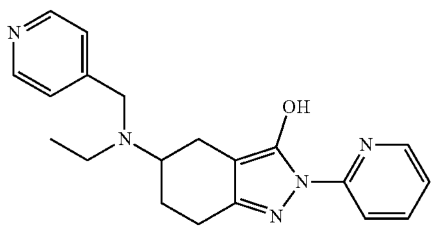 [SMILES: CCN(Cc1ccncc1)C1CCc2nn(-c3ccccn3)c(O)c2C1] | 350.2 | 5-[Ethyl(pyridin-4-ylmethyl)amino]-2-(pyridin-2-yl)-4,5,6,7-tetrahydro-2H-indazol-3-ol |
| 67 | 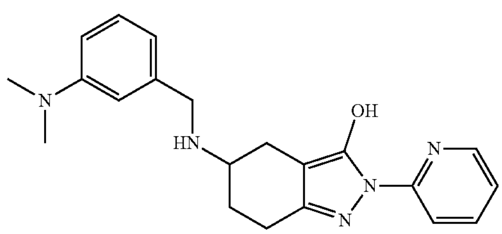 [SMILES: CN(C)c1cccc(CNC2CCc3nn(-c4ccccn4)c(O)c3C2)c1] | 364.2 | 5-[(3-Dimethylaminobenzyl)amino]-2-(pyridin-2-yl)-4,5,6,7-tetrahydro-2H-indazol-3-ol |
| 68 | 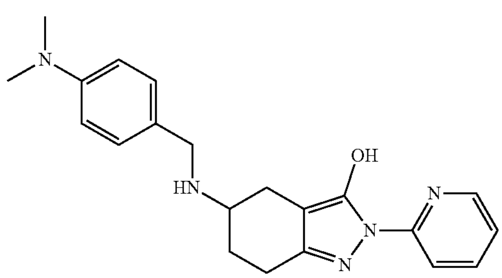 [SMILES: CN(C)c1ccc(CNC2CCc3nn(-c4ccccn4)c(O)c3C2)cc1] | 364.2 | 5-[(4-Dimethylaminobenzyl)amino]-2-(pyridin-2-yl)-4,5,6,7-tetrahydro-2H-indazol-2-ol |
| 69 | 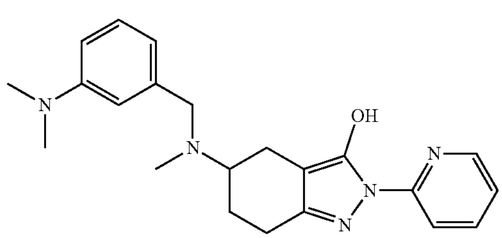 [SMILES: CN(C)c1cccc(CN(C)C2CCc3nn(-c4ccccn4)c(O)c3C2)c1] | 378.2 | 5-[(3-Dimethylaminobenzyl)methylamino)]-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 70 | 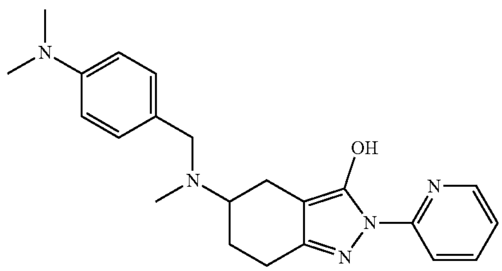 [SMILES: CN(C)c1ccc(CN(C)C2CCc3nn(-c4ccccn4)c(O)c3C2)cc1] | 378.3 | 5-[(4-Dimethylamino)benzylmethylamino]-2-(pyridin-2-yl)-4,5,6,7-tetrahydro-2H-indazol-3-ol |
| 71 | 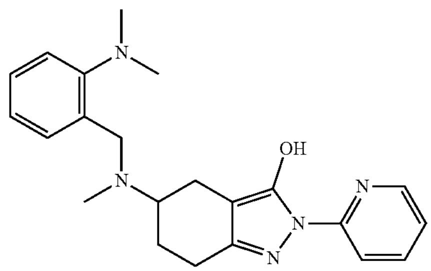 [SMILES: CN(C)c1ccccc1CN(C)C1CCc2nn(-c3ccccn3)c(O)c2C1] | 378.3 | 5-[(2-Dimethylamino)benzylmethylamino]-2-(pyridin-2-yl)-4,5,6,7-tetrahydro-2H-indazol-3-ol |
| 72 | 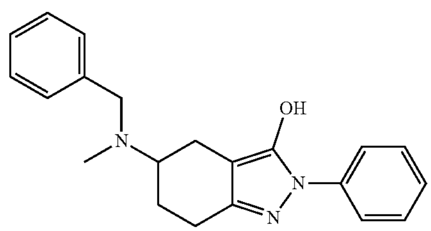 [SMILES: CN(Cc1ccccc1)C1CCc2nn(-c3ccccc3)c(O)c2C1] | 334.2 | 5-(Benzylmethylamino)-2-phenyl-4,5,6,7-tetrahydro-2H-indazol-3-ol |
| 73 | 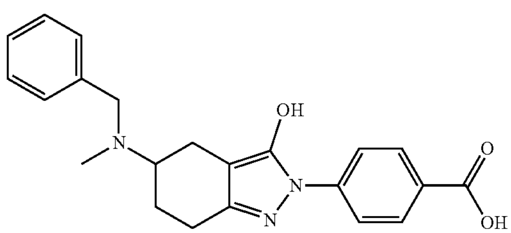 [SMILES: CN(Cc1ccccc1)C1CCc2nn(-c3ccc(C(=O)O)cc3)c(O)c2C1] | 378.2 | 4-[(5-Benzylmethylamino)-3-hydroxy-4,5,6,7-tetrahydro-2H-indazol-2-yl]benzoic acid |
| 74 | 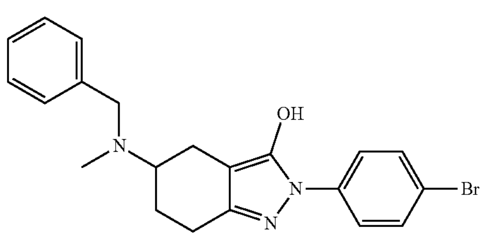 [SMILES: CN(Cc1ccccc1)C1CCc2nn(-c3ccc(Br)cc3)c(O)c2C1] | 412.1 | 5-(Benzylmethylamino)-2-(4-bromophenyl)-4,5,6,7-tetrahydro-2H-indazol-3-ol |
| 75 | 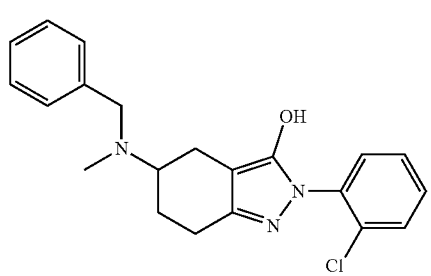 [SMILES: CN(Cc1ccccc1)C1CCc2nn(-c3ccccc3Cl)c(O)c2C1] | 368.2 | 5-(Benzylmethylamino)-2-(2-chlorophenyl)-4,5,6,7-tetrahydro-2H-indazol-3-ol |

TABLE 1-continued

| No. | Structure | MS (ESI+) | IUPAC name |
|---|---|---|---|
| 76 | 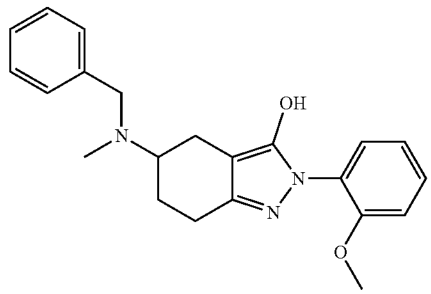 [SMILES: COc1ccccc1-n1nc2c(c1O)CC(N(C)Cc1ccccc1)CC2] | 364.2 | 5-(Benzylmethylamino)-2-(2-methoxyphenyl)-4,5,6,7-tetrahydro-2H-indazol-3-ol |
| 77 | 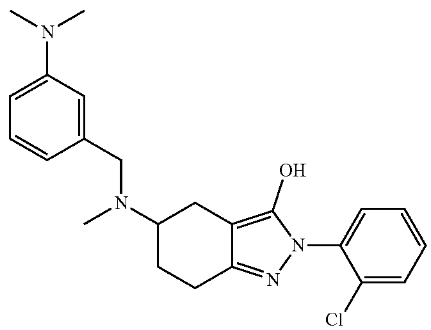 [SMILES: CN(C)c1cccc(CN(C)C2CCc3nn(-c4ccccc4Cl)c(O)c3C2)c1] | 411.2 | 2-(2-Chlorophenyl)-5-[(3-다이 methylaminobenzyl)methylamino]-4,5,6,7-tetrahydro-2H-indazol-3-ol |
| 78 | 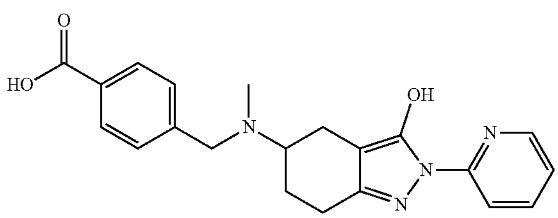 [SMILES: CN(Cc1ccc(C(=O)O)cc1)C1CCc2nn(-c3ccccn3)c(O)c2C1] | 379.2 | 4-(((3-Hydroxy-2-(pyridin-2-yl)-4,5,6,7-tetrahydro-2H-indazol-5-yl)(methyl)amino)methyl)bezoic acid |
| 79 | 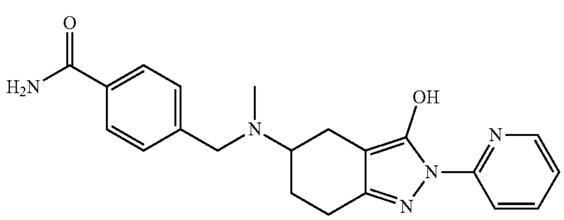 [SMILES: CN(Cc1ccc(C(N)=O)cc1)C1CCc2nn(-c3ccccn3)c(O)c2C1] | 378.2 | 4-(((3-Hydroxy-2-(pyridin-2-yl)-4,5,6,7-tetrahydro-2H-indazol-5-yl)(methyl)amino)methyl)benzamide |
| 80 | 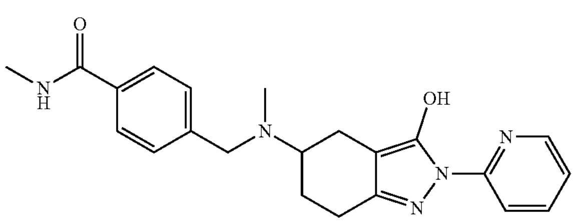 [SMILES: CN(C)C(=O)c1ccc(CN(C)C2CCc3nn(-c4ccccn4)c(O)c3C2)cc1] | 392.2 | 4-(((3-Hydroxy-2-(pyridin-2-yl)-4,5,6,7-tetrahydro-2H-indazol-5-yl)(methyl)amino)methyl)-N-methylbenzamide |
| 81 | 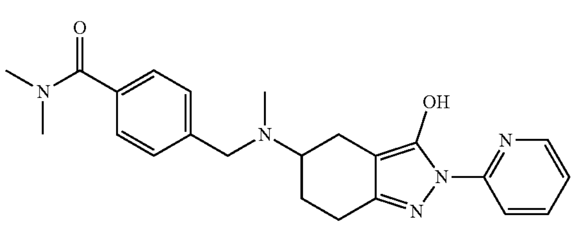 | 406.2 | 4-(((3-Hydroxy-2-(pyridin-2-yl)-4,5,6,7-tetrahydro-2H-indazol-5-yl)(methyl)amino)methyl)-N,N-dimethylbenzamide |

TABLE 1-continued

| No. | Structure | MS (ESI+) | IUPAC name |
|---|---|---|---|
| 82 | 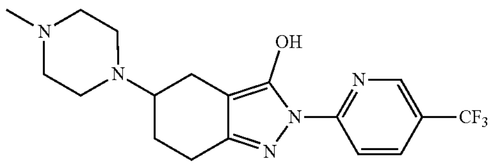 [SMILES: CN1CCN(C2CCc3nn(-c4ccc(C(F)(F)F)cn4)c(O)c3C2)CC1] | 382.3 | 5-(4-Methylpiperazin-1-yl)-2-(5-(trifluoromethyl)pyridin-2-yl)-4,5,6,7-tetrahydro-2H-indazol-3-ol |
| 83 | 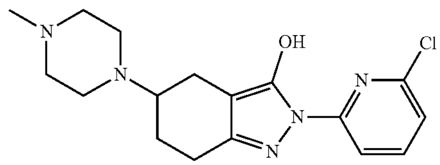 [SMILES: CN1CCN(C2CCc3nn(-c4cccc(Cl)n4)c(O)c3C2)CC1] | 348.2 | 2-(6-Chloropyridin-2-yl)-5-(4-methylpiperazin-1-yl)-4,5,6,7-tetrahydro-2H-indazol-3-ol |
| 84 | 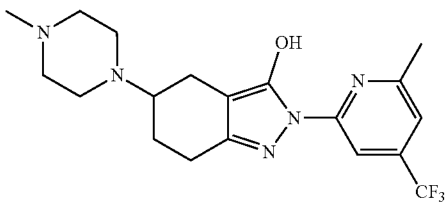 [SMILES: Cc1cc(C(F)(F)F)cc(-n2nc3c(c2O)CC(N2CCN(C)CC2)CC3)n1] | 396.3 | 2-(6-Methyl-4-(trifluoromethyl)pyridin-2-yl)-5-(4-methylpiperazin-1-yl)-4,5,6,7-tetrahydro-2H-indazol-3-ol |
| 85 | 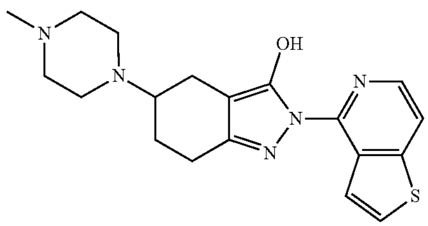 [SMILES: CN1CCN(C2CCc3nn(-c4nccc5sccc45)c(O)c3C2)CC1] | 370.2 | 5-(4-Methylpiperazin-1-yl)-2-(thieno[3,2-c]pyridin-4-yl)-4,5,6,7-tetrahydro-2H-indazol-3-ol |
| 86 | 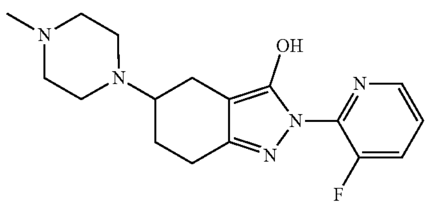 [SMILES: CN1CCN(C2CCc3nn(-c4ncccc4F)c(O)c3C2)CC1] | 332.3 | 2-(3-Fluoropyridin-2-yl)-5-(4-methylpiperazin-1-yl)-4,5,6,7-tetrahydro-2H-indazol-3-ol |
| 87 | 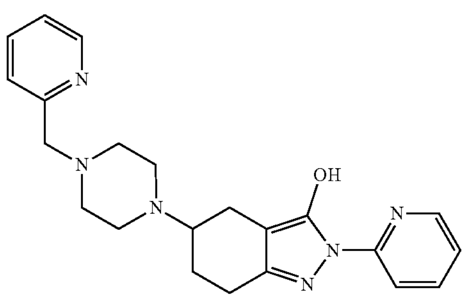 [SMILES: Oc1c2c(nn1-c1ccccn1)CCC(N1CCN(Cc3ccccn3)CC1)C2] | 391.3 | 2-(Pyridin-2-yl)-5-(4-(pyridin-2-ylmethyl)piperazin-1-yl)-4,5,6,7-tetrahydro-2H-indazol-3-ol |
| 88 | 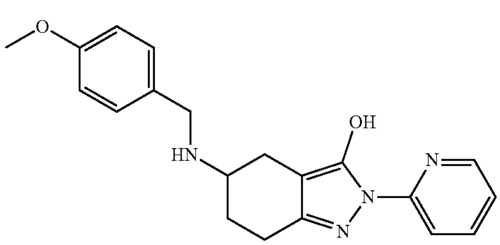 [SMILES: COc1ccc(CNC2CCc3nn(-c4ccccn4)c(O)c3C2)cc1] | 351.3 | 5-((4-Methoxybenzyl)amino)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 89 | 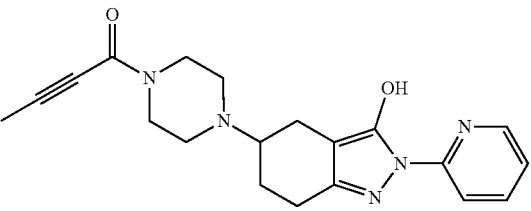 [SMILES: CC#CC(=O)N1CCN(C2CCc3nn(-c4ccccn4)c(O)c3C2)CC1] | 366.2 | 1-(4-(3-Hydroxy-2-(pyridin-2-yl)-4,5,6,7-tetrahydro-2H-indazol-5-yl)piperazin-1-yl)but-2-en-1-one |
| 90 | 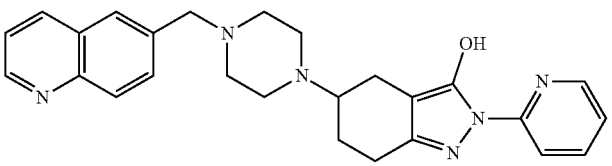 [SMILES: Oc1c2c(nn1-c1ccccn1)CCC(N1CCN(Cc3ccc4ncccc4c3)CC1)C2] | 441.4 | 2-(Pyridin-2-yl)-5-(4-(quinolin-6-ylmethyl)piperazin-1-yl)-4,5,6,7-tetrahydro-2H-indazol-3-ol |
| 91 | 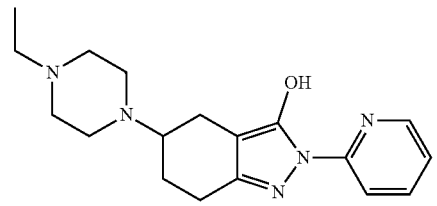 [SMILES: CCN1CCN(C2CCc3nn(-c4ccccn4)c(O)c3C2)CC1] | 328.4 | 5-(4-Ethylpiperazin-1-yl)-2-(pyridin-2-yl)-4,5,6,7-tetrahydro-2H-indazol-3-ol |
| 92 | 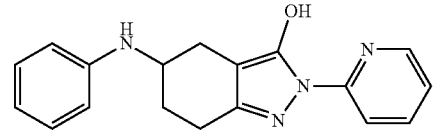 [SMILES: Oc1c2c(nn1-c1ccccn1)CCC(Nc1ccccc1)C2] | 307.3 | 5-(Phenylamino)-2-(pyridin-2-yl)-4,5,6,7-tetrahydro-2H-indazol-3-ol |
| 93 | 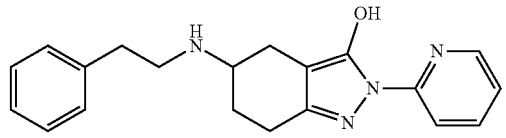 [SMILES: Oc1c2c(nn1-c1ccccn1)CCC(NCCc1ccccc1)C2] | 335.3 | 5-(Penethylamino)-2-(pyridin-2-yl)-4,5,6,7-tetrahydro-2H-indazol-3-ol |
| 94 | 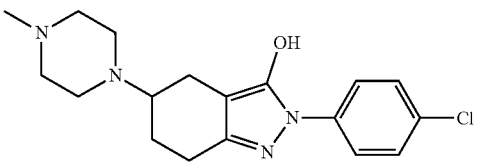 [SMILES: CN1CCN(C2CCc3nn(-c4ccc(Cl)cc4)c(O)c3C2)CC1] | 347.3 | 2-(4-Chlorophenyl)-5-(4-methylpiperazin-1-yl)-4,5,6,7-tetrahydro-2H-indazol-3-ol |
| 95 | 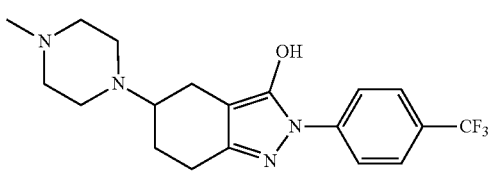 | 381.2 | 5-(4-Methylpiperazin-1-yl)-2-(4-(trifluoromethyl)phenyl)-4,5,6,7-tetrahydro-2H-indazol-3-ol |
| 96 | 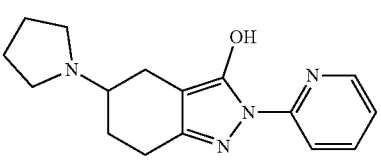 [SMILES: Oc1c2c(nn1-c1ccccn1)CCC(N1CCCC1)C2] | 285.4 | 2-(Pyridin-2-yl)-5-(pyrrolidin-1-yl)-4,5,6,7-tetrahydro-2H-indazol-3-ol |

TABLE 1-continued

| No. | Structure | MS (ESI+) | IUPAC name |
|---|---|---|---|
| 97 | 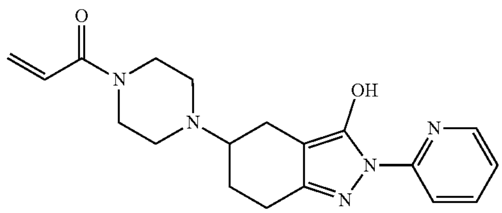 [SMILES: C=CC(=O)N1CCN(C2CCc3nn(-c4ccccn4)c(O)c3C2)CC1] | 354.3 | 1-(4-(3-Hydroxy-2-(pyridin-2-yl)-4,5,6,7-tetrahydro-2H-indazol-5-yl)piperazin-1-yl)prop-2-en-1-one |
| 98 | 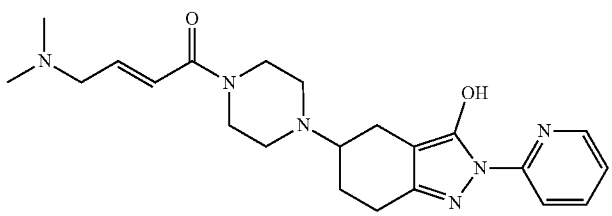 [SMILES: CN(C)C/C=C/C(=O)N1CCN(C2CCc3nn(-c4ccccn4)c(O)c3C2)CC1] | 411.3 | (E)-4-(dimethylamino)-1-(4-(3-hydroxy-2-(pyridin-2-yl)-4,5,6,7-tetrahydro-2H-indazol-5-yl)piperazin-1-yl)but-2-en-1-one |
| 99 | 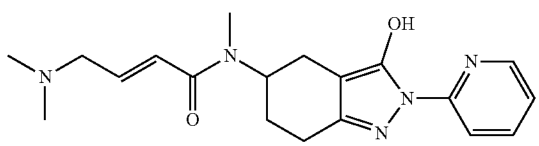 [SMILES: CN(C)C/C=C/C(=O)N(C)C1CCc2nn(-c3ccccn3)c(O)c2C1] | 356.2 | (E)-4-(dimethylamino)-N-(3-hydroxy-2-(pyridin-2-yl)-4,5,6,7-tetrahydro-2H-indazol-5-yl)-N-methylbut-2-enamide |
| 100 | 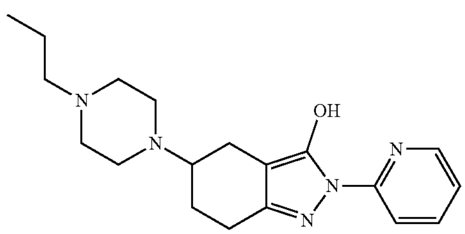 [SMILES: CCCN1CCN(C2CCc3nn(-c4ccccn4)c(O)c3C2)CC1] | 342.4 | 5-(4-Propylpiperazin-1-yl)-2-(pyridin-2-yl)-4,5,6,7-tetrahydro-2H-indazol-3-ol |
| 101 | 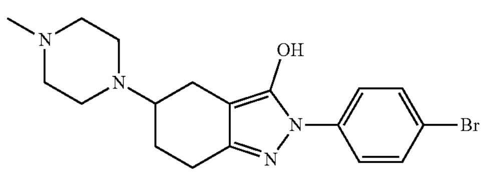 [SMILES: CN1CCN(C2CCc3nn(-c4ccc(Br)cc4)c(O)c3C2)CC1] | 391.2 | 2-(4-Bromophenyl)-5-(4-methylpiperazin-1-yl)-4,5,6,7-tetrahydro-2H-indazol-3-ol |
| 102 | 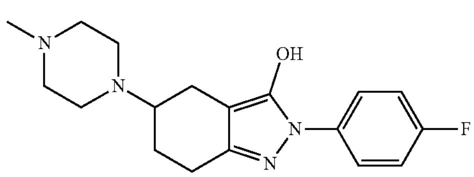 [SMILES: CN1CCN(C2CCc3nn(-c4ccc(F)cc4)c(O)c3C2)CC1] | 331.4 | 2-(4-Fluorophenyl)-5-(4-methylpiperazin-1-yl)-4,5,6,7-tetrahydro-2H-indazol-3-ol |
| 103 | 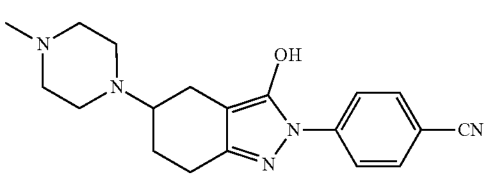 [SMILES: CN1CCN(C2CCc3nn(-c4ccc(C#N)cc4)c(O)c3C2)CC1] | 338.2 | 4-(3-Hydroxy-5-(4-methylpiperazin-1-yl)-4,5,6,7-tetrahydro-2H-indazol-2-yl)benzonitrile |

TABLE 1-continued

| No. | Structure | MS (ESI+) | IUPAC name |
|---|---|---|---|
| 104 | 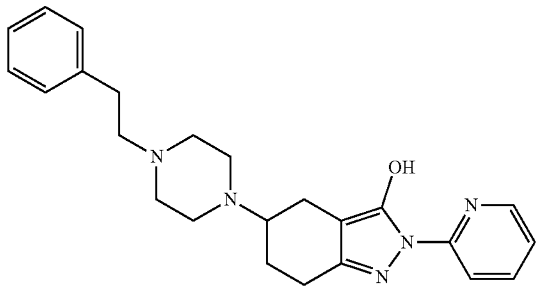 [SMILES: Oc1c2c(nn1-c1ccccn1)CCC(N1CCN(CCc3ccccc3)CC1)C2] | 404.3 | 5-(4-Penethylpiperazin-1-yl)-2-(pyridin-2-yl)-4,5,6,7-tetrahydro-2H-indazol-3-ol |
| 105 | 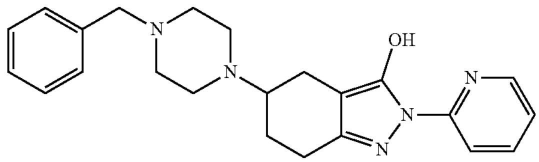 [SMILES: Oc1c2c(nn1-c1ccccn1)CCC(N1CCN(Cc3ccccc3)CC1)C2] | 390.3 | 5-(4-Benzylpiperazin-1-yl)-2-(pyridin-2-yl)-4,5,6,7-tetrahydro-2H-indazol-3-ol |
| 106 | 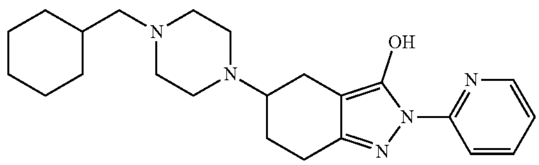 [SMILES: Oc1c2c(nn1-c1ccccn1)CCC(N1CCN(CC3CCCCC3)CC1)C2] | 396.3 | 5-(4-(Cyclohexylmethyl)piperazin-1-yl)-2-(pyridin-2-yl)-4,5,6,7-tetrahydro-2H-indazol-3-ol |
| 107 | 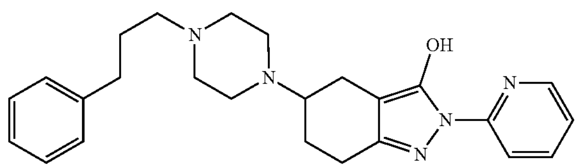 [SMILES: Oc1c2c(nn1-c1ccccn1)CCC(N1CCN(CCCc3ccccc3)CC1)C2] | 418.3 | 5-(4-(3-Phenylpropyl)piperazin-1-yl)-2-(pyridin-2-yl)-4,5,6,7-tetrahydro-2H-indazol-3-ol |
| 108 | 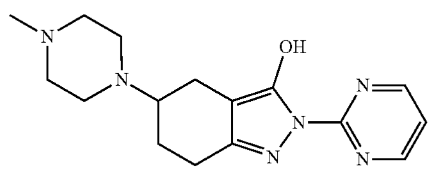 [SMILES: CN1CCN(C2CCc3nn(-c4ncccn4)c(O)c3C2)CC1] | 315.3 | 5-(4-Methylpiperazin-1-yl)-2-(pyrimidin-2-yl)-4,5,6,7-tetrahydro-2H-indazol-3-ol |
| 109 | 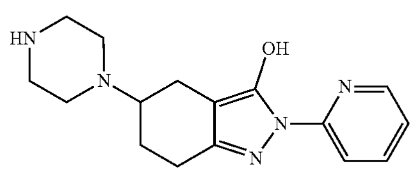 [SMILES: Oc1c2c(nn1-c1ccccn1)CCC(N1CCNCC1)C2] | 300.2 | 5-(Piperazin-1-yl)-2-(pyridin-2-yl)-4,5,6,7-tetrahydro-2H-indazol-3-ol |
| 110 | 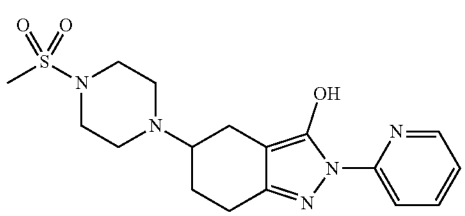 [SMILES: CS(=O)(=O)N1CCN(C2CCc3nn(-c4ccccn4)c(O)c3C2)CC1] | 378.2 | 5-(4-(Methylsulfonyl)piperazin-1-yl)-2-(pyridin-2-yl)-4,5,6,7-tetrahydro-2H-indazol-3-ol |
| 111 | 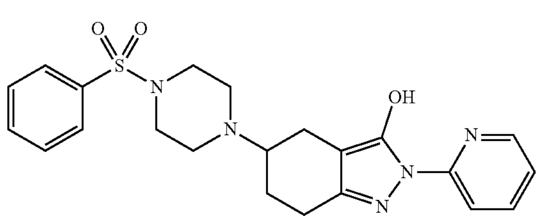 [SMILES: O=S(=O)(c1ccccc1)N1CCN(C2CCc3nn(-c4ccccn4)c(O)c3C2)CC1] | 440.2 | 5-(4-(Phenylsulfonyl)piperazin-1-yl)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 112 | 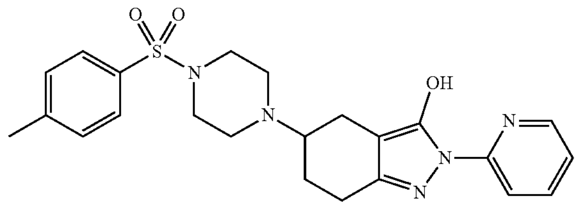 [SMILES: Cc1ccc(S(=O)(=O)N2CCN(C3CCc4nn(-c5ccccn5)c(O)c4C3)CC2)cc1] | 454.2 | 2-(Pyridin-2-yl)-5-(4-tosylpiperazin-1-yl)-4,5,6,7-tetrahydro-2H-indazol-3-ol |
| 113 | 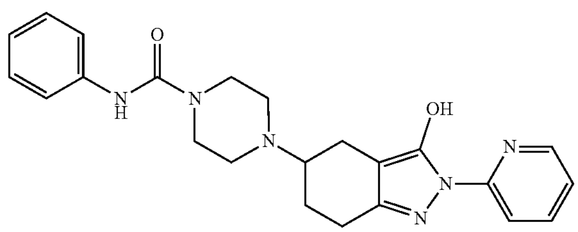 [SMILES: O=C(Nc1ccccc1)N1CCN(C2CCc3nn(-c4ccccn4)c(O)c3C2)CC1] | 419.2 | 4-(3-Hydroxy-2-(pyridin-2-yl)-4,5,6,7-tetrahydro-2H-indazol-5-yl)-N-phenylpiperazin-1-carboxamide |
| 114 | 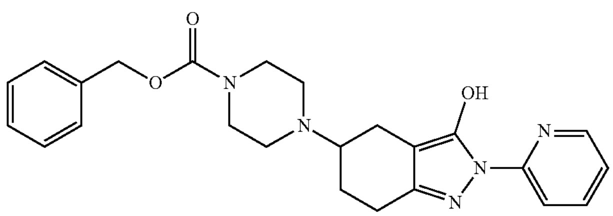 [SMILES: O=C(OCc1ccccc1)N1CCN(C2CCc3nn(-c4ccccn4)c(O)c3C2)CC1] | 434.2 | Benzyl 4-(3-hydroxy-2-(pyridin-2-yl)-4,5,6,7-tetrahydro-2H-indazol-5-yl)piperazin-1-carboxylate |
| 115 | 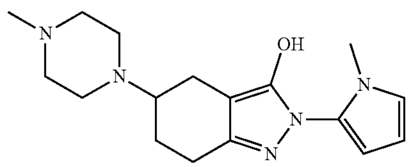 [SMILES: CN1CCN(C2CCc3nn(-c4cccn4C)c(O)c3C2)CC1] | 316.2 | 2-(1-Methyl-1H-pyrrol-2-yl)-5-(4-methylpiperazin-1-yl)-4,5,6,7-tetrahydro-2H-indazol-3-ol |
| 116 | 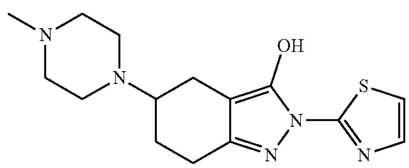 [SMILES: CN1CCN(C2CCc3nn(-c4ncco4)c(O)c3C2)CC1] | 320.2 | 5-(4-Methylpiperazin-1-yl)-2-(thiazol-2-yl)-4,5,6,7-tetrahydro-2H-indazol-3-ol |
| 117 | 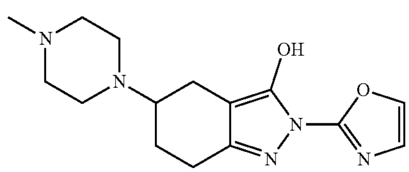 | 304.2 | 5-(4-Methylpiperazin-1-yl)-2-(oxazol-2-yl)-4,5,6,7-tetrahydro-2H-indazol-3-ol |
| 118 | 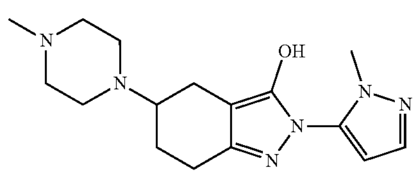 [SMILES: CN1CCN(C2CCc3nn(-c4ccnn4C)c(O)c3C2)CC1] | 317.2 | 2-(1-Methyl-1H-pyrazol-5-yl)-5-(4-methylpiperazin-1-yl)-4,5,6,7-tetrahydro-2H-indazol-3-ol |
| 119 | 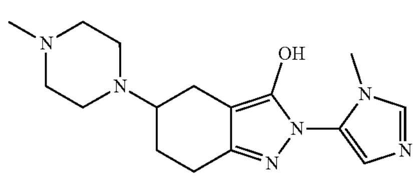 [SMILES: CN1CCN(C2CCc3nn(-c4cncn4C)c(O)c3C2)CC1] | 317.2 | 2-(1-Methyl-1H-imidazol-5-yl)-5-(4-methylpiperazin-1-yl)-4,5,6,7-tetrahydro-2H-indazol-3-ol |

TABLE 1-continued

| No. | Structure | MS (ESI+) | IUPAC name |
|---|---|---|---|
| 120 | 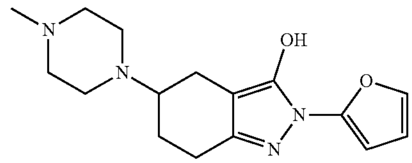 [SMILES: CN1CCN(C2CCc3nn(-c4ccco4)c(O)c3C2)CC1] | 303.2 | 2-(1-Methyl-1H-imidazol-5-yl)-5-(4-methylpiperazin-1-yl)-4,5,6,7-tetrahydro-2H-indazol-3-ol |
| 121 | 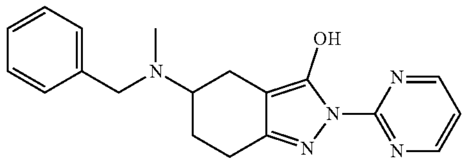 [SMILES: CN(Cc1ccccc1)C1CCc2nn(-c3ncccn3)c(O)c2C1] | 336.2 | 5-(Benzyl(methyl)amino)-2-(pyrimidin-2-yl)-4,5,6,7-tetrahydro-2H-indazol-3-ol |
| 122 | 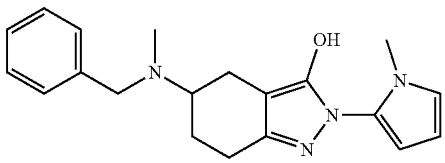 [SMILES: CN(Cc1ccccc1)C1CCc2nn(-c3cccn3C)c(O)c2C1] | 337.2 | 5-(Benzyl(methyl)amino)-2-(1-methyl-1H-pyrrol-2-yl)-4,5,6,7-tetrahydro-2H-indazol-3-ol |
| 123 | 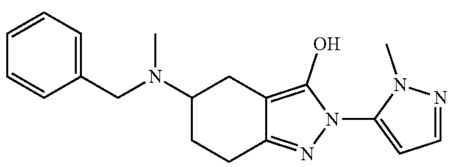 [SMILES: CN(Cc1ccccc1)C1CCc2nn(-c3ccnn3C)c(O)c2C1] | 338.2 | 5-(Benzyl(methyl)amino)-2-(1-methyl-1H-pyrazol-5-yl)-4,5,6,7-tetrahydro-2H-indazol-3-ol |
| 124 | 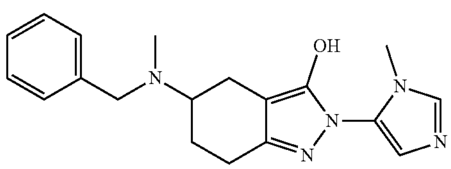 [SMILES: CN(Cc1ccccc1)C1CCc2nn(-c3cncn3C)c(O)c2C1] | 338.2 | 5-(Benzyl(methyl)amino)-2-(1-methyl-1H-imidazol-5-yl)-4,5,6,7-tetrahydro-2H-indazol-3-ol |
| 125 | 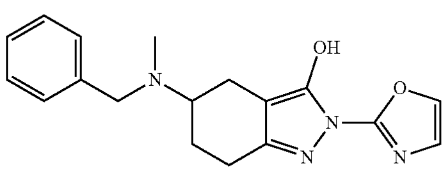 [SMILES: CN(Cc1ccccc1)C1CCc2nn(-c3ncco3)c(O)c2C1] | 325.2 | 5-(Benzyl(methyl)amino)-2-(oxazol-2-yl)-4,5,6,7-tetrahydro-2H-indazol-3-ol |
| 126 | 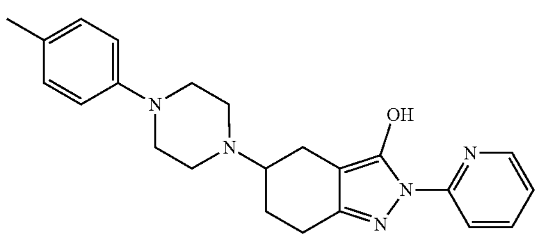 [SMILES: Cc1ccc(N2CCN(C3CCc4nn(-c5ccccn5)c(O)c4C3)CC2)cc1] | 390.3 | 2-(Pyridin-2-yl)-5-(4-(p-tolyl)piperazin-1-yl)-4,5,6,7-tetrahydro-2H-indazol-3-ol |
| 127 | 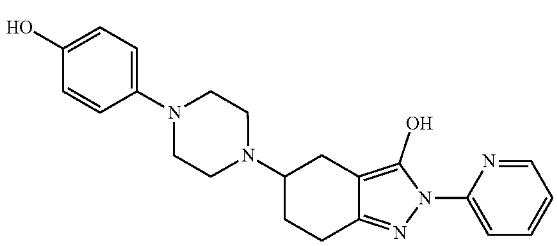 [SMILES: Oc1ccc(N2CCN(C3CCc4nn(-c5ccccn5)c(O)c4C3)CC2)cc1] | 392.2 | 5-(4-(4-Hydroxyphenyl)piperazin-1-yl)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 128 | 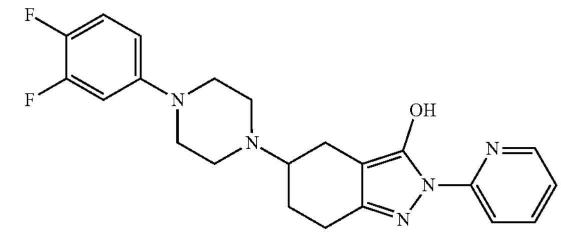 [SMILES: Oc1c2c(nn1-c1ccccn1)CCC(N1CCN(c3ccc(F)c(F)c3)CC1)C2] | 412.2 | 5-(4-(3,4-Difluorophenyl)piperazin-1-yl)-2-(pyridin-2-yl)-4,5,6,7-tetrahydro-2H-indazol-3-ol |
| 129 | 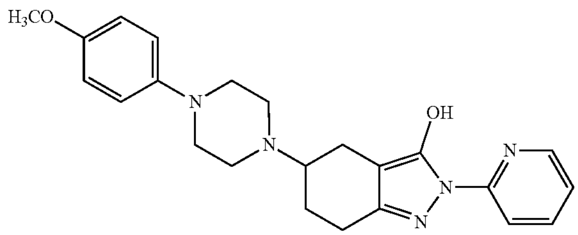 [SMILES: COc1ccc(N2CCN(C3CCc4nn(-c5ccccn5)c(O)c4C3)CC2)cc1] | 406.3 | 5-(4-(4-Methoxyphenyl)piperazin-1-yl)-2-(pyridin-2-yl)-4,5,6,7-tetrahydro-2H-indazol-3-ol |
| 130 | 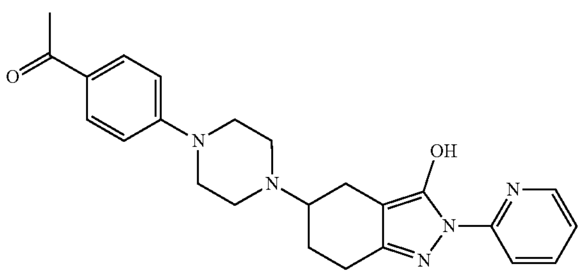 [SMILES: CC(=O)c1ccc(N2CCN(C3CCc4nn(-c5ccccn5)c(O)c4C3)CC2)cc1] | 418.3 | 1-(4-(4-(3-Hydroxy-2-(pyridin-2-yl)-4,5,6,7-tetrahydro-2H-indazol-5-yl)piperazin-1-yl)phenyl)ethan-1-one |
| 131 | 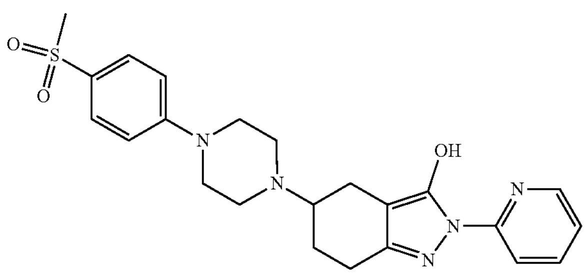 [SMILES: CS(=O)(=O)c1ccc(N2CCN(C3CCc4nn(-c5ccccn5)c(O)c4C3)CC2)cc1] | 454.2 | 5-(4-(4-(Methylsulfonyl)phenyl)piperazin-1-yl)-2-(pyridin-2-yl)-4,5,6,7-tetrahydro-2H-indazol-3-ol |
| 132 | 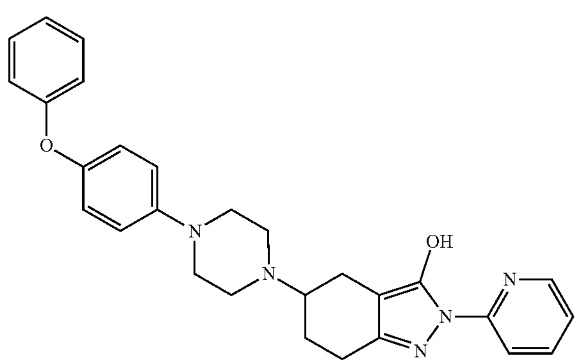 [SMILES: Oc1c2c(nn1-c1ccccn1)CCC(N1CCN(c3ccc(Oc4ccccc4)cc3)CC1)C2] | 468.2 | 5-(4-(4-Phenoxyphenyl)piperazin-1-yl)-2-(pyridin-2-yl)-4,5,6,7-tetrahydro-2H-indazol-3-ol |
| 133 | 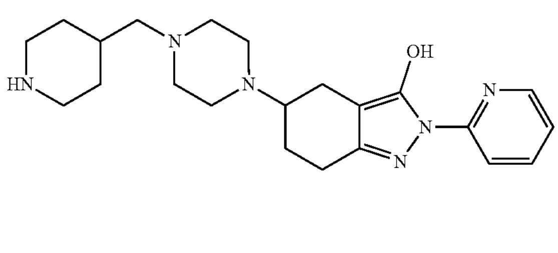 [SMILES: Oc1c2c(nn1-c1ccccn1)CCC(N1CCN(CC3CCNCC3)CC1)C2] | 397.3 | 5-(4-(Piperidin-4-ylmethyl)piperazin-1-yl)-2-(pyridin-2-yl)-4,5,6,7-tetrahydro-2H-indazol-3-ol |

TABLE 1-continued

| No. | Structure | MS (ESI+) | IUPAC name |
|---|---|---|---|
| 134 | 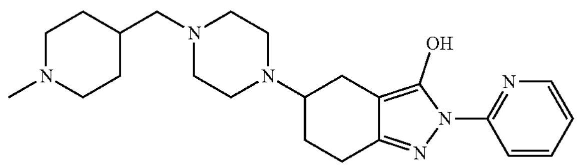 [SMILES: CN1CCC(CN2CCN(C3CCc4nn(-c5ccccn5)c(O)c4C3)CC2)CC1] | 411.3 | 5-(4-((1-Methylpiperidin-4-yl)methyl)piperazin-1-yl)-2-(pyridin-2-yl)-4,5,6,7-tetrahydro-2H-indazol-3-ol |
| 135 | 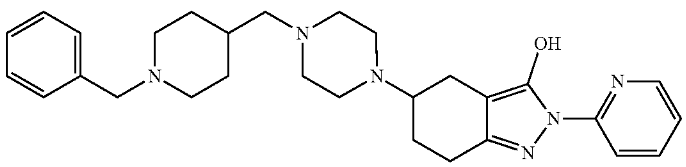 [SMILES: Oc1c2c(nn1-c1ccccn1)CCC(N1CCN(CC3CCN(Cc4ccccc4)CC3)CC1)C2] | 487.4 | 5-(4-((1-Benzylpiperidin-4-yl)methyl)piperazin-1-yl)-2-(pyridin-2-yl)-4,5,6,7-tetrahydro-2H-indazol-3-ol |
| 136 | 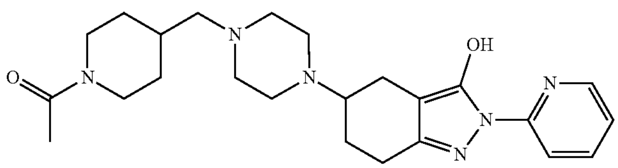 [SMILES: CC(=O)N1CCC(CN2CCN(C3CCc4nn(-c5ccccn5)c(O)c4C3)CC2)CC1] | 439.3 | 1-(4-((4-(3-Hydroxy-2-(pyridin-2-yl)-4,5,6,7-tetrahydro-2H-indazol-5-yl)piperazin-1-yl)methyl)piperidin-1-yl)ethan-1-one |
| 137 | 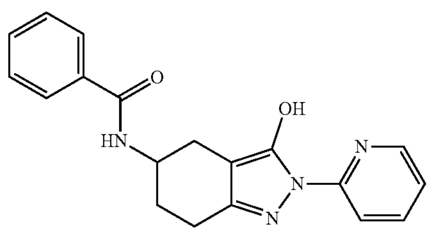 [SMILES: O=C(NC1CCc2nn(-c3ccccn3)c(O)c2C1)c1ccccc1] | 335.1 | N-(3-Hydroxy-2-(pyridin-2-yl)-4,5,6,7-tetrahydro-2H-indazol-5-yl)benzamide |
| 138 | 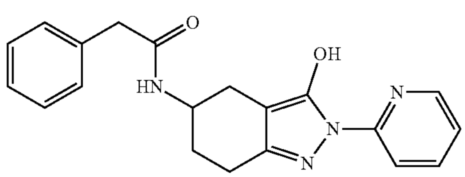 [SMILES: O=C(Cc1ccccc1)NC1CCc2nn(-c3ccccn3)c(O)c2C1] | 349.2 | N-(3-Hydroxy-2-(pyridin-2-yl)-4,5,6,7-tetrahydro-2H-indazol-5-yl)-2-phenylacetamide |
| 139 | 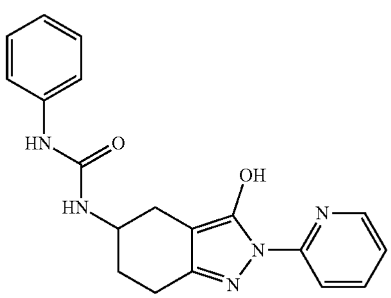 [SMILES: O=C(Nc1ccccc1)NC1CCc2nn(-c3ccccn3)c(O)c2C1] | 350.2 | 1-(3-Hydroxy-2-(pyridin-2-yl)-4,5,6,7-tetrahydro-2H-indazol-5-yl)-3-phenylurea |
| 140 | 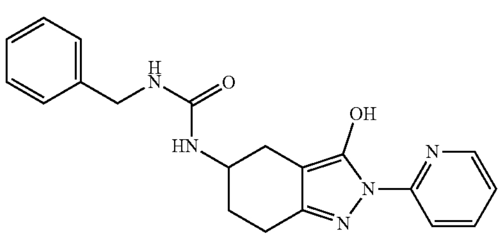 [SMILES: O=C(NCc1ccccc1)NC1CCc2nn(-c3ccccn3)c(O)c2C1] | 364.2 | 1-Benzyl-3-(3-hydroxy-2-(pyridin-2-yl)-4,5,6,7-tetrahydro-2H-indazol-5-yl)urea |

TABLE 1-continued

| No. | Structure | MS (ESI+) | IUPAC name |
|---|---|---|---|
| 141 | 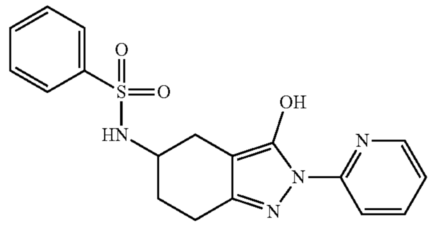 [SMILES: O=S(=O)(NC1CCc2nn(-c3ccccn3)c(O)c2C1)c1ccccc1] | 371.1 | N-(3-hydroxy-2-(pyridin-2-yl)-4,5,6,7-tetrahydro-2H-indazol-5-yl)benzenesulfonamide |
| 142 | 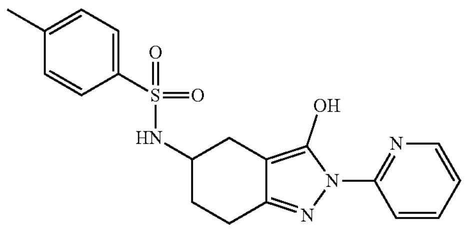 [SMILES: Cc1ccc(S(=O)(=O)NC2CCc3nn(-c4ccccn4)c(O)c3C2)cc1] | 385.1 | N-(3-hydroxy-2-(pyridin-2-yl)-4,5,6,7-tetrahydro-2H-indazol-5-yl)-4-methylbenzenesulfonamide |
| 143 | 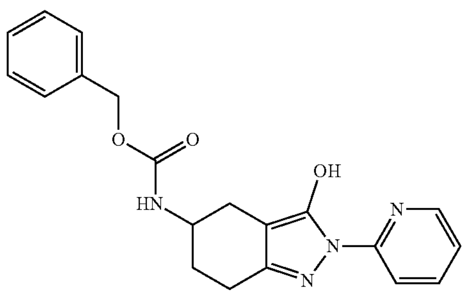 [SMILES: O=C(NC1CCc2nn(-c3ccccn3)c(O)c2C1)OCc1ccccc1] | 365.2 | Benzyl (3-hydroxy-2-(pyridin-2-yl)-4,5,6,7-tetrahydro-2H-indazol-5-yl)carbamate |
| 144 | 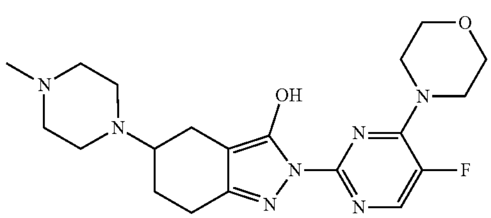 [SMILES: CN1CCN(C2CCc3nn(-c4ncc(F)c(N5CCOCC5)n4)c(O)c3C2)CC1] | 418.2 | 2-(5-Fluoro-4-morpholinopyrimidin-2-yl)-5-(4-methylpiperazin-1-yl)-4,5,6,7-tetrahydro-2H-indazol-3-ol |
| 145 | 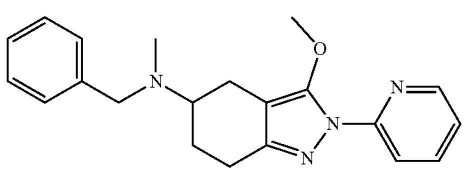 [SMILES: COc1c2c(nn1-c1ccccn1)CCC(N(C)Cc1ccccc1)C2] | 349.2 | N-benzyl-3-methoxy-N-methyl-2-(pyridin-2-yl)-4,5,6,7-tetrahydro-2H-indazol-5-amine |
| 146 | 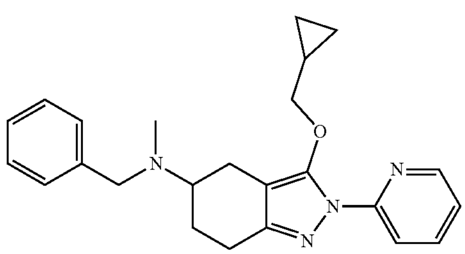 [SMILES: CN(Cc1ccccc1)C1CCc2nn(-c3ccccn3)c(OCC3CC3)c2C1] | 389.2 | N-benzyl-3-(cyclopropylmethoxy)-N-methyl-2-(pyridin-2-yl)-4,5,6,7-tetrahydro-2H-indazol-5-amine |

TABLE 1-continued

| No. | Structure | MS (ESI+) | IUPAC name |
|---|---|---|---|
| 147 | 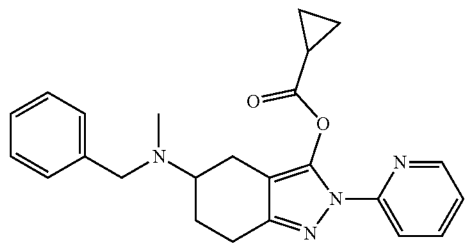 [SMILES: CN(Cc1ccccc1)C1CCc2nn(-c3ccccn3)c(OC(=O)C3CC3)c2C1] | 403.2 | 5-(Benzyl(methyl)amino)-2-(pyridin-2-yl)-4,5,6,7-tetrahydro-2H-indazol-3-ylcyclopropane carboxylate |
| 148 | 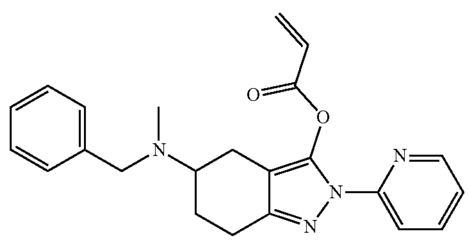 [SMILES: C=CC(=O)Oc1c2c(nn1-c1ccccn1)CCC(N(C)Cc1ccccc1)C2] | 389.2 | 5-(Benzyl(methyl)amino)-2-(pyridin-2-yl)-4,5,6,7-tetrahydro-2H-indazol-3-ylacrylate |
| 149 | 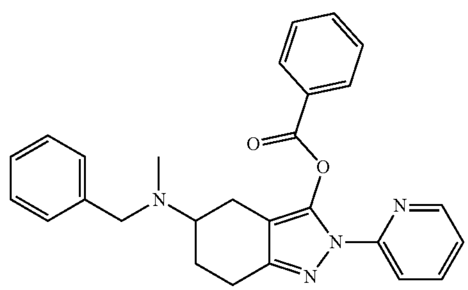 [SMILES: CN(Cc1ccccc1)C1CCc2nn(-c3ccccn3)c(OC(=O)c3ccccc3)c2C1] | 439.2 | 5-(Benzyl(methyl)amino)-2-(pyridin-2-yl)-4,5,6,7-tetrahydro-2H-indazol-3-ylbenzoate |
| 150 | 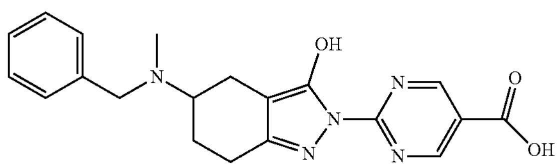 [SMILES: CN(Cc1ccccc1)C1CCc2nn(-c3ncc(C(=O)O)cn3)c(O)c2C1] | 380.2 | 2-(5-(Benzyl(methyl)amino)-3-hydroxy-4,5,6,7-tetrahydro-2H-indazol-2-yl)pyrimidin-5-carboxylic acid |
| 151 | 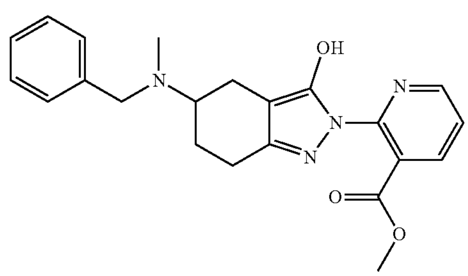 [SMILES: COC(=O)c1cccnc1-n1nc2c(c1O)CC(N(C)Cc1ccccc1)CC2] | 393.2 | Methyl 2-(5-(benzyl(methyl)amino)-3-hydroxy-4,5,6,7-tetrahydro-2H-indazol-2-yl)nicotinate |
| 152 | 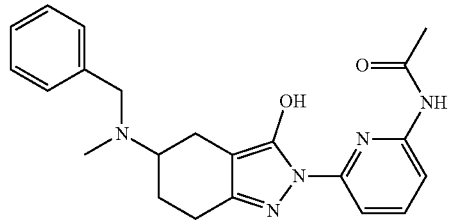 [SMILES: CC(=O)Nc1cccc(-n2nc3c(c2O)CC(N(C)Cc2ccccc2)CC3)n1] | 392.2 | N-(6-(5-(benzyl(methyl)amino)-3-hydroxy-4,5,6,7-tetrahydro-2H-indazol-2-yl)pyridin-2-yl)acetamide |

TABLE 1-continued

| No. | Structure | MS (ESI+) | IUPAC name |
|---|---|---|---|
| 153 | 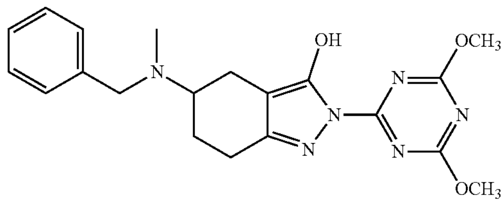 [SMILES: COc1nc(OC)nc(-n2nc3c(c2O)CC(N(C)Cc2ccccc2)CC3)n1] | 397.2 | 5-(Benzyl(methyl)amino)-2-(4,6-dimethoxy-1,3,5-triazin-2-yl)-4,5,6,7-tetrahydro-2H-indazol-3-ol |
| 154 | 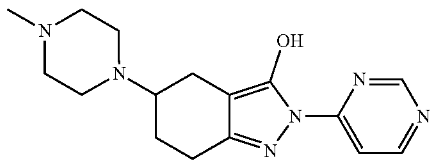 [SMILES: CN1CCN(C2CCc3nn(-c4ccncn4)c(O)c3C2)CC1] | 315.2 | 5-(4-Methylpiperazin-1-yl)-2-(pyrimidin-4-yl)-4,5,6,7-tetrahydro-2H-indazol-3-ol |
| 155 | 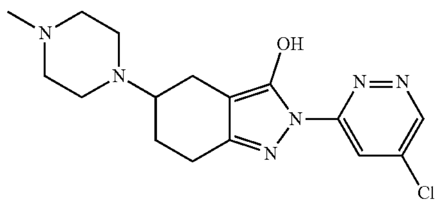 [SMILES: CN1CCN(C2CCc3nn(-c4cc(Cl)cnn4)c(O)c3C2)CC1] | 349.2 | 2-(5-Chloropyridazin-3-yl)-5-(4-methylpiperazin-1-yl)-4,5,6,7-tetrahydro-2H-indazol-3-ol |
| 156 | 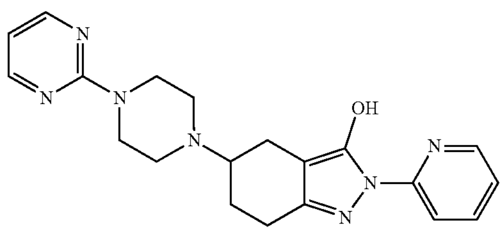 [SMILES: Oc1c2c(nn1-c1ccccn1)CCC(N1CCN(c3ncccn3)CC1)C2] | 378.2 | 2-(Pyridin-2-yl)-5-(4-(pyrimidin-2-yl)piperazin-1-yl)-4,5,6,7-tetrahydro-2H-indazol-3-ol |
| 157 | 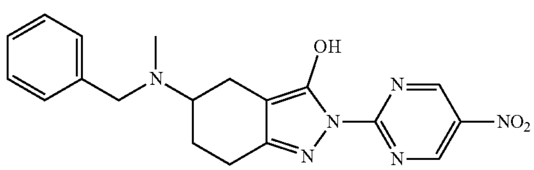 [SMILES: CN(Cc1ccccc1)C1CCc2nn(-c3ncc([N+](=O)[O-])cn3)c(O)c2C1] | 381.2 | 5-(Benzyl(methyl)amino)-2-(5-nitropyrimidin-2-yl)-4,5,6,7-tetrahydro-2H-indazol-3-ol |
| 158 | 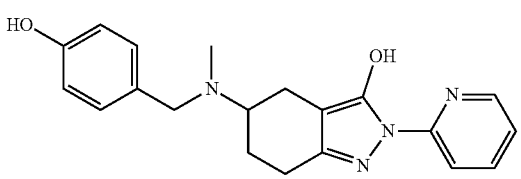 [SMILES: CN(Cc1ccc(O)cc1)C1CCc2nn(-c3ccccn3)c(O)c2C1] | 351.2 | 5-((4-Hydroxybenzyl)(methyl)amino)-2-(pyridin-2-yl)-4,5,6,7-tetrahydro-2H-indazol-3-ol |
| 159 | 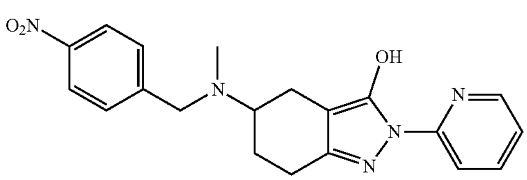 [SMILES: CN(Cc1ccc([N+](=O)[O-])cc1)C1CCc2nn(-c3ccccn3)c(O)c2C1] | 380.2 | 5-(Methyl(4-nitrobenzyl)amino)-2-(pyridin-2-yl)-4,5,6,7-tetrahydro-2H-indazol-3-ol |
| 160 | 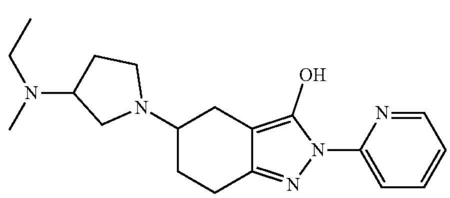 [SMILES: CCN(C)C1CCN(C2CCc3nn(-c4ccccn4)c(O)c3C2)C1] | 342.2 | 5-(3-(Ethyl(methyl)amino)pyrrolidin-1-yl)-2-(pyridin-2-yl)-4,5,6,7-tetrahydro-2H-indazol-3-ol; |

TABLE 1-continued

| No. | Structure | MS (ESI+) | IUPAC name |
|---|---|---|---|
| 161 | [structure] | 396.2 | 2,2,2-Trifluoro-N-(1-(3-hydroxy-2-(pyridin-2-yl)-4,5,6,7-tetrahydro-2H-indazol-5-yl)pyrrolidin-3-yl)acetamide |

<Example 1> Analysis of Change in ROS Production Induced by PMA Treatment, in HL-60 Cells Differentiated into Neutrophil Cells by DMSO Treatment In order to confirm the effect of the compounds of Synthetic examples on ROS production from fibroblasts and specific substrate cells, ROS production was induced by stimulation of PMA (phorbol 12-myristate 13-acetate), TGF-β1, palmitate or high concentration-glucose, or the like, in HL-60 cells differentiated into neutrophil cells by DMSO treatment, NHLF (normal human lung fibroblast, Lonza), LX-2 (human hepatic stellate cells, Sigma), ARPE19 (human retinal pigment epithelial cell, ATCC), and KEL-FIB (Keloid fibroblast, ATCC) cells, and under this condition, the inhibitory effect of ROS production of the compounds of Synthetic Examples was observed.

HL-60 cells (human leukemia cells, ATCC) were suspended in a medium containing 1.25% DMSO (RPMI+10% FBS) and cultured under the condition of 5% $CO_2$, 37° C. for 6 days, thereby inducing differentiation into neutrophil cells. The HL-60 cells differentiated into neutrophil cells were aliquoted at a concentration of $2 \times 10^4$ cells/well on a 96 well plate, and the compounds of Synthetic examples were treated into the cells at a concentration of 0.5 mM for 30 minutes. Then, to each well comprising the cells and drug, 200 nM PMA was treated to induce ROS production, and such ROS production was measured by observing the luminescence level of each well using 100 μM L-012.

The NHLF (normal human lung fibroblast, Lonza), LX-2 (human hepatic stellate cells, Sigma), ARPE19 (human retinal pigment epithelial cell, ATCC), KEL-FIB (keloid fibroblast, ATCC) cells were suspended in a culture medium containing 10% FBS and aliquoted on a 96 well plate and then cultured under the condition of 5% $CO_2$, 37° C. for 24 hours. After pre-treating the compounds of Synthetic examples at a concentration of 10, 20, 30, 40, 60 and 80 μM for 30 minutes to 1 hour, the ROS stimulus was treated to each well containing the cells and drug. After additional culturing for 48 hours, the ROS production level was confirmed using L-012 or DCF-DA.

As the result of the experiment, the compounds of Synthetic compounds inhibited ROS production by the ROS stimulus in all the NHLF, LX-2, ARPE19, KEL-FIB cells. Specifically, the result of Table 2 shows the result that ROS production induced by PMA is inhibited, when the compounds of Synthetic examples are treated by 0.5 uM in the HL-60 cells induced into neutrophils. FIG. 1 shows the result that ROS production induced by PMA is inhibited all, when Compound 1 and Compound 17 of Synthetic examples are treated into the LX-2 and NHLF cells.

Accordingly, it was confirmed that ROS production was effectively inhibited, when the compounds of Synthetic examples were treated to the differentiated HL-60 cells or various fibroblasts or specific substrate cells in which ROS production was induced.

TABLE 2

[ROS production inhibitory effect in differentiated HL-60 cells]

| Synthetic example compound number | ROS inhibition |
|---|---|
| 1 | **** |
| 2 | **** |
| 3 | **** |
| 4 | **** |
| 5 | **** |
| 6 | **** |
| 7 | **** |
| 8 | * |
| 9 | *** |
| 10 | ** |
| 11 | * |
| 12 | **** |
| 13 | **** |
| 14 | *** |
| 15 | **** |
| 16 | **** |
| 17 | **** |
| 18 | **** |
| 19 | **** |
| 20 | ** |
| 21 | ** |
| 22 | * |
| 23 | *** |
| 24 | ** |
| 25 | ** |
| 26 | * |
| 27 | ** |
| 28 | *** |
| 29 | ** |
| 32 | *** |
| 33 | *** |
| 34 | ** |
| 37 | ** |
| 38 | **** |
| 62 | **** |
| 63 | **** |
| 70 | ** |
| 71 | *** |
| 82 | *** |
| 83 | **** |
| 84 | *** |
| 85 | *** |
| 86 | ** |
| 87 | *** |
| 88 | *** |
| 89 | **** |
| 90 | **** |
| 91 | *** |
| 92 | ** |
| 93 | ** |
| 94 | **** |
| 95 | *** |

TABLE 2-continued

[ROS production inhibitory effect in differentiated HL-60 cells]

| Synthetic example compound number | ROS inhibition |
|---|---|
| 96 | *** |
| 97 | *** |
| 98 | *** |
| 99 | *** |
| 100 | *** |
| 102 | **** |
| 103 | **** |
| 104 | *** |
| 105 | **** |
| 106 | **** |
| 107 | **** |
| 108 | **** |
| 126 | **** |
| 129 | **** |
| 130 | **** |
| 131 | **** |

<*: <30%, : 30< <50%, *: 50< <70%, ****: >70%>

<Example 2> Analysis of Change in Expression of αSMA Induced by TGF-β1

It has been reported that a cancer associated fibroblast (CAF) is formed or fibrosis of various tissues is caused, as a fibroblast is differentiated into a myofibroblast.

In order to confirm whether the compounds of Synthetic examples of the present invention affect differentiation of fibroblasts into myofibroblasts, the inhibitory effect of the compounds of Synthetic examples on increase in expression of αSMA (biomarker for confirming differentiation into myofibroblasts) induced by TGF-β1 on HFF-1 (human foreskin fibroblast, ATCC), NHLF (normal human lung fibroblast, Lonza), LX-2 (human hepatic stellate cells, Sigma), ARPE19 (human retinal pigment epithelial cell, ATCC), and KEL-FIB (Keloid fibroblast, ATCC) cells was to be observed.

Each cell was suspended in a DMEM medium containing 10% FBS and aliquoted at a concentration of $1\times10^4$ to $1.5\times10$ 5 cells/well in a 4-well chamber slide (Nunc) and the compounds of Synthetic examples and TGF-β1 (both TGF β1 and TGF-β have the same meaning) were treated to prepare cells to be used for confirming αSMA expression. The confirmation of αSMA expression in the prepared cells was performed by immunocytochemistry as follows. For the cells, fixation with 4% paraformaldehyde for 10 minutes and permeabilization using 0.1% Triton x-100 were performed, and then processes of treating the primary antibody (anti-αSMA Ab, 1:200, at 4° C. for 16 hours) and secondary antibody (Alexa-594 conjugated Ab, 1:800, at a room temperature for 1 hour) against αSMA were progressed in order, and then the expression level of αSMA was observed using a fluorescence microscope.

FIG. 3 observes the effect of treating various compounds of Synthetic examples by 10, 20 and 40 μM, after inducing αSMA expression by treatment of TGF-β1(10 ng/ml) into HFF cells. Compound 1, Compound 23, Compound 12, Compound 5, Compound 14 and Compound 33 of Synthetic examples showed the effect of inhibiting αSMA expression of 35%-70% all, although there was a difference in degree.

In addition, also in the LX-2, NHLF, ARPE19, KEL-FIB cells, it was confirmed that the increase in expression of αSMA induced by TGF-01 (10 ng/ml) was significantly inhibited by treatment of 10 μM Synthetic example Compound 1, as could be confirmed in FIG. 4.

<Example 3> Analysis of Change in Gel Contraction Induced by TGF-β1

In order to confirm the effect of the compounds of Synthetic examples on differentiation of fibroblasts into myofibroblasts, the inhibitory effect of the compounds of Synthetic examples on the phenomenon of contraction of gel induced by interaction of human foreskin fibroblasts (HFF-1, ATCC) and collagen was observed.

The mixed solution of the HFF-1 cells and collagen (bovine type I collagen) prepared at a concentration of $3\times10^6$ cells/ml was aliquoted in a 24 well plate, respectively, and then cultured under the condition of 5% $CO_2$, 37° C. for 1 hour to induce gel polymerization. Then, after suspending the gel attached on the plate from the plate using a spoon, a medium comprising TGF-β1 and Synthetic example compounds was added to each well. After culturing for 72 hours, the Synthetic example compounds were treated by 10, 20, 30, 40, 60 and 80 μM to measure the size of the gel, and thereby, the degree of contraction of the gel by drug treatment was confirmed.

As the result of the experiment, as could be confirmed in FIG. 7, it was observed that the contraction of the gel induced by TGF-β1 (10 ng/ml) was effectively inhibited by treatment of Compound 1, Compound 5, Compound 12, Compound 13, Compound 14, Compound 16, Compound 23, Compound 33, Compound 38, Compound 63 and Compound 62 of Synthetic examples.

<Example 4> Analysis of Change in ROS Production on Dopaminergic Neural Cells

In order to confirm the effect of the compounds of Synthetic examples on ROS production from dopaminergic neural cells, ROS production was induced by alpha-synuclein preformed fibril (PFF) stimulation on N27 (rat dopaminergic neural cell, Sigma) cells and under this condition, the inhibitory effect of ROS production of the compounds of Synthetic examples was observed.

The N27 cells were cultured in RPMI medium containing 10% FBS, 1 μM angiotensin II, and the prepared cells were aliquoted at a concentration of $4\times10^3$ cells/well on a 6-well plate. The ROS production stimulus, PFF (preformed fibril) and the compounds of Synthetic examples were treated to the cells. After treating the compounds of Synthetic examples for 24 hours, fluorescence of each well was measured using CellROX-Deep Red reagent, thereby confirming the degree of ROS production.

As the result of the experiment, as could be confirmed in FIG. 2, it was confirmed that the ROS production induced by PFF was effectively inhibited by treatment of 0.001 μM Synthetic Example Compound 12, Compound 16, Compound 32 and Compound 82.

<Example 5> Analysis of Change in Expression of IL-1β Induced by LPS

In order to confirm the effect of the compounds of Synthetic examples of the present invention on inflammation reaction in human-derived fibroblasts, whether IL-10 increased by LPS treatment inhibited expression by the compounds of Synthetic examples in fibroblasts derived from various tissues was observed.

After inoculating 2×10⁵ cells in a 6 well plate and then culturing for 24 hours, they were further cultured in a serum-free culture solution for 16 hours and then the Synthetic example 1 Compound was pre-treated for 20 minutes according to each condition and inflammation reaction was induced with LPS (1 μg/ml) for 6 hours. The expression of IL-1β was confirmed using RT-PCR. Total RNA was separated from the cells using RNeasy mini kit (Qiagen), and for the separated RNA 2 ug, cDNA was synthesized using PrimeScript™ II 1$^{st}$ strand cDNA synthesis kit (TaKaRa) and then PCR was performed with AccuPower® PCR PreMix (Bioneer) to amplify genes. The nucleotide sequences for target primers are as follows. IL-1β (forward: 5'-CCACAGACCTTCCAGGAGAATG-3'(SEQ ID NO: 1), reverse: 5'-GTGCAGTTCAGTGATCGTACAGG-3'(SEQ ID NO: 2)); GAPDH (forward: 5'-GTGGCTGGCTCAGAAAAAGG-3'(SEQ ID NO: 3), reverse: 5'-GGTGGTCCAGGGGTCTTACT-3'(SEQ ID NO: 4)); β-actin (forward: 5'-CACCATTGGCAAT-GAGCGGTTC-3'(SEQ ID NO: 5), reverse: 5'-AGGTCTTTGCGGATGTCCACGT-3'(SEQ ID NO: 6)). The PCR product was confirmed by electrophoresis in 1.5% agarose gel.

As the result of the experiment, as could be confirmed in FIG. 8, it was observed that the IL-1β induced by LPS was effectively inhibited in a concentration-dependent manner by treatment of 10 μM of the Synthetic example Compound 1.

<Example 6> Analysis of Change in Expression of IL-6 and IL8 Cancer Associated Fibroblasts In order to confirm the effect of the compounds of Synthetic examples of the present invention on inflammation reaction in cancer associated fibroblasts, whether the expression of IL6 and IL8 was inhibited by the compounds of Synthetic examples in pancreatic cancer associated fibroblasts (P.CAF) was observed.

After inoculating 1.5×10⁵ cells in a 6 well plate and then culturing in P.CAF complete media for 48 hours, the compounds of Synthetic examples were treated by 10, 20, 30, 40, 60 and 80 μM for 48 hours according to each condition, and then the expression of IL-6 and IL-8 was confirmed by performing ELISA with Quantkine ELISA kit (R&D systems) as follows.

100 μl of the culture solution in which the compounds of Synthetic examples were treated for 48 hours was added to the microplate strip for analysis including a 100 μl assay diluent and left at a room temperature for 2 hours and then the contents were removed, and then it was washed with 400 μl wash buffer 4 times. 200 μl of a human IL-6 or IL-8 conjugate was added and left at a room temperature for 2 hours and then the contents were removed, and then it was washed with 400 μl wash buffer 4 times. 200 μl of substrate solution was added and left at a room temperature for 20 minutes and left at a room temperature for 20 minutes and then 50 μl of stop solution was added, and the absorbance at a wavelength of 450 nm was measured within 30 minutes to confirm the expression level of IL-6 and IL-8.

As the result of the experiment, as could be confirmed in FIGS. 5 and 6, it was observed that IL-6 and IL-8 expressed in P.CAF was effectively inhibited by treatment of Compound 1, Compound 5, Compound 12 to Compound 16, Compound 23, Compound 33, Compound 38, Compound 63 and Compound 62 of Synthetic examples.

<Example 7> Confirmation of Brain Damage Treatment Effect

In order to test the effect for preventing or treating brain disease or disorder of the compounds of Synthetic examples, it was evaluated using an alpha-synuclein preformed fibril (PFF) injection Parkinson's disease mouse model.

C57B1/6 mice were used, and all the mice were maintained under the standard condition. The experiment was conducted by dividing the experimental animals into a normal control group in which distilled water was orally administered (negative control), an alpha-synuclein preformed fibril (PFF) injection Parkinson's disease induction group (vehicle control), and an experimental group in which the compound of Synthetic example 16 of 25 mg/kg was orally administered into the alpha-synuclein preformed fibril (PFF) injection Parkinson's induction group daily (Synthetic example) with 8 animals in each group. For the normal control group, physiological saline solution was administered, and the Synthetic example compound was orally administered once a day for 7 weeks, and then a behavior change experiment and a histopathological experiment were performed.

The behavior change was analyzed by Rota rod, pole test and hindlimb clasping, and the average value of the 3 experiments per each animal was measured.

After completion of the test, the animals were anesthetized, and brain tissues were extracted for each individual, and the tissues were fixed in 4% neutral buffered formalin solution (10% buffered neutral formalin). After the fixed tissues were cut to a certain thickness, it was embedded in paraffin through a general tissue treatment process to prepare tissue sections of 4~5 μm. Thereafter, in order to confirm whether the Parkinson's disease pathological index was improved according to the level of protein aggregation in the striatum, it was first labeled with phosphorylated-Serin-129 alpha-synuclein, and then Thioflavin-T staining was performed to observe histopathological opinions.

As the result of the experiment, as the result of analyzing the behavior change such as the climedown time, Rota rod, pole test and hindlimb clasping, and the like in the administration group of the compound of Synthetic example 16, it was observed that Parkinson-like behavior symptoms were improved by 50% or more, and aggregation and accumulation of a-synuclein, an important pathological indicator of Parkinson's disease, were improved by 50% or more.

In conclusion, it was confirmed that the compounds of Synthetic examples of the present invention effectively improved Parkinson's disease.

The invention claimed is:

1. A compound of Chemical formula I below, or a stereoisomer thereof, a solvate thereof, an isotopic variant thereof, a tautomer thereof, or a pharmaceutically acceptable salt thereof:

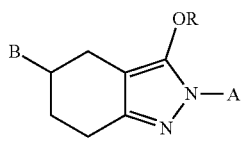

in the formula,

A is a substituted or unsubstituted 5-membered to 20-membered heteroaryl or substituted or unsubstituted $C_5$-$C_{20}$ aryl; and then, the 5-membered to 20-membered heteroaryl or $C_6$-$C_{20}$ aryl of A are unsubstituted, or are substituted with 1, 2, 3 or 4 kinds of substituents consisting of cyano, halo, $C_1$-$C_6$ haloalkyl, nitro, —C(=O)$R_1$, —C(=O)O$R_1$, —NH—C(=O)$R_1$, $C_1$-$C_{10}$ alkoxy group, substituted or unsubstituted $C_1$-$C_{10}$ alkyl, substituted or unsubstituted $C_3$-$C_8$ cycloalkyl, substituted or unsubstituted amino, substituted or unsubstituted $C_5$-$C_{20}$ aryl, substituted or unsubstituted 5-membered to 20-membered heteroaryl and substituted or unsubstituted 5-membered to 20-membered heterocycloalkyl, and then, the $R_1$ is hydrogen, heavy hydrogen, or $C_1$-$C_{10}$ alkyl, two or more adjacent substituents of the 5-membered to 20-membered heteroaryl or $C_6$-$C_{20}$ aryl of A are combined with each other to form an unsubstituted 5-membered to 10-membered heteroaryl ring comprising 0, 1, 2 or 3 heteroatoms selected from N, O and S or a $C_5$-$C_{10}$ aryl ring; and R is hydrogen, heavy hydrogen, cyano, halo, nitro, $C_1$-$C_6$ haloalkyl, substituted or unsubstituted $C_1$-$C_{10}$ alkyl, substituted or unsubstituted $C_3$-$C_8$ cycloalkyl, substituted or unsubstituted $C_5$-$C_{20}$ aryl, substituted or unsubstituted 5-membered to 20-membered heteroaryl, or —C(=O)$R_2$, and then, the $R_2$ is $C_3$-$C_8$ cycloalkyl, $C_1$-$C_{10}$ alkyl, $C_2$-$C_{10}$ alkenyl, or $C_6$-$C_{10}$ aryl; and B is -N(K)M or substituted or unsubstituted 5-membered to 20-membered heteroaryl or substituted or unsubstituted 5-membered to 20-membered heterocycloalkyl; and K is hydrogen, heavy hydrogen, cyano, halo, nitro, $C_1$-$C_6$ haloalkyl, substituted or unsubstituted $C_1$-$C_{10}$ alkyl, unsubstituted $C_1$-$C_{10}$ alkoxy, —C(=O)R', —C(=O)OR', —SO$_2$—R", substituted or unsubstituted $C_3$-$C_8$ cycloalkyl, substituted or unsubstituted $C_6$-$C_{20}$ aryl, substituted or unsubstituted $C_6$-$C_{20}$ aryl $C_1$-$C_{10}$ alkyl, substituted or unsubstituted 5-membered to 20-membered heteroaryl or substituted or unsubstituted 5-membered to 20-membered heteroaryl $C_1$-$C_{10}$ alkyl;

M is cyano, halo, nitro, $C_1$-$C_6$ haloalkyl, substituted or unsubstituted $C_1$-$C_{10}$ alkyl, unsubstituted $C_1$-$C_{10}$ alkoxy, —C(=O)R', —C(=O)OR', —SO$_2$-R", substituted or unsubstituted $C_3$-$C_8$ cycloalkyl, substituted or unsubstituted $C_6$-$C_{20}$ aryl, substituted or unsubstituted $C_6$-$C_{20}$ aryl $C_1$-$C_{10}$ alkyl, substituted or unsubstituted 5-membered to 20-membered heteroaryl or substituted or unsubstituted 5-membered to 20-membered heteroaryl $C_1$-$C_{10}$ alkyl;

wherein the $C_1$-$C_{10}$ alkyl is unsubstituted, or substituted with 1, 2, 3 or 4 kinds of substituents selected from the group consisting of heavy hydrogen, halo, hydroxy, cyano, nitro, carboxyl, substituted or unsubstituted amino, substituted or unsubstituted $C_1$-$C_{10}$ alkyl, substituted or unsubstituted $C_1$-$C_{10}$ haloalkyl, substituted or unsubstituted $C_1$-$C_{10}$ hydroxyalkyl, substituted or unsubstituted $C_3$-$C_8$ cycloalkyl, $C_1$-$C_{10}$ alkoxy, $C_1$-$C_{10}$ alkylsulfonyl, $C_5$-$C_{20}$ arylsulfonyl, $C_5$-$C_{20}$ aryloxy, substituted or unsubstituted $C_6$-$C_{20}$ aryl, substituted or unsubstituted 5-membered to 20-membered heteroaryl and substituted or unsubstituted 5-membered to 20-membered heterocycloalkyl; and the $C_3$-$C_8$ cycloalkyl is unsubstituted, or substituted with 1, 2, 3 or 4 kinds of substituents selected from the group consisting of heavy hydrogen, halogen, cyano, nitro, carboxyl, substituted or unsubstituted amino, substituted or unsubstituted $C_6$-$C_{20}$ aryl or 5-membered to 20-membered heteroaryl, $C_1$-$C_{10}$ alkoxy and $C_1$-$C_{10}$ haloalkyl; and the 5-membered to 20-membered heteroaryl, 5-membered to 20-membered heterocycloalkyl, or $C_6$-$C_{20}$ aryl is unsubstituted, or substituted with 1, 2, 3 or 4 kinds of substituents selected from the group consisting of heavy hydrogen, halo, cyano, nitro, —C(=O)R', —C(=O)OR', —NH—C(=O)R", substituted or unsubstituted amino, substituted or unsubstituted $C_1$-$C_{10}$ alkyl, unsubstituted $C_1$-$C_{10}$ alkoxy, substituted or unsubstituted $C_1$-$C_{10}$ haloalkyl, substituted or unsubstituted $C_1$-$C_{10}$ hydroxyalkyl, substituted or unsubstituted $C_1$-$C_{10}$ alkylsulfonyl, substituted or unsubstituted $C_5$-$C_{20}$ arylsulfonyl, substituted or unsubstituted $C_3$-$C_8$ cycloalkyl, substituted or unsubstituted $C_3$-$C_8$ cycloalkyl $C_1$-$C_{10}$ alkyl, substituted or unsubstituted $C_6$-$C_{20}$ aryl, substituted or unsubstituted $C_6$-$C_{20}$ aryl $C_1$-$C_{10}$ alkyl, substituted or unsubstituted 5-membered to 12-membered heterocycloalkyl, substituted or unsubstituted $C_1$-$C_{10}$ alkyl $C_3$-$C_8$ cycloalkyl and substituted or unsubstituted $C_1$-$C_{10}$ alkyl 5-membered to 20-membered heterocycloalkyl, and then, the R' and R" are each independently hydrogen, heavy hydrogen, substituted or unsubstituted amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_g$ cycloalkyl, substituted or unsubstituted $C_6$-$C_{10}$ aryl or substituted or unsubstituted $C_6$-$C_{10}$ aryl $C_1$-$C_6$ alkyl, and then, the $C_2$-$C_6$ alkenyl or $C_2$-$C_6$ alkynyl is unsubstituted or substituted with 1, 2, 3 or 4 kinds of mono $C_1$-$C_6$ alkylamine or di $C_1$-$C_6$ alkylamine; and the substituted amino group is substituted with 1 kind or 2 kinds of $C_1$-$C_{10}$ alkyl, $C_6$-$C_{10}$ aryl or $C_6$-$C_{10}$ aryl $C_1$-$C_6$ alkyl groups; and the heteroatom of the heterocycloalkyl or heteroaryl ring is one or more kinds selected from N, S and O.

2. The compound, or stereoisomer thereof, solvate thereof, isotopic variant thereof, tautomer, or pharmaceutically acceptable salt thereof according to claim 1, wherein the A is a unsubstituted, or substituted 5-membered to 12-membered heteroaryl or $C_6$-$C_{10}$ aryl, and then, the 5-membered to 12-membered heteroaryl or $C_6$-$C_{10}$ aryl of A is substituted with 1, 2, 3 or 4 kinds of substituents selected from the group consisting of cyano, halo, $C_1$-$C_6$ haloalkyl, nitro, —C(=O)$R_1$, —C(=O)O$R_1$, —NH—C(=O)$R_1$, $C_1$-$C_6$ alkyl, $C_1$-$C_6$ alkoxy, $C_3$-$C_6$ cycloalkyl, amino, $C_6$-$C_{10}$ aryl, 5-membered to 12-membered heteroaryl, and 5-membered to 12-membered heterocycloalkyl, and then the $R_1$ is hydrogen, heavy hydrogen or $C_1$-$C_6$ alkyl; and the two or more adjacent groups of the 5-membered to 12-membered heteroaryl or $C_6$-$C_{10}$ aryl of A are combined with each other to form an unsubstituted 5-membered to 7-membered heteroaryl ring comprising 0, 1, 2 or 3 heteroatoms selected from N, O and S or a $C_6$-$C_9$ aryl ring.

3. The compound, or stereoisomer thereof, solvate thereof, isotopic variant thereof, tautomer, or pharmaceutically acceptable salt thereof according to claim 1, wherein the R is hydrogen, heavy hydrogen, cyano, halo, nitro, unsubstituted or $C_3$-$C_6$ cycloalkyl-substituted $C_1$-$C_6$ alkyl, $C_1$-$C_6$ haloalkyl, $C_3$-$C_6$ cycloalkyl, $C_6$-$C_{10}$ aryl, 5-membered to 12-membered heteroaryl, —C(=O)$R_2$, and then, the $R_2$ is $C_3$-$C_6$ cycloalkyl, $C_1$-$C_6$ alkyl, $C_2$-$C_6$ alkenyl, or $C_6$-$C_{10}$ aryl.

4. The compound, or stereoisomer thereof, solvate thereof, isotopic variant thereof, tautomer, or pharmaceutically acceptable salt thereof according to claim 1, wherein the B is -N(K)M or 5-membered to 12-membered heteroaryl or 5-membered to 12-membered heterocycloalkyl, and then, the 5-membered to 12-membered heteroaryl or 5-membered to 12-membered heterocycloalkyl is unsubstituted, or substituted with 1, 2, 3 or 4 kinds of heavy hydrogen, halo, cyano, nitro, -N$R_3R_4$, $C_1$-$C_6$ alkyl, $C_1$-$C_6$ alkoxy, $C_6$-$C_{10}$ aryl, —C(=O)$R_5$, —SO$_2$-$R_6$, and then, the $C_1$-$C_6$ alkyl, $C_1$-$C_6$ alkoxy or $C_6$-$C_{10}$ aryl is unsubstituted, or substituted with 1, 2, 3 or 4 kinds of hydroxy, $C_1$-$C_6$ alkyl, $C_1$-$C_6$ alkoxy, $C_6$-$C_{10}$ aryloxy, or unsubstituted or $C_1$-$C_6$ alkyl, $C_6$-$C_{10}$ aryl $C_1$-$C_6$ alkyl or $C_1$-$C_6$ alkylcarbonyl-substituted 4-membered to 12-membered heterocycloalkyl, and the $R_3$ and $R_4$ are each independently hydrogen, heavy hydrogen, —C(=O)—Ra, $C_1$-$C_6$ alkyl or $C_6$-$C_{10}$ aryl, and the $C_1$-$C_6$ alkyl or $C_6$-$C_{10}$ aryl is unsubstituted or substituted with 1, 2, 3 or 4 kinds of halo, hydroxy, $C_1$-$C_6$ alkyl, $C_1$-$C_6$ alkoxy or $C_6$-$C_{10}$ aryloxy, and then the $R_a$ is hydrogen, heavy hydrogen, $C_1$-$C_6$ alkyl or $C_1$-$C_6$ haloalkyl; and the $R_5$ is —$OR_b$, -$NR_cRa$, $C_1$-$C_6$ alkyl, $C_2$-$C_6$ alkenyl, $C_2$-$C_6$ alkynyl, or $C_3$-$C_8$ cycloalkyl, and then, the $C_1$-$C_6$ alkyl, $C_2$-$C_6$ alkenyl or $C_2$-$C_6$ alkynyl is unsubstituted, or substituted with 1, 2, 3 or 4 kinds of mono $C_1$-$C_6$ alkylamine or di $C_1$-$C_6$ alkylamine, and then the $R_b$, $R_c$ and $R_d$ are each independently hydrogen, heavy hydrogen, $C_6$-$C_{10}$ aryl or $C_6$-$C_{10}$ aryl $C_1$-$C_6$ alkyl, and the $R_6$ is $C_1$-$C_6$ alkyl, unsubstituted or 1, 2, 3 or 4 kinds of $C_1$-$C_6$ alkyl-substituted $C_6$-$C_{10}$ aryl, and the K is hydrogen, heavy hydrogen, cyano, halo, nitro, $C_1$-$C_6$ haloalkyl, $C_1$-$C_6$ alkyl, $C_1$-$C_6$ alkoxy, —C(=O)R', —C(=O)OR', —$SO_2$-R'', $C_3$-$C_8$ cycloalkyl, $C_6$-$C_{10}$ aryl, $C_6$-$C_{10}$ aryl $C_1$-$C_6$ alkyl-, 5-membered to 12-membered heteroaryl, or 5-membered to 12-membered heteroaryl $C_1$-$C_6$ alkyl, and then the $C_1$-$C_6$ alkyl, $C_1$-$C_6$ alkoxy, $C_6$-$C_{10}$ aryl, $C_3$-$C_8$ cycloalkyl or 5-membered to 12-membered heteroaryl is substituted with 1, 2, 3 or 4 kinds of cyano, halo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylsulfonyl, $C_6$-$C_{10}$ arylsulfonyl, —C(=O)$R_9$, 5-membered to 12-membered heterocyclyl, hydroxy, nitro, or $C_6$-$C_{10}$ aryl, and then, the 5-membered to 12-membered heterocyclyl or $C_6$-$C_{10}$ aryl is unsubstituted or substituted with $C_1$-$C_6$ alkyl, the M is cyano, halo, nitro, $C_1$-$C_6$ haloalkyl, $C_1$-$C_6$ alkyl, $C_1$-$C_6$ alkoxy, —C(=O)R', —C(=O)OR', —$SO_2$-R'', $C_3$-$C_8$ cycloalkyl, $C_6$-$C_{10}$ aryl, $C_6$-$C_{10}$ aryl $C_1$-$C_6$ alkyl-, 5-membered to 12-membered heteroaryl, or 5-membered to 12-membered heteroaryl $C_1$-$C_6$ alkyl, and then the $C_1$-$C_6$ alkyl, $C_1$-$C_6$ alkoxy, $C_6$-$C_{10}$ aryl, $C_3$-$C_8$ cycloalkyl or 5-membered to 12-membered heteroaryl is substituted with 1, 2, 3 or 4 kinds of cyano, halo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylsulfonyl, $C_6$-$C_{10}$ arylsulfonyl, —C(=O)$R_9$, 5-membered to 12-membered heterocyclyl, hydroxy, nitro, or $C_6$-$C_{10}$ aryl, and then, the 5-membered to 12-membered heterocyclyl or $C_6$-$C_{10}$ aryl is unsubstituted or substituted with $C_1$-$C_6$ alkyl, and then, the R' and R'' are each independently hydrogen, heavy hydrogen, substituted or unsubstituted amino, $C_1$-$C_6$ alkyl, substituted or unsubstituted $C_2$-$C_6$ alkenyl, $C_3$-$C_8$ cycloalkyl, substituted or unsubstituted $C_6$-$C_{10}$ aryl or substituted or unsubstituted $C_6$-$C_{10}$ aryl $C_1$-$C_6$ alkyl, and then, the $C_2$-$C_6$ alkenyl is unsubstituted or substituted with 1, 2, 3 or 4 kinds of mono $C_1$-$C_6$ alkylamine or di $C_1$-$C_6$ alkylamine, the $C_6$-$C_{10}$ aryl are substituted with $C_1$-$C_{10}$ alkyl;

the substituted amino group is substituted with 1 kind or 2 kinds of $C_1$-$C_{10}$ alkyl, $C_6$-$C_{10}$ aryl or $C_6$-$C_{10}$ aryl $C_1$-$C_6$ alkyl groups; and the $R_9$ is -$OR_e$, -$NR_eR_f$, unsubstituted or 1, 2, 3 or 4 kinds of -$NR_eR_f$-substituted $C_2$-$C_6$ alkenyl, or $C_6$-$C_{10}$ aryl, and then, the Re and $R_f$ are each independently hydrogen, heavy hydrogen, $C_1$-$C_6$ alkyl, $C_6$-$C_{10}$ aryl, or $C_1$-$C_6$ alkyl.

5. The compound, or stereoisomer thereof, solvate thereof, isotopic variant thereof, tautomer, or pharmaceutically acceptable salt thereof according to claim 1, wherein the compound of Chemical formula I is a compound of Chemical formula 1-1 below:

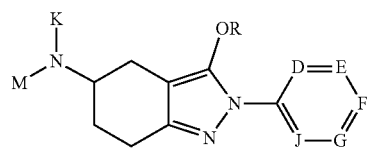

[Chemical formula I-1]

in the formula, the definition of K, M and R is same as the Chemical formula I; and D is $CR_{10}$, N, O or S, or E is $CR_{11}$, N, O or S, or F is $CR_{12}$, N, O or S, or G is $CR_{13}$, N, O or S, or J is $CR_{14}$, N, O or S, but N, O and S are one or more; and the $R_{10}$ to $R_{14}$ are same or different, and are each dependently substituted with 1, 2, 3 or 4 kinds of substituents consisting cyano, halo, $C_1$-$C_6$ haloalkyl, nitro, —C(=O) $R_1$, —C(=O)$OR_1$, —NH—C(=O)$R_1$, $C_1$-$C_{10}$ alkoxy, substituted or unsubstituted $C_1$-$C_{10}$ alkyl, substituted or unsubstituted $C_3$-$C_8$ cycloalkyl, substituted or unsubstituted amino, substituted or unsubstituted $C_6$-$C_{20}$ aryl, substituted or unsubstituted 5-membered to 12-membered heteroaryl and substituted or unsubstituted 5-membered to 12-membered heterocycloalkyl, and then the $R_1$ may be is hydrogen, heavy hydrogen, $C_1$-$C_{10}$alkyl; and two or more adjacent groups among $R_{10}$ to $R_{14}$ are combined with each other to form an unsubstituted a 5-membered to 10-membered heteroaryl ring comprising 0, 1, 2 or 3 heteroatoms selected from N, O and S or a $C_6$-$C_{10}$ aryl ring.

6. The compound, or stereoisomer thereof, solvate thereof, isotopic variant thereof, tautomer, or pharmaceutically acceptable salt thereof according to claim 1, wherein the compound of Chemical formula I is a compound of Chemical formula 1-2 below:

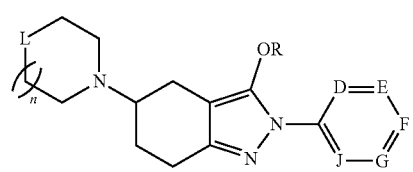

[Chemical formula I-2]

in the formula, the definition of R is same as the Chemical formula I; and

D is $CR_{10}$, N, O or S, or E is $CR_{11}$, N, O or S, or F is $CR_{12}$, N, O or S, or G is $CR_{13}$, N, O or S, or J is $CR_{14}$, N, O or S, but N, O and S are one or more; and the $R_{10}$ to $R_{14}$ are same or different, and are each independently substituted with 1, 2, 3 or 4 kinds of substituents consisting of cyano, halo, $C_1$-$C_6$haloalkyl, nitro, —C(=O)$R_1$, —C(=O)$OR_1$, —NH—C(=O)$R_1$, $C_1$-$C_{10}$ alkoxy, substituted or unsubstituted $C_1$-$C_{10}$ alkyl, substituted or unsubstituted $C_3$-$C_8$ cycloalkyl, substituted or unsubstituted amino, substituted or unsubstituted $C_6$-$C_{20}$ aryl, substituted or unsubstituted 5-membered to 12-membered heteroaryl and substituted or unsubstituted 5-membered to 12-membered heterocycloalkyl, and then the $R_1$ is hydrogen, heavy hydrogen, or $C_1$-$C_{10}$ alkyl; and two or more adjacent groups among $R_{10}$ to $R_{14}$ are combined with each other to form an unsubstituted 5-membered to 10-membered heteroaryl ring comprising 0, 1, 2 or 3 heteroatoms selected from N, O and S or a $C_6$-$C_{10}$ aryl ring, and n is an integer of 0, 1 or 2; and L is $CH_2$, NH or O; and

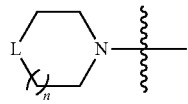

is unsubstituted, or substituted with 1, 2, 3 or 4 kinds of heavy hydrogen, halo, cyano, nitro, -$NR_3R_4$, $C_1$-$C_6$ alkyl, $C_1$-$C_6$ alkoxy, $C_6$-$C_{10}$ aryl, —C(=O)$R_5$, -$SO_2$-$R_6$, and then, when the substituent is 2 kinds or more, two or more adjacent groups among said substituents are combined with each other to form a substituted or unsubstituted 5-membered to 20-membered heteroaryl or substituted or unsubstituted 5-membered to 20-membered heterocycloalkyl with

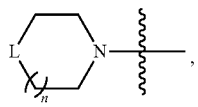

and then the $C_1$-$C_6$ alkyl, $C_1$-$C_6$ alkoxy or $C_6$-$C_{10}$ aryl is unsubstituted, or substituted with 1, 2, 3 or 4 kinds of hydroxy, $C_1$-$C_6$ alkyl, $C_1$-$C_6$ alkoxy, $C_6$-$C_{10}$ aryloxy, or unsubstituted or $C_1$-$C_6$ alkyl, $C_6$-$C_{10}$ aryl $C_1$-$C_6$ alkyl or $C_1$-$C_6$ alkylcarbonyl-substituted 4-membered to 12-membered heterocycloalkyl, and the $R_3$ and $R_4$ are each independently hydrogen, heavy hydrogen, —C(=O)—Ra, $C_1$-$C_6$ alkyl or $C_6$-$C_{10}$ aryl, and the $C_1$-$C_6$ alkyl or $C_6$-$C_{10}$ aryl is unsubstituted or substituted with 1, 2, 3 or 4 kinds of halo, hydroxy, $C_1$-$C_6$ alkyl, $C_1$-$C_6$ alkoxy or $C_6$-$C_{10}$ aryloxy, and then the $R_a$ is hydrogen, heavy hydrogen, $C_1$-$C_6$ alkyl or $C_1$-$C_6$ haloalkyl; and the $R_5$ is —$OR_b$, -$NR_cR_d$, $C_1$-$C_6$ alkyl, $C_2$-$C_6$ alkenyl, $C_2$-$C_6$ alkynyl, or $C_3$-$C_8$ cycloalkyl, and then, the $C_1$-$C_6$ alkyl, $C_2$-$C_6$ alkenyl or $C_2$-$C_6$ alkynyl is unsubstituted, or substituted with 1, 2, 3 or 4 kinds of mono $C_1$-$C_6$ alkylamine or di $C_1$-$C_6$ alkylamine, and the $R_b$, $R_c$ and $R_d$ are each independently hydrogen, heavy hydrogen, $C_6$-$C_{10}$ aryl or $C_6$-$C_{10}$ aryl $C_1$-$C_6$ alkyl, and the $R_6$ is $C_1$-$C_6$ alkyl, unsubstituted or 1, 2, 3 or 4 kinds of $C_1$-$C_6$ alkyl-substituted $C_6$-$C_{10}$ aryl.

7. The compound, or stereoisomer thereof, solvate thereof, isotopic variant thereof, tautomer, or pharmaceutically acceptable salt thereof according to claim 1, wherein the compound of Chemical formula I is a compound of Chemical formula I-3 below:

[Chemical formula I-3]

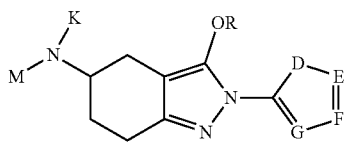

in the formula, the definition of K, M and R is same as the Chemical formula I; and D is $CR_{10}$, N, O or S, or E is $CR_{11}$, N, O or S, or F is $CR_{12}$, N, O or S, or G is $CR_{13}$, N, O or S, but N, O and S are one or more; and the $R_{10}$ to $R_{13}$ are same or different, and are each independently substituted with 1, 2, 3 or 4 kinds of substituents consisting of cyano, halo, $C_1$-$C_6$ haloalkyl, nitro, —C(=O)$R_1$, —C(=O)$OR_1$, —NH—C(=O)$R_1$, $C_1$-$C_{10}$ alkoxy, substituted or unsubstituted $C_1$-$C_{10}$ alkyl, substituted or unsubstituted $C_3$-$C_8$ cycloalkyl, substituted or unsubstituted amino, substituted or unsubstituted $C_6$-$C_{20}$ aryl, substituted or unsubstituted 5-membered to 12-membered heteroaryl and substituted or unsubstituted 5-membered to 12-membered heterocycloalkyl, and then, the $R_1$ is hydrogen, heavy hydrogen, $C_1$-$C_{10}$ alkyl; and two or more adjacent groups among $R_{10}$ to $R_{13}$ are combined with each other to form an unsubstituted 5-membered to 10-membered heteroaryl ring comprising 0, 1, 2 or 3 heteroatoms selected from N, O and S or a $C_6$-$C_{10}$ aryl ring.

8. The compound, or stereoisomer thereof, solvate thereof, isotopic variant thereof, tautomer, or pharmaceutically acceptable salt thereof according to claim 1, wherein the compound of Chemical formula I is a compound of Chemical formula I-4 below:

[Chemical formula I-4]

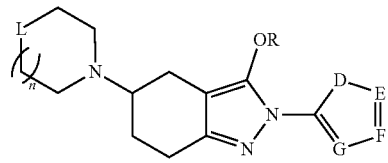

in the formula, the definition of R is same as the Chemical formula I; and

D is $CR_{10}$, N, O or S, or E is $CR_{11}$, N, O or S, or F is $CR_{12}$, N, O or S, or G is $CR_{13}$, N, O or S, but N, O and S are one or more; and the $R_{10}$ to $R_{13}$ are same or different, and are each independently substituted with 1, 2, 3 or 4 kinds of substituents consisting of cyano, halo, $C_1$-$C_6$haloalkyl, nitro, —C(=O)$R_1$, —C(=O)$OR_1$, —NH—C(=O)$R_1$, $C_1$-$C_{10}$ alkoxy, substituted or unsubstituted $C_1$-$C_{10}$ alkyl, substituted or unsubstituted $C_3$-$C_8$ cycloalkyl, substituted or unsubstituted amino, substituted or unsubstituted $C_5$-$C_{20}$ aryl, substituted or unsubstituted 5-membered to 12-membered heteroaryl and substituted or unsubstituted 5-membered to 12-membered heterocycloalkyl, and then the $R_1$ is hydrogen, heavy hydrogen, $C_1$-$C_{10}$ alkyl; and two or more adjacent groups among $R_{10}$ to $R_{13}$ are combined with each other to form an unsubstituted 5-membered to 10-membered heteroaryl ring comprising 0, 1, 2 or 3 heteroatoms selected from N, O and S or a $C_6$-$C_{10}$ aryl ring, and n is an integer of 0, 1 or 2; and L is $CH_2$, NH or O; and

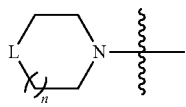

is unsubstituted, or substituted with 1, 2, 3 or 4 kinds of heavy hydrogen, halo, cyano, nitro, -NR$_3$R$_4$, C$_1$-C$_6$ alkyl, C$_1$-C$_6$ alkoxy, C$_6$-C$_{10}$ aryl, —C(=O)R$_5$, —SO$_2$-R$_6$, and then, when the substituent is 2 kinds or more, two or more adjacent groups among said substituents are combined with each other to form a substituted or unsubstituted 5-membered to 20-membered heteroaryl or substituted or unsubstituted 5-membered to 20-membered heterocycloalkyl with

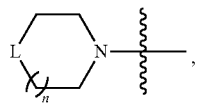

and then the C$_1$-C$_6$ alkyl, C$_1$-C$_6$ alkoxy or C$_6$-C$_{10}$ aryl is unsubstituted, or substituted with 1, 2, 3 or 4 kinds of hydroxy, C$_1$-C$_6$ alkyl, C$_1$-C$_6$ alkoxy, C$_6$-C$_{10}$ aryloxy, or unsubstituted or C$_1$-C$_6$ alkyl, C$_6$-C$_{10}$ aryl C$_1$-C$_6$ alkyl or C$_1$-C$_6$ alkylcarbonyl-substituted 4-membered to 12-membered heterocycloalkyl, and the R$_3$ and R$_4$ are each independently hydrogen, heavy hydrogen, —C(=O)—R$_a$, C$_1$-C$_6$ alkyl or C$_6$-C$_{10}$ aryl, and the C$_1$-C$_6$ alkyl or C$_6$-C$_{10}$ aryl is unsubstituted or substituted with 1, 2, 3 or 4 kinds of halo, hydroxy, C$_1$-C$_6$ alkyl, C$_1$-C$_6$ alkoxy or C$_6$-C$_{10}$ aryloxy, and then the R$_a$ is hydrogen, heavy hydrogen, C$_1$-C$_6$ alkyl or C$_1$-C$_6$ haloalkyl; and the R$_5$ is —OR$_b$, -NR$_c$R$_d$, C$_1$-C$_6$ alkyl, C$_2$-C$_6$ alkenyl, C$_2$-C$_6$ alkynyl, C$_3$-Cg cycloalkyl, and then, the C$_1$-C$_6$ alkyl, C$_2$-C$_6$ alkenyl or C$_2$-C$_6$ alkynyl is unsubstituted or substituted with 1, 2, 3 or 4 kinds of mono C$_1$-C$_6$ alkylamine or di C$_1$-C$_6$ alkylamine, and then the R$_b$, R$_c$ and R$_d$ are each independently hydrogen, heavy hydrogen, C$_6$-C$_{10}$ aryl or C$_6$-C$_{10}$ aryl C$_1$-C$_6$ alkyl, and the R$_6$ is C$_1$-C$_6$ alkyl, unsubstituted or 1, 2, 3 or 4 kinds of C$_1$-C$_6$ alkyl-substituted C$_6$-C$_{10}$ aryl.

9. The compound, or stereoisomer thereof, solvate thereof, isotopic variant thereof, tautomer, or pharmaceutically acceptable salt thereof according to claim 1, wherein the compound represented by Chemical formula I is selected from the compounds 1) to 161) below:

1. 5-(Benzylmethylamino)-2-(pyridin-2-yl)-4,5,6,7-tetrahydro-2H-indazol-3-ol;
2. 5-(Benzylcyclopropylamino)-2-(pyridin-2-yl)-4,5,6,7-tetrahydro-2H-indazol-3-ol;
3. 4-{[(3-Hydroxy-2-(pyridin-2-yl)-4,5,6,7-tetrahydro-2H-indazol-5-yl)methylamino]methyl}benzonitrile;
4. 5-[(4-Fluorobenzyl)methylamino]-2-(pyridin-2-yl)-4,5,6,7-tetrahydro-2H-indazol-3-ol;
5. 5-[(2,4-Difluorobenzyl)methylamino]-2-(pyridin-2-yl)-4,5,6,7-tetrahydro-2H-indazol-3-ol;
6) 5-[(2-Chlorobenzyl)methylamino]-2-(pyridin-2-yl)-4,5,6,7-tetrahydro-2H-indazol-3-ol;
7) 5-[(3-Chlorobenzyl)methylamino]-2-(pyridin-2-yl)-4,5,6,7-tetrahydro-2H-indazol-3-ol;
8) 5-[Methyl-(4-trifluoromethylbenzyl)amino]-2-pyridin-2-yl-4,5,6,7-tetrahydro-2H-indazol-3-ol;
9) 5-[Methyl-(3-methylbenzyl)amino]-2-(pyridin-2-yl)-4,5,6,7-tetrahydro-2H-indazol-3-ol;
10) 5-[Methyl-(3-trifluoromethylbenzyl)-amino]-2-pyridin-2-yl-4,5,6,7-tetrahydro-2H-indazol-3-ol;
11) 5-[Methyl-(2-trifluoromethylbenzyl)-amino]-2-pyridin-2-yl-4,5,6,7-tetrahydro-2H-indazol-3-ol;
12) 5-[(4-Methanesulfonylbenzyl)methylamino]-2-(pyridin-2-yl)-4,5,6,7-tetrahydro-2H-indazol-3-ol;
13) 5-[(3-Methoxybenzyl)methylamino]-2-(pyridin-2-yl)-4,5,6,7-tetrahydro-2H-indazol-3-ol;
14) 5-Piperidin-1-yl-2-(pyridin-2-yl)-4,5,6,7-tetrahydro-2H-indazol-3-ol;
15) 5-Morpholino-4-yl-2-(pyridin-2-yl)-4,5,6,7-tetrahydro-2H-indazol-3-ol;
16) 5-(4-Methylpiperazin-1-yl)-2-(pyridin-2-yl)-4,5,6,7-tetrahydro-2H-indazol-3-ol;
17) 5-(4-(2-(2-Hydroxymethoxy)ethyl)piperazin-1-yl)-2-(pyridin-2-yl)-4,5,6,7-tetrahydro-2H-indazol-3-ol;
18) 5-(3,4-Dihydro-1H-isoquinolin-2-yl)-2-(pyridin-2-yl)-4,5,6,7-tetrahydro-2H-indazol-3-ol;
19) 5-[(4-Chlorobenzyl)methylamino]-2-(pyridin-2-yl)-4,5,6,7-tetrahydro-2H-indazol-3-ol;
20) 5-(Benzylethylamino)-2-(pyridin-2-yl)-4,5,6,7-tetrahydro-2H-indazol-3-ol;
21) 5-(Benzylpropylamino)-2-(pyridin-2-yl)-4,5,6,7-tetrahydro-2H-indazol-3-ol;
22) 5-(Benzylbutylamino)-2-(pyridin-2-yl)-4,5,6,7-tetrahydro-2H-indazol-3-ol;
23) 5-[Methyl(3-methylsulfonylbenzyl)amino]-2-(pyridin-2-yl)-4,5,6,7-tetrahydro-2H-indazol-3-ol;
24) 5-[Methyl-(4-methylbenzyl)amino]-2-(pyridin-2-yl)-4,5,6,7-tetrahydro-2H-indazol-3-ol;
25) 3-{[(3-Hydroxy-2-(pyridin-2-yl)-4,5,6,7-tetrahydro-2H-indazol-5-yl)methylamino methyl}benzonitrile;
26) 5-[(2-Methoxybenzyl)-methylamino]-2-(pyridin-2-yl)-4,5,6,7-tetrahydro-2H-indazol-3-ol;
27) 5-[(3-Fluorobenzyl)methylamino]-2-(pyridin-2-yl)-4,5,6,7-tetrahydro-2H-indazol-3-ol;
28) 5-[(4-Methoxybenzyl)methylamino]-2-(pyridin-2-yl)-4,5,6,7-tetrahydro-2H-indazol-3-ol;
29) 5-[Methyl-(2-methylbenzyl)amino]-2-(pyridin-2-yl)-4,5,6,7-tetrahydro-2H-indazol-3-ol;
30) 5-[(2,4-Dichlorobenzyl)methylamino]-2-(pyridin-2-yl)-4,5,6,7-tetrahydro-2H-indazol-3-ol;
31) 5-[(3,4-Dichlorobenzyl)methylamino]-2-(pyridin-2-yl)-4,5,6,7-tetrahydro-2H-indazol-3-ol;
32) 5-(3,4-Difluorophenylamino)-2-(pyridin-2-yl)-4,5,6,7-tetrahydro-2H-indazol-3-ol;
33) 5-[Methyl(5,6,7,8-tetrahydroquinolin-8-yl)amino]-2-(pyridin-2-yl)-4,5,6,7-tetrahydro-2H-indazol-3-ol;
34) 5-(((3-(Hydroxymethyl)-5-(4-methylpiperazin-1-yl)imidazo[1,2-a]pyridin-2-yl)methyl)(methyl)amino)-2-(pyridin-2-yl)-4,5,6,7-tetrahydro-2H-indazol-3-ol;
35) 5-{[(3-(Hydroxymethyl)-5-(4-methylpiperazin-1-yl)imidazo[1,2-a]pyridin-2-yl)methyl]methylamino}-2-(pyridin-2-yl)-4,5,6,7-tetrahydro-2H-indazol-3-ol;
36) 5-{Methyl[3-methyl-5-(4-methylpiperazin-1-yl)imidazo[1,2-a]pyridin-2-yl]methylamino}-2-(pyridin-2-yl)-4,5,6,7-tetrahydro-2H-indazol-3-ol;
37) 5-{Methyl[5-(4-methylpiperazin-1-yl)imidazo[1,2-a]pyridin-2-yl]methylamino}-2-(pyridin-2-yl)-4,5,6,7-tetrahydro-2H-indazol-3-ol;
38) Cyclopropyl[4-(3-hydroxy-2-(pyridin-2-yl)-4,5,6,7-tetrahydro-2-indazol-5-yl)piperazin-1-yl]methanone;
39) 5-(Benzylmethylamino)-2-(5-trifluoromethylpyridin-2-yl)-4,5,6,7-tetrahydro-2H-indazol-3-ol;

40) 5-(Benzylmethylamino)-2-(5-chloropyridin-2-yl)-4,5,6,7-tetrahydro-2H-indazol-3-ol;
41) 5-(Benzylmethylamino)-2-(6-(trifluoromethyl)pyridin-2-yl)-4,5,6,7-tetrahydro-2H-indazol-3-ol;
42) 5-(Benzylmethylamino)-2-(6-methylpyridin-2-yl)-4,5,6,7-tetrahydro-2H-indazol-3-ol;
43) 5-(Benzylmethylamino)-2-(3-fluoropyridin-2-yl)-4,5,6,7-tetrahydro-2H-indazol-3-ol;
44) 6-(5-(Benzylmethylamino)-3-hydroxy-4,5,6,7-tetrahydro-2H-indazol-2-yl)nicotinonitrile;
45) 5-(Benzylmethylamino)-2-(6-methyl-4-trifluoromethylpyridin-2-yl)-4,5,6,7-tetrahydro-2H-indazol-3-ol;
46) 5-(Benzylamino)-2-(pyridin-2-yl)-4,5,6,7-tetrahydro-2H-indazol-3-ol;
47) 2-(Pyridin-2-yl)-5-[(pyridin-2-ylmethyl)amino]-4,5,6,7-tetrahydro-2H-indazol-3-ol;
48) 5-[Methyl(pyridin-2-ylmethyl)amino]-2-(pyridin-2-yl)-4,5,6,7-tetrahydro-2H-indazol-3-ol;
49) 5-[Methyl(pyridin-4-ylmethyl)amino]-2-(5-trifluoromethylpyridin-2-yl)-4,5,6,7-tetrahydro-2H-indazol-3-ol;
50) 2-(5-Chloropyridin-2-yl)-5-[methyl(pyridin-4-ylmethyl)amino]-4,5,6,7-tetrahydro-2H-indazol-3-ol;
51) 5-[Methyl(pyridin-4-ylmethyl)amino]-2-(pyridin-2-yl)-4,5,6,7-tetrahydro-2H-indazol-3-ol;
52) 2-(4-Bromophenyl)-5-[methyl(pyridin-4-ylmethyl)amino]-4,5,6,7,-tetrahydro-2H-indazol-3-ol;
53) 5-(Benzylmethylamino)-2-(thieno[3,2-c]pyridin-4-yl)-4,5,6,7-tetrahydro-2H-indazol-3-ol;
54) 2-(6-Aminopyridin-2-yl)-5-(benzylmethylamino)-4,5,6,7-tetrahydro-2H-indazol-3-ol;
55) 5-Phenylamino-2-(pyridin-2-yl)-4,5,6,7-tetrahydro-2H-indazol-3-ol;
56) 5-[(2,5-Dimethylphenyl)amino]-2-(pyridin-2-yl)-4,5,6,7-tetrahydro-2H-indazol-3-ol;
57) 5-[(4-Nitrophenyl) amino]-2-(pyridin-2-yl)-4,5,6,7-tetrahydro-2H-indazol-3-ol;
58) 5-[(4-Methoxyphenyl)amino]-2-(pyridin-2-yl)-4,5,6,7-tetrahydro-2H-indazol-3-ol;
59) 5-(Phenylamino)-2-(pyridin-2-yl)-4,5,6,7-tetrahydro-2H-indazol-3-ol;
60) 2-(Pyridin-2-yl)-5-(quinolin-3-ylamino)-4,5,6,7-tetrahydro-2H-indazol-3-ol;
61) 5-[Methyl(naphathalen-2-ylmethyl)amino]-2-(pyridin-2-yl)-4,5,6,7-tetrahydro-2H-indazol-3-ol;
62) 5-[(Isoquinolin-3-ylmethyl)methylamino]-2-(pyridin-2-yl)-4,5,6,7-tetrahydro-2H-indazol-3-ol;
63) 5-[Methyl(quinolin-6-ylmethyl)amino]-2-(pyridin-2-yl)-4,5,6,7-tetrahydro-2H-indazol-3-ol;
64) 5-[(Isoquinolin-3-ylmethyl)amino]-2-(pyridin-2-yl)-4,5,6,7-tetrahydro-2H-indazol-3-ol;
65) 5-[Methyl(pyridin-2-ylmethyl)amino]-2-phenyl-4,5,6,7-tetrahydro-2H-indazol-3-ol;
66) 5-[Ethyl(pyridin-4-ylmethyl)amino]-2-(pyridin-2-yl)-4,5,6,7-tetrahydro-2H-indazol-3-ol;
67) 5-[(3-Dimethylaminobenzyl)amino]-2-(pyridin-2-yl)-4,5,6,7-tetrahydro-2H-indazol-3-ol;
68) 5-[(4-Dimethylaminobenzyl)amino]-2-(pyridin-2-yl)-4,5,6,7-tetrahydro-2H-indazol-2-ol;
69) 5-[(3-Dimethylaminobenzyl)methylamino)]-2-(pyridin-2-yl)-4,5,6,7-tetrahydro-2H-indazol-3-ol;
70) 5-[(4-Dimethylamino)benzylmethylamino]-2-(pyridin-2-yl)-4,5,6,7-tetrahydro-2H-indazol-3-ol;
71) 5-[(2-Dimethylamino)benzylmethylamino]-2-(pyridin-2-yl)-4,5,6,7-tetrahydro-2H-indazol-3-ol;
72) 5-(Benzylmethylamino)-2-phenyl-4,5,6,7-tetrahydro-2H-indazol-3-ol;
73) 4-[(5-Benzylmethylamino)-3-hydroxy-4,5,6,7-tetrahydro-2H-indazol-2-yl]benzoic acid;
74) 5-(Benzylmethylamino)-2-(4-bromophenyl)-4,5,6,7-tetrahydro-2H-indazol-3-ol;
75) 5-(Benzylmethylamino)-2-(2-chlorophenyl)-4,5,6,7-tetrahydro-2H-indazol-3-ol;
76) 5-(Benzylmethylamino)-2-(2-methoxyphenyl)-4,5,6,7-tetrahydro-2H-indazol-3-ol;
77) 2-(2-Chlorophenyl)-5-[(3-dimethylaminobenzyl)methylamino]-4,5,6,7-tetrahydro-2H-indazol-3-ol;
78) 4-(((3-Hydroxy-2-(pyridin-2-yl)-4,5,6,7-tetrahydro-2H-indazol-5-yl)(methyl)amino)methyl)bezoic acid;
79) 4-(((3-Hydroxy-2-(pyridin-2-yl)-4,5,6,7-tetrahydro-2H-indazol-5-yl)(methyl)amino)methyl)benzamide;
80) 4-(((3-Hydroxy-2-(pyridin-2-yl)-4,5,6,7-tetrahydro-2H-indazol-5-yl)(methyl)amino)methyl)-N-methylbenzamide;
81) 4-(((3-Hydroxy-2-(pyridin-2-yl)-4,5,6,7-tetrahydro-2H-indazol-5-yl)(methyl)amino)methyl)-N,N-dimethylbenzamide;
82) 5-(4-Methylpiperazin-1-yl)-2-(5-(trifluoromethyl)pyridin-2-yl)-4,5,6,7-tetrahydro-2H-indazol-3-ol;
83) 2-(6-Chloropyridin-2-yl)-5-(4-methylpiperazin-1-yl)-4,5,6,7-tetrahydro-2H-indazol-3-ol;
84) 2-(6-Methyl-4-(trifluoromethyl)pyridin-2-yl)-5-(4-methylpiperazin-1-yl)-4,5,6,7-tetrahydro-2H-indazol-3-ol;
85) 5-(4-Methylpiperazin-1-yl)-2-(thieno[3,2-c]pyridin-4-yl)-4,5,6,7-tetrahydro-2H-indazol-3-ol;
86) 2-(3-Fluoropyridin-2-yl)-5-(4-methylpiperazin-1-yl)-4,5,6,7-tetrahydro-2H-indazol-3-ol;
87) 2-(Pyridin-2-yl)-5-(4-(pyridin-2-ylmethyl)piperazin-1-yl)-4,5,6,7-tetrahydro-2H-indazol-3-ol;
88) 5-((4-Methoxybenzyl)amino)-2-(pyridin-2-yl)-4,5,6,7-tetrahydro-2H-indazol-3-ol;
89) 1-(4-(3-Hydroxy-2-(pyridin-2-yl)-4,5,6,7-tetrahydro-2H-indazol-5-yl)piperazin-1-yl)but-2-en-1-one;
90) 2-(Pyridin-2-yl)-5-(4-(quinolin-6-ylmethyl)piperazin-1-yl)-4,5,6,7-tetrahydro-2H-indazol-3-ol;
91) 5-(4-Ethylpiperazin-1-yl)-2-(pyridin-2-yl)-4,5,6,7-tetrahydro-2H-indazol-3-ol;
92) 5-(Phenylamino)-2-(pyridin-2-yl)-4,5,6,7-tetrahydro-2H-indazol-3-ol;
93) 5-(Penethylamino)-2-(pyridin-2-yl)-4,5,6,7-tetrahydro-2H-indazol-3-ol;
94) 2-(4-Chlorophenyl)-5-(4-methylpiperazin-1-yl)-4,5,6,7-tetrahydro-2H-indazol-3-ol;
95) 5-(4-Methylpiperazin-1-yl)-2-(4-(trifluoromethyl)phenyl)-4,5,6,7-tetrahydro-2H-indazol-3-ol;
96) 2-(Pyridin-2-yl)-5-(pyrrolidin-1-yl)-4,5,6,7-tetrahydro-2H-indazol-3-ol;
97) 1-(4-(3-Hydroxy-2-(pyridin-2-yl)-4,5,6,7-tetrahydro-2H-indazol-5-yl)piperazin-1-yl)prop-2-en-1-one;
98) (E)-4-(dimethylamino)-1-(4-(3-hydroxy-2-(pyridin-2-yl)-4,5,6,7-tetrahydro-2H-indazol-5-yl)piperazin-1-yl)but-2-en-1-one;
99. (E)-4-(dimethylamino)-N-(3-hydroxy-2-(pyridin-2-yl)-4,5,6,7-tetrahydro-2H-indazol-5-yl)-N-methylbut-2-enamide;
100) 5-(4-Propylpiperazin-1-yl)-2-(pyridin-2-yl)-4,5,6,7-tetrahydro-2H-indazol-3-ol;
101) 2-(4-Bromophenyl)-5-(4-methylpiperazin-1-yl)-4,5,6,7-tetrahydro-2H-indazol-3-ol;
102) 2-(4-Fluorophenyl)-5-(4-methylpiperazin-1-yl)-4,5,6,7-tetrahydro-2H-indazol-3-ol;
103) 4-(3-Hydroxy-5-(4-methylpiperazin-1-yl)-4,5,6,7-tetrahydro-2H-indazol-2-yl)benzonitrile;

104) 5-(4-Penethylpiperazin-1-yl)-2-(pyridin-2-yl)-4,5,6,7-tetrahydro-2H-indazol-3-ol;
105) 5-(4-Benzylpiperazin-1-yl)-2-(pyridin-2-yl)-4,5,6,7-tetrahydro-2H-indazol-3-ol;
106) 5-(4-(Cyclohexylmethyl)piperazin-1-yl)-2-(pyridin-2-yl)-4,5,6,7-tetrahydro-2H-indazol-3-ol;
107) 5-(4-(3-Phenylpropyl)piperazin-1-yl)-2-(pyridin-2-yl)-4,5,6,7-tetrahydro-2H-indazol-3-ol;
108) 5-(4-Methylpiperazin-1-yl)-2-(pyrimidin-2-yl)-4,5,6,7-tetrahydro-2H-indazol-3-ol;
109) 5-(Piperazin-1-yl)-2-(pyridin-2-yl)-4,5,6,7-tetrahydro-2H-indazol-3-ol;
110) 5-(4-(Methylsulfonyl)piperazin-1-yl)-2-(pyridin-2-yl)-4,5,6,7-tetrahydro-2H-indazol-3-ol;
111) 5-(4-(Phenylsulfonyl)piperazin-1-yl)-2-(pyridin-2-yl)-4,5,6,7-tetrahydro-2H-indazol-3-ol;
112) 2-(Pyridin-2-yl)-5-(4-tosylpiperazin-1-yl)-4,5,6,7-tetrahydro-2H-indazol-3-ol;
113) 4-(3-Hydroxy-2-(pyridin-2-yl)-4,5,6,7-tetrahydro-2H-indazol-5-yl)-N-phenylpiperazin-1-carboxamide;
114. Benzyl 4-(3-hydroxy-2-(pyridin-2-yl)-4,5,6,7-tetrahydro-2H-indazol-5-yl)piperazin-1-carboxylate;
115) 2-(1-Methyl-1H-pyrrol-2-yl)-5-(4-methylpiperazin-1-yl)-4,5,6,7-tetrahydro-2H-indazol-3-ol;
116) 5-(4-Methylpiperazin-1-yl)-2-(thiazol-2-yl)-4,5,6,7-tetrahydro-2H-indazol-3-ol;
117) 5-(4-Methylpiperazin-1-yl)-2-(oxazol-2-yl)-4,5,6,7-tetrahydro-2H-indazol-3-ol;
118) 2-(1-Methyl-1H-pyrazol-5-yl)-5-(4-methylpiperazin-1-yl)-4,5,6,7-tetrahydro-2H-indazol-3-ol;
119) 2-(1-Methyl-1H-imidazol-5-yl)-5-(4-methylpiperazin-1-yl)-4,5,6,7-tetrahydro-2H-indazol-3-ol;
120) 2-(1-Methyl-1H-imidazol-5-yl)-5-(4-methylpiperazin-1-yl)-4,5,6,7-tetrahydro-2H-indazol-3-ol;
121) 5-(Benzyl(methyl)amino)-2-(pyrimidin-2-yl)-4,5,6,7-tetrahydro-2H-indazol-3-ol;
122) 5-(Benzyl(methyl)amino)-2-(1-methyl-1H-pyrrol-2-yl)-4,5,6,7-tetrahydro-2H-indazol-3-ol;
123) 5-(Benzyl(methyl)amino)-2-(1-methyl-1H-pyrazol-5-yl)-4,5,6,7-tetrahydro-2H-indazol-3-ol;
124) 5-(Benzyl(methyl)amino)-2-(1-methyl-1H-imidazol-5-yl)-4,5,6,7-tetrahydro-2H-indazol-3-ol;
125) 5-(Benzyl(methyl)amino)-2-(oxazol-2-yl)-4,5,6,7-tetrahydro-2H-indazol-3-ol;
126) 2-(Pyridin-2-yl)-5-(4-(p-tolyl)piperazin-1-yl)-4,5,6,7-tetrahydro-2H-indazol-3-ol;
127) 5-(4-(4-Hydroxyphenyl)piperazin-1-yl)-2-(pyridin-2-yl)-4,5,6,7-tetrahydro-2H-indazol-3-ol;
128) 5-(4-(3,4-Difluorophenyl)piperazin-1-yl)-2-(pyridin-2-yl)-4,5,6,7-tetrahydro-2H-indazol-3-ol;
129) 5-(4-(4-Methoxyphenyl)piperazin-1-yl)-2-(pyridin-2-yl)-4,5,6,7-tetrahydro-2H-indazol-3-ol;
130) 1-(4-(4-(3-Hydroxy-2-(pyridin-2-yl)-4,5,6,7-tetrahydro-2H-indazol-5-yl)piperazin-1-yl)phenyl)ethan-1-one;
131) 5-(4-(4-(Methylsulfonyl)phenyl)piperazin-1-yl)-2-(pyridin-2-yl)-4,5,6,7-tetrahydro-2H-indazol-3-ol;
132) 5-(4-(4-Phenoxyphenyl)piperazin-1-yl)-2-(pyridin-2-yl)-4,5,6,7-tetrahydro-2H-indazol-3-ol;
133) 5-(4-(Piperidin-4-ylmethyl)piperazin-1-yl)-2-(pyridin-2-yl)-4,5,6,7-tetrahydro-2H-indazol-3-ol;
134) 5-(4-((1-Methylpiperidin-4-yl)methyl)piperazin-1-yl)-2-(pyridin-2-yl)-4,5,6,7-tetrahydro-2H-indazol-3-ol;
135) 5-(4-((1-Benzylpiperidin-4-yl)methyl)piperazin-1-yl)-2-(pyridin-2-yl)-4,5,6,7-tetrahydro-2H-indazol-3-ol;
136) 1-(4-((4-(3-Hydroxy-2-(pyridin-2-yl)-4,5,6,7-tetrahydro-2H-indazol-5-yl)piperazin-1-yl)methyl)piperidin-1-yl)ethan-1-one;
137. N-(3-Hydroxy-2-(pyridin-2-yl)-4,5,6,7-tetrahydro-2H-indazol-5-yl)benzamide;
138. N-(3-Hydroxy-2-(pyridin-2-yl)-4,5,6,7-tetrahydro-2H-indazol-5-yl)-2-phenylacetamide;
139) 1-(3-Hydroxy-2-(pyridin-2-yl)-4,5,6,7-tetrahydro-2H-indazol-5-yl)-3-phenylurea;
140) 1-Benzyl-3-(3-hydroxy-2-(pyridin-2-yl)-4,5,6,7-tetrahydro-2H-indazol-5-yl)urea;
141. N-(3-Hydroxy-2-(pyridin-2-yl)-4,5,6,7-tetrahydro-2H-indazol-5-yl)benzenesulfonamide;
142. N-(3-hydroxy-2-(pyridin-2-yl)-4,5,6,7-tetrahydro-2H-indazol-5-yl)-4-methyl benzenesulfonamide;
143. Benzyl (3-hydroxy-2-(pyridin-2-yl)-4,5,6,7-tetrahydro-2H-indazol-5-yl)carbamate;
144) 2-(5-Fluoro-4-morpholinopyrimidin-2-yl)-5-(4-methylpiperazin-1-yl)-4,5,6,7-tetrahydro-2H-indazol-3-ol;
145. N-benzyl-3-methoxy-N-methyl-2-(pyridin-2-yl)-4,5,6,7-tetrahydro-2H-indazol-5-amine;
146. N-benzyl-3-(cyclopropylmethoxy)-N-methyl-2-(pyridin-2-yl)-4,5,6,7-tetrahydro-2H-indazol-5-amine;
147) 5-(Benzyl(methyl)amino)-2-(pyridin-2-yl)-4,5,6,7-tetrahydro-2H-indazol-3-yl cyclopropane carboxylate;
148) 5-(Benzyl(methyl)amino)-2-(pyridin-2-yl)-4,5,6,7-tetrahydro-2H-indazol-3-yl acrylate;
149) 5-(Benzyl(methyl)amino)-2-(pyridin-2-yl)-4,5,6,7-tetrahydro-2H-indazol-3-yl benzoate;
150) 2-(5-(Benzyl(methyl)amino)-3-hydroxy-4,5,6,7-tetrahydro-2H-indazol-2-yl)pyrimidin-5-carboxylic acid;
151. Methyl 2-(5-(benzyl(methyl)amino)-3-hydroxy-4,5,6,7-tetrahydro-2H-indazol-2-yl)nicotinate;
152. N-(6-(5-(benzyl(methyl)amino)-3-hydroxy-4,5,6,7-tetrahydro-2H-indazol-2-yl)pyridin-2-yl)acetamide;
153) 5-(Benzyl(methyl)amino)-2-(4,6-dimethoxy-1,3,5-triazin-2-yl)-4,5,6,7-tetrahydro-2H-indazol-3-ol;
154) 5-(4-Methylpiperazin-1-yl)-2-(pyrimidin-4-yl)-4,5,6,7-tetrahydro-2H-indazol-3-ol;
155) 2-(5-Chloropyridazin-3-yl)-5-(4-methylpiperazin-1-yl)-4,5,6,7-tetrahydro-2H-indazol-3-ol;
156) 2-(Pyridin-2-yl)-5-(4-(pyrimidin-2-yl)piperazin-1-yl)-4,5,6,7-tetrahydro-2H-indazol-3-ol;
157) 5-(Benzyl(methyl)amino)-2-(5-nitropyrimidin-2-yl)-4,5,6,7-tetrahydro-2H-indazol-3-ol;
158) 5-((4-Hydroxybenzyl)(methyl)amino)-2-(pyridin-2-yl)-4,5,6,7-tetrahydro-2H-indazol-3-ol;
159) 5-(Methyl(4-nitrobenzyl)amino)-2-(pyridin-2-yl)-4,5,6,7-tetrahydro-2H-indazol-3-ol;
160) 5-(3-(Ethyl(methyl)amino)pyrrolidin-1-yl)-2-(pyridin-2-yl)-4,5,6,7-tetrahydro-2H-indazol-3-ol; and
161) 2,2,2-Trifluoro-N-(1-(3-hydroxy-2-(pyridin-2-yl)-4,5,6,7-tetrahydro-2H-indazol-5-yl)pyrrolidin-3-yl) acetamide.

10. The compound or salt thereof according to claim 1, wherein the salt is in a form of a salt induced by one or more kinds of acids selected from the group consisting of hydrochloric acid, tartaric acid, hydrobromic acid, sulfuric acid, phosphoric acid, nitric acid, acetic acid, methanesulfonic acid, p-toluenesulfonic acid, acetic acid, trifluoroacetic acid, maleic acid, succinic acid, oxalic acid, benzoic acid, tartaric acid, fumaric acid acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid and hydroiodic acid; sodium salt;

potassium salt; calcium salt; silver salt; hydrobromide; hydrogen sulfate; hydrogen phosphate; dihydrogen phosphate; succinate; citrate; mesylate or tosylate.

11. A pharmaceutical composition comprising the compound or pharmaceutically acceptable salt thereof according to any one claim of claim 1 to claim 9 and a pharmaceutically acceptable carrier as an active ingredient.

12. The pharmaceutical composition according to claim 11, wherein the pharmaceutically acceptable carrier is one or more kinds selected from the group consisting of an excipient, a diluent, a disintegrating agent, a binding agent, a glydent, a surfactant, an emulsifier, a suspending agent and a diluent.

\* \* \* \* \*